(12) United States Patent
Hamblin et al.

(10) Patent No.: US 9,326,987 B2
(45) Date of Patent: *May 3, 2016

(54) INDAZOLE DERIVATIVES FOR USE IN THE TREATMENT OF INFLUENZA VIRUS INFECTION

(75) Inventors: Julie Nicole Hamblin, Stevenage (GB); Paul Spencer Jones, Stevenage (GB); Suzanne Elaine Keeling, Stevenage (GB); Joelle Le, Stevenage (GB); Charlotte Jane Mitchell, Stevenage (GB); Nigel James Parr, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 56 days.

This patent is subject to a terminal disclaimer.

(21) Appl. No.: 13/821,594

(22) PCT Filed: Sep. 6, 2011

(86) PCT No.: PCT/EP2011/065417
§ 371 (c)(1),
(2), (4) Date: Mar. 8, 2013

(87) PCT Pub. No.: WO2012/032065
PCT Pub. Date: Mar. 15, 2012

(65) Prior Publication Data
US 2013/0165433 A1   Jun. 27, 2013

Related U.S. Application Data

(60) Provisional application No. 61/380,752, filed on Sep. 8, 2010.

(51) Int. Cl.
| | | |
|---|---|---|
| A61K 31/535 | (2006.01) |
| A61K 31/497 | (2006.01) |
| A61K 31/445 | (2006.01) |
| A61K 31/55 | (2006.01) |
| A61K 31/5377 | (2006.01) |
| C07D 413/14 | (2006.01) |
| A61K 31/416 | (2006.01) |
| A61K 31/422 | (2006.01) |
| A61K 31/4245 | (2006.01) |
| A61K 31/427 | (2006.01) |
| A61K 31/437 | (2006.01) |
| A61K 31/4439 | (2006.01) |
| A61K 31/454 | (2006.01) |
| A61K 31/496 | (2006.01) |
| A61K 31/5386 | (2006.01) |

(52) U.S. Cl.
CPC ........... *A61K 31/5377* (2013.01); *A61K 31/416* (2013.01); *A61K 31/422* (2013.01); *A61K 31/427* (2013.01); *A61K 31/4245* (2013.01); *A61K 31/437* (2013.01); *A61K 31/4439* (2013.01); *A61K 31/454* (2013.01); *A61K 31/496* (2013.01); *A61K 31/5386* (2013.01); *C07D 413/14* (2013.01)

(58) Field of Classification Search
CPC ......................... A61K 31/5377; A61K 31/496
USPC ............ 514/234.5, 252.18, 254.02, 318, 322, 514/217.03
See application file for complete search history.

(56) References Cited

U.S. PATENT DOCUMENTS

| 8,586,583 B2 * | 11/2013 | Hamblin et al. | 514/234.5 |
| 8,586,590 B2 * | 11/2013 | Hamblin et al. | 514/254.02 |
| 8,609,657 B2 * | 12/2013 | Hamblin et al. | 514/234.5 |
| 2005/0215595 A1 * | 9/2005 | Arora et al. | 514/338 |

FOREIGN PATENT DOCUMENTS

| WO | 98/03487 A1 | 1/1998 |
| WO | 2006/135383 A2 | 12/2006 |
| WO | 2008/139161 A1 | 11/2008 |
| WO | 2009/147187 A1 | 12/2009 |
| WO | 2009/147188 A1 | 12/2009 |
| WO | 2009/147189 A1 | 12/2009 |
| WO | 2009/147190 A1 | 12/2009 |
| WO | 2010/083163 A1 | 7/2010 |
| WO | 2010/102958 A1 | 9/2010 |
| WO | 2010/125082 A1 | 11/2010 |
| WO | 2011/067364 A1 | 6/2011 |

OTHER PUBLICATIONS

Shin, et al., "Effect of the phosphatidylinositol 30-kinase/Akt pathway on influenza A virus propagation" 2007; Journal of General Virology; vol. 88(3); pp. 942-950.

Hale, et al., "PI3K signalling during influenza A virus infections." Biochemical Society Transactions; 2007; pp. 186-187; vol. 35, Part 2.

Ehrhardt, et al., "Bivalent role of the phosphatidylinositol-3-kinase (PI3K) during influenza virus infection and host cell defence." Cellular Microbiology; 2006; pp. 1336-1348; vol. 8, Issue 8.

* cited by examiner

*Primary Examiner* — Shengjun Wang
(74) *Attorney, Agent, or Firm* — Robert J. Smith

(57) ABSTRACT

The present invention is directed to compounds for use in the treatment or prevention of influenza virus infection.

3 Claims, 9 Drawing Sheets

INDAZOLE DERIVATIVES FOR USE IN THE TREATMENT OF INFLUENZA VIRUS INFECTION

CROSS-REFERENCE TO RELATED APPLICATIONS

This application is filed pursuant to 35 U.S.C. §371 as a United States National Phase Application of International Application No. PCT/EP2011/065417 filed Sep. 6, 2011 which claims priority from U.S. Provisional Application No. 61/380,752 filed Sep. 8, 2010.

FIELD OF THE INVENTION

The present invention is directed to compounds for use in the treatment or prevention of influenza virus infection. Specifically, the invention is directed to compounds which are inhibitors of the activity or function of phosphoinositide 3'OH kinase isoform delta (hereinafter PI3Kδ) for use in the treatment or prevention of influenza virus infection.

Phosphoinositide 3'OH kinases (hereinafter PI3Ks) are a family of signal transducer enzymes which are involved in various cellular functions including cell growth, proliferation and differentiation. A wide variety of retroviruses and DNA-based viruses activate the PI3K pathway as a way of preventing host cell death during viral infection and ultimately exploiting the host cell synthesis machinery for its replication (Virology 344(1) p. 131-8 (2006) by Vogt et al.; and Nat. Rev. Microbiol. 6(4) p. 265-75 (2008) by Buchkovich et al.). It has therefore been postulated that PI3K inhibitors may have potential therapeutic benefit in the treatment of viral infections such as influenza virus infection, in addition to the more established treatment of cancer and inflammatory diseases.

The Influenza NS1 protein activates Class Ia PI3Ks by binding to their regulatory subunit p85beta but not to other Class Ia regulatory subunits such as p85alpha. The recent crystal structure of the NS1-p85beta complex (Hale et al. Proc. Natl. Acad. Sci. USA. 107(5) p. 1954-1959 (2010)) is also suggestive of an interaction with the p110 kinase subunit providing a mechanism for catalytic activation of the kinase domain. This observation provides a rationale for isoform specificity not only with the p85 regulatory subunit but also potentially with the p110 catalytic subunit too. The function of PI3K during influenza virus infection has also been investigated by, for example, Ehrhardt et al. (Cell. Microbiol. 8(8) p. 1336-1348 (2006)), and the role of PI3Kδ signalling in morbidity and lung pathology induced by influenza virus infection has been reported in WO 2010/083163.

There remains a need to provide compounds which are inhibitors of the activity or function of PI3Kδ which may be useful in the treatment or prevention of influenza virus infection.

SUMMARY OF THE INVENTION

The invention is directed to compounds which are inhibitors of the activity or function of PI3Kδ for use in the treatment or prevention of influenza virus infection.

DETAILED DESCRIPTION OF THE INVENTION

Figure 1:
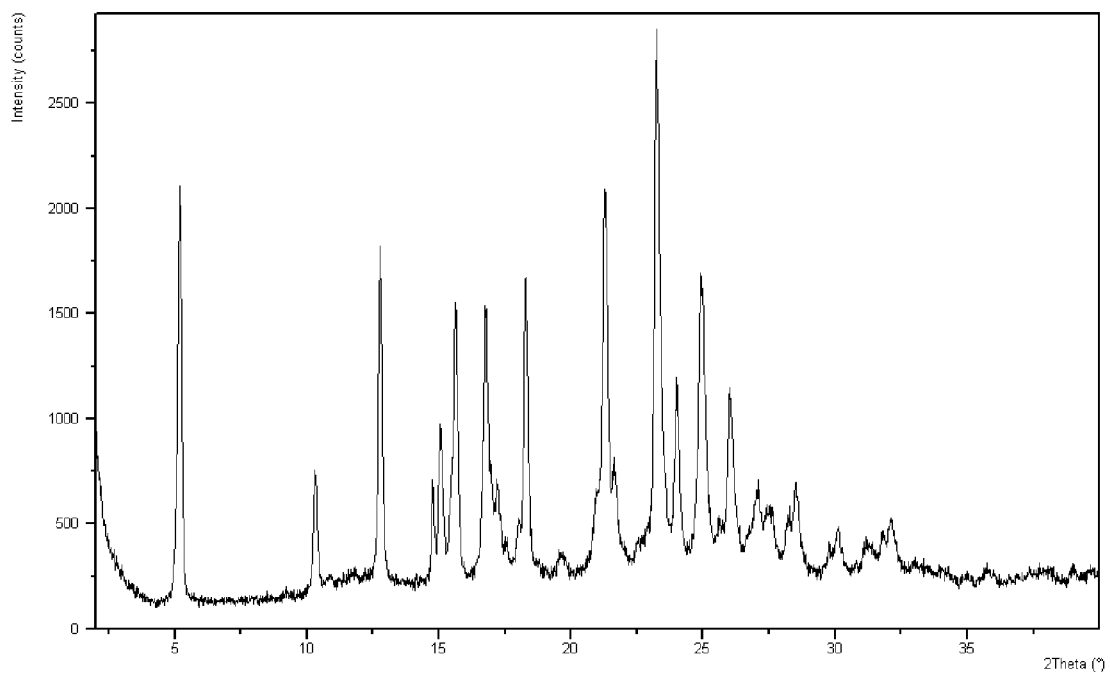
FIG. 1 shows an X-ray powder diffraction (XRPD) pattern for Example 72 (6-(1H-indol-4-yl)-4-(5-{[4-(1-methylethyl)-1-piperazinyl]methyl}-1,3-oxazol-2-yl)-1H-indazole hydrochloride).

In one embodiment, the invention is directed to compounds which are:

(a) compounds of formula (I)

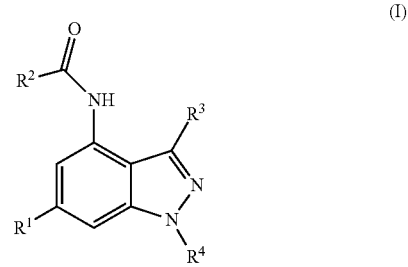

(I)

wherein
$R^1$ is phenyl substituted by one or two substituents independently selected from $C_{1-6}$alkyl, —$OR^5$, halo, —CN, —$COR^6$, $CO_2R^7$, —$CONR^8R^9$, —$NR^{10}R^{11}$, —$NHCOR^{12}$, —$SO_2R^{13}$, —$(CH_2)_mSO_2NR^{14}R^{15}$, —$NHSO_2R^{16}$, and 5-membered heteroaryl wherein the 5-membered heteroaryl contains one or two heteroatoms independently selected from oxygen and nitrogen; or pyridinyl optionally substituted by one or two substituents independently selected from $C_{1-6}$alkyl, —$OR^{17}$, halo, —$SO_2R^{18}$, —$SO_2NR^{19}R^{20}$, —$NHSO_2R^{21}$ and —$NHCOR^{24}$;

$R^2$ is —$(CH_2)_n$-phenyl optionally substituted by —CN or —$NR^{22}R^{23}$; 5- or 6-membered heteroaryl wherein the 5- or 6-membered heteroaryl contains one or two heteroatoms independently selected from oxygen, nitrogen and sulphur and is optionally substituted by $C_{1-6}$alkyl, halo or —$(CH_2)_q$$NR^{25}R^{26}$; or $C_{3-6}$cycloalkyl optionally substituted by phenyl;

$R^3$ is hydrogen or fluoro;

$R^4$ is hydrogen or methyl;
$R^7$, $R^{17}$, $R^{19}$, $R^{20}$, $R^{22}$, $R^{23}$, $R^{27}$, $R^{28}$ and $R^{29}$ are each independently hydrogen or $C_{1-6}$alkyl;
$R^5$ is hydrogen, $C_{1-6}$alkyl or —$CF_3$;
$R^6$, $R^{12}$, $R^{13}$, $R^{18}$, $R^{33}$ and $R^{34}$ are each independently $C_{1-6}$alkyl;
$R^8$ and $R^9$ are each independently hydrogen or $C_{1-6}$alkyl, or $R^8$ and $R^9$, together with the nitrogen atom to which they are attached, are linked to form a 5- or 6-membered heterocyclyl optionally containing an oxygen atom;
$R^{10}$ and $R^{11}$ are each independently hydrogen or $C_{1-6}$alkyl, or $R^{10}$ and $R^{11}$, together with the nitrogen atom to which they are attached, are linked to form a 5- or 6-membered heterocyclyl optionally containing an oxygen atom;
$R^{14}$ and $R^{15}$ are each independently hydrogen, $C_{1-6}$alkyl, $C_{3-6}$cycloalkyl or —$(CH_2)_p$phenyl, or $R^{14}$ and $R^{15}$, together with the nitrogen atom to which they are attached, are linked to form a 5- or 6-membered heterocyclyl optionally containing an oxygen atom;
$R^{16}$ is $C_{1-6}$alkyl; or phenyl optionally substituted by $C_{1-6}$alkyl;
$R^{21}$ is $C_{3-6}$cycloalkyl; $C_{1-6}$alkyl optionally substituted by —$CF_3$; phenyl optionally substituted by one or two substituents independently selected from $C_{1-6}$alkyl, —$OR^{27}$, —$CO_2R^{28}$ and halo; —$(CH_2)_u NR^{35}R^{38}$; or 5-membered heteroaryl wherein the 5-membered heteroaryl contains one or two heteroatoms independently selected from oxygen, nitrogen and sulphur and is optionally substituted by one or two substituents independently selected from $C_{1-6}$alkyl;
$R^{24}$ is $C_{1-6}$alkyl optionally substituted by —$OR^{29}$;
$R^{25}$ and $R^{26}$, together with the nitrogen atom to which they are attached, are linked to form a 5-, 6- or 7-membered heterocyclyl or a 10-membered bicyclic heterocyclyl wherein the 5-, 6- or 7-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl, $C_{3-6}$cycloalkyl, halo, oxo, phenyl optionally substituted by halo, pyridinyl, —$(CH_2)_r OR^{30}$, —$(CH_2)_s NR^{31}R^{32}$, —$COR^{33}$ and —$SO_2R^{34}$;
$R^{30}$ is hydrogen, $C_{1-6}$alkyl or —$(CH_2)_t$phenyl;
$R^{31}$ and $R^{32}$, together with the nitrogen atom to which they are attached, are linked to form a 6-membered heterocyclyl optionally containing an oxygen atom;
$R^{35}$ and $R^{36}$, together with the nitrogen atom to which they are attached, are linked to form a 5- or 6-membered heterocyclyl wherein the 5- or 6-membered heterocyclyl optionally contains an oxygen atom or a further nitrogen atom and is optionally substituted by one or two substituents independently selected from $C_{1-6}$alkyl;
m, n, p, q, r, s and t are each independently 0, 1 or 2; and
u is 1 or 2;
(b) compounds of formula (II)

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN, —$OR^{13}$ or —$NHSO_2R^{14}$; or phenyl fused to a 5-membered heterocyclyl wherein the 5-membered heterocyclyl contains one or two heteroatoms independently selected from oxygen and nitrogen and is substituted by oxo;
$R^2$ is 5-membered heteroaryl wherein the 5-membered heteroaryl contains from one to three heteroatoms independently selected from oxygen, nitrogen and sulphur and is optionally substituted by from one to three substituents independently selected from $C_{1-6}$alkyl optionally substituted by from one to three fluorine atoms; $C_{2-6}$alkenyl; $C_{3-6}$cycloalkyl; —$OR^5$; halo; —$COR^6$; —$CO_2R^7$; —$CONR^8R^9$; —$(CH_2)_m NR^{10}R^{11}$; —$CH(CH_3)NHCO$phenyl; —$NHCO_2R^{12}$; —$(CH_2)_n$phenyl; and 5-membered heteroaryl wherein the second 5-membered heteroaryl contains one or two heteroatoms independently selected from oxygen, nitrogen and sulphur and is optionally substituted by $C_{1-6}$alkyl;
$R^3$ is hydrogen or fluoro;
$R^4$ is hydrogen or methyl;
$R^5$, $R^7$, $R^{12}$ and $R^{13}$ are each independently hydrogen or $C_{1-6}$alkyl;
$R^6$, $R^{18}$ and $R^{19}$ are each independently $C_{1-6}$alkyl;
$R^8$ and $R^9$ are each independently hydrogen or $C_{1-6}$alkyl, or $R^8$ and $R^9$, together with the nitrogen atom to which they are attached, are linked to form a 5- or 6-membered heterocyclyl optionally containing an oxygen atom;
$R^{10}$ and $R^{11}$ are each independently hydrogen or $C_{1-6}$alkyl, or $R^{10}$ and $R^{11}$, together with the nitrogen atom to which they are attached, are linked to form a 5-, 6- or 7-membered heterocyclyl or a 10-membered bicyclic heterocyclyl wherein the 5-, 6- or 7-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl; $C_{3-6}$cycloalkyl; halo; oxo; phenyl optionally substituted by halo; pyridinyl; —$(CH_2)_p OR^{15}$; —$(CH_2)_q NR^{16}R^{17}$; —$COR^{18}$; and —$SO_2R^{19}$;
$R^{14}$ is $C_{1-6}$alkyl or phenyl;
$R^{15}$ is hydrogen, $C_{1-6}$alkyl or —$(CH_2)_r$phenyl;
$R^{16}$ and $R^{17}$, together with the nitrogen atom to which they are attached, are linked to form a 5- or 6-membered heterocyclyl optionally containing an oxygen atom; and
m, n, p, q, r are each independently 0, 1 or 2;
(c) compounds of formula (III)

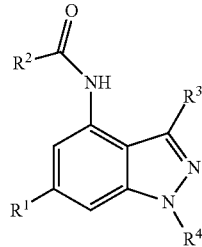

(II)

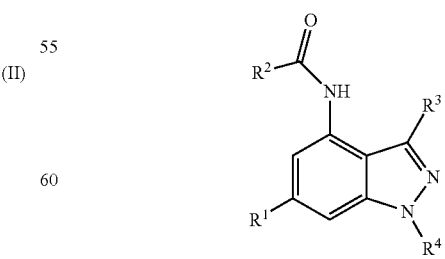

(III)

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN;

$R^2$ is pyridinyl optionally substituted by one or two substituents independently selected from $C_{1-6}$alkyl, $C_{2-6}$alkenyl, —$OR^5$, halo, —$(CH_2)_mNR^6R^7$, —$SO_2R^8$ and phenyl wherein the phenyl is optionally substituted by one or two substituents independently selected from $C_{1-6}$alkyl and —$OR^9$;

$R^3$ is hydrogen or fluoro;

$R^4$ is hydrogen, methyl or ethyl;

$R^5$ is hydrogen, $C_{1-6}$alkyl or 6-membered heterocyclyl wherein the 6-membered heterocyclyl contains one heteroatom selected from oxygen and nitrogen and is optionally substituted by $C_{1-6}$alkyl;

$R^6$ and $R^7$ are each independently hydrogen, $C_{1-6}$alkyl, $C_{3-6}$cycloalkyl or 6-membered heterocyclyl wherein the 6-membered heterocyclyl contains one heteroatom selected from oxygen and nitrogen and is optionally substituted by $C_{1-6}$alkyl, or $R^6$ and $R^7$, together with the nitrogen atom to which they are attached, are linked to form a 5- or 6-membered heterocyclyl or a 10-membered bicyclic heterocyclyl wherein the 5- or 6-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl; $C_{3-6}$cycloalkyl; halo; oxo; phenyl optionally substituted by halo; pyridinyl; —$(CH_2)_nOR^{10}$; —$(CH_2)_pNR^{11}R^{12}$; —$COR^{13}$; and —$SO_2R^{14}$;

$R^8$, $R^{13}$ and $R^{14}$ are each independently $C_{1-6}$alkyl;

$R^9$ is hydrogen or $C_{1-6}$alkyl;

$R^{10}$ is hydrogen, $C_{1-6}$alkyl or —$(CH_2)_q$phenyl;

$R^{11}$ and $R^{12}$, together with the nitrogen atom to which they are attached, are linked to form a 5- or 6-membered heterocyclyl optionally containing an oxygen atom; and m, n, p and q are each independently 0, 1 or 2;

(d) compounds of formula (IV)

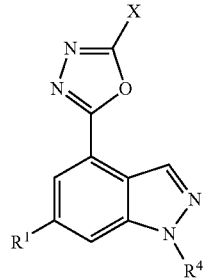

(IV)

wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN;

$R^2$ is —$NHCOR^5$,

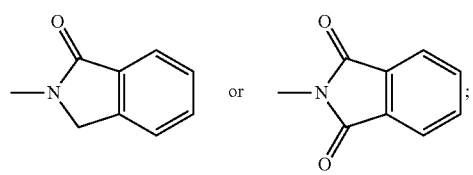

$R^3$ is hydrogen or fluoro;
$R^4$ is hydrogen or methyl;

$R^5$ is $C_{3-6}$cycloalkyl optionally substituted by phenyl;

5- or 6-membered heterocyclyl wherein the 5- or 6-membered heterocyclyl contains one or two heteroatoms independently selected from oxygen and nitrogen and is optionally substituted by one or two substituents independently selected from oxo, $C_{1-6}$alkyl, —$OR^6$, —$COR^7$, —$CO_2R^8$ and —$SO_2R^9$;

phenyl optionally substituted by one or two substituents independently selected from $C_{1-6}$alkyl, —$OR^{10}$, halo, —$NR^{11}R^{12}$, and phenyl optionally substituted by halo;

—$CH_2$-5- or 6-membered heteroaryl wherein the 5- or 6-membered heteroaryl contains one or two nitrogen atoms and is optionally substituted by $C_{1-6}$alkyl;

pyrazine optionally substituted by —$OR^{13}$; or 9- or 10-membered bicyclic heteroaryl wherein the 9- or 10-membered bicyclic heteroaryl contains one or two nitrogen atoms;

$R^6$, $R^{11}$, $R^{12}$ and $R^{13}$ are each independently hydrogen or $C_{1-6}$alkyl;

$R^7$ and $R^9$ are each independently $C_{1-6}$alkyl;

$R^8$ is hydrogen or —$(CH_2)_m$phenyl;

$R^{10}$ is $C_{1-6}$alkyl optionally substituted by from one to three fluoros; and m is 0, 1 or 2;

(e) compounds of formula (V)

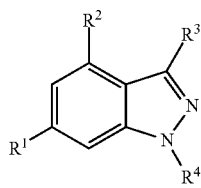

(V)

wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —$NHSO_2R^6$, or pyridinyl optionally substituted by one or two substituents independently selected from $C_{1-6}$alkyl, —$OR^6$, halo and —$NHSO_2R^7$;

X is —$CH_2NR^2R^3$, $C_{1-6}$alkyl, —$CH_2$-phenyl, —$(CH_2)_nOR^{10}$, —$CH_2SO_2R^{11}$ or —$(CH_2)_pC_{3-6}$cycloalkyl;

$R^2$ and $R^3$, together with the nitrogen atom to which they are attached, are linked to form a 6- or 7-membered heterocyclyl or a 9- or 10-membered bicyclic heterocyclyl wherein the 6- or 7-membered heterocyclyl or the 9- or 10-membered bicyclic heterocyclyl optionally contains an oxygen atom, a sulphur atom or a further nitrogen atom and is optionally substituted by from one to three substituents independently selected from oxo, $C_{1-6}$alkyl, —$(CH_2)_mNR^8R^9$, phenyl optionally substituted by halo, and 6-membered heteroaryl wherein the 6-membered heteroaryl contains one or two nitrogen atoms, a 7-membered bridged heterocyclyl wherein the 7-membered bridged heterocyclyl optionally contains a further nitrogen atom and is optionally substituted by from one to three substituents independently selected from $C_{1-6}$alkyl, or a 10-membered spiro bicyclic heterocyclyl wherein the 10-membered spiro bicyclic heterocyclyl optionally contains an oxygen atom, or $R^2$ is hydrogen and $R^3$ is $C_{1-6}$alkyl optionally substituted by one or two substituents independently selected from —$OR^{12}$ and —$NR^{13}R^{14}$;

$R^4$ is hydrogen or methyl;

$R^6$, $R^{12}$ and $R^{15}$ are each independently hydrogen or $C_{1-4}$alkyl;

$R^5$ and $R^7$ are each independently $C_{1-6}$alkyl or phenyl wherein the phenyl is optionally substituted by one or two substituents independently selected from halo and —$OR^{15}$;

$R^8$ and $R^9$, together with the nitrogen atom to which they are attached, are linked to form a 5- or 6-membered heterocyclyl optionally containing an oxygen atom;

$R^{10}$ is hydrogen, $C_{1-6}$alkyl, —$(CH_2)_q$phenyl or $C_{3-6}$cycloalkyl wherein the $C_{3-6}$cycloalkyl is optionally substituted by one or two substituents independently selected from $C_{1-6}$alkyl;

$R^{11}$ is $C_{1-6}$alkyl or phenyl;

$R^{13}$ and $R^{14}$, together with the nitrogen atom to which they are attached, are linked to form a 6-membered heterocyclyl optionally containing an oxygen atom;

m, p and q are each independently 0, 1 or 2; and n is 1 or 2;

(f) compounds of formula (VI)

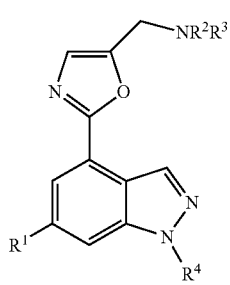

(VI)

wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —$NHSO_2R^5$, or pyridinyl optionally substituted by one or two substituents independently selected from $C_{1-6}$alkyl, —$OR^6$, halo and —$NHSO_2R^7$;

$R^2$ and $R^3$, together with the nitrogen atom to which they are attached, are linked to form a 6- or 7-membered heterocyclyl wherein the 6- or 7-membered heterocyclyl optionally contains an oxygen atom or a further nitrogen atom and is optionally substituted by one or two substituents independently selected from $C_{1-6}$alkyl;

$R^4$ is hydrogen or methyl;

$R^6$ is hydrogen or $C_{1-4}$alkyl; and $R^5$ and $R^7$ are each independently $C_{1-6}$alkyl, or phenyl optionally substituted by one or two substituents independently selected from halo; and (g) compounds of formula (VII)

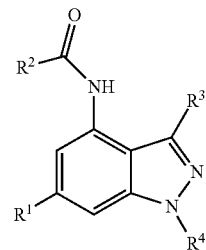

(I)

wherein $R^1$ is 9-membered bicyclic heteroaryl wherein the 9-membered bicyclic heteroaryl contains from one to three heteroatoms independently selected from oxygen and nitrogen and is optionally substituted by $C_{1-6}$alkyl, halo or —CN; or phenyl fused to pyrrolidinyl wherein the pyrrolidinyl is substituted by oxo;

$R^2$ is 5-membered heteroaryl wherein the 5-membered heteroaryl contains one or two heteroatoms independently selected from oxygen, nitrogen and sulphur and is optionally substituted by one or two substituents independently selected from $C_{1-6}$alkyl, —$CO_2R^5$ and —$CH_2NR^6R^7$; or pyridinyl substituted by $C_{1-6}$alkyl or —$CH_2NR^8R^9$;

$R^3$ is hydrogen or fluoro;

$R^4$ is hydrogen or methyl;

$R^5$ is hydrogen or $C_{1-6}$alkyl;

$R^6$ and $R^7$, together with the nitrogen atom to which they are attached, are linked to form a 6-membered heterocyclyl wherein the 6-membered heterocyclyl optionally contains an oxygen atom and is optionally substituted by $C_{1-6}$alkyl; and $R^8$ and $R^9$, together with the nitrogen atom to which they are attached, are linked to form a 6-membered heterocyclyl wherein the 6-membered heterocyclyl optionally contains a sulphur atom and is optionally substituted by one or two oxo substituents;

and pharmaceutically acceptable salts thereof for use in the treatment or prevention of influenza virus infection.

In one embodiment, the invention is directed to compounds of formula (VI)

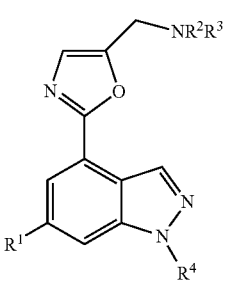

(VI)

wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —$NHSO_2R^5$, or pyridinyl optionally substituted by one or two substituents independently selected from $C_{1-6}$alkyl, —$OR^6$, halo and —$NHSO_2R^7$;

$R^2$ and $R^3$, together with the nitrogen atom to which they are attached, are linked to form a 6- or 7-membered heterocyclyl wherein the 6- or 7-membered heterocyclyl optionally contains an oxygen atom or a further nitrogen atom and is optionally substituted by one or two substituents independently selected from $C_{1-6}$alkyl;
$R^4$ is hydrogen or methyl;
$R^6$ is hydrogen or $C_{1-4}$alkyl; and
$R^5$ and $R^7$ are each independently $C_{1-6}$alkyl, or phenyl optionally substituted by one or two substituents independently selected from halo;
and pharmaceutically acceptable salts thereof for use in the treatment or prevention of influenza virus infection.

In one embodiment, in the compounds of formula (VI), $R^1$ is 9-membered bicyclic heteroaryl wherein the 9-membered bicyclic heteroaryl contains one or two nitrogen atoms, or pyridinyl optionally substituted by one or two substituents independently selected from —$OR^6$ and —$NHSO_2R^7$. In another embodiment, $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —$NHSO_2R^5$. In another embodiment, $R^1$ is 9- or 10-membered bicyclic heteroaryl wherein the 9- or 10-membered bicyclic heteroaryl contains one or two nitrogen atoms and is optionally substituted by $C_{1-6}$alkyl or halo. In another embodiment, $R^1$ is 9-membered bicyclic heteroaryl wherein the 9-membered bicyclic heteroaryl contains one or two nitrogen atoms. In another embodiment, $R^1$ is indolyl, for example 1H-indol-4-yl. In another embodiment, $R^1$ is pyridinyl optionally substituted by one or two substituents independently selected from $C_{1-6}$alkyl, —$OR^6$, halo and —$NHSO_2R^7$. In another embodiment, $R^1$ is pyridinyl optionally substituted by one or two substituents independently selected from —$OR^6$ and —$NHSO_2R^7$. In a further embodiment, $R^1$ is pyridinyl substituted by —$OR^6$ and —$NHSO_2R^7$.

In one embodiment, in the compounds of formula (VI), $R^2$ and $R^3$, together with the nitrogen atom to which they are attached, are linked to form a 6-membered heterocyclyl wherein the 6-membered heterocyclyl optionally contains an oxygen atom or a further nitrogen atom and is optionally substituted by one or two substituents independently selected from $C_{1-6}$alkyl. In another embodiment, $R^2$ and $R^3$, together with the nitrogen atom to which they are attached, are linked to form a 6-membered heterocyclyl wherein the 6-membered heterocyclyl optionally contains an oxygen atom or a further nitrogen atom and is substituted by one or two substituents independently selected from $C_{1-4}$alkyl, for example methyl. In another embodiment, $R^2$ and $R^3$, together with the nitrogen atom to which they are attached, are linked to form a 6-membered heterocyclyl wherein the 6-membered heterocyclyl contains an oxygen atom and is optionally substituted by one or two substituents independently selected from $C_{1-4}$alkyl, for example methyl. In another embodiment, $R^2$ and $R^3$, together with the nitrogen atom to which they are attached, are linked to form a 6-membered heterocyclyl wherein the 6-membered heterocyclyl contains an oxygen atom and is substituted by one or two substituents independently selected from $C_{1-6}$alkyl. In another embodiment, $R^2$ and $R^3$, together with the nitrogen atom to which they are attached, are linked to form a 6-membered heterocyclyl wherein the 6-membered heterocyclyl contains a further nitrogen atom and is optionally substituted by $C_{1-4}$alkyl, for example isopropyl. In a further embodiment, $R^2$ and $R^3$, together with the nitrogen atom to which they are attached, are linked to form a 6-membered heterocyclyl wherein the 6-membered heterocyclyl contains a further nitrogen atom and is substituted by $C_{1-4}$alkyl, for example isopropyl.

In one embodiment, in the compounds of formula (VI), $R^4$ is hydrogen.

In one embodiment, in the compounds of formula (VI), $R^5$ is $C_{1-4}$alkyl such as methyl.

In one embodiment, in the compounds of formula (VI), $R^6$ is $C_{1-4}$alkyl such as methyl.

In one embodiment, in the compounds of formula (VI), $R^7$ is $C_{1-6}$alkyl. In another embodiment, $R^7$ is $C_{1-4}$alkyl such as methyl. In a further embodiment, $R^7$ is phenyl optionally substituted by one or two substituents independently selected from halo, for example fluoro.

It is to be understood that the present invention covers the use of compounds having all combinations of substituent groups described hereinabove.

Compounds suitable for use according to the invention include the compounds of Preparative Examples 1 to 71 and 75 to 105 and pharmaceutically acceptable salts thereof.

In one embodiment, the compound for use according to the invention is a compound of formula (I) which is:
6-bromo-N-[6-(4-hydroxyphenyl)-1H-indazol-4-yl]-2-pyridinecarboxamide;
N-[6-(3-hydroxyphenyl)-1H-indazol-4-yl]cyclohexanecarboxamide;
N-[6-(3-hydroxyphenyl)-1H-indazol-4-yl]-2-pyridinecarboxamide;
N-[6-(3-hydroxyphenyl)-1H-indazol-4-yl]-3-phenylpropanamide;
4-cyano-N-[6-(3-hydroxyphenyl)-1H-indazol-4-yl]benzamide;
3-(dimethylamino)-N-[6-(3-hydroxyphenyl)-1H-indazol-4-yl]benzamide;
(1R,2R)—N-[6-(3-hydroxyphenyl)-1H-indazol-4-yl]-2-phenylcyclopropanecarboxamide;
N-[6-(3-hydroxyphenyl)-1H-indazol-4-yl]-2-furancarboxamide;
N-[6-(3-hydroxyphenyl)-1H-indazol-4-yl]cyclopropanecarboxamide;
N-{6-[5-(aminosulfonyl)-3-pyridinyl]-1H-indazol-4-yl}-2-methyl-1,3-thiazole-4-carboxamide;
N-(6-{3-[(aminosulfonyl)methyl]phenyl}-1H-indazol-4-yl)-2-methyl-1,3-thiazole-4-carboxamide;
2-methyl-N-{6-[5-(methyloxy)-3-pyridinyl]-1H-indazol-4-yl}-1,3-thiazole-4-carboxamide;
3-(4-{[(2-methyl-1,3-thiazol-4-yl)carbonyl]amino}-1H-indazol-6-yl)benzoic acid;
N-(6-{6-chloro-5-[(phenylsulfonyl)amino]-3-pyridinyl}-1H-indazol-4-yl)-2-methyl-1,3-thiazole-4-carboxamide;
N-{6-[4-(acetylamino)phenyl]-1H-indazol-4-yl}-2-pyridinecarboxamide;
N-(6-{3-[(methylsulfonyl)amino]phenyl}-1H-indazol-4-yl)-2-pyridinecarboxamide;
N-[6-(3-{[(4-methylphenyl)sulfonyl]amino}phenyl)-1H-indazol-4-yl]-2-pyridinecarboxamide;
N-{6-[3,4-bis(methyloxy)phenyl]-1H-indazol-4-yl}-2-pyridinecarboxamide;
N-{6-[3-(4-morpholinyl)phenyl]-1H-indazol-4-yl}-2-pyridinecarboxamide;
N-(6-{3-[(methylamino)carbonyl]phenyl}-1H-indazol-4-yl)-2-pyridinecarboxamide;
N-{6-[3-(2-furanyl)phenyl]-1H-indazol-4-yl}-2-pyridinecarboxamide;
N-{6-[4-(2-furanyl)phenyl]-1H-indazol-4-yl}-2-pyridinecarboxamide;
N-[6-(3-{[(phenylmethyl)amino]sulfonyl}phenyl)-1H-indazol-4-yl]-2-pyridinecarboxamide;

N-[6-(3-cyanophenyl)-1H-indazol-4-yl]-2-methyl-1,3-thiazole-4-carboxamide;
2-methyl-N-{6-[3-(methylsulfonyl)phenyl]-1H-indazol-4-yl}-1,3-thiazole-4-carboxamide;
N-[6-(3-chloro-2-fluorophenyl)-1H-indazol-4-yl]-2-methyl-1,3-thiazole-4-carboxamide;
2-methyl-N-(6-{3-[(1-methylethyl)oxy]phenyl}-1H-indazol-4-yl)-1,3-thiazole-4-carboxamide;
N-{6-[3-(ethyloxy)-2-fluorophenyl]-1H-indazol-4-yl}-2-methyl-1,3-thiazole-4-carboxamide;
N-[6-(3-fluorophenyl)-1H-indazol-4-yl]-2-methyl-1,3-thiazole-4-carboxamide;
N-(6-{3-[(diethylamino)carbonyl]phenyl}-1H-indazol-4-yl)-2-methyl-1,3-thiazole-4-carboxamide;
N-(6-{3-[(dimethylamino)carbonyl]phenyl}-1H-indazol-4-yl)-2-methyl-1,3-thiazole-4-carboxamide;
2-methyl-N-(6-{3-[(methylamino)sulfonyl]phenyl}-1H-indazol-4-yl)-1,3-thiazole-4-carboxamide;
N-[6-(3-acetylphenyl)-1H-indazol-4-yl]-2-methyl-1,3-thiazole-4-carboxamide;
N-[6-(2,3-difluorophenyl)-1H-indazol-4-yl]-2-methyl-1,3-thiazole-4-carboxamide;
2-methyl-N-{6-[3-(4-morpholinylsulfonyl)phenyl]-1H-indazol-4-yl}-1,3-thiazole-4-carboxamide;
2-methyl-N-(6-{3-[(trifluoromethyl)oxy]phenyl}-1H-indazol-4-yl)-1,3-thiazole-4-carboxamide;
2-methyl-N-{6-[3-(1-pyrrolidinylcarbonyl)phenyl]-1H-indazol-4-yl}-1,3-thiazole-4-carboxamide;
2-methyl-N-{6-[3-(1-pyrrolidinylsulfonyl)phenyl]-1H-indazol-4-yl}-1,3-thiazole-4-carboxamide;
N-{6-[3-(acetylamino)phenyl]-1H-indazol-4-yl}-2-methyl-1,3-thiazole-4-carboxamide;
N-{6-[3-(aminocarbonyl)phenyl]-1H-indazol-4-yl}-2-methyl-1,3-thiazole-4-carboxamide;
N-(6-{3-[(cyclopropylamino)sulfonyl]phenyl}-1H-indazol-4-yl)-2-methyl-1,3-thiazole-4-carboxamide;
N-{6-[3-(dimethylamino)phenyl]-1H-indazol-4-yl}-2-methyl-1,3-thiazole-4-carboxamide;
N-[6-(3-methylphenyl)-1H-indazol-4-yl]cyclopropanecarboxamide;
N-[6-(4-hydroxyphenyl)-1H-indazol-4-yl]cyclopropanecarboxamide;
N-[6-(4-hydroxyphenyl)-1H-indazol-4-yl]cyclohexanecarboxamide;
N-[6-(4-hydroxyphenyl)-1H-indazol-4-yl]-2-pyridinecarboxamide;
3-(dimethylamino)-N-[6-(4-hydroxyphenyl)-1H-indazol-4-yl]benzamide;
N-[6-(4-hydroxyphenyl)-1H-indazol-4-yl]-3-phenylpropanamide;
(1R,2R)—N-[6-(4-hydroxyphenyl)-1H-indazol-4-yl]-2-phenylcyclopropanecarboxamide;
N-[6-(4-hydroxyphenyl)-1H-indazol-4-yl]-2-furancarboxamide;
2-methyl-N-{6-[5-(methylsulfonyl)-3-pyridinyl]-1H-indazol-4-yl}-1,3-thiazole-4-carboxamide;
2-methyl-N-[6-(4-methyl-3-pyridinyl)-1H-indazol-4-yl]-1,3-thiazole-4-carboxamide;
2-methyl-N-[6-(3-pyridinyl)-1H-indazol-4-yl]-1,3-thiazole-4-carboxamide;
2-methyl-N-[6-(2-oxo-1,2-dihydro-4-pyridinyl)-1H-indazol-4-yl]-1,3-thiazole-4-carboxamide;
2-methyl-N-[6-(4-pyridinyl)-1H-indazol-4-yl]-1,3-thiazole-4-carboxamide;
2-methyl-N-(6-{6-methyl-5-[(methylsulfonyl)amino]-3-pyridinyl}-1H-indazol-4-yl)-1,3-thiazole-4-carboxamide;
N-(6-{6-chloro-5-[(methylsulfonyl)amino]-3-pyridinyl}-1H-indazol-4-yl)-2-(4-morpholinylmethyl)-1,3-thiazole-4-carboxamide;
N-(6-{6-chloro-5-[(methylsulfonyl)amino]-3-pyridinyl}-1H-indazol-4-yl)-2-(1-piperidinylmethyl)-1,3-thiazole-4-carboxamide;
N-(6-{6-chloro-5-[(methylsulfonyl)amino]-3-pyridinyl}-1H-indazol-4-yl)-2-{[4-(1-methylethyl)-1-piperazinyl]methyl}-1,3-thiazole-4-carboxamide;
N-(6-{6-chloro-5-[(methylsulfonyl)amino]-3-pyridinyl}-1H-indazol-4-yl)-2-{[(2R,6S)-2,6-dimethyl-4-morpholinyl]methyl}-1,3-thiazole-4-carboxamide;
N-(6-{6-chloro-5-[(methylsulfonyl)amino]-3-pyridinyl}-1H-indazol-4-yl)-2-{[3-methyl-4-(1-methylethyl)-1-piperazinyl]methyl}-1,3-thiazole-4-carboxamide;
2-{[4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide;
N-(6-{6-(methyloxy)-5-[(methylsulfonyl)amino]-3-pyridinyl}-1H-indazol-4-yl)-2-(4-morpholinylmethyl)-1,3-thiazole-4-carboxamide;
N-(6-{6-(methyloxy)-5-[(methylsulfonyl)amino]-3-pyridinyl}-1H-indazol-4-yl)-2-(1-piperidinylmethyl)-1,3-thiazole-4-carboxamide;
2-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide;
2-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-1,3-thiazole-4-carboxamide;
2-{[(2R,6S)-2,6-dimethyl-4-morpholinyl]methyl}-N-{6-[5-[(ethylsulfonyl)amino]-6-(methyloxy)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[3-(methyloxy)phenyl]sulfonyl}amino)-3-pyridinyl]-1H-indazol-4-yl}-1,3-thiazole-4-carboxamide;
N-{6-[5-[(cyclohexylsulfonyl)amino]-6-(methyloxy)-3-pyridinyl]-1H-indazol-4-yl}-2-{[(2R,6S)-2,6-dimethyl-4-morpholinyl]methyl}-1,3-thiazole-4-carboxamide;
2-{[(2R,6S)-2,6-dimethyl-4-morpholinyl]methyl}-N-{6-[5-{[(1-methylethyl)sulfonyl]amino}-6-(methyloxy)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[4-(methyloxy)phenyl]sulfonyl}amino)-3-pyridinyl]-1H-indazol-4-yl}-1,3-thiazole-4-carboxamide;
2-{[(2R,6S)-2,6-dimethyl-4-morpholinyl]methyl}-N-(6-{6-(methyloxy)-5-[(propylsulfonyl)amino]-3-pyridinyl}-1H-indazol-4-yl)-1,3-thiazole-4-carboxamide;
4-({[5-(4-{[(2-{[(2R,6S)-2,6-dimethyl-4-morpholinyl]methyl}-1,3-thiazol-4-yl)carbonyl]amino}-1H-indazol-6-yl)-2-(methyloxy)-3-pyridinyl]amino}sulfonyl)benzoic acid;
3-({[5-(4-{[(2-{[(2R,6S)-2,6-dimethyl-4-morpholinyl]methyl}-1,3-thiazol-4-yl)carbonyl]amino}-1H-indazol-6-yl)-2-(methyloxy)-3-pyridinyl]amino}sulfonyl)benzoic acid;
2-{[(2R,6S)-2,6-dimethyl-4-morpholinyl]methyl}-N-[6-(6-(methyloxy)-5-{[(3,3,3-trifluoropropyl)sulfonyl]amino}-3-pyridinyl)-1H-indazol-4-yl]-1,3-thiazole-4-carboxamide;

2-{[(2R,6S)-2,6-dimethyl-4-morpholinyl]methyl}-N-[6-(6-(methyloxy)-5-{[(2,2,2-trifluoroethyl)sulfonyl]amino}-3-pyridinyl)-1H-indazol-4-yl]-1,3-thiazole-4-carboxamide;

N-(6-{6-chloro-5-[(methylsulfonyl)amino]-3-pyridinyl}-1H-indazol-4-yl)-6-{[(2R,6S)-2,6-dimethyl-4-morpholinyl]methyl}-2-pyridinecarboxamide;

N-(6-{6-chloro-5-[(methylsulfonyl)amino]-3-pyridinyl}-1H-indazol-4-yl)-6-(4-morpholinylmethyl)-2-pyridinecarboxamide;

N-(6-{6-chloro-5-[(methylsulfonyl)amino]-3-pyridinyl}-1H-indazol-4-yl)-6-(1-piperidinylmethyl)-2-pyridinecarboxamide;

N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide;

N-(6-{6-chloro-5-[(methylsulfonyl)amino]-3-pyridinyl}-1H-indazol-4-yl)-6-{[3-methyl-4-(1-methylethyl)-1-piperazinyl]methyl}-2-pyridinecarboxamide;

6-[(1,1-dioxido-4-thiomorpholinyl)methyl]-N-(6-{6-(methyloxy)-5-[(methylsulfonyl)amino]-3-pyridinyl}-1H-indazol-4-yl)-2-pyridinecarboxamide;

N-(6-{6-(methyloxy)-5-[(methylsulfonyl)amino]-3-pyridinyl}-1H-indazol-4-yl)-6-(1-piperidinylmethyl)-2-pyridinecarboxamide;

N-(6-{6-(methyloxy)-5-[(methylsulfonyl)amino]-3-pyridinyl}-1H-indazol-4-yl)-6-(4-morpholinylmethyl)-2-pyridinecarboxamide;

6-{[4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide;

6-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-2-pyridinecarboxamide;

6-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide;

N-{6-[5-[(cyclopropylsulfonyl)amino]-6-(methyloxy)-3-pyridinyl]-1H-indazol-4-yl}-2-methyl-1,3-thiazole-4-carboxamide;

N-{6-[5-{[(2,4-difluorophenyl)sulfonyl]amino}-6-(methyloxy)-3-pyridinyl]-1H-indazol-4-yl}-2-methyl-1,3-thiazole-4-carboxamide;

2-methyl-N-(6-{6-(methyloxy)-5-[(methylsulfonyl)amino]-3-pyridinyl}-1H-indazol-4-yl)-1,3-thiazole-4-carboxamide;

N-{6-[5-[(2-hydroxypropanoyl)amino]-6-(methyloxy)-3-pyridinyl]-1H-indazol-4-yl}-2-methyl-1,3-thiazole-4-carboxamide;

N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide;

N-{6-[5-{[(2,4-difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;

2-[(2-methyl-4-morpholinyl)methyl]-N-(6-{6-(methyloxy)-5-[(methylsulfonyl)amino]-3-pyridinyl}-1H-indazol-4-yl)-1,3-thiazole-4-carboxamide;

N-(6-{6-(methyloxy)-5-[(methylsulfonyl)amino]-3-pyridinyl}-1H-indazol-4-yl)-2-(tetrahydro-1,4-oxazepin-4(5H)-ylmethyl)-1,3-thiazole-4-carboxamide;

2-[(2-ethyl-4-morpholinyl)methyl]-N-(6-{6-(methyloxy)-5-[(methylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-(1-methyl-6-{6-(methyloxy)-5-[(methylsulfonyl)amino]-3-pyridinyl}-1H-indazol-4-yl)-1,3-thiazole-4-carboxamide;

N-{6-[5-{[(2,4-difluorophenyl)sulfonyl]amino}-6-(methyloxy)-3-pyridinyl]-1-methyl-1H-indazol-4-yl}-2-{[(2R,6S)-2,6-dimethyl-4-morpholinyl]methyl}-1,3-thiazole-4-carboxamide;

2-{[(2R,6S)-2,6-dimethyl-4-morpholinyl]methyl}-N-(6-{6-(methyloxy)-5-[(1H-pyrazol-4-ylsulfonyl)amino]-3-pyridinyl}-1H-indazol-4-yl)-1,3-thiazole-4-carboxamide;

N-{6-[5-{[(1,2-dimethyl-1H-imidazol-5-yl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;

2-{[(2R,6S)-2,6-dimethyl-4-morpholinyl]methyl}-N-{6-[5-{[(2-methyl-1H-imidazol-4-yl)sulfonyl]amino}-6-(methyloxy)-3-pyridinyl]-1H-indazol-4-yl}-1,3-thiazole-4-carboxamide;

2-{[(2R,6S)-2,6-dimethyl-4-morpholinyl]methyl}-N-(6-{6-(methyloxy)-5-[(2-thienylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-{6-[5-[(1H-imidazol-4-ylsulfonyl)amino]-6-(methyloxy)-3-pyridinyl]-1H-indazol-4-yl}-1,3-thiazole-4-carboxamide;

2-{[(2R,6S)-2,6-dimethyl-4-morpholinyl]methyl}-N-{6-[6-(methyloxy)-5-({[2-(4-methyl-1-piperazinyl)ethyl]sulfonyl}amino)-3-pyridinyl]-1H-indazol-4-yl}-1,3-thiazole-4-carboxamide;

N-[6-(6-chloro-5-{[(2-methylphenyl)sulfonyl]amino}-3-pyridinyl)-1H-indazol-4-yl]-2-methyl-1,3-thiazole-4-carboxamide;

N-[6-(6-chloro-5-{[(5-fluoro-2-methylphenyl)sulfonyl]amino}-3-pyridinyl)-1H-indazol-4-yl]-2-methyl-1,3-thiazole-4-carboxamide;

N-[6-(6-chloro-5-{[(2,5-dimethylphenyl)sulfonyl]amino}-3-pyridinyl)-1H-indazol-4-yl]-2-methyl-1,3-thiazole-4-carboxamide;

N-(6-{6-(ethyloxy)-5-[(phenylsulfonyl)amino]-3-pyridinyl}-1H-indazol-4-yl)-2-methyl-1,3-thiazole-4-carboxamide;

N-(6-{6-chloro-5-[(methylsulfonyl)amino]-3-pyridinyl}-1-methyl-1H-indazol-4-yl)-6-methyl-2-pyridinecarboxamide;

N-(6-{6-chloro-5-[(methylsulfonyl)amino]-3-pyridinyl}-1H-indazol-4-yl)-6-methyl-2-pyridinecarboxamide;

N-{6-[6-chloro-5-({[5-methyl-2-(methyloxy)phenyl]sulfonyl}amino)-3-pyridinyl]-1H-indazol-4-yl}-2-methyl-1,3-thiazole-4-carboxamide;

N-(6-{6-chloro-5-[(cyclopropylsulfonyl)amino]-3-pyridinyl}-1H-indazol-4-yl)-2-methyl-1,3-thiazole-4-carboxamide;

N-[6-(2,3-diaminophenyl)-1H-indazol-4-yl]-2-methyl-1,3-thiazole-4-carboxamide;

2-methyl-N-(6-{5-[(methylsulfonyl)amino]-3-pyridinyl}-1H-indazol-4-yl)-1,3-thiazole-4-carboxamide;

N-{6-[4-(aminosulfonyl)phenyl]-1H-indazol-4-yl}-2-methyl-1,3-thiazole-4-carboxamide;

N-(6-{6-chloro-5-[(methylsulfonyl)amino]-3-pyridinyl}-1-methyl-1H-indazol-4-yl)-2-methyl-1,3-thiazole-4-carboxamide;

N-(6-{5-[(cyclopropylsulfonyl)amino]-6-hydroxy-3-pyridinyl}-1H-indazol-4-yl)-2-methyl-1,3-thiazole-4-carboxamide;

N-(6-{6-chloro-5-[(methylsulfonyl)amino]-3-pyridinyl}-1H-indazol-4-yl)-2-methyl-1,3-thiazole-4-carboxamide;

2-methyl-N-(6-{5-[(phenylsulfonyl)amino]-3-pyridinyl}-1H-indazol-4-yl)-1,3-thiazole-4-carboxamide;

N-[6-(5-hydroxy-3-pyridinyl)-1H-indazol-4-yl]-2-methyl-1,3-thiazole-4-carboxamide trifluoroacetate;

N-[6-(3-hydroxyphenyl)-1H-indazol-4-yl]-2-methyl-1,3-thiazole-4-carboxamide;
N-[6-(4-chloro-3-hydroxyphenyl)-1H-indazol-4-yl]-2-methyl-1,3-thiazole-4-carboxamide;
N-[6-(4-hydroxy-3-methylphenyl)-1H-indazol-4-yl]-2-methyl-1,3-thiazole-4-carboxamide;
N-[6-(3-hydroxy-4-methylphenyl)-1H-indazol-4-yl]-2-methyl-1,3-thiazole-4-carboxamide;
N-(6-{4-chloro-3-[(methylsulfonyl)amino]phenyl}-1H-indazol-4-yl)-2-methyl-1,3-thiazole-4-carboxamide;
2-methyl-N-(6-{5-[(methylamino)sulfonyl]-3-pyridinyl}-1H-indazol-4-yl)-1,3-thiazole-4-carboxamide;
N-(6-{5-[(diethylamino)sulfonyl]-3-pyridinyl}-1H-indazol-4-yl)-2-methyl-1,3-thiazole-4-carboxamide;
N-(6-{6-hydroxy-5-[(phenylsulfonyl)amino]-3-pyridinyl}-1H-indazol-4-yl)-2-methyl-1,3-thiazole-4-carboxamide;
N-(6-{6-chloro-5-[(methylsulfonyl)amino]-3-pyridinyl}-1-methyl-1H-indazol-4-yl)-2-{[(2R,6S)-2,6-dimethyl-4-morpholinyl]methyl}-1,3-thiazole-4-carboxamide;
or a pharmaceutically acceptable salt thereof.

In another embodiment, the compound for use according to the invention is a compound of formula (II) which is:

N-[6-(1H-indol-4-yl)-1H-indazol-4-yl]-5-methyl-1H-pyrazole-3-carboxamide;
N-[6-(1H-indol-4-yl)-1H-indazol-4-yl]-1-methyl-1H-imidazole-2-carboxamide;
N-[6-(1H-indol-4-yl)-1H-indazol-4-yl]-1-methyl-1H-pyrrole-2-carboxamide;
N-[6-(1H-indol-4-yl)-1H-indazol-4-yl]-1-methyl-1H-imidazole-4-carboxamide;
N-[6-(1H-indol-4-yl)-1H-indazol-4-yl]-1-methyl-1H-pyrazole-5-carboxamide;
N-[6-(1H-indol-4-yl)-1H-indazol-4-yl]-1,5-dimethyl-1H-pyrazole-3-carboxamide;
N-[6-(1H-indol-4-yl)-1H-indazol-4-yl]-2-(phenylmethyl)-1,3-thiazole-4-carboxamide;
1-ethyl-N-[6-(1H-indol-4-yl)-1H-indazol-4-yl]-1H-pyrazole-3-carboxamide;
N-[6-(1H-indol-4-yl)-1H-indazol-4-yl]-2-methyl-3-furancarboxamide;
N-[6-(1H-indol-4-yl)-1H-indazol-4-yl]-5-methyl-2-furancarboxamide;
N-[6-(1H-indol-4-yl)-1H-indazol-4-yl]-1-methyl-1H-pyrazole-3-carboxamide;
N-[6-(1H-indol-4-yl)-1H-indazol-4-yl]-3-furancarboxamide;
N-[6-(1H-indol-4-yl)-1H-indazol-4-yl]-3-thiophenecarboxamide;
N-[6-(1H-indol-4-yl)-1H-indazol-4-yl]-5-(1-pyrrolidinylmethyl)-2-furancarboxamide;
N-[6-(1H-indol-4-yl)-1H-indazol-4-yl]-2-phenyl-1,3-thiazole-4-carboxamide;
2-chloro-N-[6-(1H-indol-4-yl)-1H-indazol-4-yl]-3-furancarboxamide;
1-ethenyl-N-[6-(1H-indol-4-yl)-1H-indazol-4-yl]-1H-pyrazole-5-carboxamide;
1-ethyl-N-[6-(1H-indol-4-yl)-1H-indazol-4-yl]-1H-pyrazole-5-carboxamide;
N-[6-(1H-indol-4-yl)-1H-indazol-4-yl]-2-(trifluoromethyl)-1,3-thiazole-4-carboxamide;
N-[6-(1H-indol-4-yl)-1H-indazol-4-yl]-2-{1-[(phenylcarbonyl)amino]ethyl}-1,3-thiazole-4-carboxamide;
N-[6-(1H-indol-4-yl)-1H-indazol-4-yl]-5-(trifluoromethyl)-2-furancarboxamide;
5-[(dimethylamino)methyl]-N-[6-(1H-indol-4-yl)-1H-indazol-4-yl]-2-furancarboxamide;
3-ethyl-N-[6-(1H-indol-4-yl)-1H-indazol-4-yl]-1H-pyrazole-5-carboxamide;
5-chloro-N-[6-(1H-indol-4-yl)-1H-indazol-4-yl]-2-furancarboxamide;
N-[6-(1H-indol-4-yl)-1H-indazol-4-yl]-4-methyl-2-thiophenecarboxamide;
N-[6-(1H-indol-4-yl)-1H-indazol-4-yl]-2-(4-morpholinylmethyl)-1,3-thiazole-4-carboxamide;
N-[6-(1H-indol-4-yl)-1H-indazol-4-yl]-1H-pyrazole-3-carboxamide;
N-[6-(1H-indol-4-yl)-1H-indazol-4-yl]-1,3-thiazole-5-carboxamide;
1-(1-methylethyl)-N-[6-(1H-pyrazolo[3,4-b]pyridin-4-yl)-1H-indazol-4-yl]-1H-pyrazole-5-carboxamide;
N-[6-(1H-Indol-4-yl)-1H-indazol-4-yl]-1H-imidazole-4-carboxamide;
N-[6-(1H-indol-4-yl)-1H-indazol-4-yl]-1,3-thiazole-4-carboxamide;
N-[6-(1H-Indol-4-yl)-1H-indazol-4-yl]-5-methyl-3-isoxazolecarboxamide;
N-[6-(1H-indol-4-yl)-1H-indazol-4-yl]-1,2,3-thiadiazole-4-carboxamide;
N-[6-(1H-indol-4-yl)-1H-indazol-4-yl]-2,5-dimethyl-1,3-oxazole-4-carboxamide;
N-[6-(1H-indol-4-yl)-1H-indazol-4-yl]-2-methyl-1,3-oxazole-4-carboxamide;
N-[6-(1H-indol-4-yl)-1H-indazol-4-yl]-3-isoxazolecarboxamide;
N-[6-(1H-indol-4-yl)-1H-indazol-4-yl]-2-methyl-5-(trifluoromethyl)-1,3-oxazole-4-carboxamide;
N-[6-(1H-indol-4-yl)-1H-indazol-4-yl]-5-(2-methyl-1,3-thiazol-4-yl)-3-isoxazolecarboxamide;
4-[(dimethylamino)methyl]-N-[6-(1H-indol-4-yl)-1H-indazol-4-yl]-5-methyl-3-isoxazolecarboxamide;
N-[6-(1H-indol-4-yl)-1H-indazol-4-yl]-5-(4-morpholinylmethyl)-3-isoxazolecarboxamide;
N-[6-(1H-indol-4-yl)-1H-indazol-4-yl]-5-methyl-4-(1-piperidinylmethyl)-3-isoxazolecarboxamide;
N-[6-(1H-indol-4-yl)-1H-indazol-4-yl]-5-methyl-4-(4-morpholinylmethyl)-3-isoxazolecarboxamide;
N-[6-(1H-indol-4-yl)-1H-indazol-4-yl]-5-methyl-4-(1-pyrrolidinylmethyl)-3-isoxazolecarboxamide;
N-[6-(1H-indol-4-yl)-1H-indazol-4-yl]-2-(1-piperidinylmethyl)-1,3-thiazole-4-carboxamide;
N-[6-(1H-indol-4-yl)-1H-indazol-4-yl]-1H-imidazole-2-carboxamide;
N-1H,1'H-5,6'-biindazol-4'-yl-2-methyl-1,3-thiazole-4-carboxamide;
4-chloro-N-[6-(1H-indol-4-yl)-1H-indazol-4-yl]-1-methyl-1H-pyrazole-5-carboxamide;
N-[6-(1H-indol-4-yl)-1H-indazol-4-yl]-1,4-dimethyl-1H-pyrazole-5-carboxamide;
N-[6-(1H-indol-4-yl)-1H-indazol-4-yl]-5-(1-methylethyl)-2-(4-morpholinylmethyl)-1,3-thiazole-4-carboxamide;
4-chloro-N-[6-(1H-indol-4-yl)-1H-indazol-4-yl]-1H-pyrazole-5-carboxamide;
4-chloro-N-[6-(1H-indol-4-yl)-1H-indazol-4-yl]-1-(1-methylethyl)-1H-pyrazole-3-carboxamide;
2-chloro-N-[6-(1H-indol-4-yl)-1H-indazol-4-yl]-5-(1-methylethyl)-1,3-thiazole-4-carboxamide;
N-[6-(1H-indol-4-yl)-1H-indazol-4-yl]-2,5-dimethyl-1,3-thiazole-4-carboxamide;
4-chloro-N-[6-(1H-indol-4-yl)-1H-indazol-4-yl]-1-(1-methylethyl)-1H-pyrazole-5-carboxamide;
N-[6-(1H-indol-4-yl)-1H-indazol-4-yl]-1-methyl-4-(trifluoromethyl)-1H-pyrazole-5-carboxamide;

N-[6-(1H-indol-4-yl)-1H-indazol-4-yl]-2-methyl-5-(1-methylethyl)-1,3-thiazole-4-carboxamide;
N-[6-(1H-indol-4-yl)-1H-indazol-4-yl]-1-(1-methylethyl)-3-(4-morpholinylmethyl)-1H-pyrazole-5-carboxamide;
N-[6-(1H-indol-4-yl)-1H-indazol-4-yl]-1-(1-methylethyl)-5-(4-morpholinylmethyl)-1H-pyrazole-3-carboxamide;
N-[6-(1H-indol-4-yl)-1H-indazol-4-yl]-1-methyl-1H-1,2,4-triazole-5-carboxamide;
N-[6-(1H-indol-4-yl)-1H-indazol-4-yl]-1-(1-methylethyl)-1H-1,2,4-triazole-5-carboxamide;
1-(1,1-dimethylethyl)-N-[6-(1H-indol-4-yl)-1H-indazol-4-yl]-3-methyl-1H-pyrazole-5-carboxamide;
N-[6-(1H-indol-4-yl)-1H-indazol-4-yl]-1-(2,2,2-trifluoroethyl)-1H-pyrazole-5-carboxamide;
1-(difluoromethyl)-N-[6-(1H-indol-4-yl)-1H-indazol-4-yl]-1H-pyrazole-5-carboxamide;
1,1-dimethylethyl[4-({[6-(1H-indol-4-yl)-1H-indazol-4-yl]amino}carbonyl)-1,3-thiazol-2-yl]carbamate;
1,1-dimethylethyl3-cyclopropyl-4-({[6-(1H-indol-4-yl)-1H-indazol-4-yl]amino}carbonyl)-1H-pyrazole-1-carboxylate;
4-fluoro-N-[6-(1H-indol-4-yl)-1H-indazol-4-yl]-1-(1-methylethyl)-1H-pyrazole-5-carboxamide;
2-amino-N-[6-(1H-indol-4-yl)-1H-indazol-4-yl]-1,3-thiazole-4-carboxamide;
1-ethyl-4-fluoro-N-[6-(1H-indol-4-yl)-1H-indazol-4-yl]-1H-pyrazole-5-carboxamide;
2-amino-N-[6-(1H-indol-4-yl)-1H-indazol-4-yl]-4-(trifluoromethyl)-1,3-thiazole-5-carboxamide;
2-amino-N-[6-(1H-indol-4-yl)-1H-indazol-4-yl]-5-(1-methylethyl)-1,3-thiazole-4-carboxamide;
N-[6-(1H-indol-4-yl)-1H-indazol-4-yl]-2-(1-methylethyl)-2H-1,2,3-triazole-4-carboxamide;
4-bromo-N-[6-(1H-indol-4-yl)-1H-indazol-4-yl]-1,3-dimethyl-1H-pyrazole-5-carboxamide;
N-[6-(1H-indol-4-yl)-1H-indazol-4-yl]-5-(1-methylethyl)-1,3-thiazole-4-carboxamide;
1-(2-fluoroethyl)-N-[6-(1H-indol-4-yl)-1H-indazol-4-yl]-1H-pyrazole-5-carboxamide;
1-(2-fluoroethyl)-N-[6-(1H-indol-4-yl)-1H-indazol-4-yl]-1H-pyrazole-3-carboxamide;
5-acetyl-N-[6-(1H-indol-4-yl)-1H-indazol-4-yl]-2-methyl-1,3-thiazole-4-carboxamide;
N-[6-(1H-indol-4-yl)-1H-indazol-4-yl]-5-(1-methylethyl)-1,3-oxazole-4-carboxamide;
N-[6-(1H-indol-4-yl)-1H-indazol-4-yl]-1-(1-methylethyl)-1H-1,2,3-triazole-5-carboxamide;
N-[6-(1H-indol-4-yl)-1H-indazol-4-yl]-2-methyl-1,3-thiazole-4-carboxamide;
N-[6-(1H-indol-4-yl)-1H-indazol-4-yl]-1-methyl-1H-1,2,4-triazole-3-carboxamide;
N-[6-(1H-indol-5-yl)-1H-indazol-4-yl]-2-methyl-1,3-thiazole-4-carboxamide;
N-[6-(1H-benzimidazol-4-yl)-1H-indazol-4-yl]-2-methyl-1,3-thiazole-4-carboxamide;
2-methyl-N-[6-(2-methyl-1H-pyrrolo[2,3-b]pyridin-4-yl)-1H-indazol-4-yl]-1,3-thiazole-4-carboxamide;
N-[6-(2-cyclopropyl-1H-pyrrolo[2,3-b]pyridin-4-yl)-1H-indazol-4-yl]-2-methyl-1,3-thiazole-4-carboxamide;
N-1H,1'H-4,6'-biindazol-4'-yl-1-(1-methylethyl)-1H-pyrazole-5-carboxamide;
N-[3-fluoro-6-(1H-indol-4-yl)-1H-indazol-4-yl]-2-methyl-1,3-thiazole-4-carboxamide;
4-chloro-1-ethyl-N-[3-fluoro-6-(1H-indol-4-yl)-1H-indazol-4-yl]-1H-pyrazole-5-carboxamide;
N-[3-fluoro-6-(1H-indol-4-yl)-1H-indazol-4-yl]-1-(1-methylethyl)-1H-pyrazole-5-carboxamide;
N-[6-(6-fluoro-1H-indol-4-yl)-1H-indazol-4-yl]-2-methyl-1,3-thiazole-4-carboxamide;
N-[6-(1H-indol-4-yl)-1H-indazol-4-yl]-1-(1-methylethyl)-1H-imidazole-2-carboxamide;
4-fluoro-N-[6-(1H-indol-4-yl)-1H-indazol-4-yl]-1-methyl-1H-pyrazole-3-carboxamide;
ethyl-N-[6-(1H-indol-4-yl)-1H-indazol-4-yl]-3-methyl-1H-pyrazole-5-carboxamide;
N-[6-(1H-indol-4-yl)-1H-indazol-4-yl]-1,3-dimethyl-1H-pyrazole-5-carboxamide;
3-(1,1-dimethylethyl)-N-[6-(1H-indol-4-yl)-1H-indazol-4-yl]-1-methyl-1H-pyrazole-5-carboxamide;
4-chloro-1-ethyl-N-[6-(1H-indol-4-yl)-1H-indazol-4-yl]-1H-pyrazole-5-carboxamide;
N-[6-(1H-indol-4-yl)-1H-indazol-4-yl]-1-methyl-3-(trifluoromethyl)-1H-pyrazole-5-carboxamide;
N-[6-(1H-indol-4-yl)-1H-indazol-4-yl]-1-methyl-3-(1-methylethyl)-1H-pyrazole-5-carboxamide;
3-cyclopropyl-N-[6-(1H-indol-4-yl)-1H-indazol-4-yl]-1-methyl-1H-pyrazole-5-carboxamide;
1-ethyl-N-[6-(1H-indol-4-yl)-1H-indazol-4-yl]-3-(1-methylethyl)-1H-pyrazole-5-carboxamide;
N-[6-(1H-indol-4-yl)-1H-indazol-4-yl]-1-methyl-3-(2-methylpropyl)-1H-pyrazole-5-carboxamide;
N-[6-(1H-indol-4-yl)-1H-indazol-4-yl]-4-(methyloxy)-3-thiophenecarboxamide;
N-[6-(1H-indol-4-yl)-1H-indazol-4-yl]-1-methyl-3-(4-morpholinylcarbonyl)-1H-pyrazole-5-carboxamide;
N-[6-(1H-indol-4-yl)-1H-indazol-4-yl]-1,4-dimethyl-1H-pyrazole-3-carboxamide;
1-ethyl-N-[6-(1H-indol-4-yl)-1H-indazol-4-yl]-3-(2-methylpropyl)-1H-pyrazole-5-carboxamide;
N-[6-(1H-indol-4-yl)-1H-indazol-4-yl]-1-methyl-5-(4-morpholinylmethyl)-1H-pyrazole-3-carboxamide;
N-[6-(1H-indol-4-yl)-1H-indazol-4-yl]-1-methyl-3-(4-morpholinylmethyl)-1H-pyrazole-5-carboxamide;
2-acetyl-N-[6-(1H-indol-4-yl)-1H-indazol-4-yl]-1,3-thiazole-4-carboxamide;
N-[6-(5-isoquinolinyl)-1H-indazol-4-yl]-2-methyl-1,3-thiazole-4-carboxamide;
2-methyl-N-[6-(1-methyl-1H-indol-4-yl)-1H-indazol-4-yl]-1,3-thiazole-4-carboxamide;
N-[6-(4-isoquinolinyl)-1H-indazol-4-yl]-2-methyl-1,3-thiazole-4-carboxamide;
N-[6-(1H-indol-3-yl)-1H-indazol-4-yl]-2-methyl-1,3-thiazole-4-carboxamide;
N-[6-(1H-indol-6-yl)-1H-indazol-4-yl]-2-methyl-1,3-thiazole-4-carboxamide;
2-methyl-N-[6-(1-methyl-1H-indol-6-yl)-1H-indazol-4-yl]-1,3-thiazole-4-carboxamide;
N-[6-(1H-indol-4-yl)-1H-indazol-4-yl]-2-furancarboxamide;
N-[6-(1-benzofuran-2-yl)-1H-indazol-4-yl]-2-methyl-1,3-thiazole-4-carboxamide;
N-[6-(6-cyano-1H-indol-4-yl)-1H-indazol-4-yl]-1-(1-methylethyl)-1H-pyrazole-5-carboxamide;
1-(1-methylethyl)-N-[6-(6-methyl-1H-indol-4-yl)-1H-indazol-4-yl]-1H-pyrazole-5-carboxamide;
N-[6-(1-benzofuran-5-yl)-1H-indazol-4-yl]-1-(1-methylethyl)-1H-pyrazole-5-carboxamide;
5-bromo-N-[6-(1H-indol-4-yl)-1H-indazol-4-yl]-1,3-thiazole-4-carboxamide;
N-[6-(1H-indol-4-yl)-1H-indazol-4-yl]-5-(1-methylethyl)-4-isoxazolecarboxamide;
N-[6-(1-benzofuran-5-yl)-1H-indazol-4-yl]-2-methyl-1,3-thiazole-4-carboxamide;

N-{6-[2-(1,1-dimethylethyl)-1H-pyrrolo[2,3-b]pyridin-4-yl]-1H-indazol-4-yl}-2-methyl-1,3-thiazole-4-carboxamide;

1-(1-methylethyl)-N-[6-(2-methyl-1H-pyrrolo[2,3-b]pyridin-4-yl)-1H-indazol-4-yl]-1H-pyrazole-5-carboxamide;

1-(1-methylethyl)-N-[6-(1H-pyrrolo[2,3-b]pyridin-4-yl)-1H-indazol-4-yl]-1H-pyrazole-5-carboxamide;

1-(1-methylethyl)-N-[6-(1H-pyrrolo[2,3-c]pyridin-4-yl)-1H-indazol-4-yl]-1H-pyrazole-5-carboxamide;

1-(1-methylethyl)-N-[6-(2-oxo-2,3-dihydro-1H-indol-4-yl)-1H-indazol-4-yl]-1H-pyrazole-5-carboxamide;

1-(1-methylethyl)-N-[6-(2-oxo-2,3-dihydro-1,3-benzoxazol-7-yl)-1H-indazol-4-yl]-1H-pyrazole-5-carboxamide;

1-(1-methylethyl)-N-[6-(7H-pyrrolo[2,3-d]pyrimidin-4-yl)-1H-indazol-4-yl]-1H-pyrazole-5-carboxamide;

N-[6-(6-fluoro-1H-indol-4-yl)-1H-indazol-4-yl]-1-(1-methylethyl)-1H-pyrazole-5-carboxamide;

N-1H,1'H-4,6'-biindazol-4'-yl-2-methyl-1,3-thiazole-4-carboxamide;

2-methyl-N-[6-(1H-pyrrolo[2,3-b]pyridin-4-yl)-1H-indazol-4-yl]-1,3-thiazole-4-carboxamide;

2-methyl-N-[6-(1H-pyrrolo[2,3-c]pyridin-4-yl)-1H-indazol-4-yl]-1,3-thiazole-4-carboxamide;

1,4-dimethyl-N-[6-(2-methyl-1H-pyrrolo[2,3-b]pyridin-4-yl)-1H-indazol-4-yl]-1H-pyrazole-3-carboxamide;

1,4-dimethyl-N-[6-(1H-pyrrolo[2,3-c]pyridin-4-yl)-1H-indazol-4-yl]-1H-pyrazole-3-carboxamide;

1,4-dimethyl-N-[6-(1H-pyrrolo[2,3-b]pyridin-4-yl)-1H-indazol-4-yl]-1H-pyrazole-3-carboxamide;

N-1H,1'H-4,6'-biindazol-4'-yl-1,4-dimethyl-1H-pyrazole-3-carboxamide;

4-chloro-1-ethyl-N-[6-(2-methyl-1H-pyrrolo[2,3-b]pyridin-4-yl)-1H-indazol-4-yl]-1H-pyrazole-5-carboxamide;

4-chloro-1-ethyl-N-[6-(1H-pyrrolo[2,3-c]pyridin-4-yl)-1H-indazol-4-yl]-1H-pyrazole-5-carboxamide;

4-chloro-1-ethyl-N-[6-(1H-pyrrolo[2,3-b]pyridin-4-yl)-1H-indazol-4-yl]-1H-pyrazole-5-carboxamide;

N-1H,1'H-4,6'-biindazol-4'-yl-4-chloro-1-ethyl-1H-pyrazole-5-carboxamide;

4-chloro-1-ethyl-N-[6-(1H-pyrazolo[3,4-b]pyridin-4-yl)-1H-indazol-4-yl]-1H-pyrazole-5-carboxamide;

N-[3-fluoro-6-(6-fluoro-1H-indol-4-yl)-1H-indazol-4-yl]-2-methyl-1,3-thiazole-4-carboxamide;

2-[(4,4-dimethyl-1-piperidinyl)methyl]-N-[6-(1H-indol-4-yl)-1H-indazol-4-yl]-1,3-thiazole-4-carboxamide;

2-[(3,3-dimethyl-1-piperidinyl)methyl]-N-[6-(1H-indol-4-yl)-1H-indazol-4-yl]-1,3-thiazole-4-carboxamide;

N-[6-(1H-indol-4-yl)-1H-indazol-4-yl]-2-{[4-(2-methylpropyl)-1-piperazinyl]methyl}-1,3-thiazole-4-carboxamide;

N-[6-(1H-indol-4-yl)-1H-indazol-4-yl]-2-{[4-(1-methylethyl)-1-piperazinyl]methyl}-1,3-thiazole-4-carboxamide;

N-[6-(1H-indol-4-yl)-1H-indazol-4-yl]-2-({4-[2-(4-morpholinyl)ethyl]-1-piperazinyl}methyl)-1,3-thiazole-4-carboxamide;

N-[6-(1H-indol-4-yl)-1H-indazol-4-yl]-2-(octahydro-4H-1,4-benzoxazin-4-ylmethyl)-1,3-thiazole-4-carboxamide;

2-{[(2R,6S)-2,6-dimethyl-4-morpholinyl]methyl}-N-[6-(1H-indol-4-yl)-1H-indazol-4-yl]-1,3-thiazole-4-carboxamide;

2-{[4-(4-fluorophenyl)-1-piperazinyl]methyl}-N-[6-(1H-indol-4-yl)-1H-indazol-4-yl]-1,3-thiazole-4-carboxamide;

N-[6-(1H-indol-4-yl)-1H-indazol-4-yl]-2-(octahydro-2H-pyrido[1,2-a]pyrazin-2-ylmethyl)-1,3-thiazole-4-carboxamide;

N-[6-(1H-indol-4-yl)-1H-indazol-4-yl]-2-{[2-(1-pyrrolidinylmethyl)-4-morpholinyl]methyl}-1,3-thiazole-4-carboxamide;

N-[6-(1H-indol-4-yl)-1H-indazol-4-yl]-2-{[2-(2-methylpropyl)-4-morpholinyl]methyl}-1,3-thiazole-4-carboxamide;

N-[6-(1H-indol-4-yl)-1H-indazol-4-yl]-2-{[3-(3-pyridinyl)-1-pyrrolidinyl]methyl}-1,3-thiazole-4-carboxamide;

N-[6-(1H-indol-4-yl)-1H-indazol-4-yl]-2-{[3-methyl-4-(1-methylethyl)-1-piperazinyl]methyl}-1,3-thiazole-4-carboxamide;

N-[6-(1H-indol-4-yl)-1H-indazol-4-yl]-2-({3-[(phenylmethyl)oxy]-1-piperidinyl}methyl)-1,3-thiazole-4-carboxamide;

2-{[4-(1-ethylpropyl)-1-piperazinyl]methyl}-N-[6-(1H-indol-4-yl)-1H-indazol-4-yl]-1,3-thiazole-4-carboxamide;

2-[(4-cyclopentyl-1-piperazinyl)methyl]-N-[6-(1H-indol-4-yl)-1H-indazol-4-yl]-1,3-thiazole-4-carboxamide;

2-methyl-N-[6-(2-methyl-1H-indol-4-yl)-1H-indazol-4-yl]-1,3-thiazole-4-carboxamide;

N-[6-(6-chloro-1H-indol-4-yl)-1H-indazol-4-yl]-2-methyl-1,3-thiazole-4-carboxamide;

2-methyl-N-{6-[6-(methyloxy)-1H-indol-4-yl]-1H-indazol-4-yl}-1,3-thiazole-4-carboxamide;

N-[6-(6-cyano-1H-indol-4-yl)-1H-indazol-4-yl]-2-methyl-1,3-thiazole-4-carboxamide;

N-[6-(6-fluoro-1H-indol-4-yl)-1H-indazol-4-yl]-2-methyl-1,3-thiazole-4-carboxamide;

2-(1-piperidinylmethyl)-N-[6-(1H-pyrazolo[3,4-b]pyridin-5-yl)-1H-indazol-4-yl]-1,3-thiazole-4-carboxamide;

N-[6-(6-fluoro-1H-indol-4-yl)-1H-indazol-4-yl]-2-(1-piperidinylmethyl)-1,3-thiazole-4-carboxamide;

2-methyl-N-(6-{6-[(phenylsulfonyl)amino]-1H-indol-4-yl}-1H-indazol-4-yl)-1,3-thiazole-4-carboxamide;

2-methyl-N-(6-{6-[(methylsulfonyl)amino]-1H-indol-4-yl}-1H-indazol-4-yl)-1,3-thiazole-4-carboxamide;

2-methyl-N-[6-(7-methyl-1H-indol-4-yl)-1H-indazol-4-yl]-1,3-thiazole-4-carboxamide;

2-(4-morpholinylmethyl)-N-[6-(1H-pyrazolo[3,4-b]pyridin-5-yl)-1H-indazol-4-yl]-1,3-thiazole-4-carboxamide;

2-{[(2R,6S)-2,6-dimethyl-4-morpholinyl]methyl}-N-[6-(1H-pyrazolo[3,4-b]pyridin-5-yl)-1H-indazol-4-yl]-1,3-thiazole-4-carboxamide;

2-(4-morpholinylmethyl)-N-[6-(1H-pyrrolo[2,3-b]pyridin-4-yl)-1H-indazol-4-yl]-1,3-thiazole-4-carboxamide;

N-[6-(1H-indol-4-yl)-1H-indazol-4-yl]-2-[(2-methyl-4-morpholinyl)methyl]-1,3-thiazole-4-carboxamide;

N-[6-(1H-indol-4-yl)-1H-indazol-4-yl]-2-(6-oxa-9-azaspiro[4.5]dec-9-ylmethyl)-1,3-thiazo-4-carboxamide;

N-[6-(1H-indol-4-yl)-1H-indazol-4-yl]-2-(tetrahydro-1,4-oxazepin-4(5H)-ylmethyl)-1,3-thiazole-4-carboxamide;

2-[(1,1-dioxido-4-thiomorpholinyl)methyl]-N-[6-(1H-indol-4-yl)-1H-indazol-4-yl]-1,3-thiazole-4-carboxamide;

2-[(2,2-dimethyl-4-morpholinyl)methyl]-N-[6-(1H-indol-4-yl)-1H-indazol-4-yl]-1,3-thiazole-4-carboxamide;

2-{[(2R,6S)-2,6-dimethyl-4-morpholinyl]methyl}-N-[6-(1H-indol-4-yl)-1-methyl-1H-indazol-4-yl]-1,3-thiazole-4-carboxamide; or a pharmaceutically acceptable salt thereof.

In another embodiment, the compound for use according to the invention is a compound of formula (III) which is:

N-[6-(1H-indol-4-yl)-1H-indazol-4-yl]-3-methyl-2-pyridinecarboxamide;

3-bromo-N-[6-(1H-indol-4-yl)-1H-indazol-4-yl]-2-pyridinecarboxamide;

5-fluoro-N-[6-(1H-indol-4-yl)-1H-indazol-4-yl]-2-pyridinecarboxamide;

N-[6-(1H-indol-4-yl)-1H-indazol-4-yl]-6-[5-methyl-2-(methyloxy)phenyl]-2-pyridinecarboxamide;
N-[6-(1H-indol-4-yl)-1H-indazol-4-yl]-6-(methyloxy)-2-pyridinecarboxamide;
N-[6-(1H-indol-4-yl)-1H-indazol-4-yl]-6-methyl-2-pyridinecarboxamide;
3,5-difluoro-N-[6-(1H-indol-4-yl)-1H-indazol-4-yl]-2-pyridinecarboxamide;
N-[1-ethyl-6-(1H-indol-4-yl)-1H-indazol-4-yl]-6-methyl-2-pyridinecarboxamide;
N-[6-(1H-indol-4-yl)-1-methyl-1H-indazol-4-yl]-2-pyridinecarboxamide;
N-[6-(1H-indol-4-yl)-1H-indazol-4-yl]-3-(methyloxy)-2-pyridinecarboxamide;
6-[(dimethylamino)methyl]-N-[6-(1H-indol-4-yl)-1H-indazol-4-yl]-2-pyridinecarboxamide;
N-[6-(1H-indol-4-yl)-1H-indazol-4-yl]-6-(4-morpholinylmethyl)-2-pyridinecarboxamide;
N-[6-(1H-indol-4-yl)-1H-indazol-4-yl]-6-(1-piperidinylmethyl)-2-pyridinecarboxamide;
3-fluoro-N-[6-(1H-indol-4-yl)-1H-indazol-4-yl]-2-pyridinecarboxamide;
N-[6-(1H-indol-4-yl)-1H-indazol-4-yl]-3-pyridinecarboxamide;
N-[6-(1H-indol-4-yl)-1H-indazol-4-yl]-3-(methylsulfonyl)-2-pyridinecarboxamide;
6-chloro-3-fluoro-N-[6-(1H-indol-4-yl)-1H-indazol-4-yl]-2-pyridinecarboxamide;
6-chloro-N-[6-(1H-indol-4-yl)-1H-indazol-4-yl]-2-pyridinecarboxamide;
N-[6-(1H-indol-4-yl)-1H-indazol-4-yl]-6-(methylamino)-2-pyridinecarboxamide;
N-[6-(1H-indol-4-yl)-1H-indazol-4-yl]-6-[(1-methylethyl)amino]-2-pyridinecarboxamide;
6-(ethylamino)-N-[6-(1H-indol-4-yl)-1H-indazol-4-yl]-2-pyridinecarboxamide;
6-(diethylamino)-N-[6-(1H-indol-4-yl)-1H-indazol-4-yl]-2-pyridinecarboxamide;
6-(cyclopropylamino)-N-[6-(1H-indol-4-yl)-1H-indazol-4-yl]-2-pyridinecarboxamide;
N-[6-(1H-indol-4-yl)-1H-indazol-4-yl]-6-(4-methyl-1-piperazinyl)-2-pyridinecarboxamide;
N-[6-(1H-indol-4-yl)-1H-indazol-4-yl]-6-(1-pyrrolidinyl)-2-pyridinecarboxamide;
6-(dimethylamino)-N-[6-(1H-indol-4-yl)-1H-indazol-4-yl]-2-pyridinecarboxamide;
3,6-dichloro-N-[6-(1H-indol-4-yl)-1H-indazol-4-yl]-2-pyridinecarboxamide;
3-chloro-N-[6-(1H-indol-4-yl)-1H-indazol-4-yl]-6-(4-morpholinyl)-2-pyridinecarboxamide;
3-chloro-N-[6-(1H-indol-4-yl)-1H-indazol-4-yl]-6-(1-piperidinyl)-2-pyridinecarboxamide;
3-chloro-6-(dimethylamino)-N-[6-(1H-indol-4-yl)-1H-indazol-4-yl]-2-pyridinecarboxamide;
6-fluoro-N-[6-(1H-indol-4-yl)-1H-indazol-4-yl]-2-pyridinecarboxamide;
N-[6-(1H-indol-4-yl)-1H-indazol-4-yl]-6-[methyl(tetrahydro-2H-pyran-4-yl)amino]-2-pyridinecarboxamide;
N-[6-(1H-indol-4-yl)-1H-indazol-4-yl]-6-[(1-methyl-4-piperidinyl)amino]-2-pyridinecarboxamide;
N-[6-(1H-indol-4-yl)-1H-indazol-4-yl]-6-(tetrahydro-2H-pyran-4-ylamino)-2-pyridinecarboxamide;
6-chloro-3-(dimethylamino)-N-[6-(1H-indol-4-yl)-1H-indazol-4-yl]-2-pyridinecarboxamide;
3-(dimethylamino)-N-[6-(1H-indol-4-yl)-1H-indazol-4-yl]-6-(4-morpholinyl)-2-pyridinecarboxamide;
3-(dimethylamino)-N-[6-(1H-indol-4-yl)-1H-indazol-4-yl]-6-(1-piperidinyl)-2-pyridinecarboxamide;
3-(dimethylamino)-N-[6-(1H-indol-4-yl)-1H-indazol-4-yl]-6-(methylamino)-2-pyridinecarboxamide;
3-(dimethylamino)-6-(ethylamino)-N-[6-(1H-indol-4-yl)-1H-indazol-4-yl]-2-pyridinecarboxamide;
6-chloro-N-[6-(1H-indol-4-yl)-1H-indazol-4-yl]-3-(4-morpholinyl)-2-pyridinecarboxamide;
6-chloro-N-[6-(1H-indol-4-yl)-1H-indazol-4-yl]-3-(1-piperidinyl)-2-pyridinecarboxamide;
N-[6-(1H-indol-4-yl)-1H-indazol-4-yl]-5-(4-morpholinyl)-2-pyridinecarboxamide;
N-[6-(1H-indol-4-yl)-1H-indazol-4-yl]-5-(1-piperidinyl)-2-pyridinecarboxamide;
3-chloro-N-[6-(1H-indol-4-yl)-1H-indazol-4-yl]-2-pyridinecarboxamide;
6-amino-N-[6-(1H-indol-4-yl)-1H-indazol-4-yl]-2-pyridinecarboxamide;
5-amino-N-[6-(1H-indol-4-yl)-1H-indazol-4-yl]-2-pyridinecarboxamide;
N-[6-(1H-indol-4-yl)-1H-indazol-4-yl]-5-methyl-2-pyridinecarboxamide;
N-[6-(1H-indol-4-yl)-1H-indazol-4-yl]-2-methyl-3-pyridinecarboxamide;
3-amino-N-[6-(1H-indol-4-yl)-1H-indazol-4-yl]-2-pyridinecarboxamide;
N-[6-(1H-indol-4-yl)-1H-indazol-4-yl]-4-(methylamino)-2-pyridinecarboxamide;
N-[6-(1H-indol-4-yl)-1H-indazol-4-yl]-2-pyridinecarboxamide;
N-[6-(1H-indol-6-yl)-1H-indazol-4-yl]-2-pyridinecarboxamide;
N-[6-(1-methyl-1H-indol-5-yl)-1H-indazol-4-yl]-2-pyridinecarboxamide;
N-[6-(1H-indol-4-yl)-1H-indazol-4-yl]-2-(methyloxy)-3-pyridinecarboxamide;
2-(ethyloxy)-N-[6-(1H-indol-4-yl)-1H-indazol-4-yl]-3-pyridinecarboxamide;
5-bromo-N-[6-(1H-indol-4-yl)-1H-indazol-4-yl]-2-pyridinecarboxamide;
N-[6-(1H-indol-4-yl)-1H-indazol-4-yl]-2-(1-pyrrolidinyl)-4-pyridinecarboxamide;
N-[6-(1H-indol-4-yl)-1H-indazol-4-yl]-6-(4-morpholinyl)-2-pyridinecarboxamide;
N-[6-(1H-indol-4-yl)-1H-indazol-4-yl]-6-oxo-1,6-dihydro-2-pyridinecarboxamide;
N-[6-(1H-indol-4-yl)-1H-indazol-4-yl]-2-(1-pyrrolidinyl)-4-pyridinecarboxamide;
N-[6-(1H-indol-4-yl)-1-methyl-1H-indazol-4-yl]-6-methyl-2-pyridinecarboxamide;
N-[6-(1H-indol-4-yl)-1H-indazol-4-yl]-3-(1-methylethenyl)-2-pyridinecarboxamide;
N-[6-(1H-indol-4-yl)-1H-indazol-4-yl]-3-(1-methylethyl)-2-pyridinecarboxamide;
N-[6-(1H-indol-4-yl)-1H-indazol-4-yl]-6-(tetrahydro-2H-pyran-4-yloxy)-2-pyridinecarboxamide;
N-[6-(1H-indol-4-yl)-1H-indazol-4-yl]-6-[(4-methyl-1-piperazinyl)methyl]-2-pyridinecarboxamide;
N-[3-fluoro-6-(1H-indol-4-yl)-1H-indazol-4-yl]-3-methyl-2-pyridinecarboxamide;
6-[(4,4-dimethyl-1-piperidinyl)methyl]-N-[6-(1H-indol-4-yl)-1H-indazol-4-yl]-2-pyridinecarboxamide;
6-[(3,3-dimethyl-1-piperidinyl)methyl]-N-[6-(1H-indol-4-yl)-1H-indazol-4-yl]-2-pyridinecarboxamide;
N-[6-(1H-indol-4-yl)-1H-indazol-4-yl]-6-{[4-(2-methylpropyl)-1-piperazinyl]methyl}-2-pyridinecarboxamide;

N-[6-(1H-indol-4-yl)-1H-indazol-4-yl]-6-{[4-(1-methyl-ethyl)-1-piperazinyl]methyl}-2-pyridinecarboxamide;
N-[6-(1H-indol-4-yl)-1H-indazol-4-yl]-6-{[4-(1-methyl-ethyl)-1-piperidinyl]methyl}-2-pyridinecarboxamide;
N-[6-(1H-indol-4-yl)-1H-indazol-4-yl]-6-({4-[2-(4-morpholinyl)ethyl]-1-piperazinyl}methyl)-2-pyridinecarboxamide;
N-[6-(1H-indol-4-yl)-1H-indazol-4-yl]-6-(octahydro-4H-1,4-benzoxazin-4-ylmethyl)-2-pyridinecarboxamide;
6-{[(2R,6S)-2,6-dimethyl-4-morpholinyl]methyl}-N-[6-(1H-indol-4-yl)-1H-indazol-4-yl]-2-pyridinecarboxamide;
6-{[4-(4-fluorophenyl)-1-piperazinyl]methyl}-N-[6-(1H-indol-4-yl)-1H-indazol-4-yl]-2-pyridinecarboxamide;
N-[6-(1H-indol-4-yl)-1H-indazol-4-yl]-6-(octahydro-2H-pyrido[1,2-a]pyrazin-2-ylmethyl)-2-pyridinecarboxamide;
N-[6-(1H-indol-4-yl)-1H-indazol-4-yl]-6-{[2-(1-pyrrolidinylmethyl)-4-morpholinyl]methyl}-2-pyridinecarboxamide;
N-[6-(1H-indol-4-yl)-1H-indazol-4-yl]-6-{[2-(2-methylpropyl)-4-morpholinyl]methyl}-2-pyridinecarboxamide;
N-[6-(1H-indol-4-yl)-1H-indazol-4-yl]-6-{[3-methyl-4-(1-methylethyl)-1-piperazinyl]methyl}-2-pyridinecarboxamide;
N-[6-(1H-indol-4-yl)-1H-indazol-4-yl]-6-[(3-phenyl-1-piperidinyl)methyl]-2-pyridinecarboxamide;
N-[6-(1H-indol-4-yl)-1H-indazol-4-yl]-6-({2-[(phenyloxy)methyl]-4-morpholinyl}methyl)-2-pyridinecarboxamide;
N-[6-(1H-indol-4-yl)-1H-indazol-4-yl]-6-({3-[(phenylmethyl)oxy]-1-piperidinyl}methyl)-2-pyridinecarboxamide;
6-{[4-(1-ethylpropyl)-1-piperazinyl]methyl}-N-[6-(1H-indol-4-yl)-1H-indazol-4-yl]-2-pyridinecarboxamide;
6-[(4-cyclopentyl-1-piperazinyl)methyl]-N-[6-(1H-indol-4-yl)-1H-indazol-4-yl]-2-pyridinecarboxamide;
6-methyl-N-[1-methyl-6-(1H-pyrrolo[2,3-b]pyridin-4-yl)-1H-indazol-4-yl]-2-pyridinecarboxamide;
6-(4-morpholinylmethyl)-N-[6-(1H-pyrrolo[2,3-b]pyridin-4-yl)-1H-indazol-4-yl]-2-pyridinecarboxamide;
6-(1-piperidinylmethyl)-N-[6-(1H-pyrrolo[2,3-b]pyridin-4-yl)-1H-indazol-4-yl]-2-pyridinecarboxamide;
6-[(4-methyl-3-oxo-1-piperazinyl)methyl]-N-[6-(1H-pyrrolo[2,3-b]pyridin-4-yl)-1H-indazol-4-yl]-2-pyridinecarboxamide;
6-[(4-acetyl-1-piperazinyl)methyl]-N-[6-(1H-pyrrolo[2,3-b]pyridin-4-yl)-1H-indazol-4-yl]-2-pyridinecarboxamide;
6-{[4-(methylsulfonyl)-1-piperazinyl]methyl}-N-[6-(1H-pyrrolo[2,3-b]pyridin-4-yl)-1H-indazol-4-yl]-2-pyridinecarboxamide;
6-[(1,1-dioxido-4-thiomorpholinyl)methyl]-N-[6-(1H-pyrrolo[2,3-b]pyridin-4-yl)-1H-indazol-4-yl]-2-pyridinecarboxamide;
6-{[(2R,6S)-2,6-dimethyl-4-morpholinyl]methyl}-N-[6-(1H-pyrrolo[2,3-b]pyridin-4-yl)-1H-indazol-4-yl]-2-pyridinecarboxamide;
6-{[3-methyl-4-(1-methylethyl)-1-piperazinyl]methyl}-N-[6-(1H-pyrrolo[2,3-b]pyridin-4-yl)-1H-indazol-4-yl]-2-pyridinecarboxamide;
6-[(4,4-difluoro-1-piperidinyl)methyl]-N-[6-(1H-pyrrolo[2,3-b]pyridin-4-yl)-1H-indazol-4-yl]-2-pyridinecarboxamide;
6-(4-morpholinylmethyl)-N-[6-(1H-pyrazolo[3,4-b]pyridin-5-yl)-1H-indazol-4-yl]-2-pyridinecarboxamide;
6-{[4-(methylsulfonyl)-1-piperazinyl]methyl}-N-[6-(1H-pyrazolo[3,4-b]pyridin-5-yl)-1H-indazol-4-yl]-2-pyridinecarboxamide;
6-[(1,1-dioxido-4-thiomorpholinyl)methyl]-N-[6-(1H-pyrazolo[3,4-b]pyridin-5-yl)-1H-indazol-4-yl]-2-pyridinecarboxamide;
6-[(4,4-difluoro-1-piperidinyl)methyl]-N-[6-(1H-pyrazolo[3,4-b]pyridin-5-yl)-1H-indazol-4-yl]-2-pyridinecarboxamide;
6-{[(2R,6S)-2,6-dimethyl-4-morpholinyl]methyl}-N-[6-(1H-pyrazolo[3,4-b]pyridin-5-yl)-1H-indazol-4-yl]-2-pyridinecarboxamide;
6-{[3-methyl-4-(1-methylethyl)-1-piperazinyl]methyl}-N-[6-(1H-pyrazolo[3,4-b]pyridin-5-yl)-1H-indazol-4-yl]-2-pyridinecarboxamide; or
a pharmaceutically acceptable salt thereof.

In another embodiment, the compound for use according to the invention is a compound of formula (IV) which is:
N-[6-(1H-indol-4-yl)-1H-indazol-4-yl]benzamide;
2-fluoro-N-[6-(1H-indol-4-yl)-1H-indazol-4-yl]benzamide;
2,3-difluoro-N-[6-(1H-indol-4-yl)-1H-indazol-4-yl]benzamide;
2,5-difluoro-N-[6-(1H-indol-4-yl)-1H-indazol-4-yl]benzamide;
N-[6-(1H-indol-4-yl)-1H-indazol-4-yl]-2-methylbenzamide;
2'-chloro-N-[6-(1H-indol-4-yl)-1H-indazol-4-yl]-2-biphenylcarboxamide;
N-[6-(1H-indol-4-yl)-1H-indazol-4-yl]-1-isoquinolinecarboxamide;
2,4-difluoro-N-[6-(1H-indol-4-yl)-1H-indazol-4-yl]benzamide;
2,6-difluoro-N-[6-(1H-indol-4-yl)-1H-indazol-4-yl]benzamide;
N-[6-(1H-indol-4-yl)-1H-indazol-4-yl]-2-(methyloxy)benzamide;
2-[(difluoromethyl)oxy]-N-[6-(1H-indol-4-yl)-1H-indazol-4-yl]benzamide;
N-[6-(1H-Indol-4-yl)-1H-indazol-4-yl]pyrazolo[1,5-a]pyridine-2-carboxamide;
N-[6-(1H-indol-4-yl)-1H-indazol-4-yl]-6-(methyloxy)-2-pyrazinecarboxamide;
N-[6-(1H-indol-4-yl)-1H-indazol-4-yl]-1H-benzimidazole-2-carboxamide;
N-[6-(1H-indol-4-yl)-1H-indazol-4-yl]-1H-indole-2-carboxamide;
N-[6-(1H-indol-4-yl)-1H-indazol-4-yl]-4-methyl-2-(methyloxy)benzamide;
N-[6-(1H-indol-4-yl)-1H-indazol-4-yl]-5-methyl-2-(methyloxy)benzamide;
N-[6-(1H-indol-4-yl)-1H-indazol-4-yl]-2-(3-methyl-1H-pyrazol-1-yl)acetamide;
N-[6-(1H-indol-4-yl)-1H-indazol-4-yl]-3-methyl-2-(methyloxy)benzamide;
2-(ethyloxy)-N-[6-(1H-indol-4-yl)-1H-indazol-4-yl]benzamide;
4-acetyl-N-[6-(1H-indol-4-yl)-1H-indazol-4-yl]-2-morpholinecarboxamide;
N-[6-(1H-indol-4-yl)-1H-indazol-4-yl]-2-(2-pyridinyl)acetamide;
2-[6-(1H-indol-4-yl)-1H-indazol-4-yl]-1H-isoindole-1,3(2H)-dione;
2-[6-(1H-indol-4-yl)-1H-indazol-4-yl]-2,3-dihydro-1H-isoindol-1-one;
N-[6-(1H-indol-4-yl)-1H-indazol-4-yl]-3-methylbenzamide;
N-[6-(1H-indol-4-yl)-1H-indazol-4-yl]-4-methyl-2-morpholinecarboxamide;
1-acetyl-N-[6-(1H-indol-4-yl)-1H-indazol-4-yl]-4-piperidinecarboxamide;

N-[6-(1H-indol-4-yl)-1H-indazol-4-yl]-1-methyl-4-piperidinecarboxamide;
N-[6-(1H-indol-4-yl)-1H-indazol-4-yl]-1-(methylsulfonyl)-4-piperidinecarboxamide;
N-[6-(1H-indol-4-yl)-1H-indazol-4-yl]-5-oxo-3-pyrrolidinecarboxamide;
N-[6-(1H-indol-4-yl)-1H-indazol-4-yl]-1-(1-methylethyl)-5-oxo-3-pyrrolidinecarboxamide;
N-[6-(1H-indol-4-yl)-1H-indazol-4-yl]cyclopropanecarboxamide;
3-(dimethylamino)-N-[6-(1H-indol-4-yl)-1H-indazol-4-yl]benzamide;
4-amino-N-[6-(1H-indol-4-yl)-1H-indazol-4-yl]benzamide;
(1R,2R)—N-[6-(1H-indol-4-yl)-1H-indazol-4-yl]-2-phenylcyclopropanecarboxamide;
N-[6-(1H-indol-4-yl)-1H-indazol-4-yl]cyclohexanecarboxamide; phenylmethyl 3-hydroxy-4-({[6-(1H-indol-4-yl)-1H-indazol-4-yl]amino}carbonyl)-1-pyrrolidinecarboxylate; or
a pharmaceutically acceptable salt thereof.

In another embodiment, the compound for use according to the invention is a compound of formula (V) which is:
6-(1H-indol-4-yl)-4-[5-(4-morpholinylmethyl)-1,3,4-oxadiazol-2-yl]-1H-indazole;
N-(2-chloro-5-{4-[5-(4-morpholinylmethyl)-1,3,4-oxadiazol-2-yl]-1H-indazol-6-yl}-3-pyridinyl)methanesulfonamide;
4-(5-{[(2R,6S)-2,6-dimethyl-4-morpholinyl]methyl}-1,3,4-oxadiazol-2-yl)-6-(1H-indol-4-yl)-1H-indazole;
6-(1H-indol-4-yl)-4-(5-{[4-(2-pyrimidinyl)-1-piperazinyl]methyl}-1,3,4-oxadiazol-2-yl)-1H-indazole;
4-{5-[(4,4-dimethyl-1-piperidinyl)methyl]-1,3,4-oxadiazol-2-yl}-6-(1H-indol-4-yl)-1H-indazole;
6-(1H-indol-4-yl)-4-(5-{[4-(2-methylpropyl)-1-piperazinyl]methyl}-1,3,4-oxadiazol-2-yl)-1H-indazole;
6-(1H-indol-4-yl)-4-(5-{[4-(1-methylethyl)-1-piperidinyl]methyl}-1,3,4-oxadiazol-2-yl)-1H-indazole;
6-(1H-indol-4-yl)-4-(5-{[2-(1-pyrrolidinylmethyl)-1-piperidinyl]methyl}-1,3,4-oxadiazol-2-yl)-1H-indazole;
4-(5-{[4-(4-fluorophenyl)-1-piperazinyl]methyl}-1,3,4-oxadiazol-2-yl)-6-(1H-indol-4-yl)-1H-indazole;
6-(1H-indol-4-yl)-4-(5-{[(1R,4R)-1,4,5-trimethyl-2,5-diazabicyclo[2.2.1]hept-2-yl]methyl}-1,3,4-oxadiazol-2-yl)-1H-indazole;
6-(1H-indol-4-yl)-4-(5-{[2-(1-pyrrolidinylmethyl)-4-morpholinyl]methyl}-1,3,4-oxadiazol-2-yl)-1H-indazole;
6-(1H-indol-4-yl)-4-(5-({4-[2-(4-morpholinyl)ethyl]-1-piperazinyl}methyl)-1,3,4-oxadiazol-2-yl)-1H-indazole;
6-(1H-indol-4-yl)-4-(5-{[4-(1-methylethyl)-1-piperazinyl]methyl}-1,3,4-oxadiazol-2-yl)-1H-indazole;
4-(5-{[(2R,6S)-2,6-dimethyl-1-piperidinyl]methyl}-1,3,4-oxadiazol-2-yl)-6-(1H-indol-4-yl)-1H-indazole;
4-(5-{[(1S,4S)-1,4-dimethyl-7-azabicyclo[2.2.1]hept-7-yl]methyl}-1,3,4-oxadiazol-2-yl)-6-(1H-indol-4-yl)-1H-indazole;
4-({5-[6-(1H-indol-4-yl)-1H-indazol-4-yl]-1,3,4-oxadiazol-2-yl}methyl)octahydro-2H-1,4-benzoxazine;
6-(1H-indol-4-yl)-4-(5-{[2-(2-methylpropyl)-4-morpholinyl]methyl}-1,3,4-oxadiazol-2-yl)-1H-indazole;
N-{2-chloro-5-[4-(5-{[4-(1-methylethyl)-1-piperazinyl]methyl}-1,3,4-oxadiazol-2-yl)-1H-indazol-6-yl]-3-pyridinyl}methanesulfonamide;
N-{2-chloro-5-[4-(5-{[(2R,6S)-2,6-dimethyl-4-morpholinyl]methyl}-1,3,4-oxadiazol-2-yl)-1H-indazol-6-yl]-3-pyridinyl}methanesulfonamide;
N-(2-chloro-5-{4-[5-(4-morpholinylmethyl)-1,3,4-oxadiazol-2-yl]-1H-indazol-6-yl}-3-pyridinyl)methanesulfonamide;
N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]methanesulfonamide;
N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;
4-(5-{[(2R,6S)-2,6-dimethyl-4-morpholinyl]methyl}-1,3,4-oxadiazol-2-yl)-6-(1H-indol-4-yl)-1-methyl-1H-indazole;
6-(1H-indol-4-yl)-1-methyl-4-(5-{[4-(1-methylethyl)-1-piperazinyl]methyl}-1,3,4-oxadiazol-2-yl)-1H-indazole;
N-[5-[1-methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;
N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]methanesulfonamide;
N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]-2,4-difluorobenzenesulfonamide;
N-[5-(4-{5-[(2,2-dimethyl-4-morpholinyl)methyl]-1,3,4-oxadiazol-2-yl}-1H-indazol-6-yl)-2-(methyloxy)-3-pyridinyl]methanesulfonamide;
6-(1H-indol-4-yl)-4-[5-(1-methylethyl)-1,3,4-oxadiazol-2-yl]-1H-indazole;
4-(5-cyclohexyl-1,3,4-oxadiazol-2-yl)-6-(1H-indol-4-yl)-1H-indazole;
4-[5-(cyclohexylmethyl)-1,3,4-oxadiazol-2-yl]-6-(1H-indol-4-yl)-1H-indazole;
6-(1H-indol-4-yl)-4-[5-(phenylmethyl)-1,3,4-oxadiazol-2-yl]-1H-indazole;
6-(1H-indol-4-yl)-4-{5-[2-(methyloxy)ethyl]-1,3,4-oxadiazol-2-yl}-1H-indazole;
6-(1H-indol-4-yl)-4-(5-{[(phenylmethyl)oxy]methyl}-1,3,4-oxadiazol-2-yl)-1H-indazole;
6-(1H-indol-4-yl)-4-[5-({[(1R,2S,5R)-5-methyl-2-(1-methylethyl)cyclohexyl]oxy}methyl)-1,3,4-oxadiazol-2-yl]-1H-indazole;
{5-[6-(1H-indol-4-yl)-1H-indazol-4-yl]-1,3,4-oxadiazol-2-yl}methanol;
6-(1H-indol-4-yl)-4-{5-[(methyloxy)methyl]-1,3,4-oxadiazol-2-yl}-1H-indazole;
6-(1H-indol-4-yl)-4-(5-methyl-1,3,4-oxadiazol-2-yl)-1H-indazole;
N-{2-chloro-5-[4-(5-methyl-1,3,4-oxadiazol-2-yl)-1H-indazol-6-yl]-3-pyridinyl}methanesulfonamide;
6-(1H-indol-4-yl)-4-{5-[(methylsulfonyl)methyl]-1,3,4-oxadiazol-2-yl}-1H-indazole;
6-(1H-indol-4-yl)-4-{5-[(phenylsulfonyl)methyl]-1,3,4-oxadiazol-2-yl}-1H-indazole;
N-(2-(methyloxy)-5-{4-[5-(6-oxa-9-azaspiro[4.5]dec-9-ylmethyl)-1,3,4-oxadiazol-2-yl]-1H-indazol-6-yl}-3-pyridinyl)methanesulfonamide;
2-[({5-[6-(1H-indol-4-yl)-1H-indazol-4-yl]-1,3,4-oxadiazol-2-yl}methyl)amino]ethanol;
1-[({5-[6-(1H-indol-4-yl)-1H-indazol-4-yl]-1,3,4-oxadiazol-2-yl}methyl)amino]-3-(4-morpholinyl)-2-propanol;
N-[5-[4-(5-{[(3R,5S)-3,5-dimethyl-4-(1-methylethyl)-1-piperazinyl]methyl}-1,3,4-oxadiazol-2-yl)-1H-indazol-6-yl]-2-(methyloxy)-3-pyridinyl]methanesulfonamide;
N-[5-(4-{5-[(1,1-dioxido-4-thiomorpholinyl)methyl]-1,3,4-oxadiazol-2-yl}-1H-indazol-6-yl)-2-(methyloxy)-3-pyridinyl]methanesulfonamide;

N-[5-(4-{5-[(2-ethyl-4-morpholinyl)methyl]-1,3,4-oxadiazol-2-yl}-1H-indazol-6-yl)-2-(methyloxy)-3-pyridinyl]methanesulfonamide;

9-({5-[6-(1H-indol-4-yl)-1H-indazol-4-yl]-1,3,4-oxadiazol-2-yl}methyl)-6-oxa-9-azaspiro[4.5]decane;

4-{5-[(2,2-dimethyl-4-morpholinyl)methyl]-1,3,4-oxadiazol-2-yl}-6-(1H-indol-4-yl)-1H-indazole;

N-[5-[4-(5-{[(3R,5S)-3,5-dimethyl-4-(1-methylethyl)-1-piperazinyl]methyl}-1,3,4-oxadiazol-2-yl)-1H-indazol-6-yl]-2-(methyloxy)-3-pyridinyl]-2,4-difluorobenzenesulfonamide;

2,4-difluoro-N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]benzenesulfonamide;

N-[5-(4-{5-[(2-methyl-4-morpholinyl)methyl]-1,3,4-oxadiazol-2-yl}-1H-indazol-6-yl)-2-(methyloxy)-3-pyridinyl]methanesulfonamide;

6-(1H-indol-4-yl)-4-{5-[(2-methyl-4-morpholinyl)methyl]-1,3,4-oxadiazol-2-yl}-1H-indazole;

N-({5-[6-(1H-indol-4-yl)-1H-indazol-4-yl]-1,3,4-oxadiazol-2-yl}methyl)-3-(4-morpholinyl)-1-propanamine;

N-(2-(methyloxy)-5-{4-[5-(tetrahydro-1,4-oxazepin-4(5H)-ylmethyl)-1,3,4-oxadiazol-2-yl]-1H-indazol-6-yl}-3-pyridinyl)methanesulfonamide;

6-(1H-indol-4-yl)-4-[5-(tetrahydro-1,4-oxazepin-4(5H)-ylmethyl)-1,3,4-oxadiazol-2-yl]-1H-indazole;

N-[5-{4-[5-({[2-hydroxy-3-(4-morpholinyl)propyl]amino}methyl)-1,3,4-oxadiazol-2-yl]-1H-indazol-6-yl}-2-(methyloxy)-3-pyridinyl]methanesulfonamide;

2,4-difluoro-N-[5-{4-[5-({[2-hydroxy-3-(4-morpholinyl)propyl]amino}methyl)-1,3,4-oxadiazol-2-yl]-1H-indazol-6-yl}-2-(methyloxy)-3-pyridinyl]benzenesulfonamide;

N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]methanesulfonamide;

2,4-difluoro-N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]benzenesulfonamide;

N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]-2,4-difluorobenzenesulfonamide;

N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]-2-(methyloxy)benzenesulfonamide; or a pharmaceutically acceptable salt thereof.

In another embodiment, the compound for use according to the invention is a compound of formula (VI) which is:

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide;

N-[5-[4-(5-{[4-(1-methylethyl)-1-piperazinyl]methyl}-1,3-oxazol-2-yl)-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]-2,4-difluorobenzenesulfonamide;

2,4-difluoro-N-[5-[4-(5-{[4-(1-methylethyl)-1-piperazinyl]methyl}-1,3-oxazol-2-yl)-1H-indazol-6-yl]-2-(methyloxy)-3-pyridinyl]benzenesulfonamide;

4-(5-{[(2R,6S)-2,6-dimethyl-4-morpholinyl]methyl}-1,3-oxazol-2-yl)-6-(1H-indol-4-yl)-1H-indazole;

6-(1H-indol-4-yl)-4-(5-{[4-(1-methylethyl)-1-piperazinyl]methyl}-1,3-oxazol-2-yl)-1H-indazole;

6-(1H-indol-4-yl)-4-[5-(4-morpholinylmethyl)-1,3-oxazol-2-yl]-1H-indazole;

N-[5-[4-(5-{[(2R,6R)-2,6-dimethyl-4-morpholinyl]methyl}-1,3-oxazol-2-yl)-1H-indazol-6-yl]-2-(methyloxy)-3-pyridinyl]methanesulfonamide;

6-(1H-indol-4-yl)-4-[5-(1-piperazinylmethyl)-1,3-oxazol-2-yl]-1H-indazole;

or a pharmaceutically acceptable salt thereof.

In another embodiment, the compound for use according to the invention is a compound of formula (VI) which is:

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide;

N-[5-[4-(5-{[4-(1-methylethyl)-1-piperazinyl]methyl}-1,3-oxazol-2-yl)-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]-2,4-difluorobenzenesulfonamide;

2,4-difluoro-N-[5-[4-(5-{[4-(1-methylethyl)-1-piperazinyl]methyl}-1,3-oxazol-2-yl)-1H-indazol-6-yl]-2-(methyloxy)-3-pyridinyl]benzenesulfonamide;

4-(5-{[(2R,6S)-2,6-dimethyl-4-morpholinyl]methyl}-1,3-oxazol-2-yl)-6-(1H-indol-4-yl)-1H-indazole;

6-(1H-indol-4-yl)-4-(5-{[4-(1-methylethyl)-1-piperazinyl]methyl}-1,3-oxazol-2-yl)-1H-indazole;

6-(1H-indol-4-yl)-4-[5-(4-morpholinylmethyl)-1,3-oxazol-2-yl]-1H-indazole;

or a pharmaceutically acceptable salt thereof.

In another embodiment, the compound for use according to the invention is a compound of formula (VI) which is:

N-[5-[4-(5-{[2,6-dimethyl-4-morpholinyl]methyl}-1,3-oxazol-2-yl)-1H-indazol-6-yl]-2-(methyloxy)-3-pyridinyl]methanesulfonamide;

or a pharmaceutically acceptable salt thereof.

In another embodiment, the compound for use according to the invention is a compound of formula (VI) which is:

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide;

or a pharmaceutically acceptable salt thereof.

In another embodiment, the compound for use according to the invention is a compound of formula (VI) which is:

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate.

In another embodiment, the compound for use according to the invention is a compound of formula (VI) which is:

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide.

In another embodiment, the compound for use according to the invention is a compound of formula (VI) which is:

6-(1H-indol-4-yl)-4-(5-{[4-(1-methylethyl)-1-piperazinyl]methyl}-1,3-oxazol-2-yl)-1H-indazole;

or a pharmaceutically acceptable salt thereof.

In another embodiment, the compound for use according to the invention is a compound of formula (VI) which is:

6-(1H-indol-4-yl)-4-(5-{[4-(1-methylethyl)-1-piperazinyl]methyl}-1,3-oxazol-2-yl)-1H-indazole hemi succinate.

In another embodiment, the compound for use according to the invention is a compound of formula (VI) which is:

6-(1H-indol-4-yl)-4-(5-{[4-(1-methylethyl)-1-piperazinyl]methyl}-1,3-oxazol-2-yl)-1H-indazole hydrochloride.

In another embodiment, the compound for use according to the invention is a compound of formula (VI) which is:

6-(1H-indol-4-yl)-4-(5-{[4-(1-methylethyl)-1-piperazinyl]methyl}-1,3-oxazol-2-yl)-1H-indazole.

In a further embodiment, the compound for use according to the invention is a compound of formula (VII) which is:

N-[6-(6-fluoro-1H-indol-4-yl)-1H-indazol-4-yl]-6-methyl-2-pyridinecarboxamide;
N-[3-fluoro-6-(1H-indol-4-yl)-1H-indazol-4-yl]-6-methyl-2-pyridinecarboxamide;
2,5-dimethyl-N-[6-(2-methyl-1H-pyrrolo[2,3-b]pyridin-4-yl)-1H-indazol-4-yl]-1,3-oxazole-4-carboxamide;
6-methyl-N-[6-(2-methyl-1H-pyrrolo[2,3-b]pyridin-4-yl)-1H-indazol-4-yl]-2-pyridinecarboxamide;
N-[6-(6-fluoro-1H-indol-4-yl)-1H-indazol-4-yl]-2,5-dimethyl-1,3-oxazole-4-carboxamide;
2,5-dimethyl-N-[6-(1H-pyrazolo[3,4-b]pyridin-5-yl)-1H-indazol-4-yl]-1,3-oxazole-4-carboxamide;
6-methyl-N-[6-(1H-pyrazolo[3,4-b]pyridin-5-yl)-1H-indazol-4-yl]-2-pyridinecarboxamide;
N-[3-fluoro-6-(1H-indol-4-yl)-1H-indazol-4-yl]-3-(1-methylethyl)-2-pyridinecarboxamide;
3-(1-methylethyl)-N-[6-(1H-pyrazolo[3,4-b]pyridin-5-yl)-1H-indazol-4-yl]-2-pyridinecarboxamide;
N-[6-(6-fluoro-1H-indol-4-yl)-1H-indazol-4-yl]-3-(1-methylethyl)-2-pyridinecarboxamide;
N-[3-fluoro-6-(1H-pyrazolo[3,4-b]pyridin-5-yl)-1H-indazol-4-yl]-2,5-dimethyl-1,3-oxazole-4-carboxamide;
N-[3-fluoro-6-(1H-pyrazolo[3,4-b]pyridin-5-yl)-1H-indazol-4-yl]-3-(1-methylethyl)-2-pyridinecarboxamide;
N-[3-fluoro-6-(6-fluoro-1H-indol-4-yl)-1H-indazol-4-yl]-2,5-dimethyl-1,3-oxazole-4-carboxamide;
N-[3-fluoro-6-(1H-indol-4-yl)-1H-indazol-4-yl]-2,5-dimethyl-1,3-oxazole-4-carboxamide;
N-[3-fluoro-6-(2-methyl-1H-pyrrolo[2,3-b]pyridin-4-yl)-1H-indazol-4-yl]-2-methyl-1,3-thiazole-4-carboxamide;
N-[6-(6-cyano-1H-indol-4-yl)-1H-indazol-4-yl]-1,4-dimethyl-1H-pyrazole-3-carboxamide;
2-methyl-N-[6-(2-oxo-2,3-dihydro-1H-indol-4-yl)-1H-indazol-4-yl]-1,3-thiazole-4-carboxamide;
N-[6-(5-fluoro-1H-pyrrolo[2,3-b]pyridin-4-yl)-1H-indazol-4-yl]-2-methyl-1,3-thiazole-4-carboxamide;
N-[6-(1H-benzimidazol-5-yl)-1H-indazol-4-yl]-2-methyl-1,3-thiazole-4-carboxamide;
2-methyl-N-[6-(1H-pyrrolo[2,3-b]pyridin-3-yl)-1H-indazol-4-yl]-1,3-thiazole-4-carboxamide;
N-1H,1'H-5,6'-biindazol-4'-yl-2-methyl-1,3-thiazole-4-carboxamide;
2-methyl-N-[6-(1H-pyrrolo[2,3-c]pyridin-3-yl)-1H-indazol-4-yl]-1,3-thiazole-4-carboxamide;
N-(6-imidazo[1,2-a]pyridin-6-yl-1H-indazol-4-yl)-2-methyl-1,3-thiazole-4-carboxamide;
2-methyl-N-[1-methyl-6-(1H-pyrrolo[2,3-b]pyridin-4-yl)-1H-indazol-4-yl]-1,3-thiazole-4-carboxamide;
N-(6-furo[3,2-b]pyridin-6-yl-1H-indazol-4-yl)-2-methyl-1,3-thiazole-4-carboxamide;
N-[6-(1H-indol-4-yl)-1H-indazol-4-yl]-1-(1-methylethyl)-1H-pyrazole-5-carboxamide;
N-[6-(1H-pyrrolo[2,3-b]pyridin-4-yl)-1H-indazol-4-yl]-2-furancarboxamide;
1,1-dimethylethyl4-({[6-(1H-indol-4-yl)-1H-indazol-4-yl]amino}carbonyl)-3-methyl-1H-pyrazole-1-carboxylate;
2-(1-piperidinylmethyl)-N-[6-(1H-pyrrolo[2,3-b]pyridin-4-yl)-1H-indazol-4-yl]-1,3-thiazole-4-carboxamide;
2-[(2-ethyl-4-morpholinyl)methyl]-N-[6-(1H-indol-4-yl)-1H-indazol-4-yl]-1,3-thiazole-4-carboxamide;
6-[(1,1-dioxido-4-thiomorpholinyl)methyl]-N-[6-(1H-indol-4-yl)-1H-indazol-4-yl]-2-pyridinecarboxamide; or
a pharmaceutically acceptable salt thereof.

TERMS AND DEFINITIONS

"Alkyl" refers to a saturated hydrocarbon chain having the specified number of member atoms. For example, $C_{1-6}$alkyl refers to an alkyl group having from 1 to 6 member atoms, for example 1 to 4 member atoms. Alkyl groups may be optionally substituted with one or more substituents if so defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkenyl" refers to a hydrocarbon chain having the specified number of member atoms and at least one double bond. For example, $C_{2-6}$alkenyl refers to an alkenyl group having from 2 to 6 member atoms, for example 2 to 4 member atoms. Alkenyl groups may be straight or branched. Alkenyl includes ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. In one embodiment, the cycloalkyl groups have 3 or 4 member atoms. In a further embodiment, the cycloalkyl groups have 5 or 6 member atoms. Cycloalkyl groups may be optionally substituted with one or more substituents if so defined herein. It will be appreciated that the substituent may be at any position on the ring, including the carbon atom which is the point of attachment to the rest of the molecule. Cycloalkyl includes cyclopropyl, cyclobutyl, cyclopentyl, and cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halo" refers to the halogen radical fluoro, chloro, bromo, or iodo. In one embodiment, the halogen radical is fluoro, chloro or bromo.

"Heteroaryl", unless otherwise defined, refers to an aromatic group containing from 1 to 3 heteroatoms, for example 1 or 2 heteroatoms, as member atoms in the ring or rings. Heteroaryl groups containing more than one heteroatom may contain different heteroatoms. Heteroaryl groups may be optionally substituted if so defined herein. The heteroaryl groups herein are monocyclic ring systems or are fused bicyclic ring systems. The monocyclic heteroaryl rings 5 or 6 member atoms. The bicyclic heteroaryl rings have 9 or 10 member atoms. Monocyclic heteroaryl includes pyrrolyl, pyrazolyl, imidazolyl, oxazolyl, isoxazolyl, thiazolyl, isothiazolyl, furanyl, thienyl, furazanyl, triazolyl, thiadiazolyl, pyridinyl, pyrimidinyl, pyridazinyl and pyrazinyl. Bicyclic heteroaryl includes indolyl, isoindolyl, indolizinyl, benzofuranyl, isobenzofuranyl, indazolyl, purinyl, benzimidazolyl, pyrrolopyridinyl, pyrazolopyridinyl, pyrrolopyrimidinyl, quinolyl, isoquinolinyl, quinoxalinyl, quinazolinyl, cinnolinyl, benzopyranyl, benzoxazolyl, furopyridinyl and naphthridinyl.

"Heteroatom" refers to a nitrogen, sulphur, or oxygen atom.

"Heterocyclyl", unless otherwise defined, refers to a saturated or unsaturated ring containing 1 or 2 heteroatoms as member atoms in the ring. However, heterocyclyl rings are not aromatic. In certain embodiments, heterocyclyl is saturated. In other embodiments, heterocyclyl is unsaturated but not aromatic. Heterocyclyl groups containing more than one heteroatom may contain different heteroatoms. Heterocyclyl groups may be optionally substituted with one or more substituents if so defined herein. The heterocyclyl groups herein are monocyclic ring systems having 5, 6 or 7 member atoms, bicyclic ring systems having 9 or 10 member atoms, bridged ring systems having 7 member atoms, or spiro bicyclic ring systems having 10 member atoms. Monocyclic heterocyclyl includes pyrrolidinyl, pyrazolidinyl, imidazolidinyl, isoxazolidinyl, oxazolidinyl, isothiazoldinyl, thiazolidinyl, piperidinyl, piperazinyl, morpholinyl, thiomorpholinyl, hexahydro-1,4-oxazepinyl and tetrahydro-1,4-oxazepin-4(5H)-yl. Bicyclic heterocyclyl includes octahydropyrrolo[1,2-a]pyrazinyl and octahydro-2H-1,4-benzoxazinyl. Bridged heterocyclyl includes 7-azabicylo[2.2.1]heptyl and 2,5-diazabicyclo[2.2.1]heptyl. Spiro bicyclic ring systems include 6-oxa-9-azaspiro[4.5]decyl.

"Influenza virus" refers to a member of the orthomyxoviridae family of RNA viruses and includes any strain of influenza virus, for example influenza A or influenza B.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as heteroaryl, may be unsubstituted or substituted with one or more substituents as defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, salts, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Aq Aqueous
DCM Dichloromethane
DIPEA Diisopropylethylamine
DMF Dimethylformamide
DMPU 1,3-Dimethyl-3,4,5,6-tetrahydro-2-(1H)-pyrimidinone
DMSO Dimethylsulfoxide
Et Ethyl
EtOAc Ethyl acetate
g Grams
h hour(s)
HATU O-(7-Azabenzotriazol-1-yl)-N,N,N',N'-tetramethyluronium hexafluorophosphate
HPLC High performance liquid chromatography
IPA Isopropanol
LCMS Liquid chromatography mass spectroscopy
L Liter
M Molar
MDAP Mass directed automated preparative HPLC
Me Methyl
MeCN Acetonitrile
MeOH Methanol
mg Milligrams
mins Minutes
ml Milliliters
mmol Millimoles
mp Melting point
Pd(dppf)Cl$_2$ [1,1'-bis(diphenylphosphino)ferrocene]dichloropalladium(II)
Pd(dppf)Cl$_2$—CH$_2$Cl$_2$ [1,1'-Bis(diphenylphosphino)ferrocene]dichloropalladium(II) dichloromethane adduct
Pd(PPh$_3$)$_4$ Tetrakis(triphenylphosphine)palladium(0)
Rt Retention time
RT Room temperature
s Seconds
SCX Strong Cation Exchange
Solvias Catalyst chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1)
SPE Solid Phase Extraction
TEA Triethylamine
TFA Trifluoroacetic acid
THF Tetrahydrofuran
UPLC Ultra high performance liquid chromatography
UV Ultraviolet All references to brine are to a saturated aqueous solution of NaCl.

Included within the scope of the compounds for use according to the invention are all solvates (including hydrates), complexes, polymorphs, prodrugs, radiolabelled derivatives, stereoisomers and optical isomers of the compounds of formulae (I) to (VII) and pharmaceutically acceptable salts thereof.

The compounds for use according to the invention may exist in solid or liquid form. In the solid state, the compounds may exist in crystalline or noncrystalline form, or as a mixture thereof. For compounds that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The compounds for use according to the invention include all such solvates.

The skilled artisan will further appreciate that certain compounds and pharmaceutically acceptable salts thereof for use according to the invention which exist in crystalline form, including the various solvates thereof, may exhibit polymorphism (i.e. the capacity to occur in different crystalline structures). These different crystalline forms are typically known as "polymorphs". The compounds and pharmaceutically acceptable salts thereof for use according to the invention include all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

In one aspect, the present invention provides 6-(1H-indol-4-yl)-4-(5-{[4-(1-methylethyl)-1-piperazinyl]methyl}-1,3-oxazol-2-yl)-1H-indazole or a pharmaceutically acceptable salt thereof in crystalline form for use in the treatment or prevention of influenza virus infection.

In one embodiment, the present invention provides a polymorph of 6-(1H-indol-4-yl)-4-(5-{[4-(1-methylethyl)-1-piperazinyl]methyl}-1,3-oxazol-2-yl)-1H-indazole characterised in that it provides an XRPD pattern comprising peaks (° 2θ) at about 9.0, about 9.6, about 10.4 and/or about 12.5 for use in the treatment or prevention of influenza virus infection.

In another embodiment, the present invention provides a polymorph of 6-(1H-indol-4-yl)-4-(5-{[4-(1-methylethyl)-1-piperazinyl]methyl}-1,3-oxazol-2-yl)-1H-indazole characterised in that it provides an XRPD pattern comprising peaks substantially as set out in Table 6 for use in the treatment or prevention of influenza virus infection.

Figure 6:
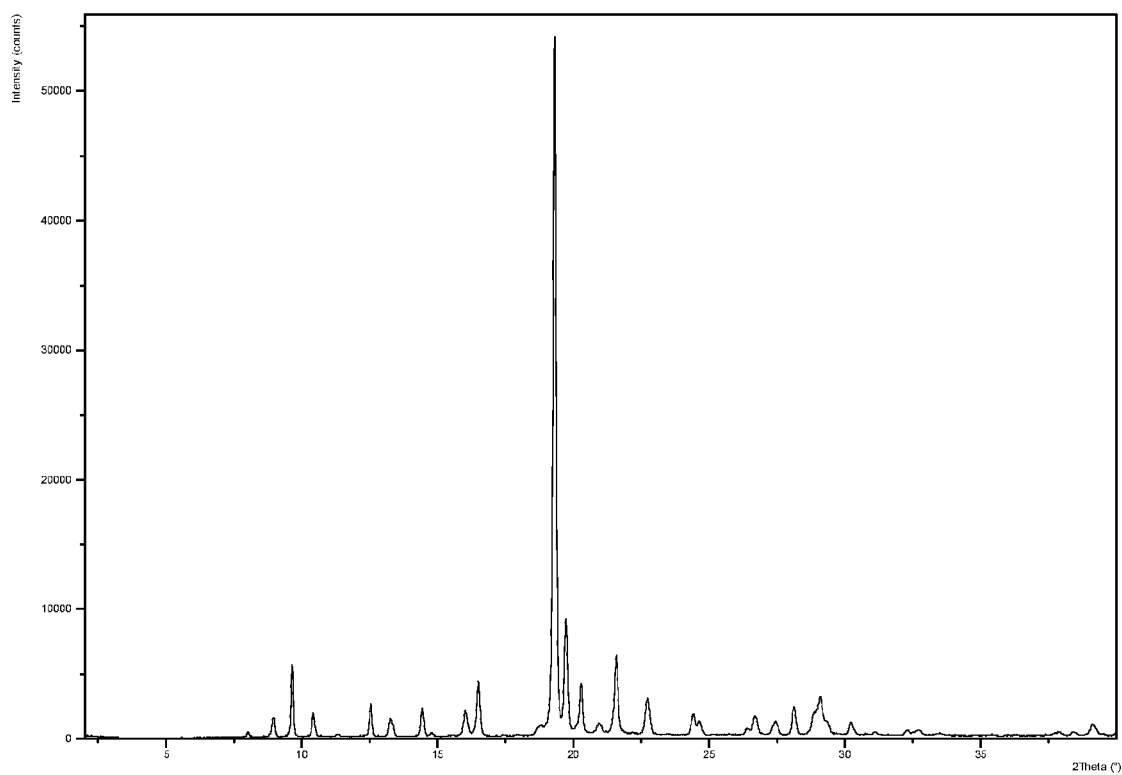
FIG. 6 shows an XRPD pattern for a polymorph of 6-(1H-indol-4-yl)-4-(5-{[4-(1-methylethyl)-1-piperazinyl]methyl}-1,3-oxazol-2-yl)-1H-indazole.

In another embodiment, the present invention provides a polymorph of 6-(1H-indol-4-yl)-4-(5-{[4-(1-methylethyl)-1-piperazinyl]methyl}-1,3-oxazol-2-yl)-1H-indazole characterised in that it provides an XRPD pattern substantially in accordance with FIG. 6 for use in the treatment or prevention of influenza virus infection.

In another embodiment, the present invention provides 6-(1H-indol-4-yl)-4-(5-{[4-(1-methylethyl)-1-piperazinyl]methyl}-1,3-oxazol-2-yl)-1H-indazole tosylate in crystalline form for use in the treatment or prevention of influenza virus infection.

In another embodiment, the present invention provides a polymorph of the tosylate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern comprising peaks (° 2θ) at about 6.3, about 9.3, about 11.3 and/or about 12.7 for use in the treatment or prevention of influenza virus infection.

In another embodiment, the present invention provides a polymorph of the tosylate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern comprising peaks substantially as set out in Table 7 for use in the treatment or prevention of influenza virus infection.

Figure 7:
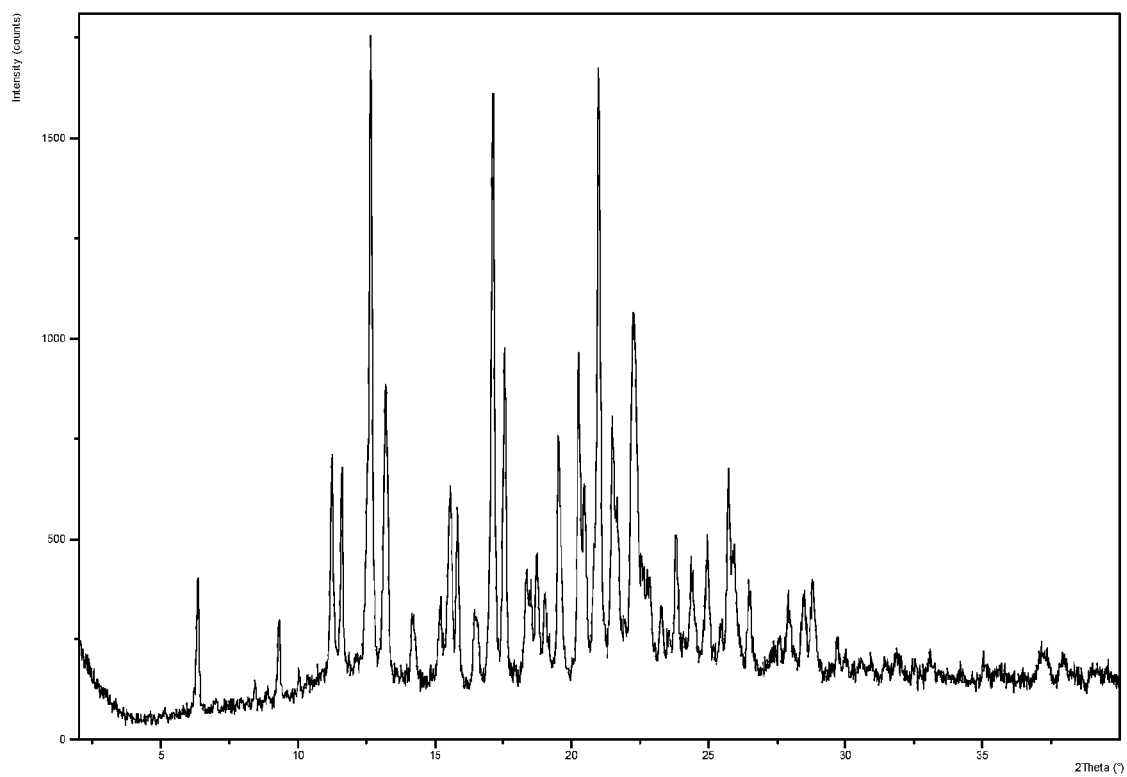
FIG. 7 shows an XRPD pattern for a polymorph of the tosylate salt of 6-(1H-indol-4-yl)-4-(5-{[4-(1-methylethyl)-1-piperazinyl]methyl}-1,3-oxazol-2-yl)-1H-indazole.

In another embodiment, the present invention provides a polymorph of the tosylate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern substantially in accordance with FIG. 7 for use in the treatment or prevention of influenza virus infection.

In another embodiment, the present invention provides 6-(1H-indol-4-yl)-4-(5-{[4-(1-methylethyl)-1-piperazinyl]methyl}-1,3-oxazol-2-yl)-1H-indazole hemi fumarate in crystalline form for use in the treatment or prevention of influenza virus infection.

In another embodiment, the present invention provides a polymorph of the hemi fumarate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern comprising peaks (° 2θ) at about 6.9, about 13.8 and/or about 14.4 for use in the treatment or prevention of influenza virus infection.

In another embodiment, the invention provides a polymorph of the hemi fumarate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern comprising peaks substantially as set out in Table 8 for use in the treatment or prevention of influenza virus infection.

Figure 8:
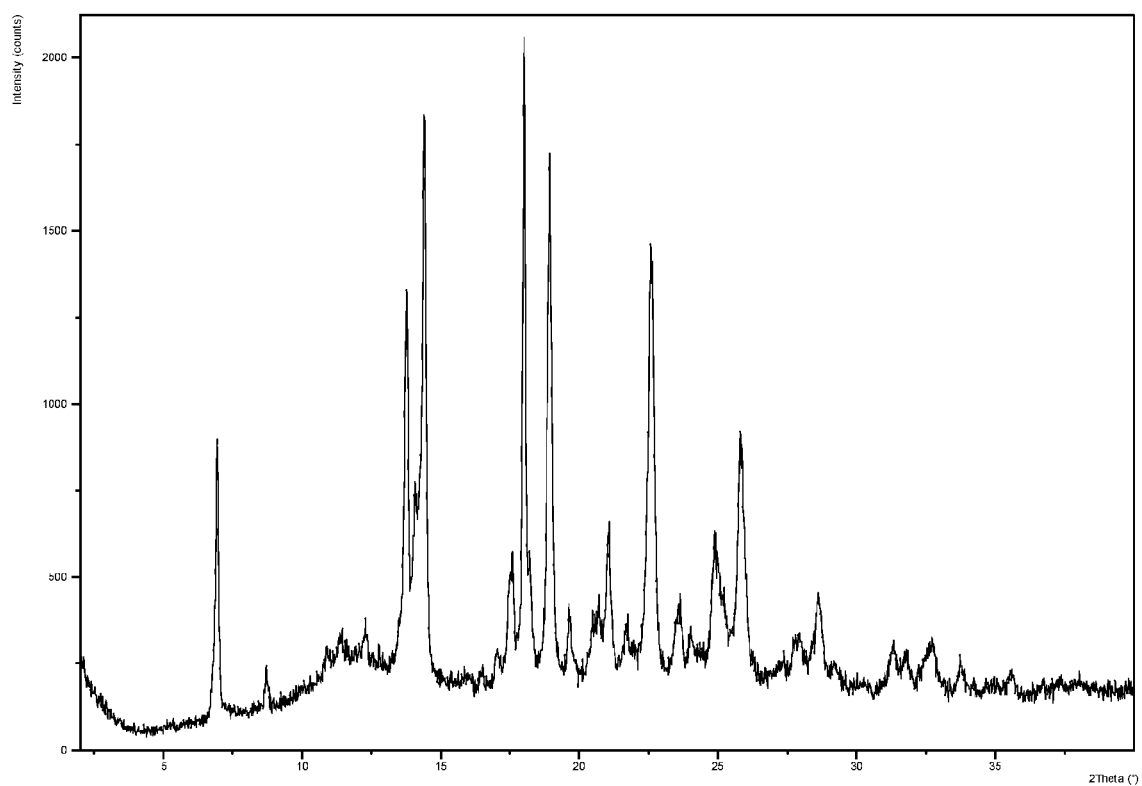
FIG. 8 shows an XRPD pattern for a polymorph of the hemi fumarate salt of 6-(1H-indol-4-yl)-4-(5-{[4-(1-methylethyl)-1-piperazinyl]methyl}-1,3-oxazol-2-yl)-1H-indazole.

In another embodiment, the invention provides a polymorph of the hemi fumarate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern substantially in accordance with FIG. 8 for use in the treatment or prevention of influenza virus infection.

In another embodiment, the present invention provides 6-(1H-indol-4-yl)-4-(5-{[4-(1-methylethyl)-1-piperazinyl]methyl}-1,3-oxazol-2-yl)-1H-indazole hemi succinate in crystalline form for use in the treatment or prevention of influenza virus infection.

In another embodiment, the invention provides a polymorph of the hemi succinate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern comprising peaks (° 2θ) at about 7.2, about 13.2 and/or about 14.0 for use in the treatment or prevention of influenza virus infection.

In another embodiment, the invention provides a polymorph of the hemi succinate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern comprising peaks substantially as set out in Table 9 for use in the treatment or prevention of influenza virus infection.

Figure 9:
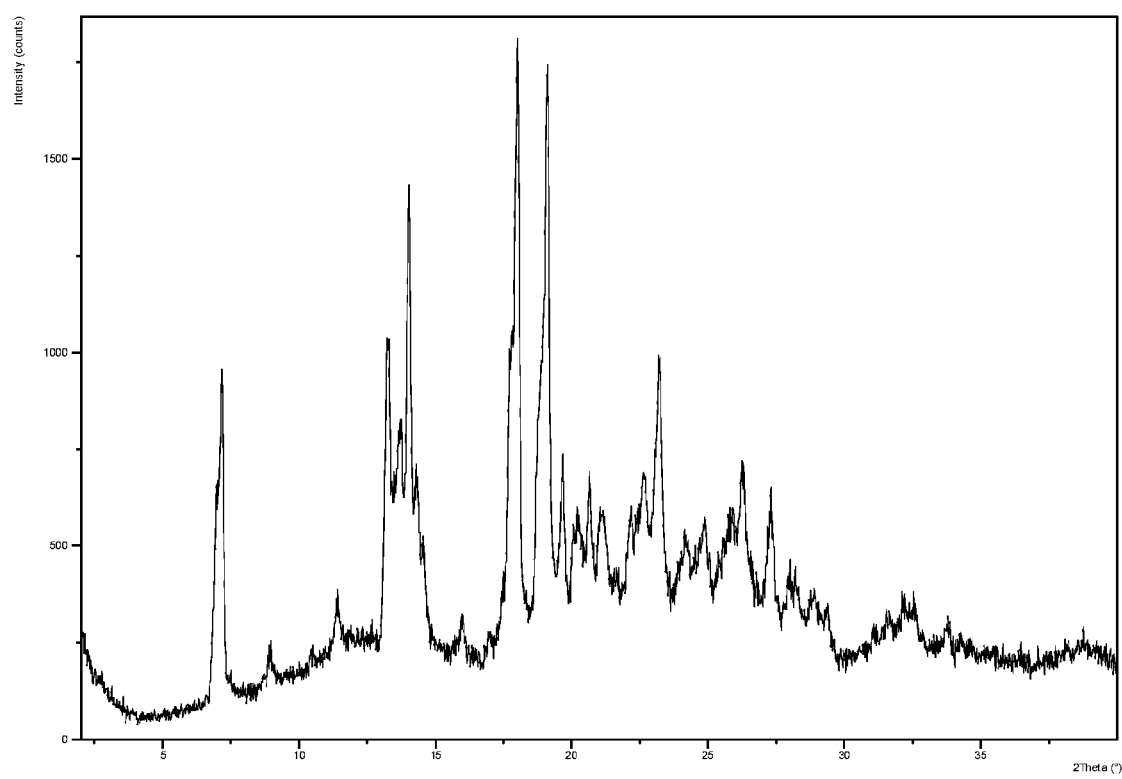
FIG. 9 shows an XRPD pattern for a polymorph of the hemi succinate salt of 6-(1H-indol-4-yl)-4-(5-{[4-(1-methylethyl)-1-piperazinyl]methyl}-1,3-oxazol-2-yl)-1H-indazole.

In another embodiment, the invention provides a polymorph of the hemi succinate salt of 6-(1H-indol-4-yl)-4-(5-{[4-(1-methylethyl)-1-piperazinyl]methyl}-1,3-oxazol-2-yl)-1H-indazole characterised in that it provides an XRPD pattern substantially in accordance with FIG. 9 for use in the treatment or prevention of influenza virus infection.

In another embodiment, the present invention provides 6-(1H-indol-4-yl)-4-(5-{[4-(1-methylethyl)-1-piperazinyl]

methyl}-1,3-oxazol-2-yl)-1H-indazole hydrochloride in crystalline form for use in the treatment or prevention of influenza virus infection.

In another embodiment, the present invention provides crystalline 6-(1H-indol-4-yl)-4-(5-{[4-(1-methylethyl)-1-piperazinyl]methyl}-1,3-oxazol-2-yl)-1H-indazole hydrochloride characterised in that it provides an XRPD (X-ray powder diffraction) pattern having peaks (° 2θ) at about 5.2, about 10.3 and/or about 12.8 for use in the treatment or prevention of influenza virus infection.

In another embodiment, the present invention provides crystalline 6-(1H-indol-4-yl)-4-(5-{[4-(1-methylethyl)-1-piperazinyl]methyl}-1,3-oxazol-2-yl)-1H-indazole hydrochloride characterised in that it provides an XRPD pattern comprising peaks substantially as set out in Table 1 for use in the treatment or prevention of influenza virus infection.

In a further embodiment, the present invention provides crystalline 6-(1H-indol-4-yl)-4-(5-{[4-(1-methylethyl)-1-piperazinyl]methyl}-1,3-oxazol-2-yl)-1H-indazole hydrochloride characterised in that it provides an XRPD pattern substantially in accordance with FIG. 1 for use in the treatment or prevention of influenza virus infection.

In a further aspect, the present invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl] methanesulfonamide or a pharmaceutically acceptable salt thereof in crystalline form for use in the treatment or prevention of influenza virus infection.

In one embodiment, the present invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl] methanesulfonamide in crystalline form for use in the treatment or prevention of influenza virus infection.

In another embodiment, the present invention provides crystalline (Form (I)) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD (X-ray powder diffraction) pattern having peaks (° 2θ) at about 4.5, about 11.7 and/or about 12.9 for use in the treatment or prevention of influenza virus infection.

In another embodiment, the present invention provides crystalline (Form (I)) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 2 for use in the treatment or prevention of influenza virus infection.

Figure 2:
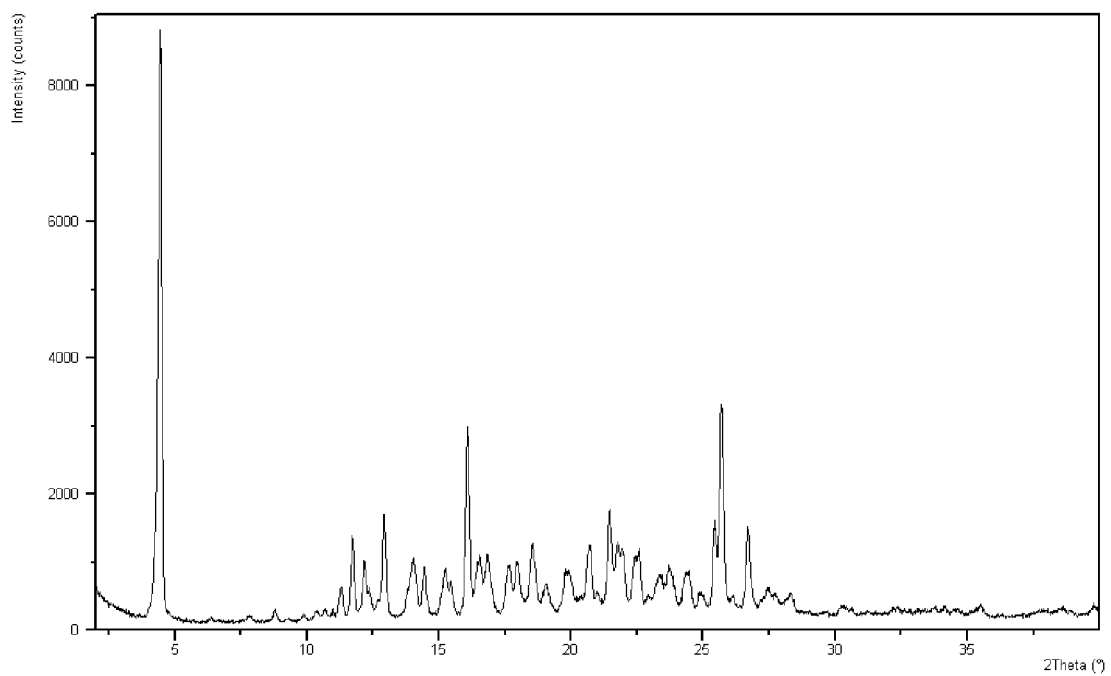
FIG. 2 shows an XRPD pattern for the Form (I) polymorph of Example 63 (N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide).

In another embodiment, the present invention provides crystalline (Form (I)) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern substantially in accordance with FIG. 2 for use in the treatment or prevention of influenza virus infection.

In another embodiment, the invention provides crystalline (Form II) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks (° 2θ) at about 4.6, about 9.2, about 11.4 and/or about 12.7 for use in the treatment or prevention of influenza virus infection.

In another embodiment, the invention provides crystalline (Form II) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 3 for use in the treatment or prevention of influenza virus infection.

Figure 3:
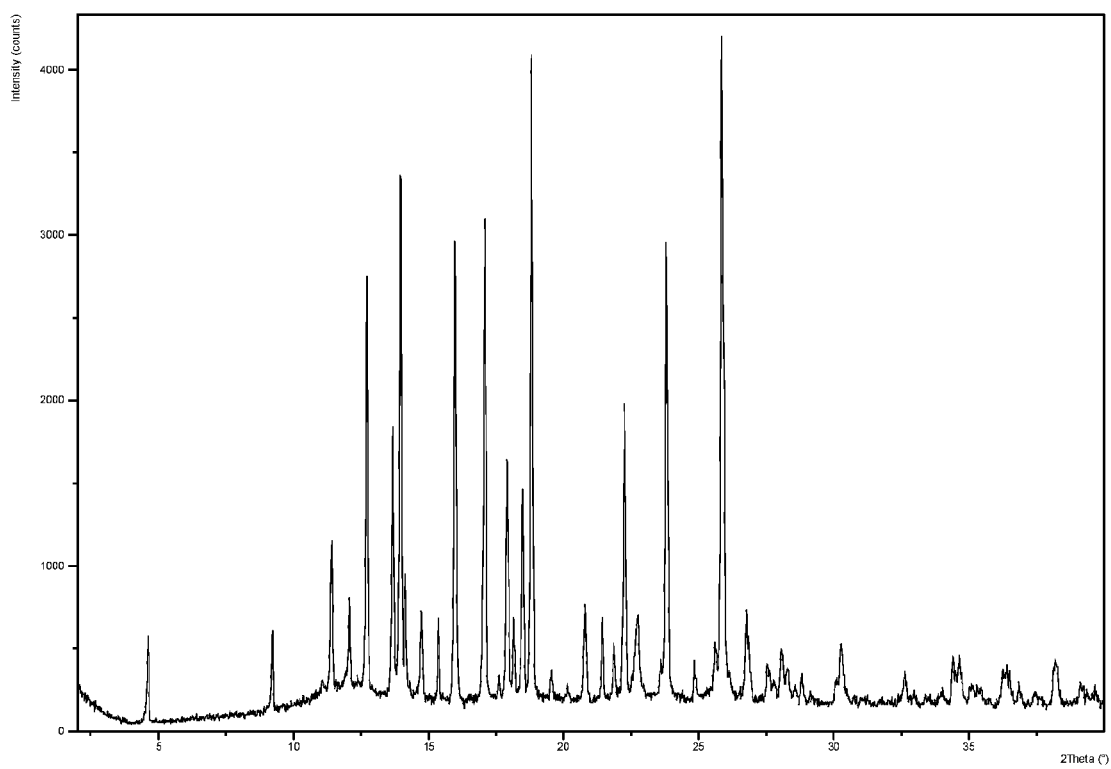
FIG. 3 shows an XRPD pattern for the Form (II) polymorph of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide.

In another embodiment, the invention provides crystalline (Form II) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern substantially in accordance with FIG. 3 for use in the treatment or prevention of influenza virus infection.

In another embodiment, the invention provides crystalline (Form III) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks (° 2θ) at about 6.7, about 8.2, about 9.7 and/or about 12.6 for use in the treatment or prevention of influenza virus infection.

In another embodiment, the invention provides crystalline (Form III) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 4 for use in the treatment or prevention of influenza virus infection.

Figure 4:
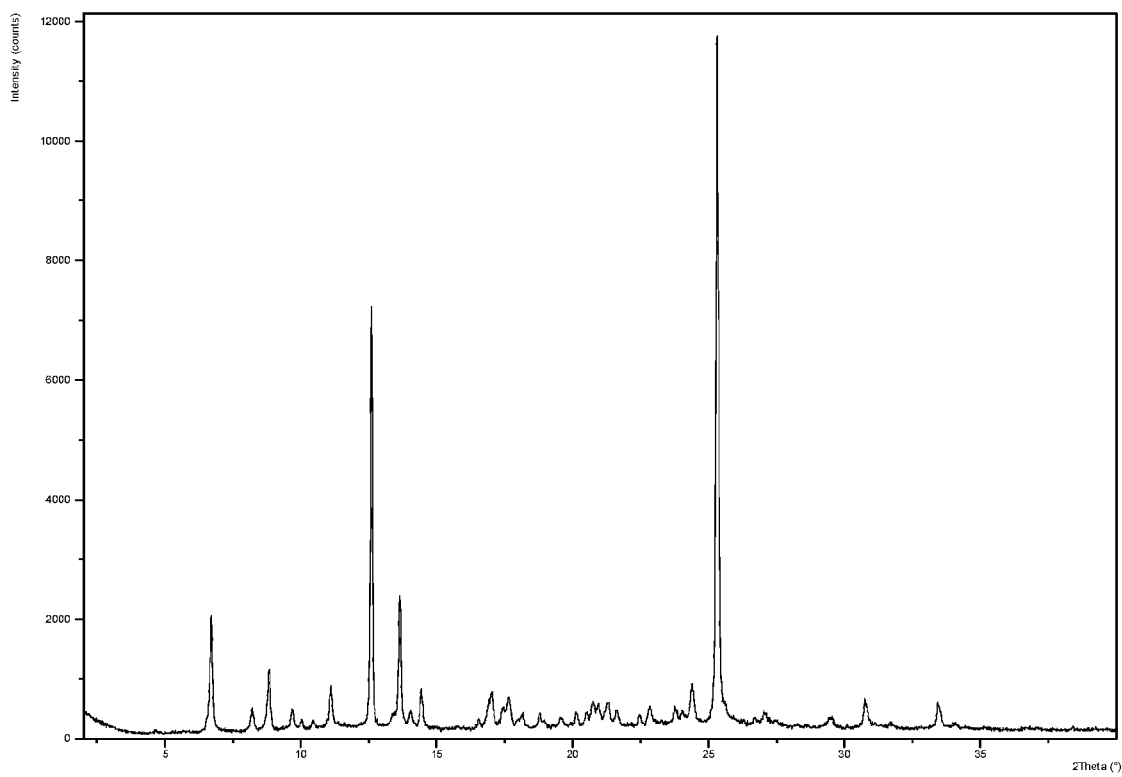
FIG. 4 shows an XRPD pattern for the Form (III) polymorph of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide.

In another embodiment, the invention provides crystalline (Form III) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern substantially in accordance with FIG. 4 for use in the treatment or prevention of influenza virus infection.

In another embodiment, the invention provides crystalline (Form IV) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks (° 2θ) at about 5.8, and/or about 11.6 for use in the treatment or prevention of influenza virus infection.

In another embodiment, the invention provides crystalline (Form IV) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 5 for use in the treatment or prevention of influenza virus infection.

Figure 5:
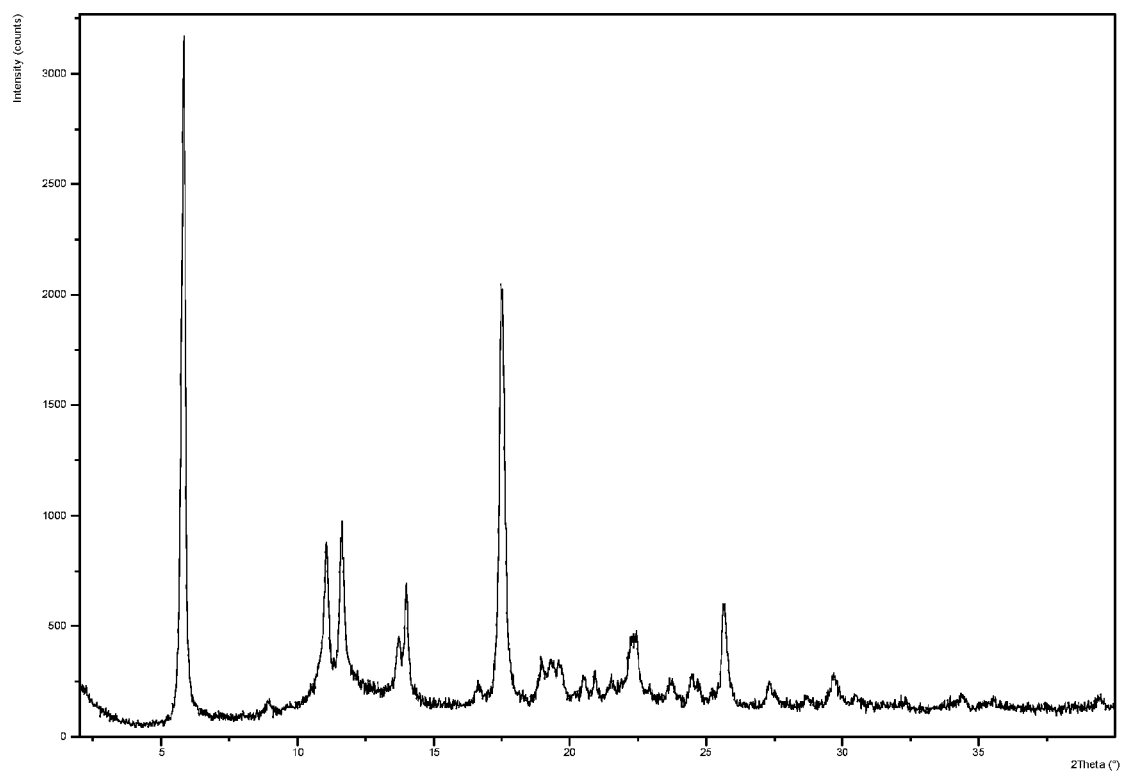
FIG. 5 shows an XRPD pattern for the Form (IV) polymorph of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide.

In a further embodiment, the invention provides crystalline (Form IV) N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern substantially in accordance with FIG. 5 for use in the treatment or prevention of influenza virus infection.

When it is indicated herein that there is a peak in an XRPD pattern at a given value, it is typically meant that the peak is within ±0.2 of the value quoted, for example within ±0.1 of the value quoted.

The invention encompasses the use of polymorphs and salts and polymorphs thereof isolated in pure form or when admixed with other materials, for example other polymorphs, or salts or solvates (inclusive of their polymorphs), or any other material.

Thus, in one aspect there is provided a polymorph or salt or a polymorph thereof in isolated or pure form. "Isolated" or "pure" form refers to a sample in which the polymorph or salt or a polymorph thereof is present in an amount of >75%, particularly >90%, more particularly >95% and even more particularly >99% relative to other materials which may be present in the sample.

The compounds for use according to the invention also include isotopically-labelled compounds, which are identical to the compounds of formulae (I) to (VII) and pharmaceutically acceptable salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^{2}H$, $^{3}H$, $^{11}C$, $^{14}C$ and $^{18}F$.

The compounds for use according to the invention may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formulae (I) to (VII), or in any chemical structure illustrated herein, is not specified the structure is intended to encompass any stereoisomer and all mixtures thereof. Thus, compounds according to formulae (I) to (VII) containing one or more chiral center may be used as racemic mixtures, enantiomerically enriched mixtures, or as enantiomerically pure individual stereoisomers.

Individual stereoisomers of a compound according to formulae (I) to (VII) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formulae (I) to (VII) may also contain centers of geometric asymmetry. Where the stereochemistry of a center of geometric asymmetry present in formulae (I) to (VII), or in any chemical structure illustrated herein, is not specified, the structure is intended to encompass the trans geometric isomer, the cis geometric isomer, and all mixtures thereof. Likewise, all tautomeric forms are also included in formulae (I) to (VII) whether such tautomers exist in equilibrium or predominately in one form.

It is to be understood that the references herein to compounds of formulae (I) to (VII) and pharmaceutically acceptable salts thereof covers the compounds of formulae (I) to (VII) as free acids or free bases, or as pharmaceutically acceptable salts thereof. Thus, in one embodiment, the invention is directed to the use of compounds of formulae (I) to (VII) as the free acid or free base. In a further embodiment, the invention is directed to the use of compounds of formulae (I) to (VII) and pharmaceutically acceptable salts thereof.

The skilled artisan will appreciate that pharmaceutically acceptable salts of the compounds according to formulae (I) to (VII) may be prepared. Indeed, in certain embodiments of the invention, pharmaceutically acceptable salts of the compounds according to formulae (I) to (VII) may be preferred over the respective free base or free acid because such salts may impart greater stability or solubility to the molecule thereby facilitating formulation into a dosage form.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form, or a non-pharmaceutically acceptable salt, with a suitable base or acid, respectively.

Salts and solvates having non-pharmaceutically acceptable counter-ions or associated solvents may be used as intermediates in the preparation of compounds of formulae (I) to (VI) and their pharmaceutically acceptable salts.

In certain embodiments, compounds according to formulae (I) to (VII) may contain an acidic functional group. Suitable pharmaceutically acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formulae (I) to (VII) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate and naphthalenedisulfonate. In one embodiment, the pharmaceutically acceptable addition salt is a hydrochloride. In a further embodiment, the pharmaceutically acceptable addition salt is a mandelate such as the (R)-mandelate.

In one aspect, the invention provides a salt of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl] methanesulfonamide selected from sodium, tosylate, maleate, hemi pamoate, hemi naphthalenedisulfonate, mesitylenesulfonate, hemi biphenyldisulfonate, 2-naphthalenesulfonate (napsylate), hemi cinnamate, hemi sebacate, hemi pyromellitate and hemi benzenediacrylate for use in the treatment or prevention of influenza virus infection.

In one embodiment, the invention provides a salt of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide selected from sodium, tosylate, maleate, hemi pamoate and hemi naphthalenedisulfonate for use in the treatment or prevention of influenza virus infection.

In one embodiment, the sodium salt is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and sodium hydroxide in a stoichiometric ratio of about 1:1. In another embodiment, the tosylate salt is the mono tosylate salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and p-toluenesulfonic acid in a stoichiometric ratio of about 1:1. In another embodiment, the maleate salt is the mono maleate salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and maleic acid in a stoichiometric ratio of about 1:1. In another embodiment, the hemipamoate salt is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and pamoic acid in a stoichiometric ratio of about 2:1. In another embodiment, the hemi naphthalenedisulfonate salt is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and naphthalenedisulfonic acid in a stoichiometric ratio of about 2:1. In another embodiment, the mesitylenesulfonate salt is the mono mesitylenesulfonate salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and mesitylenesulfonic acid dihydrate in a stoichiometric ratio of about 1:1. In another embodiment, the hemi biphenyldisulfonate salt is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and biphenyldisulfonic acid in a stoichiometric ratio of about 2:1. In another embodiment, the 2-naphthalenesulfonate (napsylate) salt is the mono 2-naphthalenesulfonate (napsylate) salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and 2-naphthalenesulfonic acid in a stoichiometric ratio of about 1:1. In another embodiment, the hemi cinnamate salt is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and trans-cinnamic acid in a stoichiometric ratio of about 2:1. In another embodiment, the hemi sebacate salt is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and sebacic acid in a stoichiometric ratio of about 2:1. In another embodiment, the hemi pyromellitate salt is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and pyromellitic acid in a stoichiometric ratio of about 2:1. In further embodiment, the hemi benzenediacrylate salt is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and 1,4-benzenediacrylic acid in a stoichiometric ratio of about 2:1.

In a further aspect, the invention provides a salt of 6-(1H-indol-4-yl)-4-(5-{[4-(1-methylethyl)-1-piperazinyl]methyl}-1,3-oxazol-2-yl)-1H-indazole selected from tosylate, hemi fumarate and hemi succinate for use in the treatment or prevention of influenza virus infection.

In one embodiment, the invention provides a salt of 6-(1H-indol-4-yl)-4-(5-{[4-(1-methylethyl)-1-piperazinyl]methyl}-1,3-oxazol-2-yl)-1H-indazole selected from hemi fumarate and hemi succinate for use in the treatment or prevention of influenza virus infection.

In another embodiment, the invention provides the hemi fumarate salt of 6-(1H-indol-4-yl)-4-(5-{[4-(1-methylethyl)-1-piperazinyl]methyl}-1,3-oxazol-2-yl)-1H-indazole for use in the treatment or prevention of influenza virus infection.

In a further embodiment, the invention provides the hemi succinate salt of 6-(1H-indol-4-yl)-4-(5-{[4-(1-methylethyl)-1-piperazinyl]methyl}-1,3-oxazol-2-yl)-1H-indazole for use in the treatment or prevention of influenza virus infection.

The tosylate salt is the mono tosylate salt formed between 6-(1H-indol-4-yl)-4-(5-{[4-(1-methylethyl)-1-piperazinyl]methyl}-1,3-oxazol-2-yl)-1H-indazole and p-toluenesulfonic acid in a stoichiometric ratio of about 1:1. The hemi fumarate salt is the salt formed between 6-(1H-indol-4-yl)-4-(5-{[4-(1-methylethyl)-1-piperazinyl]methyl}-1,3-oxazol-2-yl)-1H-indazole and fumaric acid in a stoichiometric ratio of about 2:1. The hemi succinate salt is the salt formed between 6-(1H-indol-4-yl)-4-(5-{[4-(1-methylethyl)-1-piperazinyl]methyl}-1,3-oxazol-2-yl)-1H-indazole and succinic acid in a stoichiometric ratio of about 2:1.

Compound Preparation

The compounds for use according to the invention may be made by a variety of methods, including standard chemistry. Any previously defined variable will continue to have the previously defined meaning unless otherwise indicated. Illustrative general synthetic methods are set out below and then specific compounds for use according to the invention are prepared in the Examples section.

Compounds of Formulae (I) to (IV) and (VII)

Compounds of formulae (I) to (IV) and (VII), or salts thereof, may be prepared as described in WO 2009/147187, WO 2009/147188, WO 2009/147190 and WO 2009/147189.

Compounds of Formula (V)

Compounds of formula (V) may be prepared as described in WO 2010/102958.

For example, compounds of formula (V), wherein $R^1$ and X are as defined above for compounds of formula (V) and $R^4$ is hydrogen, or salts thereof, may be prepared from compounds of formula (VA)

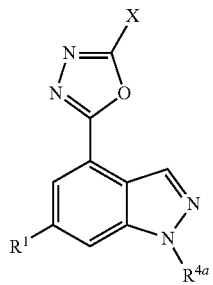

(VA)

wherein $R^1$ and X are as defined above for compounds of formula (V) and $R^{4a}$ is a suitable protecting group, for example benzenesulphonyl, by treatment with a suitable aqueous inorganic base such as aqueous sodium hydroxide, in a suitable solvent such as isopropanol or 1,4-dioxane, at a suitable temperature such as room temperature, for example about 20° C.

Process 1

Compounds of formula (VA), wherein R¹ is as defined for compounds of formula (V), R$^{4a}$ is as defined above and X is —CH$_2$NR²R³ wherein R² and R³ are as defined for compounds of formula (V), and compounds of formula (V) wherein R¹ is as defined above for compounds of formula (V), X is —CH$_2$NR²R³ wherein R² and R³ are as defined for compounds of formula (V) and R⁴ is methyl, or salts thereof, may be prepared from compounds of formula (VIII)

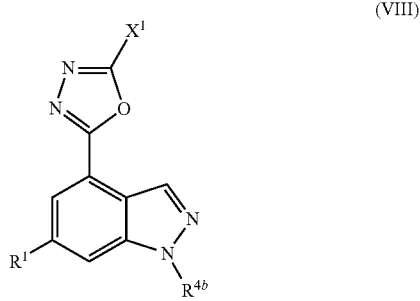

(VIII)

wherein R¹ is as defined above for compounds of formula (V), R$^{4b}$ is methyl or R$^{4a}$ as defined above, and X¹ is CH$_2$X², where X² is a suitable leaving group for example Cl, by treatment with a suitable amine of formula HNR²R³ wherein R² and R³ are as defined for compounds of formula (V) such as morpholine, in a suitable solvent such as dichloromethane, and at a suitable temperature such as from 20 to 50° C., for example about 20° C. Alternatively, this process may be carried out in a suitable solvent such as acetonitrile, in the presence of a suitable amine such as 1-(1-methylethyl)piperazine, in the presence of a suitable base such as N,N-diisopropylethylamine, in the presence of a suitable iodide such as sodium iodide, and at a suitable temperature such as from 20 to 100° C., for example about 70° C. Alternatively, this process may be carried out in the presence of a suitable amine such as morpholine, with or without the presence of a suitable solvent such as acetonitrile, under microwave irradiation at a suitable temperature such as from 50 to 120° C., for example about 80° C.

Compounds of formula (VIII), wherein R¹ is as defined for compounds of formula (V), and X¹ and R$^{4b}$ are as defined above, and compounds of formula (VA), wherein R¹ is as defined for compounds of formula (V), R$^{4a}$ is defined as above and X is C$_{1-6}$alkyl, —CH$_2$-phenyl, —(CH$_2$)$_n$OR¹⁰ or —(CH$_2$)$_p$C$_{3-6}$cycloalkyl wherein n, R¹⁰ and p are as defined for compounds of formula (V), may be prepared from compounds of formula (IX)

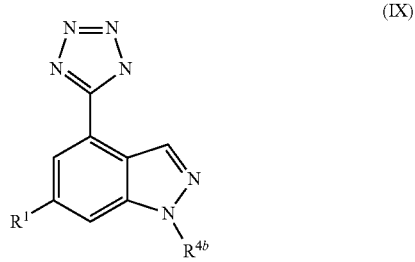

(IX)

wherein R¹ is as defined for compounds of formula (V) and R$^{4b}$ is as defined above, by treatment with a suitable acylating agent such as chloroacetyl chloride or 2-methylpropanoyl chloride, in a suitable solvent such as chloroform, under microwave irradiation at a suitable temperature such as from 50 to 120° C., for example about 100° C. Alternatively, this process may be carried out either thermally or under microwave irradiation, in a suitable solvent such as toluene, and at a suitable temperature such as from 60 to 200° C., for example about 100° C.

For compounds where R¹ contains a protecting group such as where R¹ is 1,1-dimethylethyl 1H-indole-1-carboxylate, an additional deprotection step is required, by treatment with a suitable acid such as acetic acid, at a suitable temperature such as from 50 to 130° C., for example about 100° C. Examples of suitable protection groups and the means of their removal can be found in T. W. Greene and P. G. M. Wuts 'Protective Groups in Organic Synthesis' (3$^{rd}$ Ed., J. Wiley and Sons, 1999).

Compounds of formula (IX), wherein R¹ is as defined for compounds of formula (V) and R$^{4b}$ is as defined above, may be prepared from compounds of formula (X)

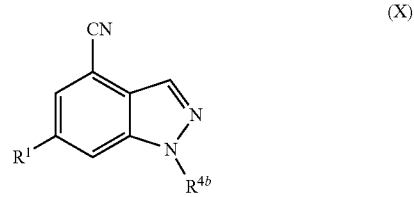

(X)

wherein R¹ is as defined for compounds of formula (V) and R$^{4b}$ is as defined above, by treatment with a suitable azide such as trimethylsilyl azide, in the presence of a suitable catalyst such as dibutyl(oxo)stannane, in a suitable solvent such as toluene, and at a suitable temperature such as from 50 to 120° C., for example about 110° C.

Compounds of formula (X), wherein R¹ is as defined for compounds of formula (V) and R$^{4b}$ is as defined above, may be prepared from compounds of formula (XI)

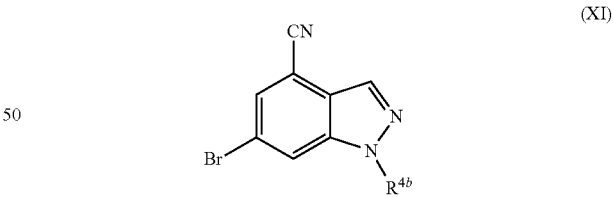

(XI)

wherein R$^{4b}$ is as defined above, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as 1,1'-bis(diphenylphosphino)ferrocene palladium dichloride, in a suitable solvent such as a mixture of 1,4-dioxane and water, in the presence of a suitable base such as tripotassium phosphate, and at a suitable temperature such as from 50 to 150° C., for example about 60° C. Alternatively, this process may be carried out under microwave irradiation, at a suitable temperature such as from 60 to 200° C., for example about 100° C.

The compound of formula (XI), wherein $R^{4b}$ is methyl, may be prepared from the compound of formula (XII)

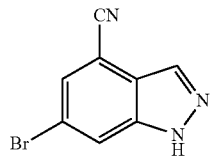
(XII)

by methylation using a suitable base such as sodium hydride, in a suitable solvent such as tetrahydrofuran, and at a suitable temperature such as about 0° C., followed by addition of an alkylating agent such as iodomethane and stirring at a suitable temperature such as room temperature. The compound of formula (XII) is commercially available.

Compounds of formula (XI), wherein $R^{4b}$ is a suitable protecting group, for example benzenesulphonyl, may be prepared from the compound of formula (XII) as defined above by treatment with a suitable sulphonylating agent such as benzenesulphonyl chloride, in the presence of a suitable base such as sodium hydride, in a suitable solvent such as N,N-dimethylformamide, and at a suitable temperature such as from 0° C. to 50° C., for example about 20° C.

Process 1b

Compounds of formula (VA), wherein $R^1$ is as defined for compounds of formula (V) and $R^{4a}$ is as defined above and X is —$CH_2SO_2R^{11}$ wherein $R^{11}$ is as defined for compounds of formula (V), and compounds of formula (V) wherein $R^1$ is as defined for compounds of formula (V), X is —$CH_2SO_2R^{11}$ wherein $R^{11}$ is as defined for compounds of formula (V) and $R^4$ is methyl, or salts thereof, may be prepared from compounds of formula (VIII) as defined above, by treatment with a suitable sulfinate salt, such as sodium methanesulfinate, in a suitable solvent such as ethanol, and under microwave irradiation at a suitable temperature such as from 50° C. to 200° C., for example about 100° C.

Process 1c

Compounds of formula (VA), wherein $R^1$ is as defined for compounds of formula (V), $R^{4a}$ is as defined above and X is —$(CH_2)_nOR^{10}$ wherein n and $R^{10}$ are as defined for compounds of formula (V), and compounds of formula (V) wherein $R^1$ is as defined for compounds of formula (V), X is —$(CH_2)_nOR^{10}$ wherein n and $R^{10}$ are as defined for compounds of formula (V) and $R^4$ is methyl, or salts thereof, may also be prepared from compounds of formula (VIII) as defined above, by treatment with a suitable alcohol such as methanol, in the presence of a suitable base such as potassium carbonate, under microwave irradiation at a suitable temperature such as from 80 to 150° C., for example about 110° C.

Process 2

For compounds of formula (VA), wherein X and $R^{4a}$ are as defined above and $R^1$ is pyridinyl substituted by —$NHSO_2R^7$ wherein $R^7$ is as defined for compounds of formula (V), and compounds of formula (V) wherein X is as defined above, $R^4$ is methyl and $R^1$ is pyridinyl substituted by —$NHSO_2R^7$ wherein $R^7$ is as defined for compounds of formula (V), or salts thereof, may be prepared from compounds of formula (XIII)

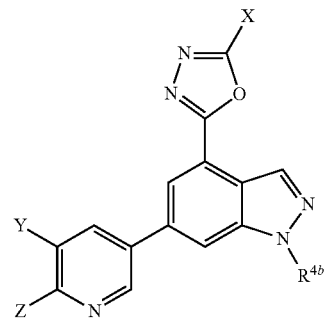
(XIII)

wherein X and $R^{4b}$ are as defined above, Y is $NH_2$ and Z is $C_{1-6}$alkyl, —$OR^6$ or halo wherein $R^6$ is as defined for compounds of formula (V), by treatment with a suitable sulfonyl chloride of formula $R^7SO_2Cl$ wherein $R^7$ is as defined for compounds of formula (V), such as 2,4-difluorobenzenesulfonyl chloride, in a suitable solvent such as chloroform, with a suitable base such as pyridine at a suitable temperature such as room temperature, for example about 20° C.

Compounds of formula (XIII) wherein X, $R^{4b}$ and Y are as defined above, compounds of formula (VA) wherein $R^1$ is as defined for compounds of formula (V) and X and $R^{4a}$ are as defined above, and compounds of formula (V) wherein $R^1$ is as defined for compounds of formula (V), X is as defined above and $R^4$ is methyl, or salts thereof, may also be prepared from compounds of formula (XIV)

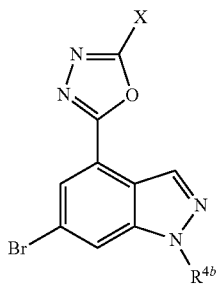
(XIV)

wherein X and $R^{4b}$ are as defined above, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as 1,1'-bis(diphenylphosphino)ferrocene palladium dichloride, in a suitable solvent such as a mixture of 1,4-dioxane and water, in the presence of a suitable base such as tripotassium phosphate or 2M sodium carbonate solution, under microwave irradiation, and at a suitable temperature such as from 50 to 200° C., for example about 85° C.

Compounds of formula (XIV), wherein $R^{4b}$ is as defined above and X is —$CH_2NR^2R^3$ wherein $R^2$ and $R^3$ are as defined for compounds of formula (V), may be prepared from compounds of formula (XV)

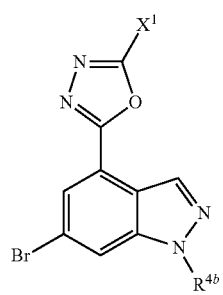
(XV)

wherein $R^{4b}$ is as defined above and $X^1$ is $CH_2X^2$, where $X^2$ is a suitable leaving group for example Cl, by treatment with an amine of formula $HNR^2R^3$ wherein $R^2$ and $R^3$ are as defined for compounds of formula (V), such as morpholine, in a suitable solvent such as dichloromethane and at a suitable temperature such as from 20 to 50° C., for example about 20° C. Alternatively, this process may be carried out in a suitable solvent such as acetonitrile, in the presence of a suitable amine such as 1-(1-methylethyl)piperazine, in the presence of a suitable base such as N,N-diisopropylethylamine, in the presence of a suitable iodide such as sodium iodide, and at a suitable temperature such as from 20 to 100° C., for example about 80° C.

Compounds of formula (XV), wherein $R^{4b}$ is as defined above and $X^1$ is —$CH_2Cl$ or $CH_2Br$, may be prepared from compounds of formula (XVI)

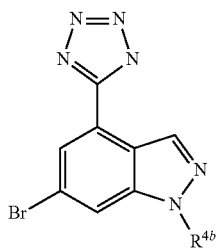

(XVI)

wherein $R^{4b}$ is as defined above, by treatment with a suitable acylating agent such as chloroacetyl chloride, in the presence of a suitable solvent such as toluene, under microwave irradiation, and at a suitable temperature such as from 60 to 200° C., for example about 115° C.

Compounds of formula (XIV) where $R^{4b}$ is defined as above and X is $C_{1-6}$alkyl, may be prepared directly from compounds of formula (XVI) wherein $R^{4b}$ is defined as above by treatment with a suitable acylating agent, such as acetyl chloride, in a suitable solvent such as toluene, under microwave irradiation at a suitable temperature such as from 80 to 150° C., for example about 130° C.

Compounds of formula (XVI), wherein $R^{4b}$ is as defined above, may be prepared from compounds of formula (XI), as defined above, by treatment with a suitable azide such as trimethylsilyl azide, in the presence of a suitable catalyst such as dibutyl(oxo)stannane, in a suitable solvent such as toluene, under microwave irradiation, and at a suitable temperature such as from 50 to 120° C., for example about 110° C.

Process 3

Compounds of formula (XIV), wherein $R^{4b}$ is as defined above and X is —$CH_2NR^2R^3$ wherein $R^2$ and $R^3$ are as defined for compounds for formula (V), may be prepared from compounds of formula (XVII)

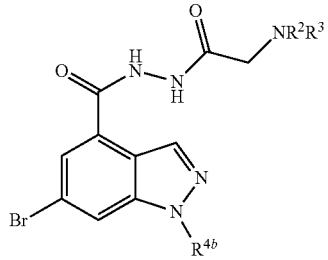

(XVII)

wherein $R^2$ and $R^3$ as defined for compounds for formula (V), and $R^{4b}$ is as defined above, by treatment with a suitable dehydrating agent such as (methoxycarbonylsulfamoyl)triethylammonium hydroxide, inner salt (Burgess reagent), in a suitable solvent such as tetrahydrofuran, under microwave irradiation, and at a suitable temperature such as from 50 to 150° C., for example about 100° C.

Compounds of formula (XVII), wherein $R^2$ and $R^3$ as defined for compounds for formula (V) and $R^{4b}$ is 2-tetrahydro-2H-pyran, may be prepared from compounds of formula (XVIII)

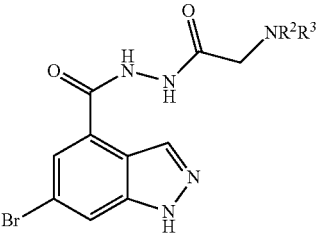

(XVIII)

wherein $R^2$ and $R^3$ are as defined for compounds of formula (V), by treatment with 3,4-dihydro-2H-pyran, in the presence of a suitable acid catalyst such as trifluoroacetic acid, in a suitable solvent such as ethyl acetate, and at a suitable temperature such as from 20 to 100° C., for example about 50° C.

Compounds of formula (XVIII), wherein $R^2$ and $R^3$ are as defined for compounds of formula (V), may be prepared from the compound of formula (XIX)

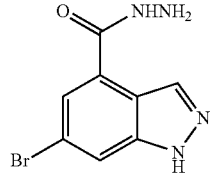

(XIX)

by treatment with a suitable $R^2R^3N$-acetic acid such as 4-morpholinylacetic acid, in the presence of a suitable amide coupling reagent such as O-(7-azabenzotriazol-1-yl)-N,N,N',N'-tetramethyluronium hexafluorophosphate, in the presence of a suitable base such as N,N-diisopropylethylamine, in a suitable solvent such as N,N-dimethylformamide, and at a suitable temperature such as from 20 to 50° C., for example about 20° C.

The compound of formula (XIX) may be prepared from the compound of formula (XX)

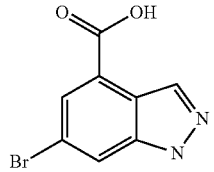

(XX)

by treatment with a suitable hydrazide such as t-butylcarbazate in the presence of a suitable amide coupling reagent such as O-(7-azabenzotriazol-1-yl)-N,N,N',N'-tetramethyluronium hexafluorophosphate, in the presence of a suitable base such as N,N-diisopropylethylamine, in a suitable solvent such as N,N-dimethylformamide and at a suitable temperature such as room temperature, for example 20° C. Followed by deprotection, by treatment with a suitable acid such as hydrogen chloride, in a suitable solvent such as 1,4-dioxane and at a suitable temperature such as room temperature, for example 20° C. The compound of formula (XX) is commercially available.

Process 4

Compounds of formula (X), wherein $R^1$ is as defined for compounds of formula (V) and $R^{4b}$ is as defined above may be prepared from compounds of formula (XXI)

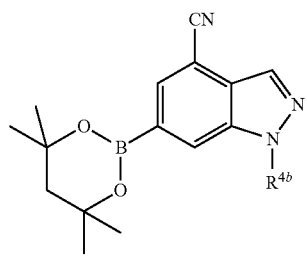

(XXI)

wherein $R^{4b}$ is as defined above, by treatment with a suitable halide such as N-(5-bromo-2-chloro-3-pyridinyl)methanesulfonamide (commercially available), in the presence of a suitable palladium catalyst such as chloro(di-2-norbonylphosphino)(2'-dimethylamino-1,1'-biphenyl-2-yl)palladium (II), in a suitable solvent such as a mixture of 1,4-dioxane and water, in the presence of a suitable base such as tripotassium phosphate, under microwave irradiation, and at a suitable temperature such as from 50 to 200° C., for example about 100° C.

Compounds of formula (XXI), wherein $R^{4b}$ is as defined above, may be prepared from compounds of formula (XI), as defined above, by treatment with a suitable borinane such as 4,4,4',4',6,6,6',6'-octamethyl-2,2'-bi-1,3,2-dioxaborinane (commercially available), in the presence of a suitable palladium catalyst such as 1,1'-bis(diphenylphosphino)ferrocene palladium dichloride, in a suitable solvent such as 1,4-dioxane, in the presence of a suitable base such as potassium acetate, under microwave irradiation, and at a suitable temperature such as from 50 to 150° C., for example about 80° C.

Process 5

Compounds of formula (XIV), wherein $R^{4b}$ is defined as above and X is $CH_2NR^2R^3$ wherein $R^2$ and $R^3$ are defined for compounds of formula (V), may be prepared from compounds of formula (XXII)

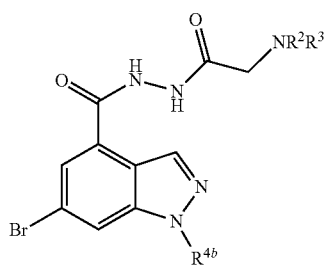

(XXII)

wherein $R^2$ and $R^3$ are as defined for compounds of formula (V), and $R^{4b}$ is as defined above, by treatment with a suitable dehydrating agent such as (methoxycarbonylsulfamoyl)triethylaminonium hydroxide, in a suitable solvent such a tetrahydrofuran, at a suitable temperature such as from 50 to 150° C., for example 75° C.

Compounds of formula (XXII), wherein $R^2$ and $R^3$ are as defined for compounds of formula (V), and $R^{4b}$ is as defined above, may be prepared from compounds of formula (XXIII)

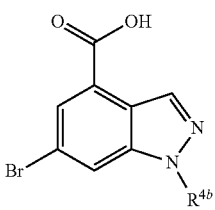

(XXIII)

wherein $R^{4b}$ is defined as above, by treatment with a suitable chlorinating agent such as thionyl chloride at a suitable temperature such as from 50 to 150° C., for example 100° C., followed by treatment with a suitable hydrazide such as 2-[(2R,6S)-2,6-dimethyl-4-morpholinyl]acetohydrazide and a suitable base such a N,N-diisopropylethylamine in a suitable solvent such as tetrahydrofuran at a suitable temperature such as from 20° C. to 100° C., for example 20° C.

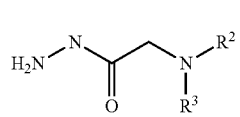

(XXIV)

Hydrazides of formula (XXIV), wherein $R^2$ and $R^3$ are as defined for compounds of formula (V), may be prepared from compounds of formula (XXV)

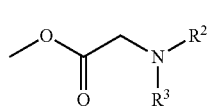

(XXV)

wherein $R^2$ and $R^3$ are as defined for compounds of formula (V), by treatment with a suitable hydrazine such as hydrazine hydrate, in a suitable solvent such as methanol, at a suitable temperature such as from 50 to 150° C., for example about 70° C. Compounds of formula (XXV) may be prepared as described in the literature. For the compound wherein and $NR^2R^3$ is (2R,6S)-2,6-dimethylmorpholine, see Journal of Fluorine Chemistry, 1998, 193-201).

Compounds of formula (XXIII), wherein $R^{4b}$ is defined as above, may be prepared from compounds of formula (XXVI)

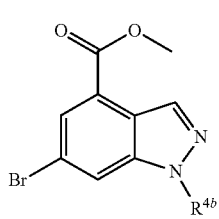

(XXVI)

wherein $R^{4b}$ is defined as above, by treatment with a suitable base such as lithium hydroxide, in a suitable solvent such as a mixture of tetrahydrofuran and water, at a suitable temperature such as room temperature, for example about 20° C.

Compounds of formula (XXVI), wherein $R^{4b}$ is methyl, may be prepared from the compound of formula (XXVII)

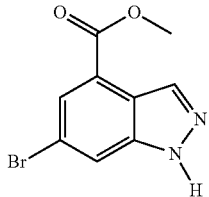
(XXVII)

by methylation using a suitable base such as sodium hydride, in a suitable solvent such as tetrahydrofuran, and at a suitable temperature such as about 0° C., followed by addition of an alkylating agent such as iodomethane and stirring at a suitable temperature such as from 0° C. to room temperature.

Compounds of formula (XXVI), wherein $R^{4b}$ is a suitable protecting group, for example benzenesulphonyl, may be prepared from compounds of formula (XXVII) by treatment with a suitable sulphonylating agent such as benzenesulphonyl chloride, in the presence of a suitable base such as sodium hydride, in a suitable solvent such as N,N-dimethylformamide, and at a suitable temperature such as from 0° C. to 50° C., for example about 20° C.

The compound of formula (XXVII) may be prepared from the compound of formula (XXVIII)

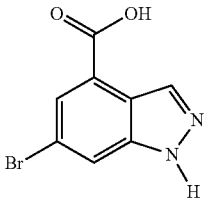
(XXVIII)

by treatment with a suitable acid such as concentrated hydrochloric acid and a suitable alcohol such as methanol, at a suitable temperature such as from 50 to 150° C., for example about 70° C. The compound of formula (XXVIII) is commercially available.

Process 6

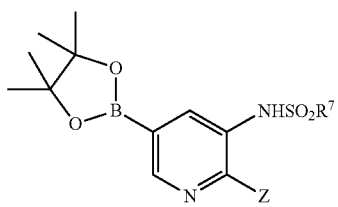
(XXIX)

Boronic esters of formula (XXIX), wherein $R^7$ is as defined for compounds of formula (V) and Z is $OR^6$ as defined for compounds of formula (V) or halo, may be prepared from compounds of formula (XXX)

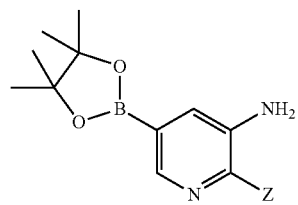
(XXX)

wherein Z is $OR^6$ as defined for compounds of formula (V) or halo, by treatment with a suitable sulphonyl chloride such as methane sulfonyl chloride, in a suitable solvent such a pyridine, at a suitable temperature such as room temperature, for example about 20° C.

Compounds of formula (XXX) where Z is $OR^6$ as defined for compounds of formula (V) or halo, may be prepared from compounds of formula (XXXI)

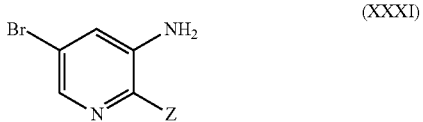
(XXXI)

wherein Z is $OR^6$ as defined for compounds of formula (V) or halo, by treatment with a suitable borolane such as 4,4,4',4', 5,5,5',5'-octamethyl-2,2'-bi-1,3,2-dioxaborolane, in the presence of a suitable palladium catalyst such as dichloro[1,1'-bis (diphenylphosphino)ferrrocene]palladium (II) dichloromethane adduct, in the presence of a suitable base such as potassium acetate, in a suitable solvent such as 1,4-dioxane and at a suitable temperature such as from 50 to 120° C., for example about 80° C. Compounds of formula (XXXI) are commercially available.

Compounds of Formula (VI)

Compounds of formula (VI) may be prepared as described in WO 2010/125082.

Process 1A

Compounds of formula (VI), wherein $R^1$, $R^2$, $R^3$ and $R^4$ are as defined for compounds of formula (VI), or salts thereof, may be prepared from compounds of formula (XXXV)

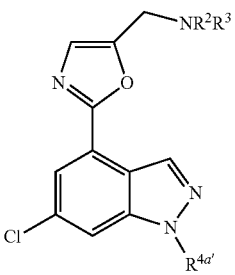
(XXXV)

wherein $R^2$ and $R^3$ are as defined for compounds of formula (VI) and $R^{4a'}$ is methyl or a suitable protecting group such as benzenesulphonyl, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as chloro[2'-(dimethylamino)-2-biphenylyl]palladium-(1R,4S)-bicyclo[2.2.1]hept-2-yl[(1S,4R)-bicyclo[2.2.1]hept-2-yl]phosphane, in a suitable solvent such as a mixture of 1,4-dioxane and water in a suitable ratio, for example about 4:1, in the presence of a suitable base such as sodium bicarbonate, and at a suitable temperature such as from about 80° C. to about 150° C., for example about 120° C.

The $R^1$ group introduced via the boronic acid or boronate ester may be protected by a suitable protecting group such as a tert-butyldimethylsilyl group and an additional deprotection step may be required, for example treatment with a suitable fluoride such as tetra-n-butylammonium fluoride, in a suitable solvent such as tetrahydrofuran, and at a suitable temperature such as room temperature, for example about 20° C.

If necessary, for compounds of formula (XXXV) wherein $R^{4a'}$ is a suitable protecting group, the protecting group such as benzenesulphonyl may subsequently be removed by treatment with a suitable aqueous inorganic base such as aqueous sodium hydroxide, in a suitable solvent such as isopropanol, and at a suitable temperature such as room temperature, for example about 20° C.

Compounds of formula (XXXV), wherein $R^2$ and $R^3$ are as defined for compounds of formula (VI) and $R^{4a'}$ is as defined above, may be prepared from compounds of formula (XXXVI)

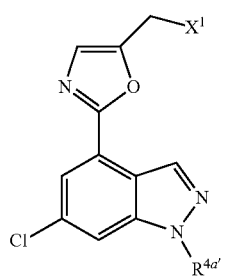
(XXXVI)

wherein $R^{4a'}$ is as defined above and $X^1$ is a suitable leaving group such as Br, by treatment with an amine of formula $HNR^2R^3$, wherein $R^2$ and $R^3$ are as defined for compounds of formula (VI), in a suitable solvent such as dichloromethane, and at a suitable temperature such as room temperature, for example about 20° C.

Compounds of formula (XXXVI), wherein $R^{4a'}$ is as defined above and $X^1$ is Br, may be prepared from compounds of formula (XXXVII)

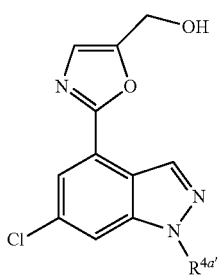
(XXXVII)

wherein $R^{4a'}$ is as defined above, by treatment with a suitable brominating agent such as carbon tetrabromide and a suitable phosphine such as triphenylphosphine, in a suitable solvent such as dichloromethane, and at a suitable temperature such as from about 0° C. to about 50° C., for example about 0° C. warming to about 20° C. after addition.

Or, alternatively, compounds of formula (XXXVI), wherein $R^{4a'}$ is as defined above and $X^1$ is Br, may be prepared from compounds of formula (XXXVII) wherein $R^{4a'}$ is as defined above, by treatment with a suitable brominating agent such as triphenylphosphine dibromide, in a suitable solvent such as dichloromethane, and at a suitable temperature such as from about 0° C. to about 50° C., for example about 0° C.

Compounds of formula (XXXVII), wherein $R^{4a'}$ is as defined above, may be prepared from compounds of formula (XXXVIII)

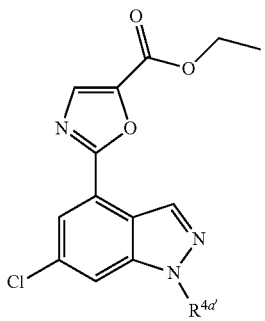
(XXXVIII)

wherein $R^{4a'}$ is as defined above, by treatment with a suitable reducing agent such as diisobutylaluminium hydride, in a suitable solvent such as tetrahydrofuran, and at a suitable temperature such as from about −50° C. to about 0° C., for example about 0° C.

Compounds of formula (XXXVIII), wherein $R^{4a'}$ is as defined above, may be prepared from compounds of formula (XXXIX)

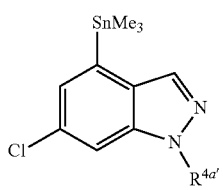
(XXXIX)

wherein $R^{4a'}$ is as defined above, by treatment with a suitable halide such as ethyl 2-chloro-1,3-oxazole-5-carboxylate (commercially available), in the presence of a suitable palladium catalyst such as tetrakis(triphenylphosphine)palladium (0), in a suitable solvent such as a N,N-dimethylformamide, in the presence of a suitable iodide such as sodium iodide, and under microwave irradiation at a suitable temperature such as from about 80° C. to about 150° C., for example about 100° C.

Or, alternatively, compounds of formula (XXXVIII), wherein $R^{4a'}$ is as defined above, may be prepared from compounds of formula (XXXX) as defined below, by treatment with a suitable stannane such as hexamethylditin, in the presence of a suitable palladium catalyst such as tetrakis(triphenylphosphine)palladium (0) and a suitable base such as triethylamine, in a suitable solvent such as toluene, and at a suitable temperature such as from about 100° C. to about 200° C., for example about 120° C., followed by treatment with a suitable halide such as methyl 2-chloro-1,3-oxazole-5-carboxylate (commercially available), in the presence of a suitable iodide such as copper (I) iodide, and a suitable palladium catalyst such as tetrakis(triphenylphosphine)palladium (0), in a suitable solvent such as 1,3-dimethyl-3,4,5,6-tetrahydro-2(1H)-pyrimidinone, and at a suitable temperature such as from about 50° C. to about 150° C., for example about 85° C.

Compounds of formula (XXXIX), wherein $R^{4a'}$ is as defined above, may be prepared from compounds of formula (XXXX)

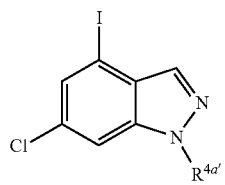

(XXXX)

wherein $R^{4a'}$ is as defined above, by treatment with a suitable stannane such as hexamethylditin, in the presence of a suitable palladium catalyst such as tetrakis(triphenylphosphine) palladium (0), in a suitable solvent such as xylene, in the presence of a suitable base such as triethylamine, and at a suitable temperature such as from about 100° C. to about 200° C., for example about 150° C.

Compounds of formula (XXXX), wherein $R^{4a'}$ is methyl, may be prepared from compounds such as the compound of formula (XXXXI)

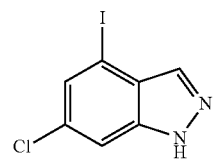

(XXXXI)

by methylation using a suitable base such as sodium hydride, in a suitable solvent such as tetrahydrofuran, and at a suitable temperature such as about 0° C., followed by addition of an alkylating agent such as iodomethane and stirring at a suitable temperature such as room temperature, for example about 20° C.

The compound of formula (XXXXI) is commercially available.

Compounds of formula (XXXX), wherein $R^{4a'}$ is a suitable protecting group such as benzenesulphonyl, may be prepared from the compound with formula (XXXXI) as defined above, by treatment with a suitable base such as sodium hydride in a suitable solvent such as N,N-dimethylformamide, and at a suitable temperature such as from about 0° C. to about 20° C., for example about 0° C., followed by treatment with a suitable sulphonylating agent such as benzensulphonyl chloride, at a suitable temperature such as from about 0° C. to about 50° C., for example about 0° C. warming to about 20° C. after addition.

Or alternatively, compounds of formula (XXXX), wherein $R^{4a'}$ is a suitable protecting group such as benzenesulphonyl, may be prepared from the compound with formula (XXXXI) as defined above, by treatment with a suitable base, such as sodium hydroxide and a suitable phase transfer catalyst such as tetra-n-butylammonium bisulphate, in a suitable solvent such as tetrahydrofuran and at a suitable temperature such as from about 0° C. to about 20° C., for example about 20° C., followed by treatment with a suitable sulphonylating agent such as benzene sulphonyl chloride, at a suitable temperature such as from about 0° C. to about 50° C., for example about 25° C.

Process 2A

Compounds of formula (VI), wherein $R^1$, $R^2$ and $R^3$ are as defined for compounds of formula (VI) and $R^4$ is hydrogen, or salts thereof, may be prepared from compounds of formula (XXXXII)

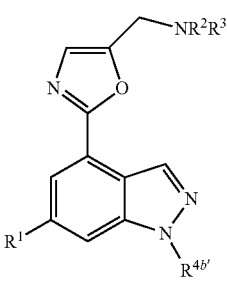

(XXXXII)

wherein $R^1$, $R^2$ and $R^3$ are as defined for compounds of formula (VI) and $R^{4b'}$ is a suitable protecting group such as benzenesulphonyl, by treatment with a suitable aqueous inorganic base such as aqueous sodium hydroxide, in a suitable solvent such as 1,4-dioxane, and at a suitable temperature such as room temperature, for example about 20° C.

Compounds of formula (XXXXII), wherein $R^1$, $R^2$ and $R^3$ are as defined for compounds of formula (VI) and $R^{4b'}$ are as defined above, may be prepared from compounds of formula (XXXXIII)

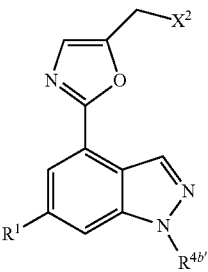

(XXXXIII)

wherein, $R^1$ is as defined for compounds of formula (VI), $R^{4b'}$ is as defined above and $X^2$ is a suitable leaving group such as Br, by treatment with an amine of formula $HNR^2R^3$, wherein $R^2$ and $R^3$ are as defined for compounds of formula (VI), in a suitable solvent such as dichloromethane, and at a suitable temperature such as room temperature, for example about 20° C.

Compounds of formula (XXXXIII), wherein $R^1$ is as defined for compounds of formula (VI), $R^{4b'}$ is as defined above and $X^2$ is Br, may be prepared from compounds of formula (XXXXIV)

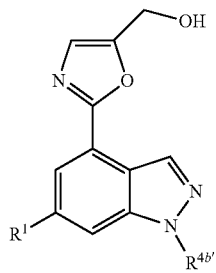

(XXXXIV)

wherein $R^1$ is as defined for compounds of formula (VI) and $R^{4b'}$ is as defined above, by treatment with a suitable brominating agent such as carbon tetrabromide and a suitable phosphine such as triphenylphosphine, in a suitable solvent such as dichloromethane, and at a suitable temperature such as from about 0° C. to about 50° C., for example about 0° C. warming to room temperature after addition.

Compounds of formula (XXXXIV), wherein $R^1$ is as defined for compounds of formula (VI) and $R^{4b'}$ is as defined above, may be prepared from compounds of formula (XXXXV)

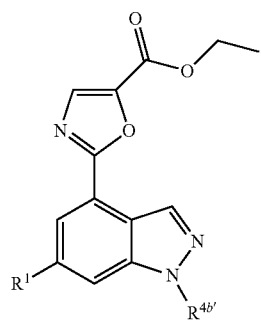

(XXXXV)

wherein $R^1$ is as defined for compounds of formula (VI) and $R^{4b'}$ is as defined above, by treatment with a suitable reducing agent such as diisobutylaluminium hydride, in a suitable solvent such as dichloromethane, and at a suitable temperature such as from about −50° C. to about 0° C., for example about −20° C.

Compounds of formula (XXXXV), wherein $R^1$ is as defined for compounds of formula (VI) and $R^{4b'}$ is as defined above, may be prepared from compounds of formula (XXXXVI)

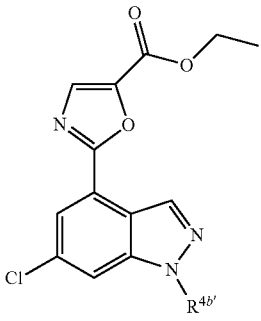

(XXXXVI)

wherein $R^{4b'}$ is as defined above, by treatment with a suitable boronic acid or boronate ester such as {1-[(1,1-dimethylethyl)(dimethyl)silyl]-1H-indol-4-yl}boronic acid (commercially available), in the presence of a suitable palladium catalyst such as chloro[2'-(dimethylamino)-2-biphenylyl]palladium-(1R,4S)-bicyclo[2.2.1]hept-2-yl[(1S,4R)-bicyclo[2.2.1]hept-2-yl]phosphane, in a suitable solvent such as a mixture of 1,4-dioxane and water in a suitable ratio, for example about 10:1, in the presence of a suitable base such as potassium phosphate tribasic, and at a suitable temperature such as about 80° C. to about 150° C., for example about 100° C. Alternatively, this process may be carried out under microwave irradiation, and at a suitable temperature such as from about 80° C. to about 150° C., for example about 120° C.

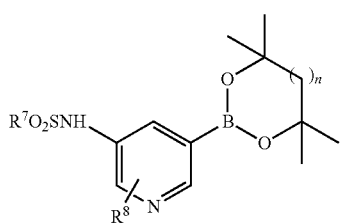

(XXXXVII)

Boronate esters of formula (XXXXVII), wherein $R^7$ is as defined for compounds of formula (VI), $R^8$ is $C_{1-6}$alkyl, $-OR^6$ or halo, wherein $R^6$ is as defined for compounds of formula (VI) and n=0 or 1, may be prepared from compounds of formula (XXXXVIII)

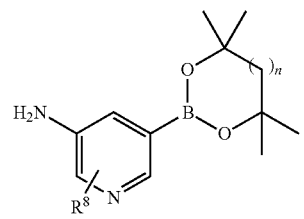

(XXXXVIII)

wherein $R^8$ is as defined for compounds of formula (VI) and n=0 or 1, by treatment with a suitable sulphonyl chloride of formula $R^7SO_2Cl$ wherein $R^7$ is as defined for compounds of formula (VI), such as methanesulphonyl chloride, in a suitable solvent such as pyridine, and at a suitable temperature such as room temperature, for example about 20° C.

Compounds of formula (XXXXVIII) wherein $R^8$ is as defined for compounds of formula (VI) and n=0 or 1, may be prepared from compounds of formula (XXXXIX)

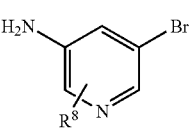

(XXXXIX)

wherein $R^8$ is as defined for compounds of formula (VI), for which a range of analogues are commercially available, by treatment with a suitable borolane such as 4,4,4',4',5,5,5',5'-octamethyl-2,2'-bi-1,3,2-dioxaborolane, in the presence of a suitable palladium catalyst such as dichloro[1,1'-bis(diphenylphosphino)ferrocene]palladium (II) dichloromethane adduct, in the presence of a suitable base such as potassium acetate, in a suitable solvent such as 1,4-dioxane, and at a suitable temperature such as from about 50° C. to about 120° C., for example about 80° C.

Methods of Use

The methods of treatment of the invention comprise administering a safe and effective amount of a compound of formulae (I) to (VII) as defined above or a pharmaceutically acceptable salt thereof to a patient in need thereof. Individual embodiments of the invention include methods of treating or preventing influenza virus infection by administering a safe and effective amount of a compound of formulae (I) to (VII) as defined above or a pharmaceutically acceptable salt thereof to a patient in need thereof.

As used herein, "treat or prevent" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

In one embodiment, the methods of the invention are directed to treating influenza virus infection. In another embodiment, the methods of the invention are directed to preventing influenza virus infection.

As used herein, "safe and effective amount" in reference to a compound of formulae (I) to (VII) as defined above or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formulae (I) to (VII) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formulae (I) to (VII) or pharmaceutically acceptable salts thereof may be administered orally. In another embodiment, the compounds of formulae (I) to (VII) or pharmaceutically acceptable salts thereof may be administered by inhalation. In a further embodiment, the compounds of formulae (I) to (VII) or pharmaceutically acceptable salts thereof may be administered intranasally.

The compounds of formulae (I) to (VII) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formulae (I) to (VII) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formulae (I) to (VII) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formulae (I) to (VII) may be administered as prodrugs. As used herein, a "prodrug" of a compound of formulae (I) to (VII) is a functional derivative of the compound which, upon administration to a patient, eventually liberates the compound of formulae (I) to (VII) in vivo. Administration of a compound of formulae (I) to (VII) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

In one aspect, the invention thus provides a method of treating or preventing influenza virus infection comprising administering a safe and effective amount of a compound of formulae (I) to (VII) or a pharmaceutically acceptable salt thereof to a patient in need thereof. In one embodiment, the invention provides a method of treating or preventing influenza virus infection comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof to a patient in need thereof. In another embodiment, the invention provides a method of treating or preventing influenza virus infection comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate to a patient in need thereof. In another embodiment, the invention provides a method of treating or preventing influenza virus infection comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide to a patient in need thereof. In another embodiment, the invention provides a method of treating or preventing influenza virus infection comprising administering a safe and effective amount of 6-(1H-indol-4-yl)-4-(5-{[4-(1-methylethyl)-1-piperazinyl]methyl}-1,3-oxazol-2-yl)-1H-indazole or a pharmaceutically acceptable salt thereof to a patient in need thereof. In another embodiment, the invention provides a method of treating or preventing influenza virus infection comprising administering a safe and effective amount of 6-(1H-indol-4-yl)-4-(5-{[4-(1-methylethyl)-1-piperazinyl]methyl}-1,3-oxazol-2-yl)-1H-indazole hemi succinate to a patient in need thereof. In a further embodiment, the invention provides a method of treating or preventing influenza virus infection comprising administering a safe and effective amount of 6-(1H-indol-4-yl)-4-(5-{[4-(1-methylethyl)-1-piperazinyl]methyl}-1,3-oxazol-2-yl)-1H-indazole hydrochloride to a patient in need thereof.

In one aspect, the invention provides a compound of formulae (I) to (VII) or a pharmaceutically acceptable salt thereof for use in the treatment or prevention of influenza virus infection. In one embodiment, the invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof for use in the treatment or prevention of influenza virus infection. In another embodiment, the invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate for use in the treatment or prevention of influenza virus infection. In another embodiment, the invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide for use in the treatment or prevention of influenza virus infection. In another embodiment, the invention provides 6-(1H-indol-4-yl)-4-(5-{[4-(1-methylethyl)-1-piperazinyl]methyl}-1,3-oxazol-2-yl)-1H-indazole or a pharmaceutically acceptable salt thereof for use in the treatment or prevention of influenza virus infection. In another embodiment, the invention provides 6-(1H-indol-4-yl)-4-(5-{[4-(1-methylethyl)-1-piperazinyl]methyl}-1,3-oxazol-2-yl)-1H-indazole hemi succinate or a pharmaceutically acceptable salt thereof for use in the treatment or prevention of influenza virus infection. In a further embodiment, the invention provides 6-(1H-indol-4-yl)-4-(5-{[4-(1-methylethyl)-1-piperazinyl]methyl}-1,3-oxazol-2-yl)-1H-indazole hydrochloride for use in the treatment or prevention of influenza virus infection.

In a further aspect, the invention provides the use of a compound of formulae (I) to (VII) or a pharmaceutically acceptable salt thereof in the manufacture of a medicament for use in the treatment or prevention of influenza virus infection. In one embodiment, the invention provides the use of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof in the manufacture of a medicament for use in the treatment or prevention of influenza virus infection. In another embodiment, the invention provides the use of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate in the manufacture of a medicament for use in the treatment or prevention of influenza virus infection. In another embodiment, the invention provides the use of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide in the manufacture of a medicament for use in the treatment or prevention of influenza virus infection. In another embodiment, the invention provides the use of 6-(1H-indol-4-yl)-4-(5-{[4-(1-methylethyl)-1-piperazinyl]methyl}-1,3-oxazol-2-yl)-1H-indazole or a pharmaceutically acceptable salt thereof in the manufacture of a medicament for use in the treatment or prevention of influenza virus infection. In another embodiment, the invention provides the use of 6-(1H-indol-4-yl)-4-(5-{[4-(1-methylethyl)-1-piperazinyl]methyl}-1,3-oxazol-2-yl)-1H-indazole hemi succinate or a pharmaceutically acceptable salt thereof in the manufacture of a medicament for use in the treatment or prevention of influenza virus infection. In a further embodiment, the invention provides the use of 6-(1H-indol-4-yl)-4-(5-{[4-(1-methylethyl)-1-piperazinyl]methyl}-1,3-oxazol-2-yl)-1H-indazole hydrochloride in the manufacture of a medicament for use in the treatment or prevention of influenza virus infection.

Compositions

The compounds of formulae (I) to (VII) and pharmaceutically acceptable salts thereof will normally, but not necessarily, be formulated into pharmaceutical compositions prior to administration to a patient.

Accordingly, in one aspect the invention is directed to pharmaceutical compositions comprising a compound of formulae (I) to (VII) or a pharmaceutically acceptable salt thereof, and one or more pharmaceutically acceptable excipients for use in the treatment or prevention of influenza virus infection.

In one embodiment, the present invention provides a pharmaceutical composition comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof, and one or more pharmaceutically acceptable excipients for use in the treatment or prevention of influenza virus infection.

In another embodiment, the present invention provides a pharmaceutical composition comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide, and one or more pharmaceutically acceptable excipients for use in the treatment or prevention of influenza virus infection.

In another embodiment, the present invention provides a pharmaceutical composition comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R) mandelate, and one or more pharmaceutically acceptable excipients for use in the treatment or prevention of influenza virus infection.

In another embodiment, the present invention provides a pharmaceutical composition comprising 6-(1H-indol-4-yl)-4-(5-{[4-(1-methylethyl)-1-piperazinyl]methyl}-1,3-oxazol-2-yl)-1H-indazole or a pharmaceutically acceptable salt thereof, and one or more pharmaceutically acceptable excipients for use in the treatment or prevention of influenza virus infection.

In another embodiment, the present invention provides a pharmaceutical composition comprising 6-(1H-indol-4-yl)-4-(5-{[4-(1-methylethyl)-1-piperazinyl]methyl}-1,3-oxazol-2-yl)-1H-indazole hemi succinate or a pharmaceutically acceptable salt thereof, and one or more pharmaceutically acceptable excipients for use in the treatment or prevention of influenza virus infection.

In a further embodiment, the present invention provides a pharmaceutical composition comprising 6-(1H-indol-4-yl)-4-(5-{[4-(1-methylethyl)-1-piperazinyl]methyl}-1,3-oxazol-2-yl)-1H-indazole hydrochloride, and one or more pharmaceutically acceptable excipients for use in the treatment or prevention of influenza virus infection.

In another aspect the invention is directed to pharmaceutical compositions comprising 0.05 to 1000 mg of a compound of formulae (I) to (VII) or a pharmaceutically acceptable salt thereof and 0.1 to 2 g of one or more pharmaceutically acceptable excipients for use in the treatment or prevention of influenza virus infection.

In a further aspect the invention is directed to a pharmaceutical composition for the treatment or prevention of influenza virus infection comprising a compound of formulae (I) to (VII) or a pharmaceutically acceptable salt thereof.

In one embodiment, the present invention is provides a pharmaceutical composition for the treatment or prevention of influenza virus infection comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof.

In one embodiment, the present invention is provides a pharmaceutical composition for the treatment or prevention of influenza virus infection comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R) mandelate.

In one embodiment, the present invention is provides a pharmaceutical composition for the treatment or prevention of influenza virus infection comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide.

In one embodiment, the present invention is provides a pharmaceutical composition for the treatment or prevention of influenza virus infection comprising 6-(1H-indol-4-yl)-4-(5-{[4-(1-methylethyl)-1-piperazinyl]methyl}-1,3-oxazol-2-yl)-1H-indazole or a pharmaceutically acceptable salt thereof.

In one embodiment, the present invention is provides a pharmaceutical composition for the treatment or prevention of influenza virus infection comprising 6-(1H-indol-4-yl)-4-(5-{[4-(1-methylethyl)-1-piperazinyl]methyl}-1,3-oxazol-2-yl)-1H-indazole hemi succinate.

In a further embodiment, the present invention is provides a pharmaceutical composition for the treatment or prevention of influenza virus infection comprising 6-(1H-indol-4-yl)-4-(5-{[4-(1-methylethyl)-1-piperazinyl]methyl}-1,3-oxazol-2-yl)-1H-indazole hydrochloride.

The pharmaceutical compositions for use according to the invention may be prepared and packaged in bulk form wherein a safe and effective amount of a compound of formulae (I) to (VII) or a pharmaceutically acceptable salt thereof can be extracted and then given to the patient such as with powders or syrups. Alternatively, the pharmaceutical compositions for use according to the invention may be prepared and packaged in unit dosage form wherein each physically discrete unit contains a compound of formulae (I) to (VII) or a pharmaceutically acceptable salt thereof. When prepared in unit dosage form, the pharmaceutical compositions for use according to the invention typically may contain, for example, from 0.5 mg to 1 g, or from 1 mg to 700 mg, or from 5 mg to 100 mg of a compound of formulae (I) to (VII) or a pharmaceutically acceptable salt thereof.

The pharmaceutical compositions for use according to the invention typically contain one compound of formulae (I) to (VII) or a pharmaceutically acceptable salt thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formulae (I) to (VII) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

The compound of formulae (I) to (VII) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formulae (I) to (VII) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions for use according to the invention are prepared using techniques and methods known to those skilled in the art. Some of the methods commonly used in the art are described in *Remington's Pharmaceutical Sciences* (Mack Publishing Company).

A pharmaceutical composition comprising a compound of formulae (I) to (VII) or a pharmaceutically acceptable salt thereof may be prepared by, for example, admixture at ambient temperature and atmospheric pressure.

In one embodiment, the compounds of formulae (I) to (VII) or pharmaceutically acceptable salts thereof will be formulated for oral administration. In another embodiment, the compounds of formulae (I) to (VII) or pharmaceutically acceptable salts thereof will be formulated for inhaled administration. In a further embodiment, the compounds of formulae (I) to (VII) or pharmaceutically acceptable salts thereof will be formulated for intranasal administration.

In one aspect, the composition for use according to the invention is a solid oral dosage form such as a tablet or capsule comprising a safe and effective amount of a compound of formulae (I) to (VII) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formulae (I) to (VII) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formulae (I) to (VII) or pharmaceutically acceptable salts thereof may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In another aspect, the composition for use according to the invention is a liquid oral dosage form. Oral liquids such as solution, syrups and elixirs can be prepared in dosage unit form so that a given quantity contains a predetermined amount of a compound of formulae (I) to (VII) or a pharmaceutically acceptable salt thereof. Syrups can be prepared by dissolving the compound of formulae (I) to (VII) or a pharmaceutically acceptable salt thereof in a suitably flavored aqueous solution, while elixirs are prepared through the use of a non-toxic alcoholic vehicle. Suspensions can be formulated by dispersing the compound of formulae (I) to (VII) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the composition for use according to the invention is a dosage form adapted for administration to a patient by inhalation, for example as a dry powder, an aerosol, a suspension, or a solution composition. In one embodiment, the composition for use according to the invention is a dosage form adapted for administration to a patient by inhalation as a dry powder. In a further embodiment, the composition for use according to the invention is a dosage form adapted for administration to a patient by inhalation via a nebulizer.

Dry powder compositions for delivery to the lung by inhalation typically comprise a compound of formulae (I) to (VII) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of formulae (I) to (VII) or a pharmaceutically acceptable salt thereof.

Aerosols may be formed by suspending or dissolving a compound of formulae (I) to (VII) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Thus the composition for use according to the invention may be a pharmaceutical aerosol formulation comprising a compound of formulae (I) to (VII) or a pharmaceutically acceptable salt thereof and a fluorocarbon or hydrogen-containing chlorofluorocarbon as propellant, optionally in combination with a surfactant and/or a cosolvent.

In another aspect the composition for use according to the invention may be a pharmaceutical aerosol formulation wherein the propellant is selected from 1,1,1,2-tetrafluoroethane, 1,1,1,2,3,3,3-heptafluoro-n-propane and mixtures thereof.

The formulations for use according to the invention may be buffered by the addition of suitable buffering agents.

Capsules and cartridges for use in an inhaler or insufflator, of for example gelatine, may be formulated containing a powder mix for inhalation of a compound of formulae (I) to (VII) or a pharmaceutically acceptable salt thereof and a suitable powder base such as lactose or starch. Each capsule or cartridge may generally contain from 20 µg to 10 mg of the compound of formulae (I) to (VII) or pharmaceutically acceptable salt thereof. Alternatively, the compound of formulae (I) to (VII) or pharmaceutically acceptable salt thereof may be presented without excipients such as lactose.

The proportion of the active compound of formulae (I) to (VII) or pharmaceutically acceptable salt thereof in the local compositions for use according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 µg to 10 mg, preferably from 20 µg to 2000 µg, more preferably from about 20 µg to 500 µg of a compound of formulae (I) to (VII). Administration may be once daily or several times daily, for example 2, 3, 4 or 8 times, giving for example 1, 2 or 3 doses each time. The overall daily dose with an aerosol will be within the range from 100 µg to 10 mg, preferably from 200 µg to 2000 µg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations for use according to the invention may be prepared by dispersal or dissolution of the medicament and a compound of formulae (I) to (VII) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations for use according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations for use according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channeling device. Suitable channeling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment the metallic internal surface of the can is coated with a fluoropolymer, more preferably blended with a non-fluoropolymer. In another embodiment the metallic internal surface of the can is coated with a polymer blend of polytetrafluoroethylene (PTFE) and polyethersulfone (PES). In a further embodiment the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179, 118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formulae (I) to (VII) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formulae (I) to (VII) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formulae (I) to (VII) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the composition for use according to the invention is a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formulae (I) to (VII) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formulae (I) to (VII) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formulae (I) to (VII) or a pharmaceutically acceptable salt thereof may be employed with either a paraffinic or a water-miscible ointment base. Alternatively, the compound of formulae (I) to (VII) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

According to the invention, compounds of formulae (I) to (VII) and pharmaceutically acceptable salts thereof may be used in combination with one or more other therapeutic agents, for example selected from anti-infective agents, anti-inflammatory agents and immunomodulators, in the treatment or prevention of influenza virus infection.

The invention thus provides, in a further aspect, a compound of formulae (I) to (VII) or a pharmaceutically acceptable salt thereof together with one or more other therapeutically active agents for use in the treatment or prevention of influenza virus infection.

In one embodiment, the invention encompasses a method of treating or preventing influenza virus infection comprising administering a safe and effective amount of a combination comprising a compound of formulae (I) to (VII) or a pharmaceutically acceptable salt thereof together with one or more therapeutically active agents.

One embodiment of the invention encompasses the use of combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

Suitable anti-infective agents include antibiotics and anti-virals.

Suitable anti-inflammatory agents include corticosteroids. Suitable corticosteroids which may be used in combination with the compounds of formulae (I) to (VII) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17α-carbothioic acid S-(2-oxo-tetrahydro-furan-35-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compounds of formulae (I) to (VII) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Suitable immunomodulators include COX-2 inhibitors.

The invention thus provides, in one aspect, a combination comprising a compound of formulae (I) to (VII) or a pharmaceutically acceptable salt thereof together with an anti-infective agent for use in the treatment or prevention of influenza virus infection.

The invention thus provides, in another aspect, a combination comprising a compound of formulae (I) to (VII) or a pharmaceutically acceptable salt thereof together with an anti-inflammatory agent for use in the treatment or prevention of influenza virus infection.

The invention thus provides, in a further aspect, a combination comprising a compound of formulae (I) to (VII) or a pharmaceutically acceptable salt thereof together with an immunomodulator for use in the treatment or prevention of influenza virus infection.

The combinations referred to above may conveniently be presented for use in the form of a pharmaceutical composition and thus pharmaceutical compositions comprising a combination as defined above together with a pharmaceutically acceptable diluent or carrier for use in the treatment or prevention of influenza virus infection represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formulae (I) to (VII) or a pharmaceutically acceptable salt thereof together with another therapeutically active agent for use in the treatment or prevention of influenza virus infection.

The invention thus provides, in one aspect, a pharmaceutical composition comprising a combination of a compound of formulae (I) to (VII) or a pharmaceutically acceptable salt thereof together with an anti-infective agent for use in the treatment or prevention of influenza virus infection.

The invention thus provides, in another aspect, a pharmaceutical composition comprising a combination of a compound of formulae (I) to (VII) or a pharmaceutically acceptable salt thereof together with an anti-inflammatory agent for use in the treatment or prevention of influenza virus infection.

The invention thus provides, in a further aspect, a pharmaceutical composition comprising a combination of a compound of formulae (I) to (VII) or a pharmaceutically acceptable salt thereof together with an immunomodulator for use in the treatment or prevention of influenza virus infection.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

When the name of a commercial supplier is given after the name of a compound or a reagent, for instance "compound X (Aldrich)" or "compound X/Aldrich", this means that compound X is obtainable from a commercial supplier, such as the commercial supplier named. If not referenced herein the compound or reagent can be purchased from a standard supplier such as Sigma Aldrich, Lancaster, Fluorochem, TCI etc.

The names of the Examples have been obtained using a compound naming programme which matches structure to name (e.g. ACD/Name Batch v 9.0).

General Experimental Details

Liquid Chromatography Mass Spectroscopy (LCMS) Methods

LCMS analysis has been carried out using one of the methods listed below.

Method A:

LCMS instrumentation consists of the following:
Column: Acquity UPLC BEH $C_{18}$ 1.7 µm 2.1 mm×50 mm. Column oven set to 40 degrees centigrade
Solvent A: Water 0.1% Formic Acid+10 mM Ammonium Acetate
Solvent B: MeCN:Water 95:5+0.05% Formic Acid
Injection volume: 0.5 µl
Injection technique: Partial loop overfill
UV detection: 220 to 330 nm
UV sampling rate: 40 points per second
MS scan range: 100 to 1000 amu
MS scanning rate: 0.2 second scan with a 0.1 second inter scan delay
MS scan function: Electrospray with pos neg switching
Cycle time: 2 minutes and 30 seconds
Gradient:

| Time | Flow ml/min | % A | % B |
| --- | --- | --- | --- |
| 0 | 1 | 97 | 3 |
| 0.1 | 1 | 97 | 3 |
| 1.4 | 1 | 0 | 100 |
| 1.9 | 1 | 0 | 100 |
| 2 | 1 | 97 | 3 |

Method B:

The HPLC analysis was conducted on a Sunfire C18 column (30 mm×4.6 mm i.d. 3.5 µm packing diameter) at 30 degrees centigrade.
Solvent A=0.1% v/v solution of Formic Acid in Water.
Solvent B=0.1% v/v solution of Formic Acid in Acetonitrile.
The gradient employed was:

| Time (min) | Flow Rate (ml/min) | % A | % B |
| --- | --- | --- | --- |
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

Method C:

The HPLC analysis was conducted on a Phenomenex Luma C18(2) (50 mm×2 mm i.d. 3 µm packing diameter, or validated equivalent) at 40 degrees centigrade.
Solvent A=0.05% v/v solution of TFA in Water.
Solvent B=0.05% v/v solution of TFA in Acetonitrile.
The gradient employed was:

| Time (min) | Flow Rate (ml/min) | % A | % B |
| --- | --- | --- | --- |
| 0 | 1 | 100 | 0 |
| 8 | 1 | 5 | 95 |
| 8.01 | 1 | 100 | 0 |

The UV detection wavelength was analyte dependent and mass spectra were recorded on a mass spectrometer using positive ion electrospray.

Method D:

The HPLC analysis was conducted on a Phenomenex Luma C18(2) (50 mm×2 mm i.d. 3 µm packing diameter, or validated equivalent) at 60 degrees centigrade.
Solvent A=0.05% v/v solution of TFA in Water.
Solvent B=0.05% v/v solution of TFA in Acetonitrile.
The gradient employed was:

| Time (min) | Flow Rate (ml/min) | % A | % B |
| --- | --- | --- | --- |
| 0 | 1.5 | 100 | 0 |
| 2.5 | 1.5 | 5 | 95 |
| 2.7 | 1.5 | 5 | 95 |
| 2.9 | 1.5 | 100 | 0 |

The UV detection wavelength was analyte dependent and mass spectra were recorded on a mass spectrometer using positive ion electrospray.

Method E:

The HPLC analysis was conducted on a Acquity UPLC BEH C18 column (50 mm×2.1 mm i.d. 1.7 µm packing diameter) at 40 degrees centigrade.
Solvent A=0.1% v/v solution of Formic Acid in Water.
Solvent B=0.1% v/v solution of Formic Acid in Acetonitrile.
The gradient employed was:

| Time (min) | Flow Rate (ml/min) | % A | % B |
| --- | --- | --- | --- |
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

Method F:

Waters ZQ mass spectrometer operating in positive ion electrospray mode, mass range 100-1000 amu.
UV wavelength: 215-330 nm
Column: 3.3 cm×4.6 mm i.d., 3 µm ABZ+PLUS
Flow Rate: 3 ml/min
Injection Volume: 5 µl
Solvent A: 95% MeCN+0.05% of a 1% v/v solution of formic acid in water
Solvent B: 0.1% v/v solution of formic acid in 10 mmol ammonium acetate (aq)
Gradient: Mixtures of Solvent A and Solvent B are used according to the following gradient profiles (expressed as % Solvent A in the mixture): 0% A; 0.7 min, 0-100% A; 3.5 min, 100% A; 0.4 min, 100-0% A; 0.2 min.

Mass Directed Automated Preparative HPLC Methods

The methods for the mass-directed automated preparative HPLC used for the purification of compounds are described below:

Method A

Column

The column used is typically a Supelco LCABZ++ column whose dimensions are 20 mm internal diameter by 100 mm in length. The stationary phase particle size is 5 µm.

Solvents

A: Aqueous solvent=Water+0.1% Formic Acid
B: Organic solvent=MeCN:Water 95:5+0.05% Formic Acid
Make up solvent=MeOH:Water 80:20+50 mMol Ammonium Acetate
Needle rinse solvent=MeOH: Water:DMSO 80:10:10

Methods

There are five methods used depending on the analytical retention time of the compound of interest.

They all have a 15-minute runtime, which comprises of a 10-minute gradient followed by a 5-minute column flush and re-equilibration step.

MDP 1.5-2.2=0-30% B
MDP 2.0-2.8=5-30% B
MDP 2.5-3.0=15-55% B
MDP 2.8-4.0=30-80% B
MDP 3.8-5.5=50-90% B

Flow Rate

All of the above methods have a flow rate of 20 ml/min

It is thought that basic compounds isolated by this method are formate salts.

Method B

Columns

Small Scale Prep Column

Supelcosil ABZ+Plus column whose dimensions are 21.2 mm internal diameter by 100 mm in length. The stationary phase particle size is 5 µm.

Large scale Prep Column

Supelcosil ABZ+Plus column whose dimensions are 30.0 mm internal diameter by 150 mm in length. The stationary phase particle size is 12 µm.

Solvents

A: Aqueous solvent=Water+0.1% Formic Acid
B: Organic solvent=MeCN:Water 95:5+0.05% Formic Acid
Make up solvent to ZQ=MeOH:Water 80:20+50 mMol Ammonium Acetate
2767 Needle rinse solvent=MeOH: Water:DMSO 80:10:10

Methods for Small Scale Prep for up to 30 mg

There are ten methods available for use. The choice of method is dependant on the analytical retention time of the compound of interest (MDP=retention time as determined by LCMS Method A above).

Five methods have a 15-minute runtime, this comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.

MDP 1.5-2.2=00-30% B
MDP 2.0-2.8=10-40% B
MDP 2.5-3.0=15-55% B
MDP 2.8-4.0=30-80% B
MDP 3.8-5.5=60-90% B

Flow rates for the above methods are 20 ml/min

Methods for Large Scale Prep for up to 90 mgs

Due to the different column dimension and the phase particle size the percentage organic content varies slightly to the small scale methods. As for small scale there are ten methods available for use. The choice of method is dependant on the analytical retention time of the compound of interest interest (MDP=retention time as determined by LCMS Method A above).

Five methods have a 15-minute runtime, which comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.

MDP 1.5-2.2=00-30% B
MDP 2.0-2.8=10-40% B
MDP 2.5-3.0=25-55% B
MDP 2.8-4.0=40-75% B
MDP 3.8-5.5=60-90% B

Flow rates for the above methods are 40 ml/min

It is thought that basic compounds isolated by this method are formate salts.

Method C

Column Details:

Zorbax Eclipse XDB-C18 prep HT (dimensions 212×100 mm, 5 um packing)

Software/Hardware:

Agilent 1100 series LC/MSD hardware, chemstation 32 purification software. Collects on uv/mass ion trigger Solvents:

A=0.1% v/v solution of Trifluoroacetic Acid in Water.
B=0.1% v/v solution of Trifluoroacetic Acid in Acetonitrile.

20 ml/min solvent speed, gradient elution:

1 min 90% Water (0.1% TFA): 10% MECN (0.1% TFA) increasing over 9 mins to 5% Water (0.1% TFA): 95% MECN (0.1% TFA) to elute compounds.

Method D

Column Details:

XBRIDGE C18 column (100 mm×19 mm id 5 uM packing diameter)

Solvents

A=10 mM ammonium bicarbonate in water adjusted to pH 10 with aq. ammonia solution
B=Acetonitrile The UV detection was an averaged signal from wavelength of 210 nm to 350 nm and mass spectra were recorded on a mass spectrometer using an alternate-scan positive and negative mode electrospray ionization.

Method E—High pH

Column Details:

Waters_XBRIDGE Prep C18 column 5 um OBD (19×100 mm)

The solvents employed were:

A=10 mM Ammonium Bicarbonate in water adjusted to pH 10 with aq. Ammonia solution
B=Acetonitrile+0.1% aq. Ammonia Collection was triggered by uv, ms or a combination of the two. The UV detection was at a selected wavelength generally 230 nm, 210 nm or 254 nm. Mass spectra were recorded on a mass spectrometer using an alternate-scan positive and negative mode electrospray ionization.

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method F—Low pH
Column Details:
 SUNFIRE C18 column (100 mm×19 mm id 5 uM packing diameter)
 The solvents employed were:
A=0.1% v/v solution of Trifluoroacetic Acid in Water.
B=0.1% v/v solution of Trifluoroacetic Acid in Acetonitrile.
 Collection was triggered by uv, ms or a combination of the two.
 The UV detection was at a selected wavelength generally 230 nm, 210 nm or 254 nm. Mass spectra were recorded on a mass spectrometer using an alternate-scan positive and negative mode electrospray ionization.

Method G
 The HPLC purification was conducted on a Sunfire C18 column (100 mm×19 mm i.d. 5 μm packing diameter) at ambient temperature.
 The solvents employed were:
A=0.1% v/v solution of Formic Acid in Water.
B=0.1% v/v solution of Formic Acid in Acetonitrile.
 The gradient employed was:

| Time (min) | Flow Rate (ml/min) | % A | % B |
| --- | --- | --- | --- |
| 0 | 20 | 85 | 15 |
| 1 | 20 | 85 | 15 |
| 10 | 20 | 45 | 55 |
| 10.5 | 20 | 1 | 99 |
| 15 | 20 | 1 | 99 |

The UV detection was an averaged signal from wavelength of 210 nm to 350 nm.

Method H—High pH
Column Details:
 Waters_XBRIDGE Prep C18 column 5 um OBD (30×150 mm)
 The solvents employed were:
A=10 mM Ammonium Bicarbonate in water adjusted to pH 10 with aq. Ammonia solution
B=Acetonitrile+0.1% aq. Ammonia
 Collection was triggered by uv, ms or a combination of the two. The UV detection was an averaged signal from wavelength of 210 nm to 350 nm. Mass spectra were recorded on a mass spectrometer using an alternate-scan positive and negative mode electrospray ionization.

Method I—Low pH
Column Details:
 SUNFIRE C18 column (30×150 mm id 5 uM packing diameter)
 The solvents employed were:
A=0.1% v/v solution of Formic Acid in Water.
B=0.1% v/v solution of Formic Acid in Acetonitrile.
 Collection was triggered by uv, ms or a combination of the two. The UV detection was an averaged signal from wavelength of 210 nm to 350 nm. Mass spectra were recorded on a mass spectrometer using an alternate-scan positive and negative mode electrospray ionization.

Method J
Column Details:
 XBRIDGE Shield RP18 column (100×19 mm, 5 uM packing diameter
 The solvents employed were:
A=10 mM Ammonium Bicarbonate in water adjusted to pH 10 with aq. Ammonia solution
B=Methanol
 Collection was triggered by uv, ms or a combination of the two. The UV detection was an averaged signal from wavelength of 210 nm to 350 nm. Mass spectra were recorded on a mass spectrometer using an alternate-scan positive and negative mode electrospray ionization.

Method K
Stationary Phase
 The stationary phase used for this purification was Sunfire C18 with a particle size of 5 μm.
Small Scale Preparative Column
Column Dimension: 100 mm×19 mm i.d.
Large Scale Preparative Column
Column Dimension: 150 mm×30 mm i.d.
Eluent
 The eluents employed were:
A=0.1% v/v solution of formic acid in water.
B=0.1% v/v solution of formic acid in acetonitrile.
Methods for Small Scale Prep for Up to 30 Mg of Crude Sample
 There are ten focused small scale preparative methods available for use. The choice of method is dependent on two factors
 1. The retention time (RT) of the component/s of interest on the generic analytical LCMS method.
 2. The presence of closely eluting impurities to the component/s of interest.
 From the analytical RT the choice of one of five small scale focused prep methods is made. Small scale prep methods contain a 10 minute gradient over a specified organic range, followed by a 5 minute flush, except the most polar method which contains a 7 minute gradient over a specified organic range followed by an 8 minute flush. The total run time is 15 minutes.
 If there are closely eluting impurities to the component/s of interest then there are five extended small scale focused prep methods available. Extended small scale prep methods contain a 20 minute gradient over the specified organic range followed by a 5 minute flush, except the most polar method which contains a 14 minute gradient over the specified organic range followed by an 11 minute flush. The total run time is 25 minutes.
 Flow rates for all small scale methods are 20 ml/min and the purification is performed at ambient temperature.
 The injection volume for small scale prep is 500 μl.
 The 10 small scale prep methods and the organic ranges of the gradients are shown below. The gradients are the same for normal or extended runs.
5-30% B
15-55% B
30-85% B
50-99% B
80-99% B
 In the flush step eluent B is raised to 99% in 0.5 minutes then held there for a further 4.5 minutes.
Methods for Large Scale Prep for Up to 90 mg of Crude Sample
 There are ten focused large scale prep methods available for use. The choice of method is dependent on the same two factors as for small scale prep. The run times (gradient and flush) are the same as for small scale prep methods.
 Flow rates for all large scale methods are 40 ml/min and the purification is performed at ambient temperature.
 The injection volume for large scale prep is 980 μl.
 The 5 large scale method names and the organic ranges of the gradients are shown below. The gradients are the same for either normal or extended runs.
5-30% B
15-55% B
30-85% B 50-99% B
80-99% B In the flush step eluent B is raised to 99% in 0.5 minutes then held there for a further 4.5 minutes.

UV Detection

The UV detection for all methods is an averaged signal from all wavelengths from 210 nm to 350 nm.

MS Conditions
MS: Waters ZQ
Ionisation mode: Alternate-scan positive and negative electrospray
Scan range: 100 to 1000 amu
Scan time: 0.50 seconds
Inter scan delay: 0.20 seconds Method L
Sunfire, Low pH
Column Details:
SUNFIRE C18 column (100 mm×19 mm id. 5 um)
The solvents employed were:
A=0.1% v/v solution of Formic Acid in Water.
B=0.1% v/v solution of Formic Acid in Acetonitrile.

Method A

| Time (min) | Flow Rate (ml/min) | % A | % B |
|---|---|---|---|
| 0.0 | 20 | 95 | 5 |
| 1.0 | 20 | 95 | 5 |
| 10 | 20 | 70 | 30 |
| 10.5 | 20 | 5 | 95 |
| 12.5 | 20 | 5 | 95 |
| 13 | 20 | 95 | 5 |
| 14 | 20 | 95 | 5 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method B

| Time (min) | Flow Rate (ml/min) | % A | % B |
|---|---|---|---|
| 0.0 | 20 | 85 | 15 |
| 1.0 | 20 | 85 | 15 |
| 10 | 20 | 45 | 55 |
| 10.5 | 20 | 5 | 95 |
| 12.5 | 20 | 5 | 95 |
| 13 | 20 | 85 | 15 |
| 14 | 20 | 85 | 15 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method C

| Time (min) | Flow Rate (ml/min) | % A | % B |
|---|---|---|---|
| 0.0 | 20 | 70 | 30 |
| 1.0 | 70 | 70 | 30 |
| 10 | 20 | 15 | 85 |
| 10.5 | 20 | 5 | 95 |
| 12.5 | 20 | 5 | 95 |
| 13 | 20 | 70 | 30 |
| 14 | 20 | 70 | 30 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method D

| Time (min) | Flow Rate (ml/min) | % A | % B |
|---|---|---|---|
| 0.0 | 20 | 50 | 50 |
| 1.0 | 20 | 50 | 50 |
| 10 | 20 | 1 | 99 |
| 12.5 | 20 | 1 | 99 |
| 13 | 20 | 50 | 50 |
| 14 | 20 | 50 | 50 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method E

| Time (min) | Flow Rate (ml/min) | % A | % B |
|---|---|---|---|
| 0.0 | 20 | 20 | 80 |
| 1.0 | 20 | 20 | 80 |
| 7.0 | 20 | 1 | 99 |
| 12.5 | 20 | 1 | 99 |
| 13 | 20 | 20 | 80 |
| 14 | 20 | 20 | 80 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method M
Column Details:
SUNFIRE C18 column (100 mm×19 mm id. 5 um)
The solvents employed were:
A=0.1% v/v solution of Trifluoroacetic Acid in Water.
B=0.1% v/v solution of Trifluoroacetic Acid in Acetonitrile.

Methods below are selected based on the analytical retention time of the compounds being purified.

Method 1

| Time (min) | Flow Rate (ml/min) | % A | % B |
|---|---|---|---|
| 0.0 | 20 | 95 | 5 |
| 1.0 | 20 | 95 | 5 |
| 10 | 20 | 70 | 30 |
| 10.5 | 20 | 5 | 95 |
| 12.5 | 20 | 5 | 95 |
| 13 | 20 | 95 | 5 |
| 14 | 20 | 95 | 5 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.
Method 2

| Time (min) | Flow Rate (ml/min) | % A | % B |
|---|---|---|---|
| 0.0 | 20 | 85 | 15 |
| 1.0 | 20 | 85 | 15 |
| 10 | 20 | 45 | 55 |
| 10.5 | 20 | 5 | 95 |
| 12.5 | 20 | 5 | 95 |
| 13 | 20 | 85 | 15 |
| 14 | 20 | 85 | 15 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.
Method 3

| Time (min) | Flow Rate (ml/min) | % A | % B |
|---|---|---|---|
| 0.0 | 20 | 70 | 30 |
| 1.0 | 70 | 70 | 30 |
| 10 | 20 | 15 | 85 |
| 10.5 | 20 | 5 | 95 |
| 12.5 | 20 | 5 | 95 |
| 13 | 20 | 70 | 30 |
| 14 | 20 | 70 | 30 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.
Method 4

| Time (min) | Flow Rate (ml/min) | % A | % B |
|---|---|---|---|
| 0.0 | 20 | 50 | 50 |
| 1.0 | 20 | 50 | 50 |
| 10 | 20 | 1 | 99 |
| 12.5 | 20 | 1 | 99 |
| 13 | 20 | 50 | 50 |
| 14 | 20 | 50 | 50 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.
Method 5

| Time (min) | Flow Rate (ml/min) | % A | % B |
|---|---|---|---|
| 0.0 | 20 | 20 | 80 |
| 1.0 | 20 | 20 | 80 |
| 7.0 | 20 | 1 | 99 |
| 12.5 | 20 | 1 | 99 |
| 13 | 20 | 20 | 80 |
| 14 | 20 | 20 | 80 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

PREPARATIVE EXAMPLES

Intermediate 1

6-Bromo-1-[(4-methylphenyl)sulfonyl]-1H-indazole-4-carbonitrile

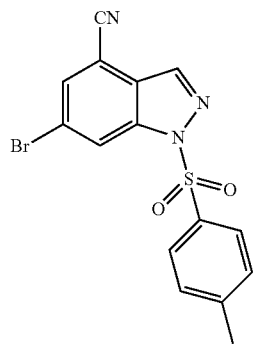 [SMILES: Cc1ccc(S(=O)(=O)n2ncc3c(C#N)cc(Br)cc32)cc1]

Sodium hydride (0.108 g, 4.50 mmol) was added to a stirred solution of 6-bromo-1H-indazole-4-carbonitrile (0.5 g, 2.252 mmol) in N,N-dimethylformamide (10 ml) at room temperature. The mixture was stirred at room temperature for 10 mins when p-toluenesulphonyl chloride (0.558 g, 2.93 mmol) was then added. The pale yellow suspension was stirred for 20 mins at room temperature. The mixture was poured into stirring water (100 ml) and the precipitated product collected by filtration. The cream coloured solid was dried in vacuo at 65° C. to give the title compound (0.794 g).
LCMS (Method B): Rt 3.38 mins, MH+ 377.8.

Intermediate 2a

6-Bromo-1-[(4-methylphenyl)sulfonyl]-4-(1H-tetrazol-5-yl)-1H-indazole

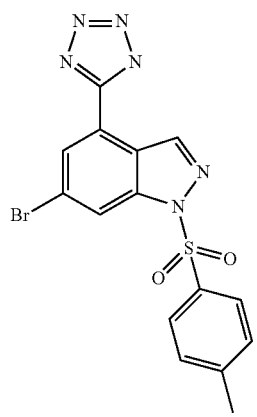 [SMILES: Cc1ccc(S(=O)(=O)n2ncc3c(-c4nnn[nH]4)cc(Br)cc32)cc1]

A stirred solution of 6-bromo-1-[(4-methylphenyl)sulfonyl]-1H-indazole-4-carbonitrile (0.79 g, 2.1 mmol), trimethylsilyl azide (0.484 g, 4.20 mmol) and dibutyltin oxide (0.105 g, 0.420 mmol) in toluene (10 ml) was heated at 110° C. for 1 h in the microwave (biotage initiator). The resulting cream coloured solid was collected by filtration, washed with toluene and dried in vacuo at 65° C. to give the title compound as a near colourless solid (0.3 g). The mother liquor was evaporated and the residue triturated with cyclohexane (10 ml) to give a further quantity of the title compound as a pale yellow solid (0.38 g).

LCMS (Method B): Rt 3.48 mins, MH+ 420.

Intermediate 2b 6-bromo-1-(phenylsulfonyl)-4-(1H-tetrazol-5-yl)-1H-indazole

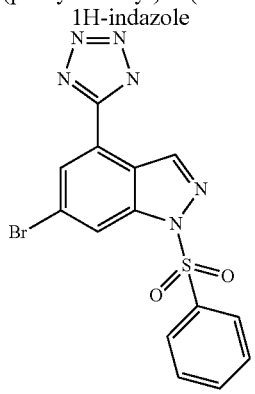

To 6-Bromo-1-(phenylsulfonyl)-1H-indazole-4-carbonitrile (18.34 g, 50.6 mmol) in toluene (700 ml) was added dibutyl(oxo)stannane (2.52 g, 10.13 mmol) and trimethylsilyl azide (13.32 ml, 101 mmol) over 2 mins. The mixture was stirred at 110° C., under nitrogen for 4 h. The reaction was cooled, then evaporated to solid and dried under vacuum overnight. The solid was triturated with diethyl ether (50 ml) and ground up then filtered under vacuum to give a beige solid (18.07 g). This solid was re-combined with the filtrate, triturated in methanol (45 ml), filtered and washed with methanol to give a pale peach solid. This was re-combined with the filtrate and stirred in methanol (300 ml) for ~20 mins, then filtered to give the title compound as a pale peach solid (17.9 g).

LCMS (Method A): Rt 1.16 mins, MH+ 407.

Intermediate 3a

6-Bromo-4-[5-(chloromethyl)-1,3,4-oxadiazol-2-yl]-1-[(4-methylphenyl)sulfonyl]-1H-indazole

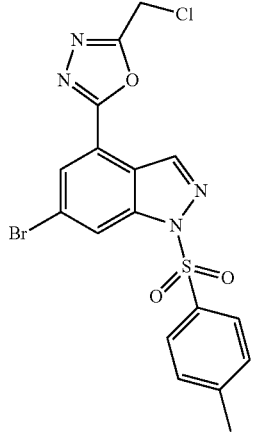 [SMILES: Cc1ccc(S(=O)(=O)n2ncc3c(-c4nnc(CCl)o4)cc(Br)cc32)cc1]

A stirred mixture of 6-bromo-1-[(4-methylphenyl)sulfonyl]-4-(1H-tetrazol-5-yl)-1H-indazole (0.237 g, 0.565 mmol) and chloroacetyl chloride (0.136 ml, 1.696 mmol) in toluene (3 ml) was heated at 130° C. in the microwave (biotage initiator) for 20 mins. The solvent was removed in vacuo and triturated with ether (10 ml) to give the title compound as a colourless solid (0.18 g).

LCMS (Method B): Rt 3.52 mins, MH+ 468.

Similarly prepared was:

Intermediate 3b

6-Bromo-4-[5-(chloromethyl)-1,3,4-oxadiazol-2-yl]-1-(phenylsulfonyl)-1H-indazole

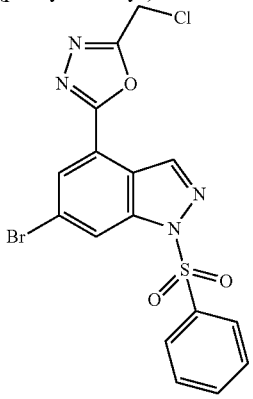

LCMS (Method A) Rt 1.38 mins, MH+ 454.

Intermediate 4

6-Bromo-1-[(4-methylphenyl)sulfonyl]-4-[5-(4-morpholinylmethyl)-1,3,4-oxadiazol-2-yl]-1H-indazole

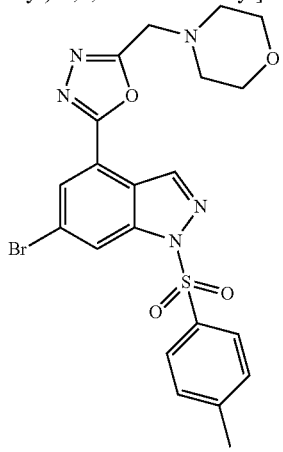

A stirred mixture of 6-bromo-4-[5-(chloromethyl)-1,3,4-oxadiazol-2-yl]-1-[(4-methylphenyl)sulfonyl]-1H-indazole (0.1 g, 0.214 mmol) and morpholine (0.056 ml, 0.641 mmol) in acetonitrile (2.5 ml) was heated at 80° C. in the microwave (biotage initiator) for 45 mins. The mixture was evaporated and the residual solid triturated with ether (10 ml) to afford the title compound as a cream coloured solid which was collected by filtration (0.07 g).

LCMS (Method B): Rt 2.90 mins, MH+ 520.

Intermediate 5

6-(1H-Indol-4-yl)-1-[(4-methylphenyl)sulfonyl]-4-[5-(4-morpholinylmethyl)-1,3,4-oxadiazol-2-yl]-1H-indazole

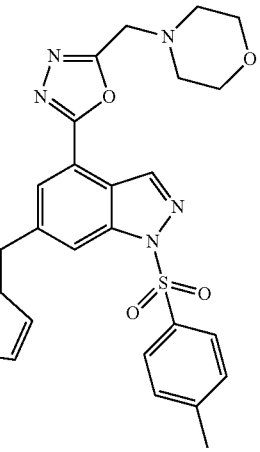

A stirred mixture of 6-bromo-1-[(4-methylphenyl)sulfonyl]-4-[5-(4-morpholinylmethyl)-1,3,4-oxadiazol-2-yl]-1H-indazole (75 mg, 0.145 mmol), 4-(4,4,5,5-tetramethyl-1,3,2-dioxaborolan-2-yl)-1H-indole (52.8 mg, 0.217 mmol), 1,1'-bis(diphenylphosphino)-ferrocene palladium dichloride (5.29 mg, 7.23 μmol) and tripotassium phosphate (92 mg, 0.434 mmol) in 1,4-dioxane (2 ml) and water (0.2 ml) was heated at 100° C. in the microwave (Biotage initiator) for 30 mins. The mixture was poured into water (40 ml) and extracted into ethyl acetate (2×30 ml). The combined extracts were washed with water (30 ml), dried (frit) and evaporated. The residual solid was purified on a silica (5 g) cartridge using ether and ethyl acetate/ether (2:1) as the eluent. The appropriate fractions were evaporated to dryness to give the title compound as a cream coloured solid (24 mg).

LCMS (Method B): Rt 2.85 mins, MH+ 555.

Intermediate 6

6-Bromo-1-(phenylsulfonyl)-1H-indazole-4-carbonitrile

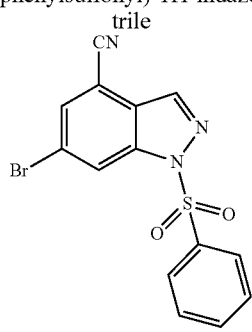

To a solution of 6-bromo-1H-indazole-4-carbonitrile (5 g, 22.52 mmol) in N,N-dimethylformamide (50 ml) was added, in portions, sodium hydride (1.351 g, 33.8 mmol) and the mixture stirred at 20° C. for 15 mins then cooled to 0° C. when benzenesulfonyl chloride (3.16 ml, 24.77 mmol) was added dropwise. The mixture was stirred at 20° C. for 18 h then concentrated in vacuo and the residue partitioned between water (100 ml) and dichloromethane (100 ml). The organic layer was separated by hydrophobic frit and evaporated in vacuo to give the title compound as a yellow solid (7.94 g).

LCMS (Method A): Rt 1.25 mins. H$^1$ NMR: (400 MHz, CDCl$_3$) –δ ppm: 8.7 (1H, s), 8.3 (1H, s), 8.05 (2H, m), 7.8 (1H, s), 7.65 (1H, t), 7.55 (2H, m).

Intermediate 7

6-(1H-Indol-4-yl)-1-(phenylsulfonyl)-1H-indazole-4-carbonitrile

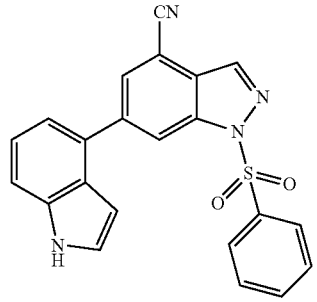 [SMILES: N#Cc1cc(-c2cccc3[nH]ccc23)cc2c1cnn2S(=O)(=O)c1ccccc1]

To a solution of 6-bromo-1-(phenylsulfonyl)-1H-indazole-4-carbonitrile (5 g, 13.80 mmol) in 1,4-dioxane (50 ml) and water (20 ml) was added 4-(4,4,5,5-tetramethyl-1,3,2-dioxaborolan-2-yl)-1H-indole (4.03 g, 16.57 mmol), 1,1'-bis(diphenylphosphino)ferrocene palladium dichloride (1.010 g, 1.380 mmol) and potassium phosphate tribasic (8.79 g, 41.4 mmol). The mixture was heated at 60° C. for 1 h, cooled and evaporated in vacuo. The residue was partitioned between water (50 ml) and dichloromethane (100 ml). The suspended solid was collected and the organics were separated by hydrophobic frit and concentrated to approx 50 ml. The precipitated solid was collected as a beige solid (1.93 g) and the filtrate purified by silica (300 g) cartridge using a gradient of ethyl acetate and cyclohexane, to give the title compound as a pale yellow solid (0.91 g). The solid collected during partitioning was purified by pre-absorbing onto florisil and purification by silica (100 g) cartridge on Flashmaster 11 using a gradient of dichloromethane and ethyl acetate to give a further quantity of the title compound as a pale yellow solid (0.45 g).

LCMS (Method A): Rt 1.24 mins, MH+ 399.

Intermediate 8

6-(1H-Indol-4-yl)-1-(phenylsulfonyl)-4-(1H-tetrazol-5-yl)-1H-indazole

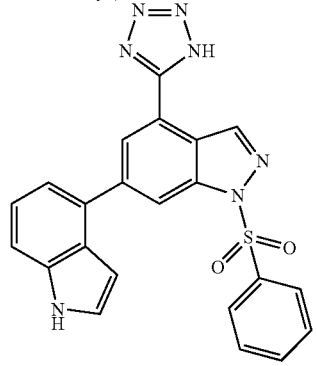

6-(1H-Indol-4-yl)-1-(phenylsulfonyl)-1H-indazole-4-carbonitrile (1.93 g, 4.84 mmol) as a slurry in toluene (90 ml) was treated with trimethylsilyl azide (1.241 ml, 9.35 mmol)

and dibutyl(oxo)stannane (0.217 g, 0.872 mmol) and heated at −120° C. for 5.75 h then left to stand at 20° C. for 18 h. The heterogeneous solution was evaporated to dryness then taken up in dichloromethane (200 ml), and this was heated in a waterbath at 40° C. to assist dissolving of the solid. This solution was then filtered and loaded directly onto a silica (100 g) cartridge which was eluted with a gradient of 0-50% methanol/dichloromethane over 60 mins using the Flashmaster II. Appropriate fractions were combined and evaporated to dryness to give the following products:

A yellow solid (0.257 g) consistent with impure desired tetrazole which was dissolved in DCM/methanol and absorbed onto silica. This was eluted with 0-25% methanol in DCM over 30 mins to give the title compound as a pale yellow solid (0.09 g).

LCMS (Method A): Rt 1.10 mins, MH+ 442.

A pale yellow solid (0.25 g) consistent with the title compound.

LCMS (Method B): Rt 2.99 mins, MH+ 442.

The original residue from the filtration [see above] was dissolved in a mixture of DCM/methanol (~250 ml) and adsorbed onto Florisil. This was eluted with 0-25% methanol over 60 min on a silica (100 g) cartridge to give a further quantity of the title compound as a pale yellow solid (1.07 g).

LCMS (Method A): 1.10 mins, MH+ 442.

Intermediate 9

4-[5-(Chloromethyl)-1,3,4-oxadiazol-2-yl]-6-(1H-indol-4-yl)-1-(phenylsulfonyl)-1H-indazole

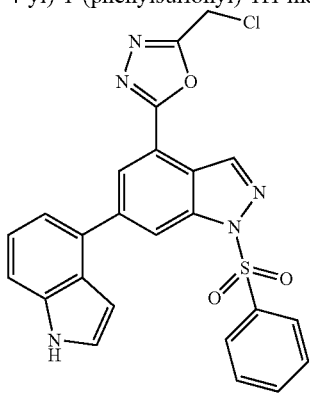

6-(1H-Indol-4-yl)-1-(phenylsulfonyl)-4-(1H-tetrazol-5-yl)-1H-indazole (1.41 g, 3.19 mmol) was slurried into anhydrous chloroform (20 ml), treated with chloroacetyl chloride (1.023 ml, 12.78 mmol) and heated at 100° C. in a Biotage Initiator microwave for 30 mins, the mixture was split into 4 batches for the microwave reaction. The mixtures were allowed to cool to room temperature and the resultant precipitate collected by filtration to give the title compound as a yellow/brown solid (0.237 g). LCMS (Method A): Rt 1.25 mins, MH+ 490.

The filtrate was concentrated in vacuo to give a yellow/brown solid. This was triturated with chloroform (~7 ml) and the resultant yellow precipitate collected by filtration and washed with chloroform (2 ml) and the solid air dried overnight to afford the title compound (0.562 g). LCMS (Method A): Rt 1.25 mins, MH+ 490.

The filtrate was evaporated in vacuo and then dissolved in chloroform (5 ml) and left to stand overnight the mixture was loaded onto a silica (100 g) cartridge and eluted with 0-100% ethyl acetate in cyclohexane over 60 mins to give the title compound (0.213 g).

LCMS (Method A): Rt 1.25 mins, MH+ 490.

Intermediate 10

N-(2-Chloro-5-{4-cyano-1-[(4-methylphenyl)sulfonyl]-1H-indazol-6-yl}-3-pyridinyl)methanesulfonamide

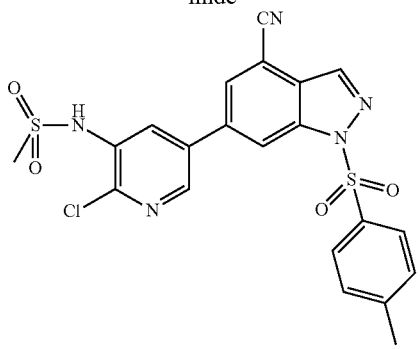

Method 1

{6-Chloro-5-[(methylsulfonyl)amino]-3-pyridinyl}boronic acid (4.9 g, 19.56 mmol), 6-bromo-1-[(4-methylphenyl)sulfonyl]-1H-indazole-4-carbonitrile (5.89 g, 15.65 mmol), 1,1'-bis(diphenylphosphino)ferrocene palladium dichloride (1.431 g, 1.956 mmol) and tripotassium phosphate (12.46 g, 58.7 mmol) were placed in 1,4-dioxane (100 ml) and water (33.3 ml) and the mixture heated at 85° C. for 2 h. The mixture was cooled to room temperature and the solvent removed. The residue was partitioned between water (200 ml) and dichloromethane (200 ml). The organic layer was collected using a hydrophobic frit and the solvent removed in vacuo. The residue was purified by chromatography on silica (3×100 g) cartridges eluting with 0-100% ethyl acetate in cyclohexane over 40 mins to a give the title compound as a pale yellow solid (0.92 g).

LCMS (Method A): Rt 1.16 min MH+ 502/504.

The column was eluted with 0-25% methanol in dichloromethane over 30 mins, and was purified further, eluting with 0-100% ethyl acetate in cyclohexane over 40 mins to give a further quantity of the title compound (0.59 g).

LCMS (Method A): Rt 1.16 mins, MH+ 502.

Method 2

Alternatively, 1-[(4-methylphenyl)sulfonyl]-6-(4,4,6,6-tetramethyl-1,3,2-dioxaborinan-2-yl)-1H-indazole-4-carbonitrile (50 mg, 0.114 mmol), N-(5-bromo-2-chloro-3-pyridinyl)methanesulfonamide (35.9 mg), tripotassium phosphate (72.8 mg, 0.343 mmol) and chloro(di-2-norbonylphosphino)(2'-dimethylamino-1,1'-biphenyl-2-yl)palladium (II) (12.82 mg, 0.023 mmol) were placed in 1,4-dioxane (2 ml) and water (0.667 ml) and the mixture heated under microwave irradiation at 80° C. for 5 mins. Additional chloro(di-2-norbonylphosphino)(2'-dimethylamino-1,1'-biphenyl-2-yl)palladium (II) (10 mg) was added and the mixture heated under microwave irradiation at 100° C. for 5 mins. Additional chloro(di-2-norbonylphosphino)(2'-dimethylamino-1,1'-biphenyl-2-yl)palladium (II) (5 mg) was added and the mixture was heated at 100° C. for a further 10 mins. The solvent was removed in vacuo and the residue partitioned between water (50 ml) and dichloromethane (50 ml). The organic layer was collected and concentrated, then the residue purified by column chromatography on silica gel, eluting with 0-100% ethyl acetate in cyclohexane to give the title compound as a pale yellow gum (10 mg).

LCMS (Method B): Rt 3.0 mins, MH+ 502.

Intermediate 11

N-{2-Chloro-5-[1-[(4-methylphenyl)sulfonyl]-4-(1H-tetrazol-5-yl)-1H-indazol-6-yl]-3-pyridinyl}methanesulfonamide

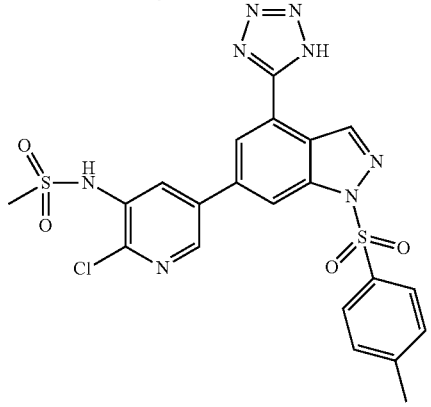 [SMILES: Cc1ccc(S(=O)(=O)n2ncc3c(-c4nnn[nH]4)cc(-c4cnc(Cl)c(NS(C)(=O)=O)c4)cc32)cc1]

N-(2-Chloro-5-{4-cyano-1-[(4-methylphenyl)sulfonyl]-1H-indazol-6-yl}-3-pyridinyl)methanesulfonamide (1.6 g, 3.19 mmol), trimethylsilyl azide (0.734 g, 6.37 mmol) and dibutyl(oxo)stannane (0.079 g, 0.319 mmol) were placed in toluene (30 ml) and the mixture heated at 100° C. for 16 h. The mixture was stirred at this temperature over the weekend. The mixture was cooled to room temperature and the solvent removed in vacuo. The residue was adsorbed onto florisil and chromatographed on silica (100 g cartridge) eluting with 0-100% ethyl acetate in cyclohexane followed by 0-20% methanol to give the title compound (1.3 g).

LCMS (Method A): Rt 1.06 mins, MH+ 545.

Intermediate 12

N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide

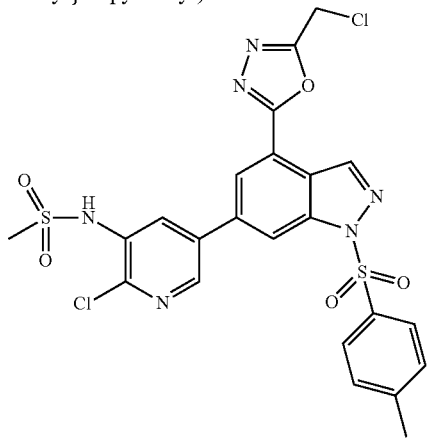

N-{2-Chloro-5-[1-[(4-methylphenyl)sulfonyl]-4-(1H-tetrazol-5-yl)-1H-indazol-6-yl]-3-pyridinyl}methanesulfonamide (1.3 g, 2.385 mmol) and chloro acetylchloride (0.285 ml, 3.58 mmol) were placed in toluene (35 ml) and the mixture heated at 105° C. for 30 mins. The temperature was increased to 115° C. and the mixture heated for 1 h. The mixture was cooled to room temperature and the solvent removed in vacuo. This was purified by chromatography on a silica (100 g) cartridge eluting with 0-100% ethyl acetate in cyclohexane followed by 0-20% methanol in dichloromethane, to give the title compound as a yellow solid (0.332 g).

LCMS (Method B): Rt 3.06 mins, MH+ 593/595.

Intermediate 13

N-(2-Chloro-5-{1-[(4-methylphenyl)sulfonyl]-4-[5-(4-morpholinylmethyl)-1,3,4-oxadiazol-2-yl]-1H-indazol-6-yl}-3-pyridinyl)methanesulfonamide

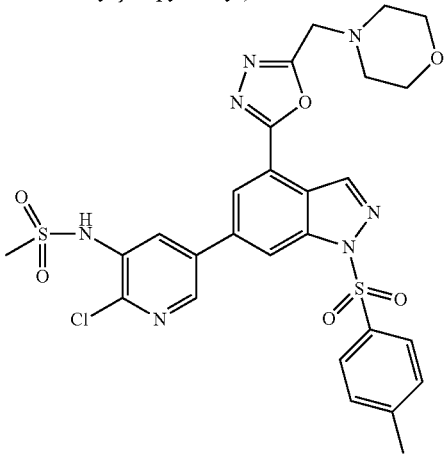 [SMILES: Cc1ccc(S(=O)(=O)n2ncc3c(-c4nnc(CN5CCOCC5)o4)cc(-c4cnc(Cl)c(NS(C)(=O)=O)c4)cc32)cc1]

N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide (50 mg, 0.084 mmol) and morpholine (0.015 ml, 0.169 mmol) were placed in acetonitrile (5 ml) and the mixture heated at 80° C. for 4 h. Further morpholine (15 µl) was added and the reaction was continued to heat overnight. The mixture was cooled to room temperature and the mixture loaded onto an SCX (5 g) cartridge. The cartridge was washed with methanol and then eluted with 2M ammonia in methanol. The mixture was purified by chromatography on silica (20 g) cartridge eluting with 0-100% ethyl acetate in cyclohexane followed by 0-20% methanol to give the title compound (52 mg).

LCMS (Method A): Rt 1.04 mins, MH+ 644.

Intermediate 14

N-(5-Bromo-2-chloro-3-pyridinyl)methanesulfonamide

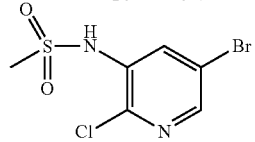

5-Bromo-2-chloro-3-pyridinamine [commercially available] (10 g, 48.2 mmol) was dissolved in pyridine (75 ml) and methanesulfonyl chloride (7.46 ml, 96 mmol) added, and the mixture stirred overnight. Further methanesulfonyl chloride (2.1 ml) was added and the reaction stirred at room temperature for 5 h. A further portion of methanesulfonyl chloride (2.1 ml) was added and the mixture stirred at room temperature overnight. The pH was adjusted to ~pH6 by the addition of 2M hydrochloric acid. The mixture was then extracted with dichloromethane (2×150 ml) the combined organic layers were dried using a hydrophobic frit and the solvent removed in vacuo. The residue was suspended in methanol (200 ml)

and 2M sodium hydroxide (50 ml) added. The mixture was stirred for 1 h and then the solvent removed in vacuo. The residue was dissolved in water (250 ml) and extracted with dichloromethane (150 ml). The aqueous layer was then acidified and the resulting precipitate collected by filtration. The solid was air dried overnight to give the title compound as an off white solid (13.45 g).

LCMS (Method A): 0.81 mins, MH− 285.

Intermediate 15

{6-Chloro-5-[(methylsulfonyl)amino]-3-pyridinyl}boronic acid

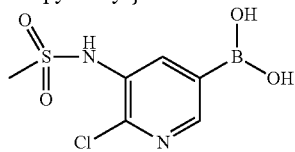

N-(5-Bromo-2-chloro-3-pyridinyl)methanesulfonamide (5 g, 17.51 mmol), potassium acetate (5.16 g, 52.5 mmol), 4,4,4',4',5,5,5',5'-octamethyl-2,2'-bi-1,3,2-dioxaborolane (4.89 g, 19.26 mmol) and 1,1'-bis(diphenylphosphino)ferrocene palladium dichloride (1.281 g, 1.751 mmol) were placed in 1,4-dioxane (51 ml) and the mixture heated for 16 h at 90° C. The reaction was left stirring at 90° C. for a further 5 h. Further catalyst (0.3 g), potassium acetate (1.7 g) and 4,4,4',4',5,5,5',5'-octamethyl-2,2'-bi-1,3,2-dioxaborolane (1.5 g) were added and the mixture stirred at 95° C. overnight. The mixture was cooled to room temperature then the mixture was filtered through a hydrophobic frit and the solvent removed in vacuo. The residue was partitioned between water (250 ml) and dichloromethane (250 ml). the organic layer was collected and the solvent removed in vacuo. The residue was columned on silica (3×100 g) cartridges eluting with 0-25% methanol in dichloromethane over 40 mins gave the title compound as a dark brown oil (4.9 g).

LCMS (Method A): Rt 0.46 mins, MH+ 251.

Intermediate 16

1,1-Dimethylethyl 2-[(6-bromo-1H-indazol-4-yl)carbonyl]hydrazinecarboxylate

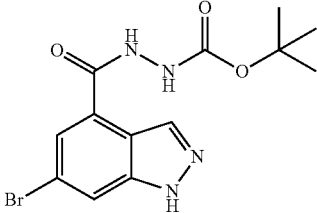 [SMILES: CC(C)(C)OC(=O)NNC(=O)c1cc(Br)cc2[nH]ncc12]

To 6-bromo-1H-indazole-4-carboxylic acid (5 g, 20.74 mmol) in N,N-dimethylformamide (20 ml) was added O-(7-azabenzotriazol-1-yl)-N,N,N'N'-tetramethyluronium hexafluorophosphate (8.68 g, 22.82 mmol) followed by N,N-diisopropyethylamine (5.42 ml, 31.1 mmol), and the clear solution was stirred for 10 mins at 20° C. To this was added t-butylcarbazate (3.29 g, 24.89 mmol) and the heterogeneous reaction was stirred for 24 h at 20° C. under nitrogen. The mixture was left to stand for 7 days. Dichloromethane (200 ml) and saturated aqueous sodium hydrogen carbonate (50 ml) were added. Ethyl acetate (100 ml) added and the monophasic mixture was left to stand for 30 mins then the mixture was filtered through a filter paper under vacuum to give a biphasic filtrate. The organic phase was separated, passed through a hydrophobic frit, then evaporated to dryness to give a yellow liquid containing N,N-dimethylformamide. The solid collected on the filter paper was dried in air to give a beige solid (6 g) which was treated with methanol (75 ml) and chloroform (75 ml) and the mixture stirred at room temperature for 2 h. The mixture was left to stand for 10 mins, then the supernatant was decanted off and loaded directly onto an aminopropyl (70 g) cartridge which had been pre-eluted with methanol. A further quantity of methanol (30 ml) and chloroform (30 ml) was added to the remaining slurry, stirred for 10 mins and heated for a couple of minutes with a heat gun. The mixture was left to stand for 10 mins and the supernatant added to the cartridge. The cartridge was then eluted with methanol, and the eluant evaporated to give the title compound as a yellow solid (3.47 g).

LCMS (Method B): Rt 2.78 mins, MH+ 355.

The aqueous was further extracted with dichloromethane (2×100 ml), the combined organics were passed through a hydrophobic frit, then evaporated to dryness to give light yellow liquid containing N,N-dimethylformamide. The two liquids from above were combined and loaded equally onto silica (2×100 g) cartridges which had been pre-eluted with cyclohexane. The cartridges were eluted with 0-100% ethyl acetate/cyhexane over 40 mins using the Flashmaster II to give further quantities of the title compound as a beige solid (0.693 g).

LCMS (Method B): Rt 2.78 mins, MH+ 355.

Intermediate 17

6-Bromo-1H-indazole-4-carbohydrazide

1,1-Dimethylethyl 2-[(6-bromo-1H-indazol-4-yl)carbonyl]hydrazinecarboxylate (3.45 g, 4.63 mmol) was treated with 4M hydrogen chloride in 1,4-dioxane (30 ml, 120 mmol) and stirred at 20° C. for 24 h under nitrogen. The solvent was blown off to leave a white solid which was azeotroped with dichloromethane (10 ml) followed by methanol (10 ml) to give a white solid (2.34 g). A portion of this material (0.505 g) was dissolved in methanol (10 ml) and purified on a SCX (10 g) cartridge which had been pre-conditioned with methanol. Methanol was eluted followed by 2M ammonia in ethanol. Basic fractions were combined and evaporated to dryness to give the title compound as a beige solid (0.180 g).

LCMS (Method B): Rt 2.06 mins, MH+ 257.

The remaining material (1.82 g) was dissolved in methanol (20 ml) and purified on an SCX (50 g) cartridge which had been pre-conditioned with methanol. Methanol was eluted followed by 2M ammonia in ethanol. Basic fractions were combined and evaporated to dryness to a further quantity of the title compound as a beige solid (0.477 g).

LCMS (Method B): Rt 2.06 mins, MH+ 255.

Intermediate 18

6-Bromo-N'-(4-morpholinylacetyl)-1H-indazole-4-carbohydrazide

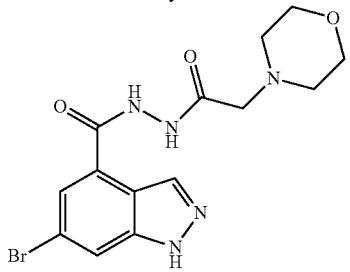

O-(7-Azabenzotriazol-1-yl)-N,N,N'N'-tetramethyluronium hexafluorophosphate (0.841 g, 2.212 mmol) was dissolved in N,N-dimethylformamide (5 ml) then treated with 4-morpholinylacetic acid (0.304 g, 2.092 mmol) and then N,N-diisopropyethylamine (0.386 ml, 2.212 mmol). The clear solution was stirred at 20° C. for 10 mins then to this was added 6-bromo-1H-indazole-4-carbohydrazide (0.513 g, 2.011 mmol) as a partial solution in N,N-dimethylformamide (8 ml). The clear solution was stirred at 20° C. for 72 h under nitrogen. It was then reduced in volume to ~1 ml, diluted with methanol (5 ml) and loaded onto an aminopropyl cartridge which had been pre-conditioned with methanol. The fully-loaded cartridge was left to stand for 2 h then eluted with methanol and the eluant evaporated to give an orange oil. This was diluted with dichloromethane (3 ml) and loaded onto a silica (10 g) cartridge. This was eluted with a gradient of methanol and ethyl acetate to give the title compound as a beige solid (0.792 g).

LCMS (Method B): Rt 1.96 mins, MH+ 384.

Intermediate 19

6-Bromo-N'-(4-morpholinylacetyl)-1-(tetrahydro-2H-pyran-2-yl)-1H-indazole-4-carbohydrazide

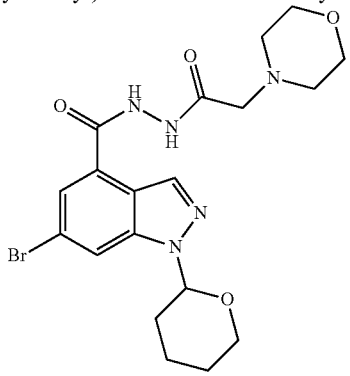

6-Bromo-N'-(4-morpholinylacetyl)-1H-indazole-4-carbohydrazide (0.232 g, 0.607 mmol) in ethyl acetate (3 ml) was treated with 3,4-dihydro-2H-pyran (0.111 ml, 1.214 mmol) then heated to 50° C. under nitrogen. Trifluoroacetic acid (4 drops) was added and heating continued for 1.5 h at 50° C. A further portion of 3,4-dihydro-2H-pyran (0.111 ml, 1.214 mmol) and trifluoroacetic acid (0.047 ml, 0.607 mmol) were added and heating continued for a further 1.5 h. The solution was left to stand at room temperature for 18 h. The clear solution was diluted with ethyl acetate (5 ml), washed with saturated aqueous sodium bicarbonate (2×10 ml), filtered through a phase separator cartridge then blown to dryness and left under vacuum. The crude product was dissolved in dichloromethane (2 ml) and purified on a silica (5 g) cartridge which was eluted with a gradient of methanol and chloroform and the appropriate fractions evaporated to give the title compound as a beige gummy solid (0.199 g).

LCMS Method (B): Rt 1.39 mins, MH+ 468.

Intermediate 20

6-Bromo-4-[5-(4-morpholinylmethyl)-1,3,4-oxadiazol-2-yl]-1-(tetrahydro-2H-pyran-2-yl)-1H-indazole

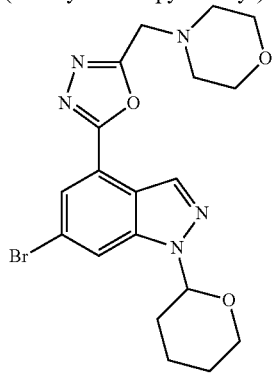

6-Bromo-N'-(4-morpholinylacetyl)-1-(tetrahydro-2H-pyran-2-yl)-1H-indazole-4-carbohydrazide (0.053 g, 0.114 mmol) in a microwave vial was treated with tetrahydrofuran (1 ml) and (methoxycarbonylsulfamoyl)triethylammonium hydroxide, inner salt (Burgess reagent) (0.054 g, 0.227 mmol). The mixture was heated in a Biotage Initiator microwave at 100° C. for 30 mins on high power. The solution was diluted with water (4 ml) and the product extracted with dichloromethane (2×10 ml). The combined organics were filtered through a hydrophobic frit then blown to dryness to give a yellow gum (60 mg). This material was dissolved in dichloromethane (1 ml) and purified on a silica (2 g) cartridge which was eluted with a gradient of methanol and chloroform to give a yellow gum (44 mg). This was dissolved in dichloromethane (2 ml) and loaded onto an SCX (1 g) cartridge which had been pre-conditioned with methanol. Methanol then 2M ammonia in ethanol was eluted. The basic fractions were blown to dryness to give the title compound (25 mg).

LCMS (Method B): Rt 2.37 mins, MH+ 450.

Intermediate 21

2-(Methyloxy)-5-(4,4,5,5-tetramethyl-1,3,2-dioxaborolan-2-yl)-3-pyridinamine

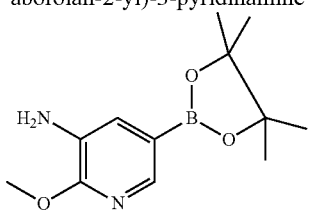

To 5-bromo-2-(methyloxy)-3-pyridinamine (18.93 g, 93 mmol, available from Asymchem) in a 1 L round-bottom flask was added nitrogen-purged 1,4-Dioxane (500 mL) followed by 4,4,4',4',5,5,5',5'-octamethyl-2,2'-bi-1,3,2-dioxaborolane (47.4 g, 186 mmol), potassium acetate (27.5 g, 280 mmol)

(0.402 g, 0.493 mmol) and PdCl2(dppf)-CH₂Cl₂ adduct (7.61 g, 9.32 mmol). The mixture was then stirred at 80° C. under nitrogen. The reaction mixture was allowed to cool then partitioned between ethyl acetate and water. The mixture was filtered through a celite pad and the aqueous layer extracted further with ethyl acetate (2×). The combined organics were washed with water, brine and dried over magnesium sulphate overnight. The residue was purified on 1.5 Kg Silica cartridge, eluting a 0-50% ethyl acetate/dichloromethane over 10 column volumes. The appropriate fractions were combined and evaporated to dryness. The residue was triturated with cyclohexane, the solid filtered off and dried in vacuo to leave the title compound as a light pink solid (1.1 g).

LCMS (Method A) Rt 0.91 mins, MH+ 251

A second crop was obtained from the above filtrate and after drying gave a further portion of the title compound as a light pink solid (2.95 g).

Intermediate 22

N-[2-(Methyloxy)-5-(4,4,5,5-tetramethyl-1,3,2-dioxaborolan-2-yl)-3-pyridinyl]methanesulfonamide

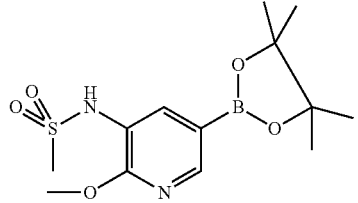 [SMILES: COc1ncc(B2OC(C)(C)C(C)(C)O2)cc1NS(C)(=O)=O]

To a solution of 2-(methyloxy)-5-(4,4,5,5-tetramethyl-1,3,2-dioxaborolan-2-yl)-3-pyridinamine (0.5 g, 1.999 mmol) in pyridine (5 ml) was added methanesulphonyl chloride (0.309 ml, 4.00 mmol) and the mixture stirred at 20° C. for 18 hr when the solvent was removed in vacuo. The residue was partitioned between saturated sodium bicarbonate solution (10 ml) and dichloromethane (20 ml), separated by hydrophobic frit and purified by silica (70 g) cartridge on Flashmaster II using a gradient of dichloromethane and methanol to give the title compound as a brown solid (0.46 g).

LCMS (Method A) Rt 0.98 mins, MH+ 329.

Intermediate 23

6-Bromo-4-(5-{[(2R,6S)-2,6-dimethyl-4-morpholinyl]methyl}-1,3,4-oxadiazol-2-yl)-1-(phenylsulfonyl)-1H-indazole

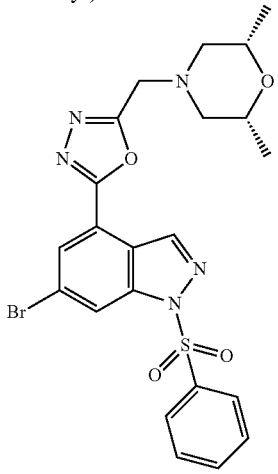

To a solution of 6-bromo-4-[5-(chloromethyl)-1,3,4-oxadiazol-2-yl]-1-(phenylsulfonyl)-1H-indazole (1.7 g, 3.75 mmol) in dichloromethane (50 ml) was added (2R,6S)-2,6-dimethylmorpholine (0.863 g, 7.49 mmol) and the mixture stirred at 50° C. for 18 hr. The crude product was purified by silica (100 g) cartridge on Flashmaster II using a gradient of dichloromethane and methanol to give the title compound as a pale yellow solid (1.79 g).

LCMS (Method A) Rt 1.22 mins, MH+ 534.

Similarly prepared was:

Intermediate 24

6-Bromo-4-(5-{[4-(1-methylethyl)-1-piperazinyl]methyl}-1,3,4-oxadiazol-2-yl)-1-(phenylsulfonyl)-1H-indazole

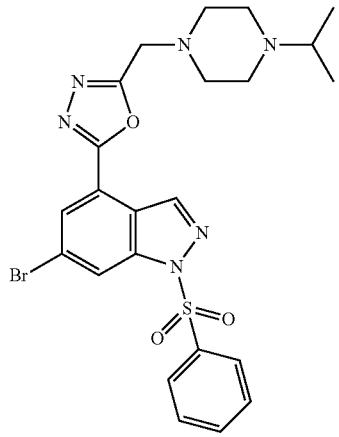 [SMILES: CC(C)N1CCN(Cc2nnc(-c3cc(Br)cc4c3cnn4S(=O)(=O)c3ccccc3)o2)CC1]

LCMS (Method A) Rt 0.93 mins, MH+ 547.

Intermediate 25

5-[4-(5-{[(2R,6S)-2,6-Dimethyl-4-morpholinyl]methyl}-1,3,4-oxadiazol-2-yl)-1-(phenylsulfonyl)-1H-indazol-6-yl]-2-(methyloxy)-3-pyridinamine

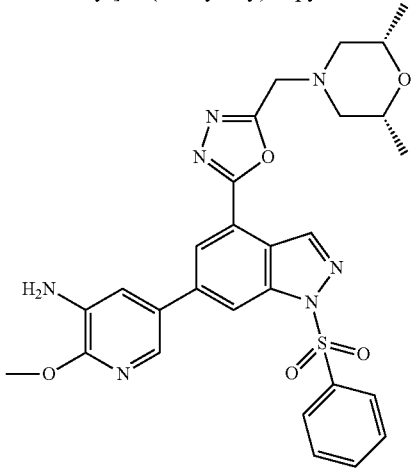

To a solution of 6-bromo-4-(5-{[(2R,6S)-2,6-dimethyl-4-morpholinyl]methyl}-1,3,4-oxadiazol-2-yl)-1-(phenylsulfonyl)-1H-indazole (0.82 g, 1.540 mmol) in 1,4-dioxane (15 ml) and water (1.5 ml) was added 2-(methyloxy)-5-(4,4,5,5-tetramethyl-1,3,2-dioxaborolan-2-yl)-3-pyridinamine (0.501 g, 2.002 mmol), 1,1'-bis(diphenylphosphino)ferrocene palladium dichloride (0.225 g, 0.308 mmol) and potassium phosphate tribasic (0.981 g, 4.62 mmol). The mixture was heated at 80° C. for 2 hr, cooled and concentrated in vacuo and the residue partitioned between dichloromethane and water (20 ml), separated by hydrophobic frit and purified by silica (100 g) cartridge on Flashmaster 11, using a gradient of dichloromethane and methanol (1% triethylamine) to give the title compound as an orange solid (0.88 g).

LCMS (Method A) Rt 1.08 mins, MH+ 576.

Intermediate 26

N-[5-[4-(5-{[(2R,6S)-2,6-Dimethyl-4-morpholinyl]methyl}-1,3,4-oxadiazol-2-yl)-1-(phenylsulfonyl)-1H-indazol-6-yl]-2-(methyloxy)-3-pyridinyl]methanesulfonamide

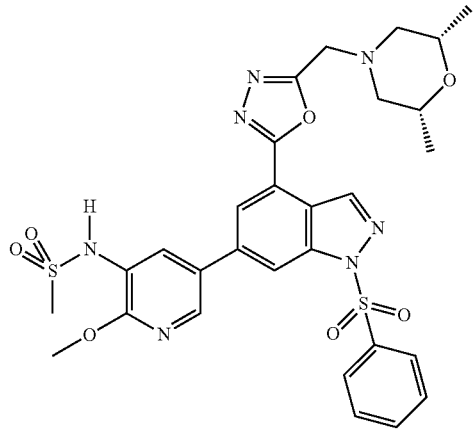 [SMILES: COc1ncc(-c2cc(-c3nnc(CN4C[C@@H](C)O[C@@H](C)C4)o3)c3cnn(S(=O)(=O)c4ccccc4)c3c2)cc1NS(C)(=O)=O]

To a solution of 5-[4-(5-{[(2R,6S)-2,6-dimethyl-4-morpholinyl]methyl}-1,3,4-oxadiazol-2-yl)-1-(phenylsulfonyl)-1H-indazol-6-yl]-2-(methyloxy)-3-pyridinamine (200 mg, 0.347 mmol) in pyridine (1 ml) was added, dropwise, methanesulphonyl chloride (0.054 ml, 0.695 mmol) and the mixture stirred at 20° C. for 18 hr. Water (10 ml) was added and the title compound was collected by filtration as a brown solid (106 mg).

LCMS (Method A) Rt 1.05 mins, MH+ 654.

Intermediate 27

N-[5-[4-(5-{[4-(1-Methylethyl)-1-piperazinyl]methyl}-1,3,4-oxadiazol-2-yl)-1-(phenylsulfonyl)-1H-indazol-6-yl]-2-(methyloxy)-3-pyridinyl]methanesulfonamide

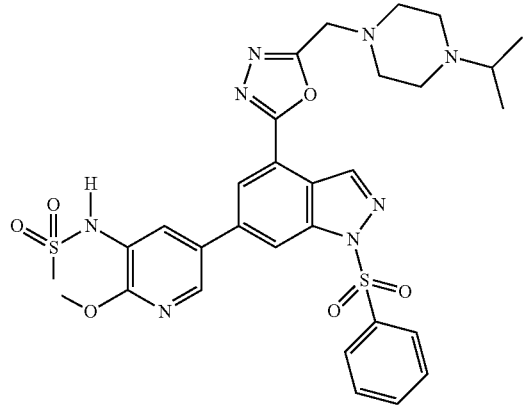 [SMILES: COc1ncc(-c2cc(-c3nnc(CN4CCN(C(C)C)CC4)o3)c3cnn(S(=O)(=O)c4ccccc4)c3c2)cc1NS(C)(=O)=O]

To a solution of 6-bromo-4-(5-{[4-(1-methylethyl)-1-piperazinyl]methyl}-1,3,4-oxadiazol-2-yl)-1-(phenylsulfonyl)-1H-indazole (100 mg, 0.183 mmol) in 1,4-dioxane (2.5 ml) and water (0.250 ml) was added N-[2-(methyloxy)-5-(4,4,5,5-tetramethyl-1,3,2-dioxaborolan-2-yl)-3-pyridinyl]methanesulfonamide (78 mg, 0.238 mmol), 1,1'-bis(diphenylphosphino)ferrocene palladium dichloride (26.8 mg, 0.037 mmol) and potassium phosphate tribasic (117 mg, 0.550 mmol). The mixture was heated under microwave irradiation at 60° C. for 10 min, then the solvent was removed in vacuo and the residue partitioned between dichloromethane (5 ml) and water (5 ml), separated by hydrophobic frit and purified by silica (5 g) cartridge using a gradient of dichloromethane and methanol to give the title compound as a brown solid (122 mg).

LCMS (Method A) Rt 0.87 mins, MH+ 667.

Intermediate 28

N-[5-Bromo-2-(methyloxy)-3-pyridinyl]-2,4-difluorobenzenesulfonamide

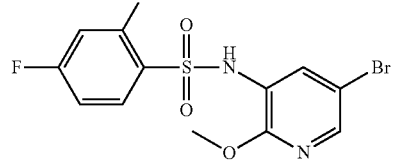

To a cooled (0° C.) solution of 5-bromo-2-(methyloxy)-3-pyridinamine (13.7 g, 67.5 mmol) in pyridine (200 ml) was added slowly 2,4-difluorobenzenesulfonyl chloride (14.37 g, 67.6 mmol) over 15 min (reaction became heterogeneous). The ice bath was removed and the reaction was stirred at ambient temperature for 16 h. Most of the pyridine was removed in vacuo and the residue diluted with water (500 mL). The solids were filtered off and washed with copious amounts of water to give 21 g of crude desired product. More solid appeared in the mother liquor and was filtered and washed with water to give an additional 1.5 g of desired material. The two batches were combined, triturated with 70 ml of methylene chloride, and dried in a vacuum oven at 50° C. to give the title compound (15

LCMS (Method B) $R_t$=1.11 min, MH+=378/380.

Intermediate 29

2,4-Difluoro-N-[2-(methyloxy)-5-(4,4,5,5-tetramethyl-1,3,2-dioxaborolan-2-yl)-3-pyridinyl]benzenesulfonamide

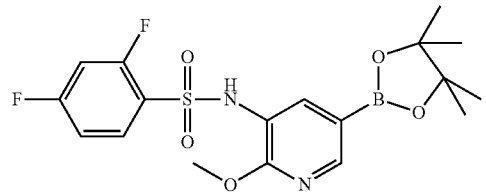 [SMILES: COc1ncc(B2OC(C)(C)C(C)(C)O2)cc1NS(=O)(=O)c1ccc(F)cc1F]

To a stirred solution of 2-(methyloxy)-5-(4,4,5,5-tetramethyl-1,3,2-dioxaborolan-2-yl)-3-pyridinamine (3 g, 12.00 mmol) in pyridine (12 ml), 2,4-difluorobenzenesulfonyl chloride (1.774 ml, 13.19 mmol) was added and the reaction mixture stirred at room temperature for 2 hours. 2 N HCl (aq) solution (20 ml) and DCM (20 ml) were added and the layers separated. The aqueous layer was washed with additional DCM (2×15 ml). Then the organic layers were combined, dried (hydrophobic frit) and evaporated in vacuo to give a brown oil. There was still some pyridine in the reaction mixture so 2M HCl was added and 15 ml DCM to extract one more time. The solvent was removed in vacuo to give the title compound as an orange solid (4.3 g).

LCMS (Method A) Rt=1.20 min, MH+=426 [NB. also observe Rt=0.73 min, MH+=344 consistent with boronic acid (hydrolysis product due to HPLC eluent)].

Intermediate 30

6-Bromo-1-methyl-1H-indazole-4-carbonitrile

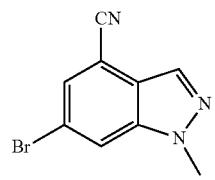

Tetrahydrofuran (27 ml) was added to a flask containing sodium hydride (0.275 g, 6.89 mmol) and the mixture was stirred for 10 minutes at 0° C. 6-Bromo-1H-indazole-4-carbonitrile (1.39 g, 6.26 mmol) was added portionwise and the mixture was stirred for 10 mins until no further effervescence was seen. Iodomethane (0.431 ml, 6.89 mmol) was added and the mixture stirred at 0° C. for 1 h. The ice bath was removed and the flask was placed in a water bath at room temperature. The reaction remained stirring for 19 h and the mixture was then evaporated in vacuo. The residual solid purified by silica (100 g) cartridge using a gradient of ethyl acetate and cyclohexane to give the title compound as a white solid (370 mg).

LCMS (Method B): Rt 2.60 mins, MH+ 237.

Intermediate 31

6-Bromo-1-methyl-4-(1H-tetrazol-5-yl)-1H-indazole

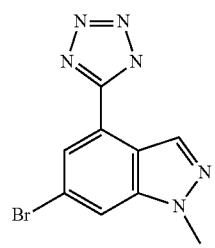 [SMILES: Cn1ncc2c(-c3nnn[nH]3)cc(Br)cc21]

6-Bromo-1-methyl-1H-indazole-4-carbonitrile (514 mg, 2.177 mmol) was dissolved in toluene (20 mL) and dibutyl (oxo)stannane (108 mg, 0.435 mmol) and trimethylsilyl azide (0.573 mL, 4.35 mmol) were added over 2 mins. The mixture was then stirred at 110° C. under nitrogen for 28 h. Further trimethylsilyl azide (0.03 mL, 0.228 mmol) was added and the mixture continued stirring at 110° C. under nitrogen for 44 h. The solvent was removed in vacuo to give a white solid. 2M sodium hydroxide in methanol was added and the mixture heated to 50° C. and then filtered whilst hot to remove insoluble impurities. The filtrate was cooled and then acidified via dropwise addition of 2M hydrochloric acid. The resultant precipitate was filtered and dried in a vacuum oven to give the title compound as a white solid (604 mg).

LCMS (Method B): Rt 2.12 mins, MH+ 279.

Intermediate 32

6-Bromo-4-[5-(chloromethyl)-1,3,4-oxadiazol-2-yl]-1-methyl-1H-indazole

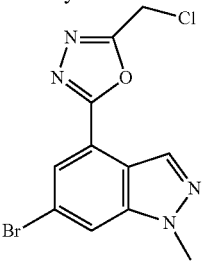

6-Bromo-1-methyl-4-(1H-tetrazol-5-yl)-1H-indazole (604.6 mg, 2.166 mmol) was dissolved in chloroform (20 ml). Chloroacetyl chloride (0.520 ml, 6.49 mmol) was added and the mixture stirred at 110° C. for 46 h. Further chloroacetyl chloride (0.174 ml, 2.166 mmol) was added and the reaction continued stirred at 110° C. for 26 h. The reaction mixture was cooled and the solvent removed in vacuo. The resultant white solid was washed with DCM, the solvent removed under vacuum and the solid dried under high vacuum for 18 h to give the title compound as a white solid (528 mg).

LCMS (Method B): Rt 2.67 mins, MH+ 329.

Intermediate 33

6-Bromo-4-(5-{[(2R,6S)-2,6-dimethyl-4-morpholinyl]methyl}-1,3,4-oxadiazol-2-yl)-1-methyl-1H-indazole

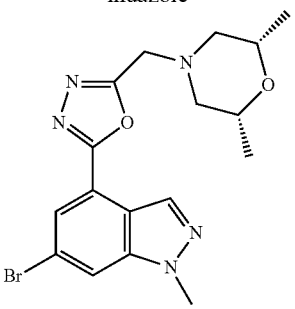

Method 1

6-Bromo-4-[5-(chloromethyl)-1,3,4-oxadiazol-2-yl]-1-methyl-1H-indazole (260 mg, 0.794 mmol) and (2R,6S)-2,6-dimethylmorpholine (1.5 ml, 0.794 mmol) were added to a microwave vial. The reaction mixture was heated under microwave irradiation at 90° C. for 15 mins. The reaction mixture was evaporated under a stream of nitrogen, dissolved in DCM (20 ml) and washed with a 10% solution of 2M hydrochloric acid in water. The organic layer was collected and the solvent removed in vacuo to give the title compound as an orange solid (240 mg).

LCMS (Method A): Rt 0.90 mins, MH+ 408.

Method 2

6-Bromo-N'-{[(2R,6S)-2,6-dimethyl-4-morpholinyl]acetyl}-1-methyl-1H-indazole-4-carbohydrazide (485 mg, 1.143 mmol) was dried on high vacuum line then added with Burgess reagent (methoxycarbonylsulfamoyl)triethylammonium hydroxide, inner salt) (409 mg, 1.715 mmol) in suspension in anhydrous Tetrahydrofuran (THF) (10 ml) and heated to 75° C. for 2 h. The solvent was then removed in vacuo and the residue partitioned between dichloromethane (10 ml) and saturated sodium bicarbonate solution (10 ml). The layers were separated, the aqueous washed with further dichloromethane (5 ml) and the combined organics concentrated in vacuo. The resultant solid was purified by column chromatography, loading in dichloromethane and purified on Flashmaster 11 silica (Si) 20 g using a 0-100% ethyl acetate-cyclohexane over 20 min. The appropriate fractions were combined and concentrated in vacuo to give the title compound as a white solid (200 mg).

LCMS (Method A) Rt=0.88 min, MH+ =408.

Intermediate 34

6-Bromo-1-methyl-4-(5-{[4-(1-methylethyl)-1-piperazinyl]methyl}-1,3,4-oxadiazol-2-yl)-1H-indazole

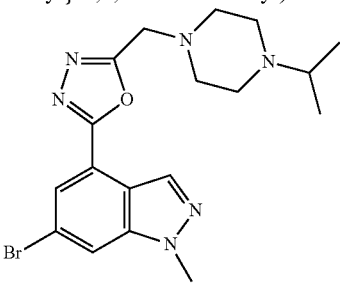

6-Bromo-4-[5-(chloromethyl)-1,3,4-oxadiazol-2-yl]-1-methyl-1H-indazole (260 mg, 0.794 mmol) and 1-(1-methylethyl)piperazine (1.5 ml, 0.794 mmol) were added to a microwave vial. The reaction mixture was heated under microwave irradiation at 90° C. for 15 mins. The reaction mixture was evaporated under a stream of nitrogen, dissolved in DCM (20 ml) and washed with a 10% solution of 2M hydrochloric acid in water. The layers were separated by hydrophobic frit and the aqueous layer was neutralised to pH=7 with 2M sodium hydroxide then extracted with DCM (20 ml). The organic layer was collected and the solvent removed in vacuo to give the title compound as an orange solid (310 mg).

LCMS (Method A): Rt 0.64 mins, MH+ 421.

Intermediate 35

6-Bromo-4-{5-[(2,2-dimethyl-4-morpholinyl)methyl]-1,3,4-oxadiazol-2-yl}-1-(phenylsulfonyl)-1H-indazole

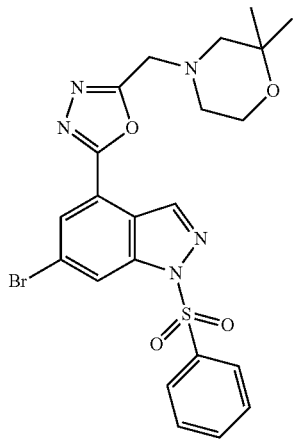 [SMILES: CC1(C)CN(Cc2nnc(-c3cc(Br)cc4c3cnn4S(=O)(=O)c3ccccc3)o2)CCO1]

To a solution of 6-bromo-4-[5-(chloromethyl)-1,3,4-oxadiazol-2-yl]-1-(phenylsulfonyl)-1H-indazole (200 mg, 0.441 mmol) in acetonitrile (2 ml) was added 2,2-dimethylmorpholine (102 mg, 0.882 mmol, available from Chembridge Corporation) and the mixture heated at 70° C. for 18 hr. The mixture was cooled to room temperature and a further portion of 2,2-dimethylmorpholine (102 mg, 0.882 mmol), DIPEA (0.154 mL, 0.882 mmol) and sodium iodide (66.1 mg, 0.441 mmol) were added. The mixture was then heated again at 70° C. for 2 hours. The mixture was cooled to room temperature, diluted with DCM and washed with water. The organic layer was separated through a hydrophobic frit and the solvent removed in vacuo. The resulting yellow oil was dried in a vacuum oven at 60° C. overnight to give a pale yellow solid, which was dissolved in DCM (10 ml) and washed with dilute HCl (10 ml) followed by water (10 ml), separating the layers using a hydrophobic frit. The DCM was removed in vacuo to give the title compound as a cream solid (214 mg).

LCMS (Method A) $R_t$=1.25 min, MH+ 534.

Intermediate 36

N-[5-[4-(5-{[(2R,6S)-2,6-Dimethyl-4-morpholinyl]methyl}-1,3,4-oxadiazol-2-yl)-1-(phenylsulfonyl)-1H-indazol-6-yl]-2-(methyloxy)-3-pyridinyl]-2,4-difluorobenzenesulfonamide

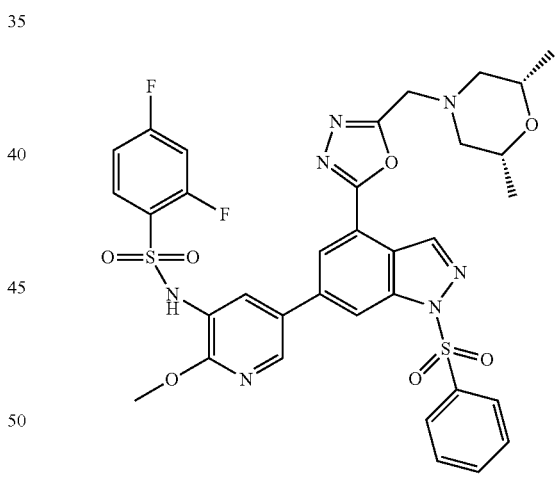

2,4-Difluorobenzenesulfonyl chloride (0.048 mL, 0.354 mmol) was added dropwise to a solution of 5-[4-(5-{[(2R,6S)-2,6-dimethyl-4-morpholinyl]methyl}-1,3,4-oxadiazol-2-yl)-1-(phenylsulfonyl)-1H-indazol-6-yl]-2-(methyloxy)-3-pyridinamine (185 mg, 0.321 mmol) in pyridine (1 ml). The mixture was stirred at room temperature for 2 h. 2,4-Difluorobenzenesulfonyl chloride (0.048 mL, 0.354 mmol) was added dropwise and the mixture continued stirring at room temperature for 1 h. Water (10 ml) was added and the resultant brown precipitate collected by filtration and dried in the vacuum oven for 72 h to give the title compound as a brown solid (194 mg).

LCMS (Method A): Rt 1.19 mins, MH+ 752.

Intermediate 37

6-(1H-Indol-4-yl)-1-[(4-methylphenyl)sulfonyl]-1H-indazole-4-carbonitrile

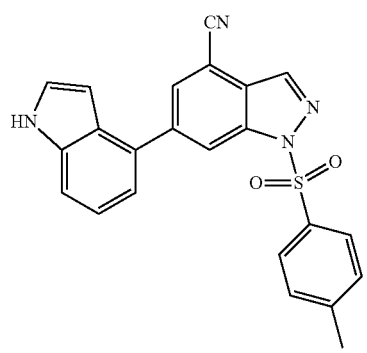 [SMILES: Cc1ccc(S(=O)(=O)n2ncc3c(C#N)cc(-c4cccc5[nH]ccc45)cc32)cc1]

To a suspension of 6-bromo-1-[(4-methylphenyl)sulfonyl]-1H-indazole-4-carbonitrile in 1,4-dioxane (100 ml) was added 4-(4,4,5,5-tetramethyl-1,3,2-dioxaborolan-2-yl)-1H-indole (4.79 g, 10.72 mmol, available from Frontier Scientific Europe), 1,1'-bis(diphenylphosphino)ferrocene palladium dichloride (2.061 g, 2.82 mmol) and potassium phosphate tribasic (8.97 g, 42.3 mmol). Water (20 ml) was added and the reaction mixture heated to 80° C. for 1 h. The solvent was removed and the residue partitioned between water (50 ml) and ethyl acetate (100 ml). The layers were filtered and the filtrate partitioned and concentrated, then purified by column chromatography, on a silica cartridge (300 g), eluting with a gradient of cyclohexane and ethyl acetate to give the title compound as a pale yellow solid (2.5 g).

LCMS (Method B): Rt 3.39 mins, MH+ 413.

Intermediate 38

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1)

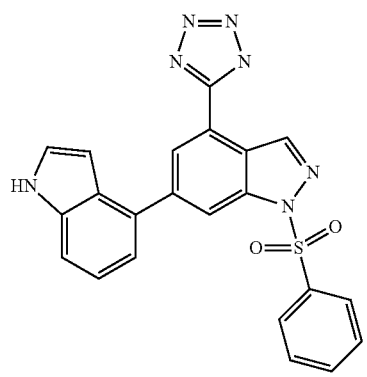

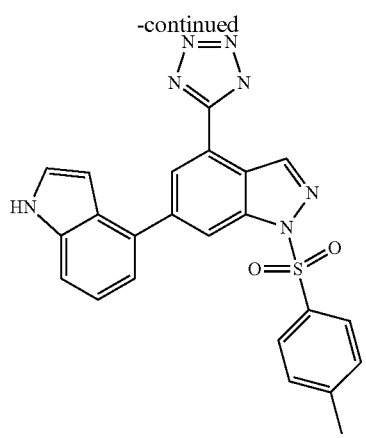

6-(1H-Indol-4-yl)-1-(phenylsulfonyl)-1H-indazole-4-carbonitrile (0.669 g, 1.679 mmol) and 6-(1H-indol-4-yl)-1-[(4-methylphenyl)sulfonyl]-1H-indazole-4-carbonitrile (0.561 g, 1.360 mmol) were slurried in toluene (60 ml) and treated with trimethylsilyl azide (0.887 ml, 6.68 mmol) and dibutyl(oxo)stannane (0.151 g, 0.608 mmol). The reaction mixture was heated, under nitrogen at 120° C. for 16 h, then additional trimethylsilyl azide (0.221 ml, 1.67 mmol) was added. After heating for a further 2 h, the solution was evaporated to dryness, treated with methanol (30 ml) and absorbed onto Florisil. The Florisil was loaded onto a silica cartridge (100 g) which was eluted with 0-30% methanol+1% triethylamine/dichloromethane. The appropriate fractions were combined and concentrated to give the title compound as a brown solid (1.724 g).

LCMS (Method B): Rt 3.08 mins, MH+ 442 and Rt 3.22 mins, MH+ 456.

Intermediate 39

1,1-Dimethylethyl 4-[4-cyano-1-(phenylsulfonyl)-1H-indazol-6-yl]-1H-indole-1-carboxylate

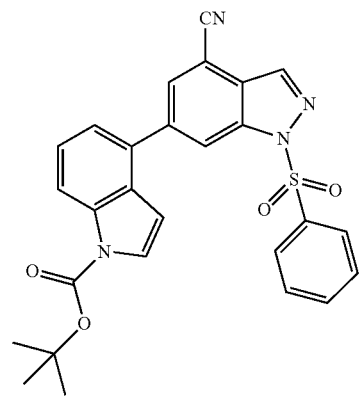 [SMILES: CC(C)(C)OC(=O)n1ccc2c(-c3cc(C#N)c4cnn(S(=O)(=O)c5ccccc5)c4c3)cccc21]

To a round bottomed flask was charged 6-bromo-1-(phenylsulfonyl)-1H-indazole-4-carbonitrile (10 g, 27.6 mmol), 1,1-dimethylethyl 4-(4,4,5,5-tetramethyl-1,3,2-dioxaborolan-2-yl)-1H-indole-1-carboxylate (14.21 g, 41.4 mmol) and potassium phosphate tribasic (17.58 g, 83 mmol). The resulting mixture was treated with 1,4-dioxane (120 ml) and water (12 ml) that had previously been purged with nitrogen. The mixture was then treated with 1'-bis(diphenylphosphino)ferrocene palladium dichloride (1.547 g, 2.76 mmol) and heated

Intermediate 40

6-(1H-Indol-4-yl)-1-(phenylsulfonyl)-4-(1H-tetrazol-5-yl)-1H-indazole

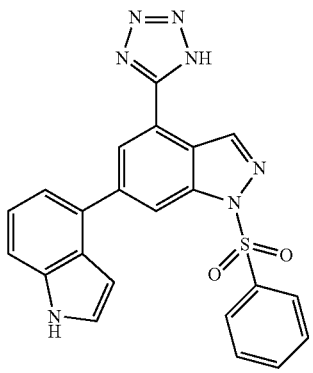 [SMILES: O=S(=O)(c1ccccc1)n1ncc2c(-c3nnn[nH]3)cc(-c3cccc4[nH]ccc34)cc21]

To a round bottomed flask was charged 1,1-dimethylethyl 4-[4-cyano-1-(phenylsulfonyl)-1H-indazol-6-yl]-1H-indole-1-carboxylate (6.16 g, 12.36 mmol) followed by toluene (250 ml). The resulting solution was then treated with dibutyl(oxo)stannane (0.554 g, 2.224 mmol) and trimethylsilyl azide (3.3 ml, 25.09 mmol). The mixture was heated to 90° C. overnight, then cooled to room temperature and concentrated in vacuo. The residue was dissolved in methanol/DCM and preabsorbed onto silica (20 g). This was placed on the top of a silica cartridge (750 g) and eluted with 0-40% methanol in DCM. The product containing fraction was evaporated to give a green foam which was placed into acetic acid (50 ml) and the mixture heated to 100° C. overnight. The mixture was heated for a further 24 h, then cooled to room temperature and water (250 ml) added. A precipitate formed, which was collected by filtration and air dried over the weekend to give the title compound as a pale grey solid (1.8 g).

LCMS (Method A): Rt 1.07 min, MH− 440.

An off white precipitate had formed in the filtrate, which was collected by filtration and dried in a vacuum oven at 45° C. overnight to afford a further quantity of the title compound as an off white solid (454 mg).

LCMS (Method A): Rt 1.07 mins, MH− 440.

to reflux, under nitrogen for 2 h. Additional 1′-bis(diphenylphosphino)ferrocene palladium dichloride (1.547 g, 2.76 mmol) was added and the mixture heated at reflux for a further 1 h. The hot reaction mixture was filtered through Celite, washed well with chloroform and the filtrate concentrated in vacuo. The residue was dissolved in DCM/cyclohexane (1:1, 50 ml) and purified by column chromatography on silica (750 g cartridge), eluting with 0-40% ethyl acetate/cyclohexane. The pure fractions were combined and concentrated to give the title compound as a yellow solid (6.16 g).

LCMS (Method A): Rt 1.50 mins, MH+ 499.

Intermediate 41

6-Bromo-4-(5-methyl-1,3,4-oxadiazol-2-yl)-1-[(4-methylphenyl)sulfonyl]-1H-indazole

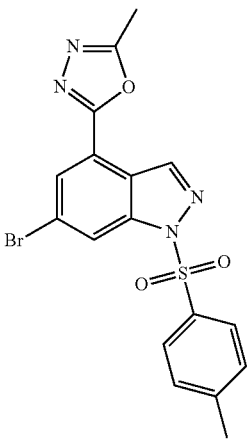 [SMILES: Cc1ccc(S(=O)(=O)n2ncc3c(-c4nnc(C)o4)cc(Br)cc32)cc1]

A stirred mixture of 6-Bromo-1-[(4-methylphenyl)sulphonyl]-4-(1H-tetrazol-5-yl)-1H-indazole (300 mg, 0.615 mmol) and acetyl chloride (0.722 ml, 10.15 mmol) in toluene (10 ml) were heated under microwave irradiation at 130° C. for 20 mins. The reaction mixture was heated for a further 20 mins at 130° C. then evaporated to dryness. The resultant yellow solid was treated with methanol (10 ml), to give a beige solid and supernatant. The supernatant was pipetted off, the process repeated twice and the resultant solid dried under vacuum to give the title compound as a beige solid (75 mg).

LCMS (Method B): Rt 3.28 mins, MH+ 433/435.

Intermediate 42

1-[(4-Methylphenyl)sulfonyl]-6-(4,4,6,6-tetramethyl-1,3,2-dioxaborinan-2-yl)-1H-indazole-4-carbonitrile

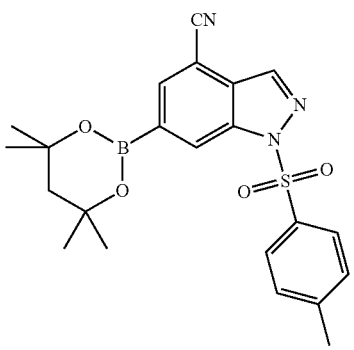 [SMILES: Cc1ccc(S(=O)(=O)n2ncc3c(C#N)cc(B4OC(C)(C)CC(C)(C)O4)cc32)cc1]

6-Bromo-1-[(4-methylphenyl)sulfonyl]-1H-indazole-4-carbonitrile (1 g, 2.66 mmol), 4,4,4′,4′,6,6,6′,6′-octamethyl-2-2′-bi-1,3,2-dioxaborinane (0.899 g, 3.19 mmol), potassium acetate (0.783 g, 7.97 mmol) and 1,1′-bis(diphenylphosphino)ferrocene palladium (0.389 g, 0.532 mmol) were heated under microwave irradiation with 1,4-dioxane (15 ml) at 80° C. for 30 mins. The solvent was removed in vacuo and the residue partitioned between dichloromethane (100 ml) and water (100 ml). The organic layer was collected and the solvent removed in vacuo. The residue was purified by column chromatography on silica gel (100 g cartridge), eluting with 0-50% ethyl actetate in cyclohexane. The resultant residue was azeotroped in toluene and dried on the vacuum line to give the title compound as a cream solid (0.99 g).

LCMS (Method A): Rt 1.53 mins, MH+ 438.

Intermediate 43

N-(2-Chloro-5-{4-(5-methyl-1,3,4-oxadiazol-2-yl)-1-[(4-methylphenyl)sulfonyl]-1H-indazol-6-yl}-3-pyridinyl)methanesulfonamide

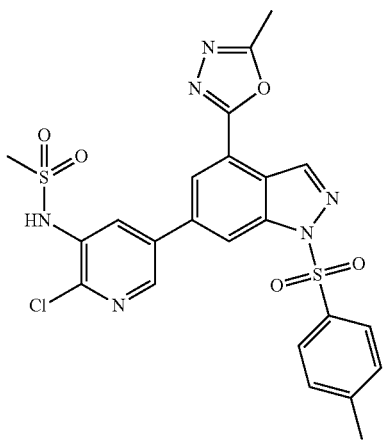 [SMILES: Cc1ccc(S(=O)(=O)n2ncc3c(-c4nnc(C)o4)cc(-c4cnc(Cl)c(NS(C)(=O)=O)c4)cc32)cc1]

N-{2-Chloro-5-[1-[(4-methylphenyl)sulfonyl]-4-(1H-tetrazol-5-yl)-1H-indazol-6-yl]-3-pyridinyl}methanesulfonamide (50 mg, 0.092 mmol) and acetyl chloride (8.48 µl, 0.119 mmol) were placed in toluene (2 ml) and left to stand for 10 mins before heating under microwave irradiation at 120° C. for 40 mins. Additional acetyl chloride (8.48 µl, 0.119 mmol) was added and the reaction mixture heated for a further 40 mins at 120° C. The solvent was removed and the residue purified by column chromatography, on a silica cartridge (20 g) eluting with 0-100% ethyl acetate/cyclohexane followed by 0-20% methanol to give the title compound as a white solid (16 mg).

LCMS (Method A): Rt 1.11 mins, MH+ 559 and [M+CH$_3$CN]+ 600.

Intermediate 44

6-Oxa-9-azaspiro[4.5]decane

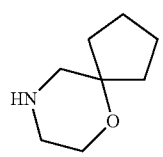

To a of solution 1,1-dimethylethyl 6-oxa-9-azaspiro[4.5]decane-9-carboxylate (200 mg, 0.829 mmol, available from Tyger Scientific Inc) in DCM (3 ml) was added trifluoroacetic acid (TFA) (0.5 ml). The resulting colourless yellow solution was stirred at room temperature for 24 hr. The solvent was evaporated to give the title compound as a grey oil (203 mg).

$^1$NMR (400 MHz, DMSO-d$_6$) δ=8.91 (2H, br. S), 3.73 (2H, dd), 2.98-3.11 (4H, m), 1.52-1.70 (6H, m)

Intermediate 45

9-({5-[6-Bromo-1-(phenylsulfonyl)-1H-indazol-4-yl]-1,3,4-oxadiazol-2-yl}methyl)-6-oxa-9-azaspiro[4.5]decane

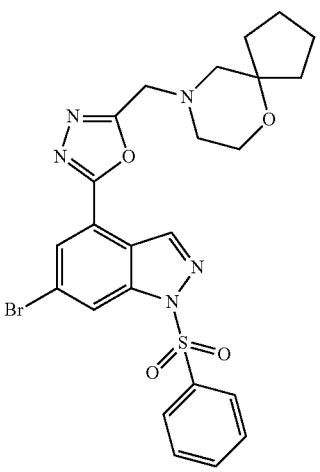 [SMILES: O=S(=O)(c1ccccc1)n1ncc2c(-c3nnc(CN4CCOC5(CCCC5)C4)o3)cc(Br)cc21]

6-Bromo-4-[5-(chloromethyl)-1,3,4-oxadiazol-2-yl]-1-(phenylsulfonyl)-1H-indazole (200 mg, 0.441 mmol) in acetonitrile (2 ml) was treated with 6-oxa-9-azaspiro[4.5]decane (160 mg, 0.793 mmol), DIPEA (0.154 ml, 0.8825 mmol) and sodium iodide (66 mg, 0.44 mmol). The reaction mixture was heated at 70° C. for 5 h, then cooled, diluted with DCM and washed with aqueous HCl. The organic layer was separated using a hydrophobic frit, washed with water and the solvent removed under a stream of nitrogen. The resulting residue was purified by loading onto a silica cartridge (20 g) and eluting with 0-100% ethyl acetate/cyclohexane over 40 mins. The appropriate fractions were combined and evaporated to give the title compound as a yellow solid (74 mg).

LCMS (Method A): Rt 1.32 mins, MH+ 558/560.

The compounds listed below were synthesised using the general method above. For each of the compounds listed below column chromatography was not required.

| Intermediate | Starting Material | Structure | Rt mins | MH+ | Name |
|---|---|---|---|---|---|
| 46 | 2-methyl-morpholine (available from Enamine Ltd) | 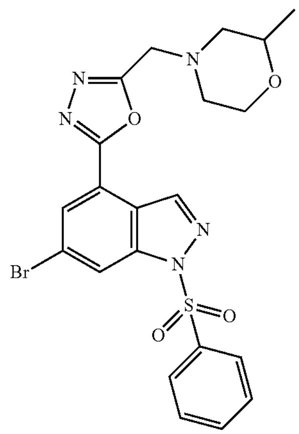 [SMILES: CC1CN(Cc2nnc(-c3cc(Br)cc4c3cnn4S(=O)(=O)c3ccccc3)o2)CCO1] | 1.11 | 518/520 | 6-bromo-4-{5-[(2-methyl-4-morpholinyl)methyl]-1,3,4-oxadiazol-2-yl}-1-(phenylsulfonyl)-1H-indazole |
| 47 | Hexahydro-1,4-oxazepine, hydrochloride (Available from Alfa Aesar) | 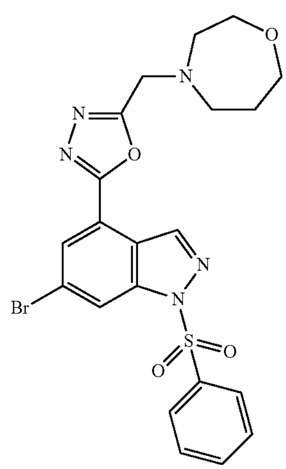 [SMILES: O=S(=O)(c1ccccc1)n1ncc2c(-c3nnc(CN4CCCOCC4)o3)cc(Br)cc21] | 0.89 | 518/520 | 6-bromo-1-(phenylsulfonyl)-4-[5-(tetrahydro-1,4-oxazepin-4(5H)-ylmethyl)-1,3,4-oxadiazol-2-yl]-1H-indazole |

Intermediate 48

6-Bromo-4-(5-{[(3R,5S)-3,5-dimethyl-4-(1-methylethyl)-1-piperazinyl]methyl}-1,3,4-oxadiazol-2-yl)-1-(phenylsulfonyl)-1H-indazole

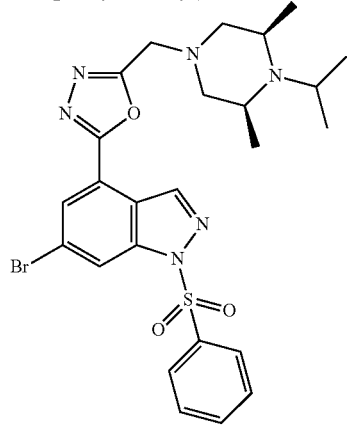 [SMILES: CC(C)N1[C@H](C)CN(Cc2nnc(-c3cc(Br)cc4c3cnn4S(=O)(=O)c3ccccc3)o2)C[C@@H]1C]

6-Bromo-4-[5-(bromomethyl)-1,3,4-oxadiazol-2-yl]-1-(phenylsulfonyl)-1H-indazole (200 mg, 0.441 mmol) in acetonitrile (2 ml) was treated with (2R,6S)-2,6-dimethyl-1-(1-methylethyl)piperazine (138 mg, 0.883 mmol, see *J. Med. Chem.*, 1999, 42, 1123-1144 for literature preparation), DIPEA (0.154 ml, 0.8825 mmol) and sodium iodide (66 mg, 0.44 mmol). The reaction mixture was heated at 70° C. for 5 h. The reaction mixture was then cooled, diluted with DCM and washed with an aqueous 2M HCl solution (5 ml). The organic layer was separated using a hydrophobic frit, washed with water and the solvent removed under a stream of nitrogen to give the title compound as a brown oil.

LCMS (Method A): Rt 0.80 mins, MH+ 573/575.

The compounds listed below were synthesised using the general method above.

| Intermediate | Starting Material | Structure | Rt mins | MH+ | Name |
|---|---|---|---|---|---|
| 49 | thiomorpholine, 1,1-dioxide (available) from Sigma-Aldrich) | 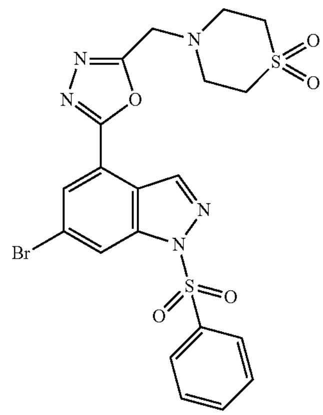 [SMILES: O=S1(=O)CCN(Cc2nnc(-c3cc(Br)cc4c3cnn4S(=O)(=O)c3ccccc3)o2)CC1] | 1.07 | 552/554 | 6-bromo-4-{5-[(1,1-dioxido-4-thiomorpholinyl)methyl]-1,3,4-oxadiazol-2-yl}-1-(phenylsulfonyl)-1H-indazole |
| 50 | 2-Ethylmorpholine (available from Bio-Farma UK) | 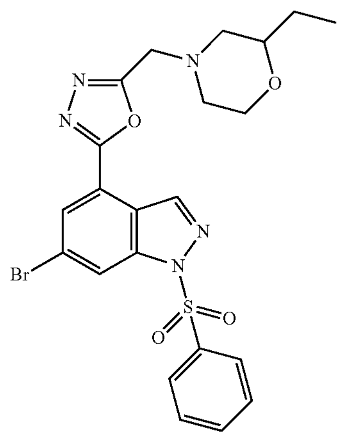 [SMILES: CCC1CN(Cc2nnc(-c3cc(Br)cc4c3cnn4S(=O)(=O)c3ccccc3)o2)CCO1] | 1.21 | 532/534 | 6-bromo-4-{5-[(2-ethyl-4-morpholinyl)methyl]-1,3,4-oxadiazol-2-yl}-1-(phenylsulfonyl)-1H-indazole |

Intermediate 51

N-{[5-(6-Bromo-1H-indazol-4-yl)-1,3,4-oxadiazol-2-yl]methyl}-3-(4-morpholinyl)-1-propanamine

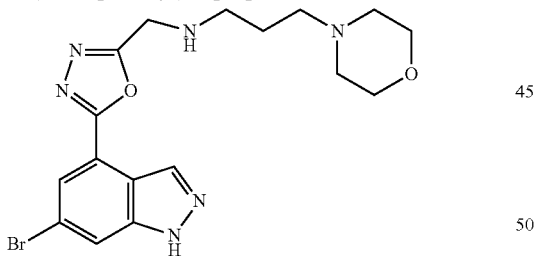

6-Bromo-4-[5-(chloromethyl)-1,3,4-oxadiazol-2-yl]-1-(phenylsulfonyl)-1H-indazole (300 mg, 0.661 mmol) and sodium iodide (99 mg, 0.661 mmol) were weighed into a round-bottomed flask and dissolved in acetonitrile (2 ml) before [3-(4-morpholinyl)propyl]amine (191 mg, 1.322 mmol, available from Sigma-Aldrich) and DIPEA (0.231 ml, 1.322 mmol) were added. The mixture was heated to 70° C. for 2 h, then cooled and the solvent removed under a stream of nitrogen. The crude residue was dissolved in DCM/MeOH (1:1) and preabsorbed onto silica which was then added to the top of a 20 g silica cartridge that was subsequently eluted with 0-15% MeOH (+1% triethylamine)/DCM over 20 mins. The appropriate fractions were combined and the solvent removed in vacuo to give the title compound as a yellow oily solid (328 mg).

LCMS (Method A): Rt 0.35 mins, MH+ 421/423.

Intermediate 52

N-(2-(Methyloxy)-5-{1-(phenylsulfonyl)-4-[5-(tetrahydro-1,4-oxazepin-4(5H)-ylmethyl)-1,3,4-oxadiazol-2-yl]-1H-indazol-6-yl}-3-pyridinyl)methanesulfonamide

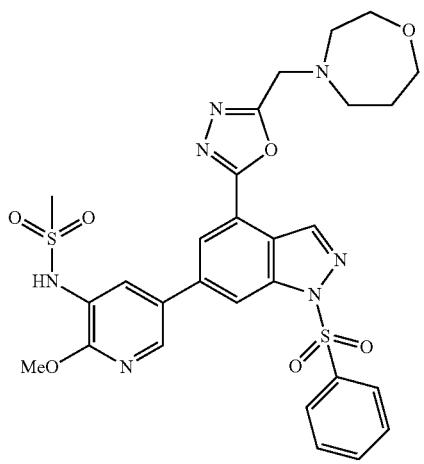 [SMILES: COc1ncc(-c2cc(-c3nnc(CN4CCCOCC4)o3)c3cnn(S(=O)(=O)c4ccccc4)c3c2)cc1NS(C)(=O)=O]

6-Bromo-1-(phenylsulfonyl)-4-[5-(tetrahydro-1,4-oxazepin-4(5H)-ylmethyl)-1,3,4-oxadiazol-2-yl]-1H-indazole (279 mg, 0.538 mmol) was dissolved in 1,4-dioxane (5 ml)

and half of the resulting solution was charged to a reaction vessel. N-[2-(methyloxy)-5-(4,4,5,5-tetramethyl-1,3,2-dioxaborolan-2-yl)-3-pyridinyl]methanesulfonamide (114 mg, 0.347 mmol), 1,1'-bis(diphenylphosphino)ferrocene palladium dichloride (39.5 mg, 0.054 mmol), potassium phosphate tribasic (171.5 mg, 0.808 mmol) and water (0.25 ml) were added. The reaction mixture was heated at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The residue was purified by preparative HPLC using the following method:

| Column Packing | Waters Sunfire c18 |
| --- | --- |
| Column Particle Size | 5.0 µm |
| Column Dimensions | 100 × 19 mm ID |
| Solvent A | 0.1% v/v formic acid in water |
| Solvent B | MeCN + 0.1% v/v of formic acid |
| Temperature | ambient |
| Flow Rate | 20 ml/min |
| Injection Volume | 500 µL |
| Injection Vehicle | 1:1 DMSO/MeCN |
| UV detection | Diode-array 210-400 nm (averaged) |
| MS detection | Electrospray, +ve/ −ve switching, 100-1000 amu, centroid mode |
| MS scan function | Electrospray, +ve/ −ve switching, centroid mode |

| Time (mins) | % A | % B | Flow rate (ml/min) |
| --- | --- | --- | --- |
| 0 | 75 | 25 | 20 |
| 1 | 75 | 25 | 20 |
| 15 | 68 | 32 | 20 |
| 15.5 | 1 | 99 | 20 |
| 18 | 1 | 99 | 20 |
| 18.5 | 75 | 25 | 20 |
| 20 | 75 | 25 | 20 |

The appropriate fractions were dried down to give the title compound as a cream solid (50 mg).

LCMS (Method A): Rt 0.78, MH+ 640

The compound listed below was synthesised using the general method above.

| Intermediate | Starting Material | Structure | Rt mins | MH+ | Name |
| --- | --- | --- | --- | --- | --- |
| 53 | 4-(4,4,5,5-tetramethyl-1,3,2-dioxaborolan-2-yl)-1H-indole (85 mg, 0.350 mmol) | 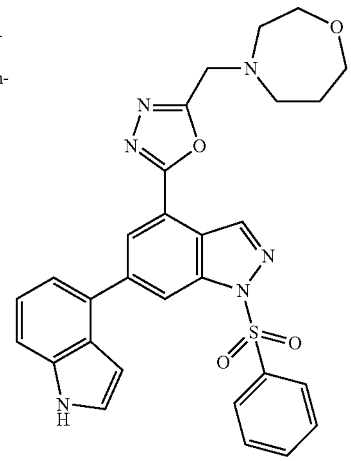 | 0.88 | 555 | 6-(1H-indol-4-yl)-1-(phenylsulfonyl)-4-[5-(tetrahydro-1,4-oxazepin-4(5H)-ylmethyl)-1,3,4-oxadiazol-2-yl]-1H-indazole |

Intermediate 54

1-[({5-[6-Bromo-1-(phenylsulfonyl)-1H-indazol-4-yl]-1,3,4-oxadiazol-2-yl}methyl)amino]-3-(4-morpholinyl)-2-propanol

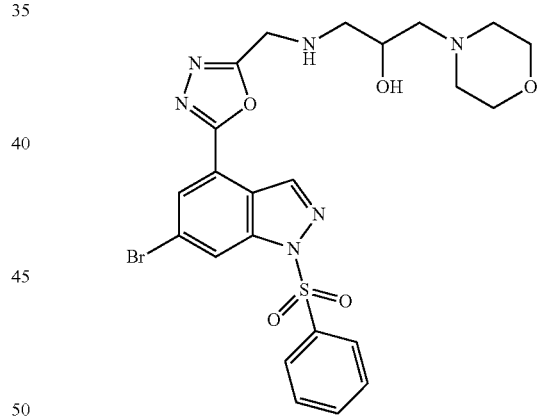

6-Bromo-4-[5-(chloromethyl)-1,3,4-oxadiazol-2-yl]-1-(phenylsulfonyl)-1H-indazole (300 mg, 0.661 mmol) and sodium iodide (138 mg, 0.921 mmol) were weighed into a round-bottomed flask and dissolved in acetonitrile (2 ml) before 1-amino-3-morpholin-4-ylpropan-2-ol (212 mg, 1.322 mmol, available from Enamine Ltd) and DIPEA (0.231 ml, 1.322 mmol) were added. The mixture was heated to 70° C. for 2 h, then cooled, diluted with DCM and washed with 2 M aqueous HCl (5 ml). The organic layer was separated with a hydrophobic frit and the aqueous layer was neutralised to pH 7 by addition of 2M NaOH resulting in the formation of a solid precipitate. This was filtered off under vacuum and dried in air for 2 h to give the title compound as a cream solid (220 mg).

LCMS (Method A): Rt 0.63 mins, MH+ 577/579.

Intermediate 55

N-[5-[4-{5-[(8aS)-Hexahydropyrrolo[1,2-a]pyrazin-2(1H)-ylmethyl]-1,3,4-oxadiazol-2-yl}-1-(phenylsulfonyl)-1H-indazol-6-yl]-2-(methyloxy)-3-pyridinyl]methanesulfonamide

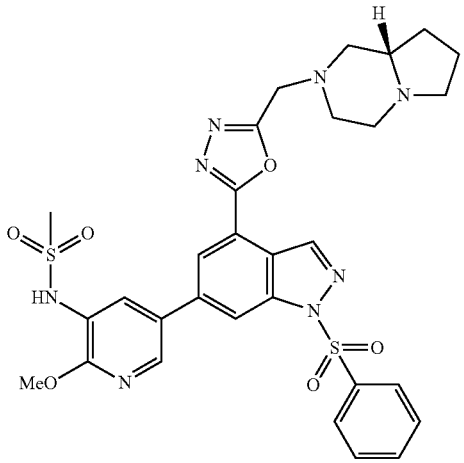 [SMILES: COc1ncc(-c2cc(-c3nnc(CN4CCN5CCC[C@H]5C4)o3)c3cnn(S(=O)(=O)c4ccccc4)c3c2)cc1NS(C)(=O)=O]

To a solution of 6-bromo-4-{5-[(8aS)-hexahydropyrrolo[1,2-a]pyrazin-2(1H)-ylmethyl]-1,3,4-oxadiazol-2-yl}-1-(phenylsulfonyl)-1H-indazole (100 mg, 0.184 mmol) was added N-[2-(methyloxy)-5-(4,4,5,5-tetramethyl-1,3,2-dioxaborolan-2-yl)-3-pyridinyl]methanesulfonamide (72.5 mg, 0.221 mmol), 1,1'-bis(diphenylphosphino)ferrocene palladium dichloride (36 mg, 0.049 mmol) and potassium phosphate tribasic (126 mg, 0.594 mmol). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The residue was dissolved in DCM and added to the top of a 10 g silica SPE cartridge that was subsequently eluted with 0-15% MeOH/DCM over 20 mins. The product-containing fractions were combined and the solvent removed in vacuo to give the title compound as an orange oil (95 mg).

LCMS (Method A). Product Rt 0.69, MH+ 665.

The compound listed below was synthesised using the general method above.

| Intermediate | Starting Material | Structure | Rt mins | MH+ | Name |
|---|---|---|---|---|---|
| 56 | 2,4-difluoro-N-[2-(methyloxy)-5-(4,4,5,5-tetramethyl-1,3,2-dioxaborolan-2-yl)-3-pyridinyl]benzenesulfonamide | 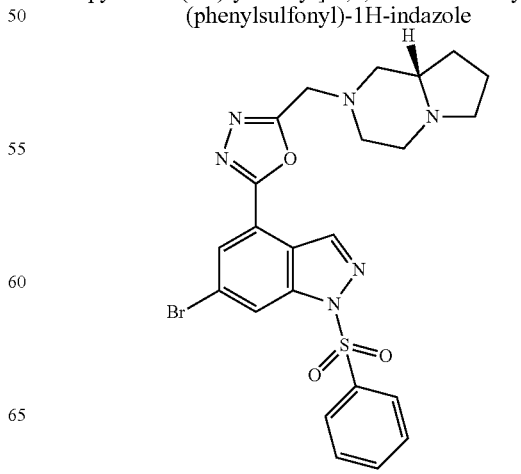 | 0.82 | 763 | 2,4-difluoro-N-[5-[4-{5-[(8aS)-hexahydropyrrolo[1,2-a]pyrazin-2(1H)-ylmethyl]-1,3,4-oxadiazol-2-yl}-1-(phenylsulfonyl)-1H-indazol-6-yl]-2-(methyloxy)-3-pyridinyl]benzenesulfonamide |

Intermediate 57

6-Bromo-4-{5-[(8aS)-hexahydropyrrolo[1,2-a]pyrazin-2(1H)-ylmethyl]-1,3,4-oxadiazol-2-yl}-1-(phenylsulfonyl)-1H-indazole 6-Bromo-4-[5-(chloromethyl)-1,3,4-oxadiazol-2-yl]-1-(phenylsulfonyl)-1H-indazole (300 mg, 0.661 mmol) and sodium iodide (99 mg, 0.661 mmol) were weighed into a round-bottomed flask and dissolved in acetonitrile (2 ml) before (S)-1,4-diazabicyclo[4.3.0]nonane (167 mg, 1.322 mmol, available from ABCR GmbH & CO. KG) and DIPEA (0.231 ml, 1.322 mmol) were added. The mixture was heated to 70° C. for 2 h. The mixture was cooled, diluted with DCM and washed with 2 M aqueous HCl (2 ml). The organic layer was separated by hydrophobic frit. The aqueous extracts were combined and neutralised to pH 7 with NaOH then extracted with more DCM (2×10 ml) which was combined with the other organic extracts and evaporated under a stream of nitrogen to give an orange oil. This was dissolved in DCM and loaded onto the top of a 10 g silica cartridge that was subsequently eluted with 0-15% MeOH (+1% triethylamine)/DCM over 15 mins. The appropriate fractions were combined and the solvent removed in vacuo to give the title compound as a cream solid (220 mg).

LCMS (Method A): Rt=0.73, MH+ 543/545.

Intermediate 58

5-[4-(5-{[(2R,6S)-2,6-Dimethyl-4-morpholinyl]methyl}-1,3,4-oxadiazol-2-yl)-1-methyl-1H-indazol-6-yl]-2-(methyloxy)-3-pyridinamine

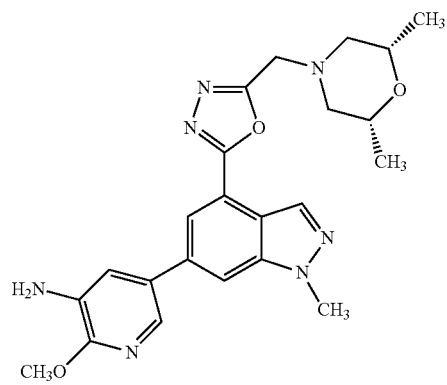

6-Bromo-4-(5-{[(2R,6S)-2,6-dimethyl-4-morpholinyl]methyl}-1,3,4-oxadiazol-2-yl)-1-methyl-1H-indazole (200 mg, 0.492 mmol), 2-(methyloxy)-5-(4,4,5,5-tetramethyl-1,3,2-dioxaborolan-2-yl)-3-pyridinamine (123 mg, 0.492 mmol), 1,1'-bis(diphenylphosphino)ferrocene palladium dichloride (72.0 mg, 0.098 mmol) and tripotassium phosphate (313 mg, 1.477 mmol) were added to 1,4-dioxane (4 ml) and water (1 ml) then heated under microwave irradiation for 20 mins at 100° C. The solvent was removed under nitrogen and the crude residue purified by chromatography (20 g Si cartridge, gradient: 0-100% EtOAc/DCM+0-20% MeOH). The appropriate fractions were combined and the solvent was removed to give the title compound as a brown solid (130 mg).

LCMS (Method A): Rt 0.76 mins, MH+ 450.

Intermediate 59

Methyl 6-bromo-1H-indazole-4-carboxylate

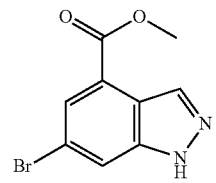

Concentrated hydrochloric acid (46.9 ml, 1543 mmol) was added to a stirred suspension of 6-bromo-1H-indazole-4-carboxylic acid (4.65 g, 19.29 mmol, available from Sinova) in methanol (100 ml) and the reaction mixture was heated to 70° C. for 18 h. The reaction mixture was allowed to cool to RT resulting in the precipitation of a solid. The mixture was cooled in ice and the yellow precipitate filtered off and washed with methanol to give the title compound as a yellow solid (2.54 g).

LCMS (Method A): Rt=0.90 mins, MH+ 255/257.

Intermediate 60

Methyl 6-bromo-1-[(4-methylphenyl)sulfonyl]-1H-indazole-4-carboxylate

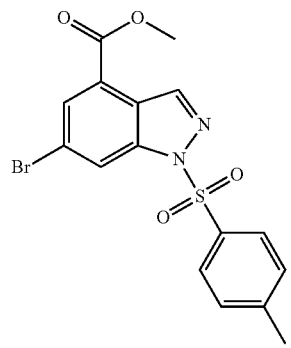 [SMILES: COC(=O)c1cc(Br)cc2c1cnn2S(=O)(=O)c1ccc(C)cc1]

Sodium hydride (1.289 g, 32.2 mmol) was added portionwise to a solution of methyl 6-bromo-1H-indazole-4-carboxylate (4.11 g, 16.11 mmol) in N,N-dimethylformamide (50 ml) at 0° C. The dark orange mixture was stirred at 0° C. for 10 mins, then treated with 4-methylbenzenesulfonyl chloride (3.38 g, 17.72 mmol). The resultant pale cream mixture was stirred for 30 mins at 0° C. then poured into water (1000 ml). The cream precipitate was filtered off under vacuum and dried in the vacuum oven at 50° C. for 18 h to give the title compound as a yellow solid (5.51 g).

LCMS (Method B): Rt 3.57 mins, MH+ 409/411.

Intermediate 61

6-Bromo-1-[(4-methylphenyl)sulfonyl]-1H-indazole-4-carboxylic acid

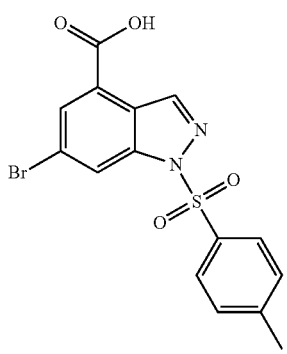 [SMILES: Cc1ccc(S(=O)(=O)n2ncc3c(C(=O)O)cc(Br)cc32)cc1]

Lithium hydroxide (0.774 g, 32.3 mmol) was added to a stirred suspension of methyl 6-bromo-1-[(4-methylphenyl)sulfonyl]-1H-indazole-4-carboxylate (5.51 g, 13.46 mmol) in tetrahydrofuran (50 ml) and water (15 ml) and the reaction mixture was stirred at RT for 1 h. The reaction mixture was poured onto 2N HCl (800 ml) with stirring. The precipitate formed was filtered off under vacuum and dried at 50° C. in a vacuum oven for 18 h to give the title compound as a yellow solid (3.5 g).

LCMS (Method B): Rt 3.10 mins, MH+ 395/397.

Intermediate 62

2-[(2R,6S)-2,6-Dimethyl-4-morpholinyl]acetohydrazide

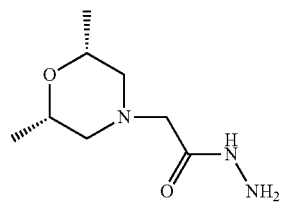

Methyl [(2R,6S)-2,6-dimethyl-4-morpholinyl]acetate (5.05 g, 27.0 mmol, see Journal of Fluorine Chemistry (1998) 193-201 for literature preparation) was dissolved in methanol (20 ml) and hydrazine hydrate (2.013 ml, 27.0 mmol) added. The reaction mixture was heated to 70° C. for 18 h. The solvent was partially concentrated in vacuo to remove the methanol and extracted with ethyl acetate (3×20 ml). The combined organic layers were dried and concentrated to afford the title compound as a yellow solid (3.35 g).

$^1$H NMR (400 MHz, chloroform-d) δ=8.06 (1H, br. S.,) 3.75-3.98 (2H, m), 3.60-3.71 (2H, m), 1.88-1.96 (2H, m), 1.15 (6H, d)

Intermediate 63

6-Bromo-N'-{[(2R,6S)-2,6-dimethyl-4-morpholinyl]acetyl}-1-[(4-methylphenyl)sulfonyl]-1H-indazole-4-carbohydrazide

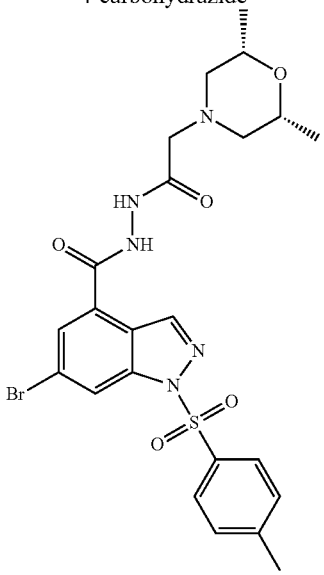

6-Bromo-1-[(4-methylphenyl)sulfonyl]-1H-indazole-4-carboxylic acid (1.5 g, 3.80 mmol) was suspended in thionyl chloride (8.31 ml, 114 mmol) and heated to 100° C. for 30 mins. The thionyl chloride was removed in vacuo and excess aziotroped with dry diethyl ether to give a yellow solid. This was dissolved in dry tetrahydrofuran (40 ml) and 2-[(2R,6S)-2,6-dimethyl-4-morpholinyl]acetohydrazide (1.066 g, 5.69 mmol) and DIPEA (2.65 ml, 15.18 mmol) added. The reaction mixture was heated to 60° C. for 20 mins. The solvent was removed in vacuo and the residue partitioned between dichloromethane (50 ml) and water (50 ml). The layers were separated and the organic concentrated in vacuo to give a yellow foam. This was purified by column chromatography, loading in dichloromethane onto a silica cartridge (50 g), eluting with 0-100% ethyl acetate-cyclohexane over 30 mins. The appropriate fractions were combined and evaporated in vacuo to give the title compound as a yellow solid (950 mg).

LCMS (Method B): Rt 2.06 mins, MH+ 564/566.

Intermediate 64

6-Bromo-4-(5-{[(2R,6S)-2,6-dimethyl-4-morpholinyl]methyl}-1,3,4-oxadiazol-2-yl)-1-[(4-methylphenyl)sulfonyl]-1H-indazole

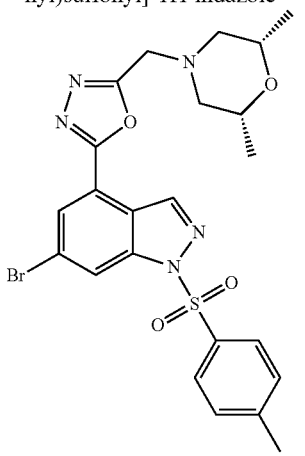

6-Bromo-N'-{[(2R,6S)-2,6-dimethyl-4-morpholinyl] acetyl}-1-[(4-methylphenyl)sulfonyl]-1H-indazole-4-carbohydrazide (950 mg, 1.683 mmol) was dried over phosphorus pentoxide in a desicator overnight. 6-bromo-N'-{[(2R,6S)-2, 6-dimethyl-4-morpholinyl]acetyl}-1-[(4-methylphenyl)sulfonyl]-1H-indazole-4-carbohydrazide (950 mg, 1.683 mmol) and methoxycarbonylsulfamoyl)triethylammonium hydroxide (602 mg, 2.52 mmol) were suspended in anhydrous tetrahydrofuran (20 ml) and heated to 75° C. for 2 h. The solvent was removed in vacuo and the residue partitioned between dichloromethane (15 ml) and saturated sodium bicarbonate solution (15 ml). The layers were separated (hydrophobic frit), the aqueous washed with further dichloromethane (5 ml) and the combined organics concentrated in vacuo to give a yellow solid. This was purified by column chromatography, loading in dichloromethane onto a silica cartridge 50 g, using a 0-100% ethyl acetate-cyclohexane over 40 mins. The appropriate fractions were combined and evaporated in vacuo to give the title compound as a white solid (680 mg).

LCMS (Method A): Rt 1.25 mins, MH+ 546/548.

Intermediate 65

5-{4-(5-{[(2R,6S)-2,6-Dimethyl-4-morpholinyl] methyl}-1,3,4-oxadiazol-2-yl)-1-[(4-methylphenyl) sulfonyl]-1H-indazol-6-yl}-2-(methyloxy)-3-pyridinamine

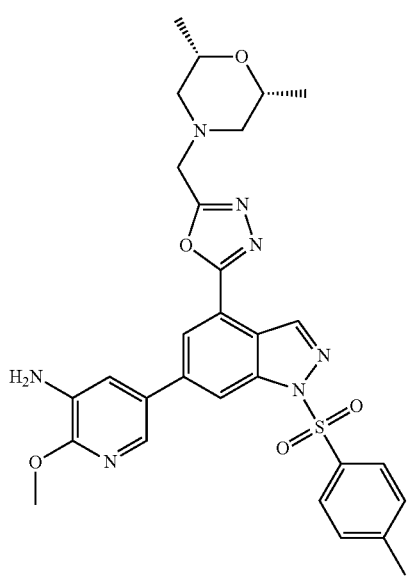 [SMILES: COc1ncc(-c2cc(-c3nnc(CN4C[C@@H](C)O[C@@H](C)C4)o3)c3cnn(S(=O)(=O)c4ccc(C)cc4)c3c2)cc1N]

6-Bromo-4-(5-{[(2R,6S)-2,6-dimethyl-4-morpholinyl] methyl}-1,3,4-oxadiazol-2-yl)-1-[(4-methylphenyl)sulfonyl]-1H-indazole (680 mg, 1.244 mmol) was dissolved in 1,4-dioxane (15 ml) and water (1.5 ml). 2-(methyloxy)-5-(4, 4,5,5-tetramethyl-1,3,2-dioxaborolan-2-yl)-3-pyridinamine (311 mg, 1.244 mmol), bis(diphenylphosphino)ferrocene palladium dichloride (182 mg, 0.249 mmol) and tripotassium phosphate monohydrate (860 mg, 3.73 mmol) were added and the reaction mixture heated at 80° C. for 2 h. 2-(methoxy)-5-(4,4,5,5-tetramethyl-1,3,2-dioxaborolan-2-yl)-3-pyridinamine (0.1 eq, 31 mg) was added and the reaction mixture heated at 80° C. for a further 18 h. The solvent was removed in vacuo and the residue partitioned between DCM (50 ml) and water (50 ml). The layers were separated (hydrophobic frit), the organic concentrated in vacuo and the residue purified by column chromatography, loading in dichloromethane and purified on a silica cartridge (100 g), using a 0-30% methanol(+1% triethylamine)-dichloromethane over 40 mins. The appropriate fractions were combined and concentrated in vacuo to a brown gum. This was purified again by column chromatography, loading in dichloromethane and purified on a silica cartridge (50 g) using a 0-100% ethyl acetate-cyclohexane+0-20% methanol over 40 mins. The appropriate fractions were combined and evaporated in vacuo to give the title compound as a yellow solid (320 mg).

LCMS (Method A): Rt 1.10 mins, MH+ 590.

Intermediate 66

Methyl 6-bromo-1-methyl-1H-indazole-4-carboxylate

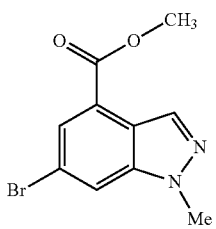

Sodium hydride (0.690 g, 17.25 mmol) was added to a 250 ml round bottom flask and tetrahydrofuran (THF) (60 mL) was added. The mixture was stirred for 10 minutes in an ice bath then methyl 6-bromo-1H-indazole-4-carboxylate (4 g, 15.68 mmol) was added portionwise and stirred until no further effervescence was seen (10 minutes). Iodomethane (5 mL, 80 mmol) was then added to the flask and the mixture stirred at 0° C. for 1 hour, then the ice bath was removed and a water bath at room temperature used and the reaction left overnight (30 hours). The solvent was removed in vacuo to give a yellow cream. The crude was partitioned between water (20 mL) and DCM (20 mL) then the solvent was removed in vacuo to give a yellow solid (2.2 g) This was purified by chromatography on silica using a 50 g Si cartridge and run on Flash Master 11 using a gradient of 0-100% EtOAc/cyclohexane over 30 min. The resultant fractions were analysed by HPLC and fractions containing the two regioisomers were independently combined and the solvent removed in vacuo. The title compound methyl 6-bromo-1-methyl-1H-indazole-4-carboxylate was isolated as white solid (730 mg).

LCMS (Method A): $R_t$ 1.03 min, MH+ 270. Regiochemistry confirmed by NMR.

Methyl 6-bromo-2-methyl-1H-indazole-4-carboxylate was also isolated as white solid (750 mg).

LCMS (Method A): $R_t$ 0.97 min, MH+ 270. Regiochemistry confirmed by NMR.

Intermediate 67

6-Bromo-1-methyl-1H-indazole-4-carboxylic acid

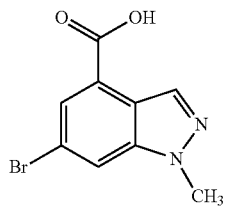

Lithium hydroxide (156 mg, 6.51 mmol) was added to a stirred suspension of methyl 6-bromo-1-methyl-1H-indazole-4-carboxylate (730 mg, 2.71 mmol) in tetrahydrofuran (THF) (25 ml) and water (5 ml) and the reaction mixture was stirred at room temperature for 1 h. During this time the cream suspension turned to a pale brown solution. The reaction mixture was poured onto 2N HCl (100 ml) with stirring. The precipitate formed was filtered off under vacuum and dried at 50° C. in a vacuum oven for 18 h to give the title compound as a white solid (480 mg).

LCMS (Method A) $R_t$ 0.79 min, MH+ 255.

Intermediate 68

6-Bromo-N'-{[(2R,6S)-2,6-dimethyl-4-morpholinyl]acetyl}-1-methyl-1H-indazole-4-carbohydrazide

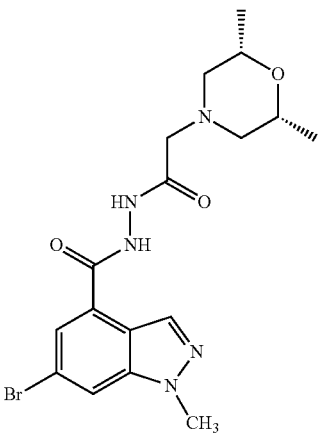 [SMILES: C[C@@H]1CN(CC(=O)NNC(=O)c2cc(Br)cc3c2cnn3C)C[C@H](C)O1]

6-Bromo-1-methyl-1H-indazole-4-carboxylic acid (480 mg, 1.882 mmol) was suspended in thionyl chloride (4.12 ml, 56.5 mmol) and heated to 100° C. for 30 mins. The thionyl chloride was removed in vacuo and excess azeotroped with dry diethyl ether to give a yellow solid. This was dissolved in dry tetrahydrofuran (THF) (15 ml) and 2-[(2R,6S)-2,6-dimethyl-4-morpholinyl]acetohydrazide (529 mg, 2.82 mmol) and DIPEA (1.315 ml, 7.53 mmol) were added. The reaction mixture was heated to 60° C. for 20 mins. Solvent was removed in vacuo and the residue partitioned between dichloromethane (15 ml) and water (15 ml). The layers were separated and the organic phase concentrated in vacuo to give a green solid which was purified by column chromatography, loading in dichloromethane and purified on Flashmaster II silica (Si) 20 g using a 0-100% ethyl acetate-cyclohexane+0-20% MeOH over 30 mins. The appropriate fractions were combined and evaporated in vacuo to afford the title compound as a yellow solid (485 mg). LCMS (Method A) Rt 0.49 min, MH+ 424.

Intermediate 69

6-Chloro-4-iodo-1-(phenylsulfonyl)-1H-indazole

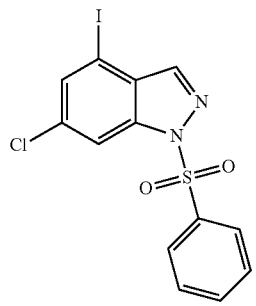 [SMILES: O=S(=O)(c1ccccc1)n1ncc2c(I)cc(Cl)cc21]

Method A

6-Chloro-4-iodo-1H-indazole (30 g, 108 mmol, available from Sinova) was dissolved in N,N-dimethylformamide (300 ml) and cooled in an ice water bath under nitrogen. Sodium hydride (5.17 g, 129 mmol) was added portionwise, maintaining the temperature below 10° C. After full addition the reaction mixture was stirred for 20 mins then benzenesulfonyl chloride (16.5 ml, 129 mmol) was added dropwise over 15 mins. The reaction was left to warm to RT overnight then poured onto ice water (2 L). The precipitated product was collected by filtration, washed with water (ca. 400 ml) and dried in a vacuum oven overnight to give the title compound (43.3 g).

LCMS (Method A): Rt 1.38 mins, MH+ 419.

Method B

To a stirred solution of 6-chloro-4-iodo-1H-indazole (633.6 g) in THF (5.7 L) was added sodium hydroxide (227.4 g) followed by tetra-n-butylammonium bisulphate (38.0 g) at 20±3° C., under a nitrogen atmosphere. The mixture was stirred at 20±3° C. for 1 h 3 min, then benzenesulphonyl chloride (319 ml) was added at such a rate as to maintain the internal temperature at <25° C. Residual benzenesulphonyl chloride was rinsed into the vessel with THF (630 mL), then the mixture stirred for 1 h 10 min. The mixture was cooled to <5° C. and water (12.7 L) added at such a rate as to maintain internal temperature below 5±3° C., then the mixture stirred at 0-5° C. for 1 h 20 min. The solids were collected by vacuum filtration, washed with water (2×1.9 L), sucked dry then further dried under vacuum with a nitrogen bleed at 40° C.±3° C. overnight to give the title compound (780.8 g).

LCMS (Method C): Rt 6.28 min, MH+ 419.

Method C

All weights, volumes and equivalents are relative to 6-chloro-4-iodo-1H-indazole.

6-Chloro-4-iodo-1H-indazole (1.0 eq., 1 wt, 50 g), sodium hydroxide (2.25 eq., 0.324 wt, 16.16 g) and tetrabutylammonium hydrogensulphate (0.05 eq., 0.061 wt, 3.05 g) are stirred in THF (9.5 vols, 475 ml) at 20±3° C. under a nitrogen atmosphere for 1 hr. The mixture is cooled to 15±3° C. and benzenesulfonyl chloride (1.10 eq., 0.51 vols, 25.5 ml) was added dropwise over 20 mins maintaining the reaction temperature at <25° C. and is washed in with THF (0.5 vols, 25 ml). The resulting mixture is then stirred under a nitrogen atmosphere at 20±3° C. for at least 1 hr before checking for completion by HPLC. The reaction mixture is then added to 0.25 M hydrochloric acid solution (18 vols, 900 ml) cooled to 0±3° C. over 15 minutes maintaining the temperature of the aqueous suspension at <20° C. This is washed in with 0.25M hydrochloric acid solution (2 vols, 100 ml). The resulting orange suspension is then stirred at 2±3° C. for at least 1 hr. The solid is filtered, washed with water (2×3 vols, 2×150 ml) and sucked dry for 20 mins, then dried under high vacuum at 40° C. (±3° C.) to constant probe temperature to afford 6-chloro-4-iodo-1-(phenylsulfonyl)-1H-indazole as an orange solid.

Intermediate 70

6-Chloro-1-(phenylsulfonyl)-4-(trimethylstannanyl)-1H-indazole

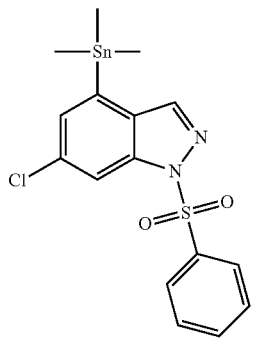 [SMILES: [CH3][Sn]([CH3])([CH3])[c]1cc(Cl)cc2c1cnn2S(=O)(=O)c1ccccc1]

6-Chloro-4-iodo-1-(phenylsulfonyl)-1H-indazole (30 g, 71.7 mmol), tetrakis(triphenylphosphine)palladium(0) (8.1 g, 7.01 mmol), xylene (200 ml), triethylamine (19.98 ml, 143 mmol) and hexamethylditin (21.8 ml, 105 mmol) were heated at 150° C. for 2 h. The reaction mixture was filtered hot through Celite, washing with further xylene and the solvent was evaporated in vacuo. The residue was triturated with cyclohexane and the precipitate collected by filtration and dried in a vacuum oven to give the title compound (14.4 g).

LCMS (Method A): Rt 1.51 mins, MH+ 457.

Intermediate 71a

Ethyl 2-[6-chloro-1-(phenylsulfonyl)-1H-indazol-4-yl]-1,3-oxazole-5-carboxylate

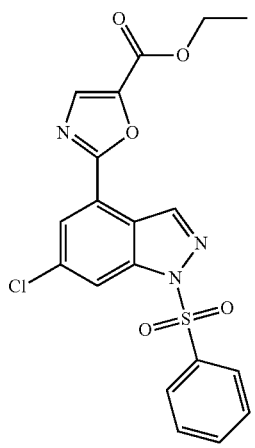 [SMILES: CCOC(=O)c1cnc(-c2cc(Cl)cc3c2cnn3S(=O)(=O)c2ccccc2)o1]

In 4 batches, tetrakis(triphenylphosphine)palladium(0) (3.37 g, 2.92 mmol), ethyl 2-chloro-1,3-oxazole-5-carboxylate (6.65 g, 37.9 mmol, available from Apollo Scientific) and copper(I) iodide (1.11 g, 5.83 mmol) were added to a solution of 6-chloro-1-(phenylsulfonyl)-4-(trimethylstannanyl)-1H-indazole (13.28 g, 29.2 mmol) in N,N-dimethylformamide (52 ml). In 3 of the batches, tetrakis(triphenylphosphine) palladium(0) (1.03 g, 0.89 mmol), ethyl 2-chloro-1,3-oxazole-5-carboxylate (2.03 g, 11.59 mmol) and copper(I) iodide (0.34 g, 1.78 mmol) were added to a solution of 6-chloro-1-(phenylsulfonyl)-4-(trimethylstannanyl)-1H-indazole (4.06 g, 8.91 mmol) in N,N-dimethylformamide (16 ml). In the fourth batch, tetrakis(triphenylphosphine)palladium(0) (0.28 g, 0.24 mmol), ethyl 2-chloro-1,3-oxazole-5-carboxylate (0.55 g, 3.14 mmol) and copper(I) iodide (0.09 g, 0.48 mmol) were added to a solution of 6-chloro-1-(phenylsulfonyl)-4-(trimethylstannanyl)-1H-indazole (1.10 g, 2.42 mmol) in N,N-dimethylformamide (4 ml). Each batch was heated and stirred at 100° C. under microwave irradiation for 30 min. The mixtures were allowed to cool to RT and the combined precipitated product suspended in diethyl ether and collected by filtration, washing with further diethyl ether then drying in a vacuum oven for 72 h. Approximately 5.2 g of the resultant solid was dissolved in dichloromethane and passed through Celite, eluting with further dichloromethane. The solvent was evaporated in vacuo to give the title compound as a pale orange solid (4.95 g).

LCMS (Method A): Rt 1.38 mins, MH+ 432.

Intermediate 71b

Methyl 2-[6-chloro-1-(phenylsulfonyl)-1H-indazol-4-yl]-1,3-oxazole-5-carboxylate

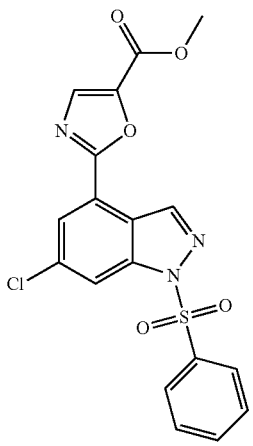 [SMILES: COC(=O)c1cnc(-c2cc(Cl)cc3c2cnn3S(=O)(=O)c2ccccc2)o1]

To a stirred solution of 6-chloro-4-iodo-1-(phenylsulphonyl)-1H-indazole (549.8 g) in toluene (1.43 L) was added triethylamine (380 ml) at 20±3° C. under an atmosphere of nitrogen. Hexamethylditin (385 ml) in toluene (825 ml) was added, followed by toluene (275 ml) then tetrakis(triphenylphosphine) palladium (0) (154.7 g). The reaction mixture was heated to 120° C. and stirred at this temperature for 3 h. The mixture was allowed to cool to 20±3° C., filtered, then washed with toluene (4.95 L). The filtrate was transferred to a clean vessel through a 5 μm Dominick hunter in-line filter, rinsing with further toluene (550 ml). The batch was then washed with 50% aqueous KF solution (5.5 L), the aqueous slurry filtered and the filtrate recombined with the organic phase. The aqueous was separated and the organics washed successively with 50% aqueous KF (5.5 L), followed by water (5.5 L). The organic layer was diluted with DMPU (2.75 L) then concentrated by vacuum distillation to ca. 5.4 vols. To the resultant solution was added copper (I) iodide (25.5 g) followed by methyl 2-chloro-1,3-oxazole-5-carboxylate (279 g, available from Apollo Scientific) at 20±3° C. The solution was degassed via vacuum and nitrogen purges (×3). Tetrakis(triphenylphosphine) palladium (0) (78 g) was added, the mixture degassed (×3) and then heated to 85-90° C. for 10 h. The mixture was diluted with DMSO (13.75 L) and cooled to 20±3° C., then water (2.75 L) added in ca. 1 vol portions over ca. 15 mins until crystallisation was initiated. The resultant suspension was aged at 20° C.±3° C. for 1.5 h. The solids were collected by vacuum filtration, washed with water (2×2.75 L), sucked dry and then further dried in vacuo with a nitrogen bleed at 45° C.±5° C. overnight to give the title compound (341.1 g).

LCMS (Method C): Rt 6.08 mins, MH+ 418

Intermediate 72

{2-[6-Chloro-1-(phenylsulfonyl)-1H-indazol-4-yl]-1,3-oxazol-5-yl}methanol

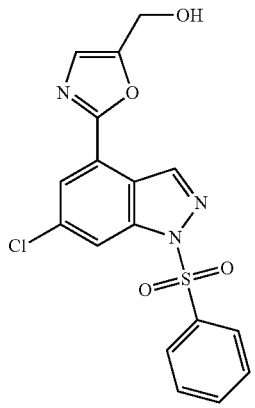 [SMILES: O=S(=O)(c1ccccc1)n1ncc2c(-c3ncc(CO)o3)cc(Cl)cc21]

Method A

A solution of ethyl 2-[6-chloro-1-(phenylsulfonyl)-1H-indazol-4-yl]-1,3-oxazole-5-carboxylate (5.11 g, 11.8 mmol) in dichloromethane (80 ml) was cooled to −25° C. in an oven dried round bottomed flask. Diisobutylaluminium hydride (25 ml, 37.5 mmol, 1.5M solution in toluene) was added dropwise and the reaction stirred at −20° C. for 3 h. A 10% aqueous solution of potassium sodium tartrate (80 ml) was added and the reaction mixture stirred for 5 min. The precipitated solid was filtered off and partitioned between ethyl acetate (500 ml) and water (500 ml). The layers were separated and the aqueous washed with further ethyl acetate (3×150 ml). The combined organics were dried and evaporated in vacuo to give the title compound as a yellow solid (1.1 g).

LCMS (Method A): Rt 1.09 mins, MH+ 390.

The remaining filtrate was largely concentrated in vacuo and the residue partitioned between ethyl acetate (500 ml) and water (500 ml). The layers were separated and the aqueous extracted with further ethyl acetate (3×150 ml). The combined organics were washed with water (2×150 ml), dried over anhydrous sodium sulfate and evaporated to give the title compound as a yellow solid (1.9 g).

LCMS (Method A): Rt 1.09 mins, MH+ 390.

Method B

To a solution of ethyl 2-[6-chloro-1-(phenylsulfonyl)-1H-indazol-4-yl]-1,3-oxazole-5-carboxylate (1.15 g) in THF (17.25 ml), stirred under nitrogen in an ice bath was added a solution of diisobutylaluminium hydride (5.08 ml, 5.64 mmol) in toluene. The reaction mixture was stirred at 0° C. for 2 h. Sodium sulphate decahydrate (2.5 g) was added, the mixture stirred at RT for 1 h, then filtered, washed with THF (2×5 vols) and concentrated under reduced pressure to give the title compound (0.98 g).

LCMS (Method D): Rt 2.20 mins, MH+ 390.

Method C

To a solution of ethyl 2-[6-chloro-1-(phenylsulfonyl)-1H-indazol-4-yl]-1,3-oxazole-5-carboxylate (604.5 g) in THF (8.7 L), stirred under nitrogen at 0±3° C. was added a solution of approximately 1.3M diisobutylaluminium hydride (1.8 kg) in toluene. The reaction mixture was stirred at 0±3° C. for 30 mins and then diluted with THF (3 L). Sodium sulphate decahydrate (1.3 kg) was added, maintaining the temperature below 5° C. The mixture was stirred at 0±3° C. for 10 mins and was then warmed to 20±3° C. and held at this temperature for 1 h. The suspension was filtered, washed with THF (4×3 L) and concentrated under reduced pressure to give the title compound (529.6 g).

LCMS (Method C): Rt 5.18 min, MH+ 390.

Method D

All weights, volumes and equivalents are relative to 6-chloro-4-iodo-1-(phenylsulfonyl)-1H-indazole.

Zinc chloride (3.6 eq, 1.17 wt, 52.7 g) in tetrahydrofuran (5 vols, 225 ml) is cooled to 0 to 5° C. A solution of the ethyl oxazole-5-carboxylate (1.1 eq, 0.37 wt, 18.1 g, corrected for 92 wt % assay) in tetrahydrofuran (5 vols, 225 ml) is added to the vessel. The suspension is cooled to −10° C. (+1-5° C.) under a nitrogen atmosphere and a 1M solution of bis-(trimethylsilyl)-lithiumamide in tetrahydrofuran (1.80 eq, 4.30 vols, 193 ml) is added over 15 minutes maintaining the temperature at −10° C. (+1-5° C.). The resulting solution is stirred under a nitrogen atmosphere at −10° C. (+1-5° C.) for 1 hour. To the solution is added 6-chloro-4-iodo-1-(phenylsulfonyl)-1H-indazole (1.0 eq, 1.0 wt, 45.0 g) and tetrakis triphenylphosphine palladium (0.03 eq, 0.083 wt, 3.73 g) (the mixture is degassed with vacuum/nitrogen 3 times) and then heated to 60° C. (+1-3° C.) for at least 6 hours. The reaction is then checked by HPLC for completion. The reaction solution is cooled to 0° C. (+/−3° C.) and a solution of 25% w/w diisobutylaluminium hydride in toluene (4.0 eq, 6.4 vols, 288 ml) is added maintaining the temperature at <5° C. The resulting reaction solution is then stirred at 0° C. (+/−3° C.) for at least 1 hour. The reaction is then checked by HPLC (generic) for completion. The reaction mixture is added portion wise to a solution of citric acid (4.0 eq, 2.0 wt, 90 g) in water (10 vols, 450 ml) at 0° C. (+/−5° C.) over ~1 h. The resulting solution is stirred at 20° C. for 15 minutes, extracted with ethyl acetate (10 vols, 450 ml), the organic layer is washed with water (2×3 vols, 2×135 ml) and filtered through a porosity 4 sinter. The organic layer is then evaporated under reduced pressure (45° C., 100 mbar) to 2 to 3 volumes, dimethyl sulphoxide (10 vols, 450 ml) is added and the solution evaporated under reduced pressure (45° C., 50 mbar) to remove all traces of other solvents. To the solution at 45° C. is added water (5 vols, 225 ml) dropwise over 30 minutes, the resulting reaction mixture is cooled to 20° C. over 3 hr and stirred at 20° C. for at least 15 hrs. The product is filtered, washed with a solution of dimethylsulphoxide:water (1:2) (2 vols, 90 ml), then washed with water (3 vols, 135 ml), then dried under high vacuum at 60° C. (±3° C.) to constant probe temperature to afford (2-(6-chloro-1-(phenylsulfonyl)-1H-indazol-4-yl)oxazol-5-yl)methanol as a beige solid.

Intermediate 73

4-[5-(Bromomethyl)-1,3-oxazol-2-yl]-6-chloro-1-(phenylsulfonyl)-1H-indazole

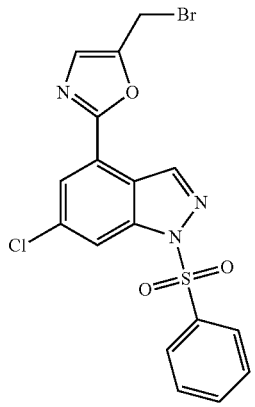 [SMILES: O=S(=O)(c1ccccc1)n1ncc2c(-c3ncc(CBr)o3)cc(Cl)cc21]

Method A

{2-[6-Chloro-1-(phenylsulfonyl)-1H-indazol-4-yl]-1,3-oxazol-5-yl}methanol (1.626 g, 4.17 mmol) was dissolved in anhydrous dichloromethane (20 ml) and carbon tetrabromide (2.77 g, 8.34 mmol) added. The reaction mixture was cooled to 0° C. and a solution of triphenylphosphine (2.188 g, 8.34 mmol) in dichloromethane (20 ml) added dropwise. After allowing to warm to RT and stirring for a further 3 h, the solvent was partially removed in vacuo and the solution purified directly by silica gel chromatography, eluting with 0-100% ethyl acetate in dichloromethane. The appropriate fractions were combined to give the title compound as a cream solid (1.16 g).

LCMS (Method B): Rt 3.70 mins, MH$^+$ 454.

Method B

Triphenylphosphine dibromide (20.60 g, 48.8 mmol) was added to a suspension of {2-[6-chloro-1-(phenylsulfonyl)-1H-indazol-4-yl]-1,3-oxazol-5-yl}methanol (9.06 g, 23.2 mmol) in dichloromethane (181 ml) at 0° C. The reaction mixture was stirred at 0° C. until completion. Water (91 ml) and saturated sodium bicarbonate solution (91 ml) were added and the mixture stirred, then separated. The aqueous layer was extracted with further dichloromethane (45 ml) and the organics combined and washed with water (91 ml). The layers were separated and the organic concentrated to dryness then redissolved in methanol (136 ml). After stirring for 30 mins the resultant white suspension was filtered and the solid dried under vacuum to give the title compound as an off-white solid (9.58 g).

LCMS (Method D): Rt 2.57 min, MH+ 452/454.

Method C

Triphenylphosphine dibromide (1.2 kg) was added to a suspension of {2-[6-chloro-1-(phenylsulfonyl)-1H-indazol-4-yl]-1,3-oxazol-5-yl}methanol (544.7 g) in dichloromethane (3.8 L) stirred under nitrogen at 10±3° C. The reaction mixture was stirred at 10±3° C. for 20 min. Water (2.7 L) and saturated sodium bicarbonate solution (5.4 L) were added and the mixture stirred, then separated. The aqueous layer was extracted with further dichloromethane (2.7 L) and the organics combined and washed with water (2.7 L). The layers were separated and the organic concentrated to dryness then redissolved in methanol (6.5 L). After stirring for 5 hours the resultant white suspension was filtered, washed with methanol (2×1.1 L) and the solid dried under vacuum at 40±5° C. to give the title compound as an off-white solid (514.0 g).

LCMS (Method C): Rt 6.40 min, MH$^+$ 453/455.

Method D

All weights, volumes and equivalents are relative to (2-(6-chloro-1-(phenylsulfonyl)-1H-indazol-4-yl)oxazol-5-yl)methanol.

(2-(6-Chloro-1-(phenylsulfonyl)-1H-indazol-4-yl)oxazol-5-yl)methanol (1.0 eq., 1 wt, 34.0 g) and triphenylphosphine dibromide (1.3 eq., 1.32 wt, 45.0 g) are stirred in dichloromethane (15 vols, 510 ml) at 20 (±3° C.) under a nitrogen atmosphere for 1 hr. The reaction is then checked by HPLC for completion. Once complete methanol (0.8 vols, 27.2 ml) is added to the reaction, with vigorous stirring 8% w/w sodium hydrogen carbonate solution (10 vols, 340 ml) is added drop wise over 15 minutes (check aqueous pH>7). The mixture is heated to 30° C. (±3° C.) and stirred together for 10 minutes, then separated, the aqueous is back extracted with dichloromethane (5 vols, 170 ml) and the combined dichloromethane layers are washed with water (5 vols, 170 ml). The dichloromethane solution is then evaporated under reduced pressure to a volume of approximately 4 vols. To the solution is added methanol (15 vols, 510 ml) and the solution evaporated under reduced pressure at 260 mbar, 20° C. to remove the remaining dichloromethane down to ~15 vols. The suspension is then stirred at 20° C. for at least 6 hrs. The solid is filtered, washed with methanol (2×1 vols, 2×34 ml), sucked dry for 20 minutes, then dried under high vacuum at 30° C. (±3° C.) to constant probe temperature to afford 5-(bromomethyl)-2-(6-chloro-1-(phenylsulfonyl)-1H-indazol-4-yl)oxazole as a beige solid.

Intermediate 74a

6-Chloro-4-(5-{[(2R,6S)-2,6-dimethyl-4-morpholinyl]methyl}-1,3-oxazol-2-yl)-1-(phenylsulfonyl)-1H-indazole

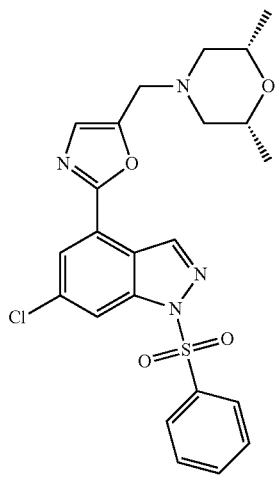 [SMILES: C[C@@H]1CN(Cc2cnc(-c3cc(Cl)cc4c3cnn4S(=O)(=O)c3ccccc3)o2)C[C@H](C)O1]

4-[5-(Bromomethyl)-1,3-oxazol-2-yl]-6-chloro-1-(phenylsulfonyl)-1H-indazole (0.580 g, 1.28 mmol) was dissolved in dichloromethane (5 ml) and (2R,6S)-2,6-dimethylmorpholine (0.317 ml, 2.56 mmol) added. The reaction mixture was stirred at RT for 3 h then the solvent removed under a stream of nitrogen. The resultant yellow solid was dissolved in dichloromethane (5 ml) and washed with water (2×2.5 ml). The layers were separated (hydrophobic frit) and the organic evaporated in vacuo to give the title compound as a pale yellow solid (0.60 g).

LCMS (Method A): Rt 0.86 mins, MH$^+$ 487.

$^1$H NMR (400 MHz, Chloroform-d) δ (ppm) 8.93 (d, J=1.0 Hz, 1H), 8.33 (dd, J=1.0, 1.5 Hz, 1H), 8.04-8.00 (m, 2H), 7.98 (d, J=1.5 Hz, 1H), 7.62 (tt, J=1.5, 7.5 Hz, 1H), 7.51 (t, J=7.5 Hz, 2H), 7.15 (s, 1H), 3.67 (s, 2H), 3.75-3.66 (m, 2H), 2.79-2.72 (m, 2H), 1.86 (dd, J=10.5, 11.0 Hz, 2H), 1.16 (d, J=6.5 Hz, 6H).

Similarly prepared using the appropriate amine was:

stirred suspension of ((2-(6-chloro-1-(phenylsulfonyl)-1H-indazol-4-yl)oxazol-5-yl)methyl)-cis-2,6-dimethylmorpholine (1 wt, 30 g) in DMSO (9 vol, 270 ml) is heated to 75-80° C. under a nitrogen atmosphere. The resulting clear solution is transferred to a crystallising vessel via a 5 μm Domnick hunter in line filter, then the line is washed with further DMSO (1.0 vol, 30 ml). The hot solution is allowed to cool to 20-25° C. over at least 2 hr, then the resulting suspension is aged at this temperature for at least 1 hr. The resulting solids are filtered, washed with DMSO (1.5 vol, 45 ml), followed by water/acetone (2:1 v/v, 2×2 vol, 2×60 ml) before being sucked dry for 0.5 hr. The batch is dried in vacuo at 45° C. to constant probe temperature to afford ((2-(6-chloro-1-(phenylsulfonyl)-1H-indazol-4-yl)oxazol-5-yl)methyl)-cis-2,6-dimethylmorpholine as an off-white solid.

| Intermediate Number | Name | Structure | Amine | LC/MS R$_t$ min | LC/MS MH$^+$ |
|---|---|---|---|---|---|
| 74b | 6-chloro-4-(5-{[4-(1-methylethyl)-1-piperazinyl]methyl}-1,3-oxazol-2-yl)-1-(phenylsulfonyl)-1H-indazole | 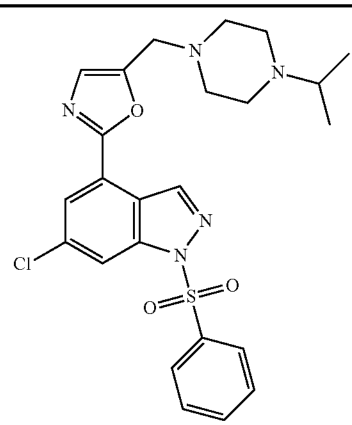 | 1-(1-methylethyl)piperazine | 0.77 | 500 |

Intermediate 74a

Intermediate 74b

Method B (2R,6S)-2,6-dimethylmorpholine (160 ml) and then triethylamine (180 ml) were added to a suspension of 4-[5-(Bromomethyl)-1,3-oxazol-2-yl]-6-chloro-1-(phenylsulfonyl)-1H-indazole (478.1 g) in acetone (3.8 L) stirred under nitrogen at less than 25° C. The reaction mixture was stirred at 20-25° C. for 2.5 hours and then water (3.8 L) was added. The resultant suspension was stirred at than 25° C. for 35 min and was then filtered, washed with a mixture of 2:1 v/v water:acetone (2×1.0 L) and the solid dried under vacuum at 45±5° C. to give the title compound as an off-white solid (500.5 g).

LCMS (Method B): Rt 3.43 min, MH$^+$ 487.

Method C

All weights, volumes and equivalents are relative to 5-(bromomethyl)-2-(6-chloro-1-(phenylsulfonyl)-1H-indazol-4-yl)oxazole (corrected for assay).

To a suspension of 5-(bromomethyl)-2-(6-chloro-1-(phenylsulfonyl)-1H-indazol-4-yl)oxazole (1 wt, 540 g) in acetone (8.7 vol, 4.7 L) is added 2,6-dimethylmorpholine (0.33 vol, 1.2 eq, 178 ml), followed by triethylamine (0.37 vol, 1.2 eq, 200 ml) at <25° C. under a nitrogen atmosphere. The resulting mixture is stirred at 20-25° C. for at least 0.5 hr, then monitored for completion by HPLC. Water (8.7 vol, 4.7 L) is then added to the mixture over ca 5 minutes. The resulting suspension is aged at <25° C. for at least 0.5 hr, then the solids are collected by vacuum filtration, washed with water/acetone (2:1 v/v, 2×2.2 vol, 2×1.2 L) and dried in vacuo with a nitrogen bleed at 45±5° C.

Recrystallisation—All weights, volumes and equivalents are relative to ((2-(6-chloro-1-(phenylsulfonyl)-1H-indazol-4-yl)oxazol-5-yl)methyl)-cis-2,6-dimethylmorpholine. A Method B Isopropylpiperazine (165 ml) was added to a suspension of 4-[5-(Bromomethyl)-1,3-oxazol-2-yl]-6-chloro-1-(phenylsulfonyl)-1H-indazole (250.1 g) in dichloromethane (2.5 L) stirred under nitrogen at 22±3° C. The reaction mixture was stirred at 22±3° C. for 1.25 hours and then water (2.5 L) was added, the mixture was stirred, then separated. The aqueous layer was extracted with further dichloromethane (0.5 L) and the organics combined and washed with water (2.5 L). The layers were separated and the organic concentrated to dryness, under vacuum, to give the title compound as a yellow solid (274.6 g).

LCMS (Method B): Rt 3.33 min, MH$^+$ 500.

Intermediate 75

2-(Methyloxy)-5-(4,4,5,5-tetramethyl-1,3,2-dioxaborolan-2-yl)-3-pyridinamine

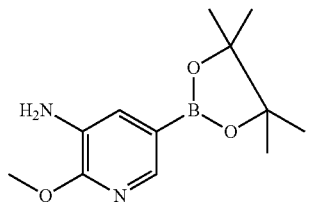

To 5-bromo-2-(methyloxy)-3-pyridinamine (18.93 g, 93 mmol, available from Asymchem International) in a 1 L round-bottom flask was added nitrogen-purged 1,4-dioxane (500 ml) followed by 4,4,4',4',5,5,5',5'-octamethyl-2,2'-bi-1,3,2-dioxaborolane (47.4 g, 186 mmol), potassium acetate (27.5 g, 280 mmol) and dichloro{1,1'-bis(diphenylphosphino)ferrocene}palladium (II) dichloromethane adduct (7.61 g, 9.32 mmol). The mixture was then stirred at 80° C. under nitrogen for 2 h. The reaction mixture was allowed to cool then partitioned between ethyl acetate and water and filtered through a Celite pad. The aqueous layer was extracted further with ethyl acetate (2×) and the combined organics washed with water, brine and dried over magnesium sulphate overnight. The mixture was filtered and the filtrate concentrated in vacuo to give a dark brown solid. The residue was purified by silica gel chromatography, eluting in 0-50% ethyl acetate/dichloromethane. The appropriate fractions were combined and evaporated to dryness and the residue triturated with cyclohexane. The resultant solid was filtered off and dried in vacuo to give the title compound as a light pink solid (11.1 g).

LCMS (Method A) Rt 0.91 mins, MH+ 251.

Intermediate 76

N-[2-(Methyloxy)-5-(4,4,5,5-tetramethyl-1,3,2-dioxaborolan-2-yl)-3-pyridinyl]methanesulfonamide

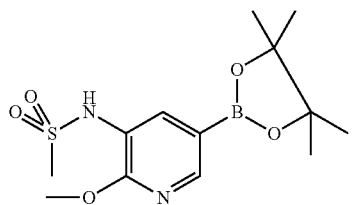 [SMILES: COc1ncc(B2OC(C)(C)C(C)(C)O2)cc1NS(C)(=O)=O]

To a solution of 2-(methyloxy)-5-(4,4,5,5-tetramethyl-1,3,2-dioxaborolan-2-yl)-3-pyridinamine (0.5 g, 1.999 mmol) in pyridine (5 ml) was added methanesulphonyl chloride (0.309 ml, 4.00 mmol) and the mixture stirred at 20° C. for 18 hr then the solvent was removed in vacuo. The residue was partitioned between saturated sodium bicarbonate solution (10 ml) and dichloromethane (20 ml), separated by hydrophobic frit and purified by silica gel chromatography, eluting with a gradient of dichloromethane and methanol to give the title compound as a brown solid (0.46 g).

LCMS (Method A): Rt 0.98 mins, MH+ 329.

Intermediate 77

2,4-Difluoro-N-[2-(methyloxy)-5-(4,4,5,5-tetramethyl-1,3,2-dioxaborolan-2-yl)-3-pyridinyl]benzenesulfonamide

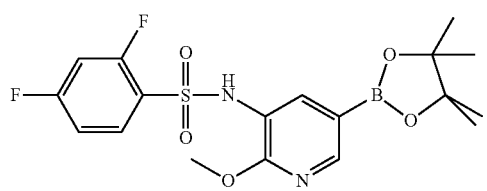 [SMILES: COc1ncc(B2OC(C)(C)C(C)(C)O2)cc1NS(=O)(=O)c1ccc(F)cc1F]

To a stirred solution of 2-(methyloxy)-5-(4,4,5,5-tetramethyl-1,3,2-dioxaborolan-2-yl)-3-pyridinamine (3 g, 12.00 mmol) in pyridine (12 ml), 2,4-difluorobenzenesulfonyl chloride (1.774 ml, 13.19 mmol) was added and the reaction mixture stirred at RT for 2 h. 2 N hydrogen chloride (aq) (20 ml) and dichloromethane (20 ml) were added and the layers separated. The aqueous layer was washed with additional dichloromethane (2×15 ml) and the organic layers combined, dried (hydrophobic frit) and evaporated in vacuo to give a brown oil. There was still some pyridine in the reaction mixture so 2M hydrogen chloride (aq) and dichloromethane (15 ml) were added to extract one more time. The solvent was removed in vacuo to give the title compound as an orange solid (4.3 g).

LCMS (Method A): Rt 1.20 min, MH+ 427 [NB. also observe Rt 0.73 min, MH+ 345 consistent with boronic acid (hydrolysis product due to HPLC eluent)].

Intermediate 78

N-[5-[4-(5-{[(2R,6S)-2,6-Dimethyl-4-morpholinyl]methyl}-1,3-oxazol-2-yl)-1-(phenylsulfonyl)-1H-indazol-6-yl]-2-(methyloxy)-3-pyridinyl]-2,4-difluorobenzenesulfonamide

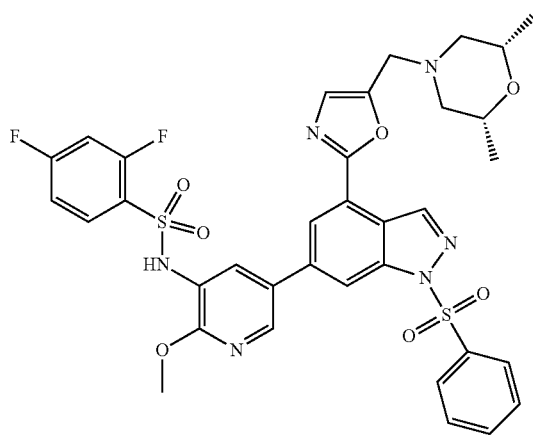 [SMILES: COc1ncc(-c2cc(-c3ncc(CN4C[C@@H](C)O[C@@H](C)C4)o3)c3cnn(S(=O)(=O)c4ccccc4)c3c2)cc1NS(=O)(=O)c1ccc(F)cc1F]

To a solution of 6-chloro-4-(5-{[(2R,6S)-2,6-dimethyl-4-morpholinyl]methyl}-1,3-oxazol-2-yl)-1-(phenylsulfonyl)-1H-indazole (0.2 g, 0.411 mmol) and 2,4-difluoro-N-[2-(methoxy)-5-(4,4,5,5-tetramethyl-1,3,2-dioxaborolan-2-yl)-3-pyridinyl]benzenesulfonamide (0.228 mg, 0.534 mmol) in 1,4-dioxane (2 ml) was added chloro[2'-(dimethylamino)-2-biphenylyl]palladium-1(1R,4S)-bicyclo[2.2.1]hept-2-yl [(1S,4R)-bicyclo[2.2.1]hept-2-yl]phosphane (11.5 mg, 0.021 mmol), potassium phosphate tribasic (0.262 g, 1.23 mmol) and water (0.2 ml). The reaction mixture was heated to 120° C. with stirring for 3 h under microwave irradiation, then filtered through a silica SPE, eluting with methanol. The solvent was removed and the residue partitioned between dichloromethane (5 ml) and water (5 ml). The layers were separated and the aqueous extracted with further dichloromethane (2×2.5 ml). The combined organics were concentrated under a stream of nitrogen and the residue dissolved in DMSO and a few drops of dichloromethane (3 ml) and purified by MDAP (method H) in 3 injections. The appropriate fractions were evaporated in vacuo to give the title compound as a pale brown solid (0.105 g).

LCMS (Method A): Rt 0.93 mins, MH+ 751.

Intermediate 79

2,4-Difluoro-N-[5-[4-(5-{[4-(1-methylethyl)-1-piperazinyl]methyl}-1,3-oxazol-2-yl)-1-(phenylsulfonyl)-1H-indazol-6-yl]-2-(methyloxy)-3-pyridinyl]benzenesulfonamide

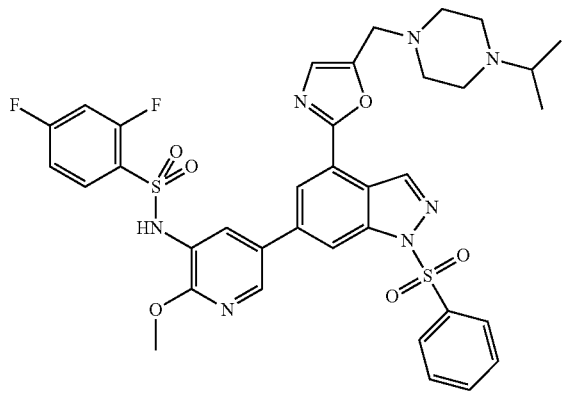 [SMILES: COc1ncc(-c2cc(-c3ncc(CN4CCN(C(C)C)CC4)o3)c3cnn(S(=O)(=O)c4ccccc4)c3c2)cc1NS(=O)(=O)c1ccc(F)cc1F]

To a solution of 6-chloro-4-(5-{[4-(1-methylethyl)-1-piperazinyl]methyl}-1,3-oxazol-2-yl)-1-(phenylsulfonyl)-1H-indazole (0.2 g, 0.40 mmol) and 2,4-difluoro-N-[2-(methoxy)-5-(4,4,5,5-tetramethyl-1,3,2-dioxaborolan-2-yl)-3-pyridinyl]benzenesulfonamide (0.222 g, 0.52 mmol) in 1,4-dioxane (2 ml) was added chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (11.2 g, 0.020 mmol), potassium phosphate tribasic (0.255 g, 1.20 mmol) and water (0.2 ml). The reaction mixture was heated to 120° C. with stirring for 3 h under microwave irradiation then filtered through a silica SPE, eluting with methanol. The solvent was removed in vacuo and the residue partitioned between dichloromethane (5 ml) and water (5 ml). The layers were separated and the aqueous extracted with further dichloromethane (2×2 ml). The combined organics were concentrated under a stream of nitrogen and the residue purified using silica gel chromatography, eluting with 0-25% methanol in dichloromethane. The appropriate fractions were evaporated in vacuo to give the title compound as a brown solid (0.081 g).

LCMS (Method A): Rt 0.85 mins, MH+ 764.

Intermediate 80

Ethyl 2-[6-{1-[(1,1-dimethylethyl)(dimethyl)silyl]-1H-indol-4-yl}-1-(phenylsulfonyl)-1H-indazol-4-yl]-1,3-oxazole-5-carboxylate

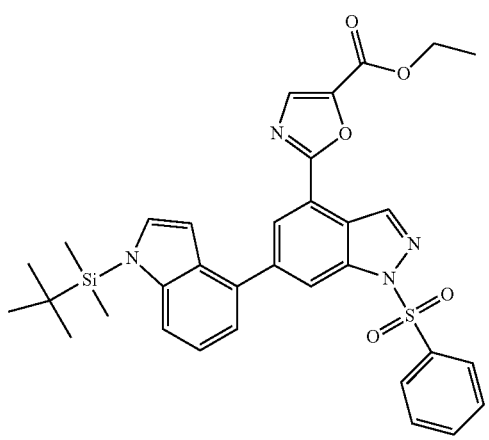 [SMILES: CCOC(=O)c1cnc(-c2cc(-c3cccc4c3ccn4[Si](C)(C)C(C)(C)C)cc3c2cnn3S(=O)(=O)c2ccccc2)o1]

To a solution of ethyl 2-[6-chloro-1-(phenylsulfonyl)-1H-indazol-4-yl]-1,3-oxazole-5-carboxylate (1.5 g, 3.47 mmol) in 1,4-dioxane (15 ml) and water (1.5 ml) was added {1-[(1,1-dimethylethyl)(dimethyl)silyl]-1H-indol-4-yl}boronic acid (1.243 g, 4.52 mmol, available from Combi-Blocks Inc.), chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (0.097 g, 0.174 mmol) and potassium phosphate tribasic (2.212 g, 10.42 mmol). The reaction mixture was heated to 100° C. for 3 h, the solvent removed in vacuo and the residue partitioned between dichloromethane (20 ml) and water (10 ml). Saturated sodium chloride solution (100 ml) was added and the organic phase separated and dried over anhydrous sodium sulphate. The crude product was purified by silica gel chromatography, eluting with a gradient of cyclohexane and ethyl acetate. The desired fractions were concentrated to give the title compound as a white solid (0.846 g), which by LCMS contained some unreacted starting material.

LCMS (Method A): Rt 1.71 mins, MH+ 627 (and Rt 1.39 min, MH+ 432 consistent with ethyl 2-[6-{1-[(1,1-dimethylethyl)(dimethyl)silyl]-1H-indol-4-yl}-1-(phenylsulfonyl)-1H-indazol-4-yl]-1,3-oxazole-5-carboxylate).

Intermediate 81

{2-[6-{1-[(1,1-Dimethylethyl)(dimethyl)silyl]-1H-indol-4-yl}-1-(phenylsulfonyl)-1H-indazol-4-yl]-1,3-oxazol-5-yl}methanol

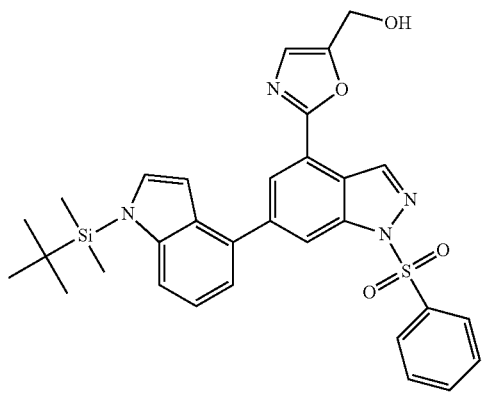 [SMILES: CC(C)(C)[Si](C)(C)n1ccc2c(-c3cc(-c4ncc(CO)o4)c4cnn(S(=O)(=O)c5ccccc5)c4c3)cccc21]

To a solution of ethyl 2-[6-{1-[(1,1-dimethylethyl)(dimethyl)silyl]-1H-indol-4-yl}-1-(phenylsulfonyl)-1H-indazol-4-yl]-1,3-oxazole-5-carboxylate (containing an impurity consistent with ethyl 2-[6-chloro-1-(phenylsulfonyl)-1H-indazol-4-yl]-1,3-oxazole-5-carboxylate)(0.84 g) in dichloromethane (10 ml) at −20° C. was added diisobutylaluminium hydride (2.68 ml, 2.68 mmol, 1M in hexanes). The reaction mixture was stirred at −20° C. for 2 h then 10% ammonium chloride solution (10 ml) added. The mixture was stirred for 5 min then extracted with dichloromethane (10 ml), the layers separated (hydrophobic frit) and the organic purified by silica gel chromatography, eluting with a gradient of cyclohexane and ethyl acetate. The desired fractions were concentrated to give the title compound as a pale yellow solid (0.36 g), which by LCMS contained an impurity consistent with 2-[6-chloro-1-(phenylsulfonyl)-1H-indazol-4-yl]-1,3-oxazol-5-yl}methanol.

LCMS (Method A): Rt 1.55 mins, MH+ 585 (and Rt 1.11 mins, MH+ 390 consistent with {2-[6-chloro-1-(phenylsulfonyl)-1H-indazol-4-yl]-1,3-oxazol-5-yl}methanol impurity).

Intermediate 82

6-Chloro-4-(5-{[(2R,6R)-2,6-dimethyl-4-morpholinyl]methyl}-1,3-oxazol-2-yl)-1-(phenylsulfonyl)-1H-indazole

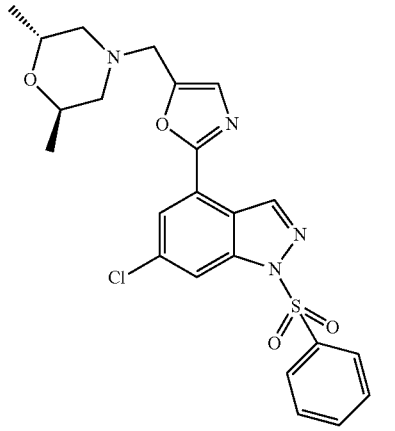 [SMILES: C[C@@H]1CN(Cc2cnc(-c3cc(Cl)cc4c3cnn4S(=O)(=O)c3ccccc3)o2)C[C@@H](C)O1]

To a solution of 4-[5-(bromomethyl)-1,3-oxazol-2-yl]-6-chloro-1-(phenylsulfonyl)-1H-indazole (750 mg, 1.657 mmol) in dichloromethane (50 mL) stirred in air at room temp, was added neat 2,6-dimethylmorpholine (191 mg, 1.657 mmol, available from Aldrich as a mixture of isomers). The reaction mixture was stirred at 20° C. for 20 hr. Volatiles were removed using a rotary evaporator then the crude material was pre-absorbed onto Fluorosil™ and purified by column chromatography on silica (100 g) using a 0-100% ethyl acetate-cyclohexane gradient over 60 mins. Two diastereoisomers were isolated. Appropriate fractions were combined and evaporated in vacuo to give the title compound as a yellow oil (226 mg).

$^1$H NMR confirmed the structure as the trans isomer. $^1$H NMR (400 MHz, Chloroform-d) δ (ppm) 8.92 (d, J=1.0 Hz, 1H), 8.32 (dd, J=1.0, 1.5 Hz, 1H), 8.04-8.00 (m, 2H), 7.97 (d, J=1.5 Hz, 1H), 7.62 (tt, J=1.5, 7.5 Hz, 1H), 7.54-7.48 (m, 2H), 7.13 (s, 1H), 4.08-3.99 (m, J=3.5, 6.0, 6.5, 6.5, 6.5 Hz, 2H), 3.66 (d, J=14.5 Hz, 1H), 3.61 (d, J=14.5 Hz, 1H), 2.56 (dd, J=3.0, 10.5 Hz, 2H), 2.23 (dd, J=6.0, 10.5 Hz, 2H), 1.24 (d, J=6.5 Hz, 6H).

Intermediate 83

1,1-Dimethylethyl 4-({2-[6-chloro-1-(phenylsulfonyl)-1H-indazol-4-yl]-1,3-oxazol-5-yl}methyl)-1-piperazinecarboxylate

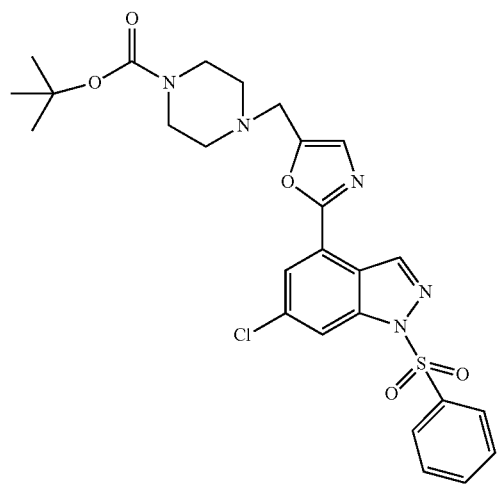 [SMILES: CC(C)(C)OC(=O)N1CCN(Cc2cnc(-c3cc(Cl)cc4c3cnn4S(=O)(=O)c3ccccc3)o2)CC1]

1,1-Dimethylethyl 1-piperazinecarboxylate (185 mg, 0.994 mmol) was dissolved in 1 ml of DCM and triethylamine (0.185 mL, 1.325 mmol) was added dropwise. The mixture was stirred for 1 h, then concentrated in vacuo to afford a yellow solid. This was dissolved in water/DCM (1:1, 50 ml) and the organic phase was collected then concentrated in vacuo to afford the title compound as a yellow gum (347 mg).

LCMS (Method A) Rt 1.16 min (poor ionisation, (M+MeCN)$^+$ 599 observed).

Intermediate 84

6-(1H-Indol-4-yl)-1H-indazol-4-amine

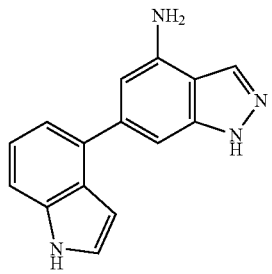 [SMILES: Nc1cc(-c2cccc3[nH]ccc23)cc2[nH]ncc12]

6-Bromo-1H-indazol-4-amine (10 g) (available from Sinova Inc.) and 4-(4,4,5,5-tetramethyl-1,3,2-dioxaborolan-2-yl)-1H-indole (16.05 g) (available from Frontier Scientific, Europe Ltd) were dissolved in 1,4-dioxane (60 ml) and water (60 ml). 2 M sodium carbonate (70.7 ml) and Pd(dppf)Cl$_2$-DCM adduct (1.93 g) were added and the mixture was heated at 115° C. for 18 h. The reaction mixture was diluted with DCM (200 ml) and the organic and aq layers were separated using a hydrophobic frit. The aq layer was extracted with further quantities of DCM (2×200 ml), using a hydrophobic frit to separate the layers. The organic layers were combined and silica (80 g) was added. The solvent was removed in vacuo to give a crude material that was purified by chromatography on silica gel (750 g cartridge, Flashmaster II) eluting with 0-100% ethyl acetate in cyclohexane over 60 min. The oil was dried in vacuo on a drying rack overnight. The yellow foam was dissolved in DCM (3×400 ml), removing the solvent in vacuo after each dissolution. ethyl acetate (50 ml) was then added and the solvent was removed in vacuo.

The solid obtained was dried in a vacuum oven to afford the title compound (12.8 g) as a yellow foam.

LCMS (Method B); R$_t$=2.71 min, MH$^+$=249.

Intermediate 85

1-(Phenylsulfonyl)-6-(trimethylstannanyl)-1H-indazol-4-amine

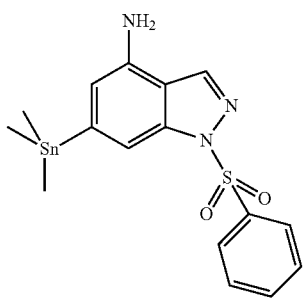 [SMILES: [CH3][Sn]([CH3])([CH3])[c]1cc(N)c2cnn(S(=O)(=O)c3ccccc3)c2c1]

A mixture of 6-bromo-1-(phenylsulfonyl)-1H-indazol-4-amine (1.3 g), hexamethylditin (2.4 g), triethylamine (1 ml)

and Pd(PPh$_3$)$_4$ (0.2 g) in toluene (15 ml) was heated under microwave irradiation at 120° C. for 1 h. The reaction was applied to a silica cartridge using light petroleum 40-60° C. as eluent. This was changed to ether:light petroleum 40-60° C. The appropriate fractions were evaporated to give title compound, 1.2 g.

LCMS (method B); R$_t$=3.3 min, MH$^+$=438.

Intermediate 86

6-Bromo-1-(phenylsulfonyl)-1H-indazol-4-amine

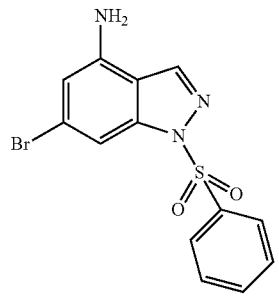 [SMILES: Nc1cc(Br)cc2c1cnn2S(=O)(=O)c1ccccc1]

6-Bromo-1H-indazol-4-amine (5 g) was dissolved in DMF (20 ml) and cooled in an ice bath. 60% Sodium hydride in mineral oil (0.94 g) was added portionwise and the reaction was left under an ice bath for 30 min. Benzenesulfonyl chloride (3 ml) in DMF (5 ml) was added slowly over 15 min and the reaction was left to warm up to RT overnight. Water (100 ml) was added and the reaction stirred for 20 min. Ethyl acetate (120 ml) was added and the water was separated, washed with ethyl acetate (50 ml×2) and the combined organics were washed with 7.5% lithium chloride (aq) (50 ml×2) then water (50 ml) before being separated and passed through a hydrophobic frit. The ethyl acetate was evaporated and the residue passed through a silica cartridge, eluting with DCM (ca. 300 ml) followed by diethyl ether (ca. 400 ml). Product containing pure fractions were combined and evaporated to dryness to give title compound, 5.9 g.

LCMS (method E); R$_t$=1.12 min, MH$^+$=354.

Intermediate 87

6-(1H-Indol-4-yl)-1-(phenylsulfonyl)-1H-indazol-4-amine

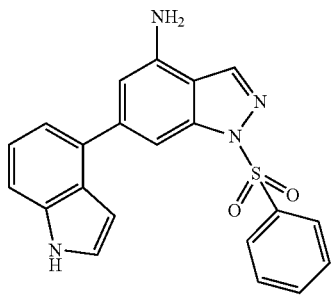 [SMILES: Nc1cc(-c2cccc3[nH]ccc23)cc2c1cnn2S(=O)(=O)c1ccccc1]

6-Bromo-1-(phenylsulfonyl)-1H-indazol-4-amine (3 g), 4-(4,4,5,5-tetramethyl-1,3,2-dioxaborolan-2-yl)-1H-indole (2.278 g), Pd(dppf)Cl$_2$ (0.623 g) and sodium carbonate (2.71 g) were divided between 2 microwave vials and dissolved in 1,4-dioxane (16 ml) and water (16 ml) to give 8 ml of each solvent in each vial. The vials were heated in the microwave at 100° C. for 10 min. The mixtures were combined and filtered through Celite, washing with ethyl acetate. The resulting mixture was partitioned between water (100 ml) and ethyl acetate (100 ml) and the layers separated. The aq layer was extracted with further ethyl acetate (2×50 ml) and the organic extracts were combined, passed through a hydrophobic frit and the solvent removed in vacuo to give a brown solid which was pre-adsorbed onto silica and added to the top of a 100 g silica SPE cartridge. This was eluted with 0-100% ethyl acetate:cyclohexane over 60 min on the FlashMaster II. The product-containing fractions were combined and the solvent was removed in vacuo to afford the title compound as orange crystals which were dried on a high vacuum line for 1 hour.

LCMS (Method E): R$_t$=1.11 min, MH$^+$=389.

Intermediate 88

2-Methyl-N-[1-(phenylsulfonyl)-6-(trimethylstannanyl)-1H-indazol-4-yl]-1,3-thiazole-4-carboxamide

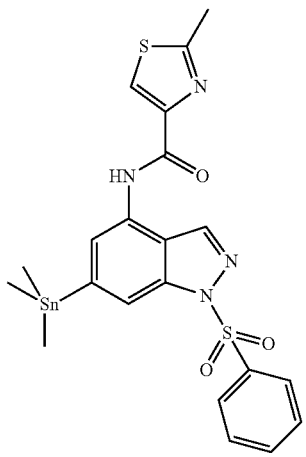 [SMILES: Cc1nc(C(=O)Nc2c[c]([Sn]([CH3])([CH3])[CH3])cc3c2cnn3S(=O)(=O)c2ccccc2)cs1]

2-Methyl-1,3-thiazole-4-carbonyl chloride (350 mg) in DCM (4 ml) was added dropwise to 1-(phenylsulfonyl)-6-(trimethylstannanyl)-1H-indazol-4-amine (300 mg) in DCM (15 ml) and pyridine (0.167 ml). The reaction was stirred at RT overnight. Saturated sodium bicarbonate (aq) (25 ml) was added and the reaction vigorously stirred for 15 min. The DCM was passed through a hydrophobic frit then evaporated to dryness. The residue was dissolved in DCM and purified on a silica cartridge, preconditioned with cyclohexane, washing with cyclohexane followed by elution with ether. The ether was evaporated to give title compound, 373 mg.

LCMS (Method E) R$_t$=1.42 min, MH$^+$=563.

Intermediate 89

6-Bromo-3-fluoro-4-nitro-1H-indazole

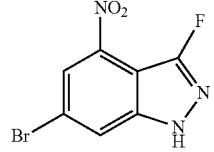

To a solution of 6-bromo-4-nitro-1H-indazole (5 g) in acetonitrile (50 ml) and acetic acid (10 ml) was added Selectfluor (9.39 g). The resulting mixture was heated to 100° C. and stirred for two days. The reaction mixture was concentrated under vacuum. The residue was dissolved in DCM and then filtered off. The sample was absorbed onto silica powder then solid loaded onto the companion where it was purified on a 120 g silica column using a 0-100% ethyl acetate:cyclohexane gradient. The appropriate fractions were combined and concentrated to yield the title compound as an orange solid, 2 g.

LCMS (Method E); $R_t$=1 min, MH$^+$=258.

Intermediate 90

6-Bromo-3-fluoro-4-nitro-1-(phenylsulfonyl)-1H-indazole

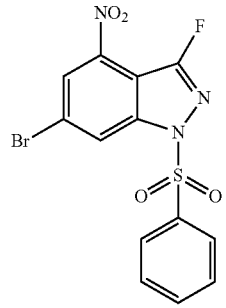

To a stirring suspension of sodium hydride (60% in mineral oil) (0.677 g) in THF (25 ml) at 0° C. was added a solution of 6-bromo-3-fluoro-4-nitro-1H-indazole (4 g) in THF (25 ml) dropwise. The reaction mixture was allowed to stir for 30 min then allowed to warm to RT before benzenesulfonyl chloride (2.17 ml) was added. After approximately two hours the reaction mixture was partitioned between ethyl acetate and water. The layers were separated and the aq was then extracted again with ethyl acetate. The combined organics were then washed with brine, dried over magnesium sulphate, filtered and concentrated. The solid was triturated with methanol (50 ml) and filtered to yield the title compound, 5.96 g as a yellow solid.

LCMS (Method E) $R_t$=1.27 min.

Intermediate 91

6-Bromo-3-fluoro-1-(phenylsulfonyl)-1H-indazol-4-amine

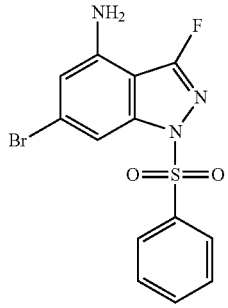 [SMILES: Nc1cc(Br)cc2c1c(F)nn2S(=O)(=O)c1ccccc1]

6-Bromo-3-fluoro-4-nitro-1-(phenylsulfonyl)-1H-indazole (5.9 g) was suspended in acetic acid (60 ml) and iron powder (4.12 g) was added. The suspension was heated to reflux. After 2 h the reaction mixture was diluted with ethyl acetate (100 ml) and filtered through celite. The filter cake was washed well with ethyl acetate then the filtrate basified to pH 8-9. The biphasic system was then stirred for ~5 min. The layers were then separated, the aq washed with ethyl acetate and the combined organics washed with brine, dried (magnesium sulphate), filtered and concentrated in vacuum to yield a crude loaded onto a 330 g silica cartridge, purified on a 0-100% ethyl acetate:cyclohexane gradient and the relevant fractions combined and concentrated to yield the title compound, 2.4 g as a yellow solid.

LCMS (Method E) $R_t$=1.17 min, MH$^+$=372.

Intermediate 92

3-Fluoro-1-(phenylsulfonyl)-6-(trimethylstannanyl)-1H-indazol-4-amine

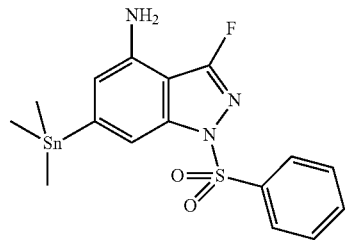 [SMILES: [CH3][Sn]([CH3])([CH3])[c]1cc(N)c2c(F)nn(S(=O)(=O)c3ccccc3)c2c1]

6-Bromo-3-fluoro-1-(phenylsulfonyl)-1H-indazol-4-amine (1.9 g), hexamethylditin (2.66 ml), triethylamine (1.431 ml) and Pd(PPh$_3$)$_4$ (0.593 g) were placed in toluene (30 ml). The mixture was split into 2 microwave vials and heated at 110° C. for 1 h in the microwave. The mixtures were combined and poured onto a 50 g silica cartridge that was eluted with cyclohexane followed by 1:1 cyclohexane:diethylether to give the title compound, 2.25 g.

LCMS (Method B) $R_t$=3.46 min, MH$^+$=456.

Intermediate 93

3-Fluoro-6-(1H-indol-4-yl)-1-(phenylsulfonyl)-1H-indazol-4-amine

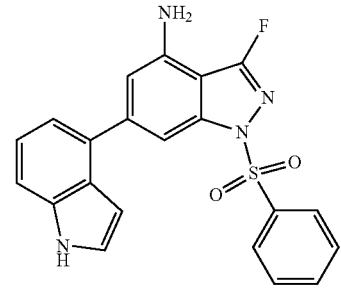 [SMILES: Nc1cc(-c2cccc3[nH]ccc23)cc2c1c(F)nn2S(=O)(=O)c1ccccc1]

6-Bromo-3-fluoro-1-(phenylsulfonyl)-1H-indazol-4-amine (350 mg), 4-(4,4,5,5-tetramethyl-1,3,2-dioxaborolan-2-yl)-1H-indole (230 mg), potassium phosphate (601 mg) and Pd(dppf)Cl$_2$ (69 mg) were placed in a microwave vial with 1,4-dioxane (5 ml) and water (2.5 ml) and the mixture heated at 110° C. for 30 min. After this time the mixture was partitioned between water (200 ml) and DCM (200 ml) and the DCM layer was collected. The aq layer was extracted with DCM (100 ml) and the combined organic layers dried using a hydrophobic frit and the solvent was removed in vacuo. The residue was adsorbed onto silica gel and purified using chromatography on silica gel eluting with 0-100% ethyl acetate in cyclohexane to give the title compound, 350 mg.

LCMS (Method E) $R_t$=1.16 min, MH$^+$=407.

Intermediate 94

6-Bromo-4-nitro-2-(tetrahydro-2H-pyran-2-yl)-2H-indazole

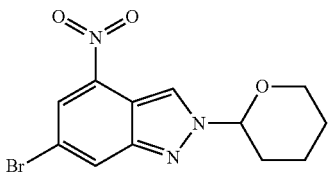 [SMILES: O=[N+]([O-])c1cc(Br)cc2nn(C3CCCCO3)cc12]

To 6-bromo-4-nitro-1H-indazole (10 g) in dihydropyran (100 ml) was added TFA (0.068 ml) and the reaction was heated for 1.5 h at reflux. After cooling, DCM (180 ml) and saturated sodium bicarbonate solution (50 ml) was added and stirred for 10 min. The DCM was separated from the aq which was re-washed with DCM (70 ml). The combined organic layers were passed through a hydrophobic frit and evaporated to dryness. The residual solid was triturated with ether then filtered. The solid material was dissolved in DCM and purified by chromatography on silica on the ISCO Companion, using an isocratic gradient of DCM. Purified fractions were combined and evaporated to dryness to afford the title compound, 7.78 g.

LCMS (method F); $R_t$=3.51 min, MH$^-$=326/328.

Intermediate 95

6-Bromo-2-(tetrahydro-2H-pyran-2-yl)-2H-indazol-4-amine

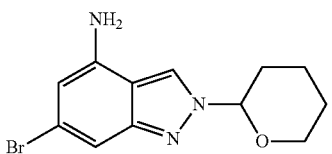 [SMILES: Nc1cc(Br)cc2nn(C3CCCCO3)cc12]

6-Bromo-4-nitro-2-(tetrahydro-2H-pyran-2-yl)-2H-indazole (6 g), iron filings (3.29 g) and ammonium chloride (0.492 g) were weighed to a 250 ml round-bottomed flask and ethanol (60 ml) then water (18 ml) were added. The reaction was heated to 80° C. for 2.5 h. The reaction mixture was cooled. Ethyl acetate (100 ml) and water (50 ml) were added. There was no visible separation of layers so the reaction was concentrated to remove the ethyl acetate and ethanol. Ethyl acetate (250 ml) was then added and the organic layer was washed with water (50 ml), before passing through a hydrophobic frit. The organic layer was evaporated to dryness. The residue was purified by column chromatography on silica (120 g silica column, ISCO Companion) eluting with a gradient of 1-2% methanol in DCM over 25 min. Fractions containing desired material were combined and evaporated to dryness to afford the title compound, 3.95 g.

LCMS (method F); $R_t$=2.87 min, MH$^-$=298.

Intermediate 96

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide

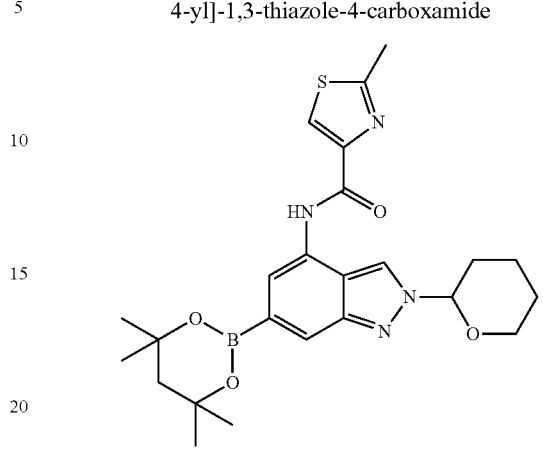

To 2 separate microwave vials was weighed N-[6-bromo-2-(tetrahydro-2H-pyran-2-yl)-2H-indazol-4-yl]-2-methyl-1,3-thiazole-4-carboxamide (1.13 g), potassium acetate (799 mg), 4,4,4',4',6,6,6',6'-octamethyl-2,2'-bi-1,3,2-dioxaborinane (2.0 g) and Pd(dppf)Cl$_2$ (348 mg). To this was added 1,4-dioxane (17 ml) and the reaction was heated for 30 min at 80° C. in the microwave. Vial 2 was heated for a further 30 min at 80° C. using the microwave. Hence combined reaction mixtures were washed through a silica cartridge (10 g) with methanol, preconditioned with methanol. The solution was dried down. The solid was separated between DCM and water and the DCM layer was dried down. The material was dissolved in DCM and methanol (few drops) and adsorbed onto fluorisil then purified on the ISCO companion, silica column (80 g) using 40-100% ethyl acetate in cyclohexane. Appropriate fractions were combined to give title compound, 1.25 g.

LCMS (method E) $R_t$=1.35 min, MH$^+$=483.

Intermediate 97

N-[6-Bromo-2-(tetrahydro-2H-pyran-2-yl)-2H-indazol-4-yl]-2-methyl-1,3-thiazole-4-carboxamide

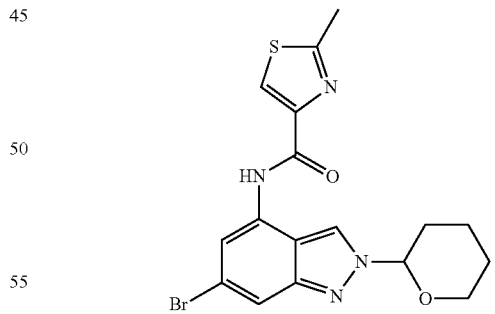

In a round bottom flask was introduced 6-bromo-2-(tetrahydro-2H-pyran-2-yl)-2H-indazol-4-amine (2.77 g) dissolved in DCM (120 ml) followed by the addition of pyridine (1.135 ml). The reaction mixture was left to stir for a few minutes before the addition of 2-methyl-1,3-thiazole-4-carbonyl chloride (2.267 g). The reaction mixture was left to stir at RT for 1 h. After this time the reaction mixture was extracted between DCM and saturated sodium bicarbonate aq. The extracted organic layer was dried down. The crude was dissolved in DCM and adsorbed onto fluorisil before purification by solid loading on companion using Si Column (40 g) eluting with 40-100% ethyl acetate in cyclohexane. The appropriate fractions were combined and evaporated to dryness to yield the title compound, 2.6 g.
LCMS (method E); $R_t$=1.17 min, MH$^+$=339.

Intermediate 98

1,4-Dimethyl-N-[1-(phenylsulfonyl)-6-(trimethylstannanyl)-1H-indazol-4-yl]-1H-pyrazole-3-carboxamide

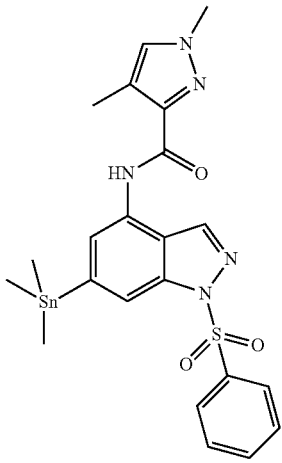 [SMILES: Cc1cn(C)nc1C(=O)Nc1c[c]([Sn]([CH3])([CH3])[CH3])cc2c1cnn2S(=O)(=O)c1ccccc1]

1-(Phenylsulfonyl)-6-(trimethylstannanyl)-1H-indazol-4-amine (250 mg) was dissolved in DCM (10 ml) and pyridine (0.051 ml) was added. 1,4-Dimethyl-1H-pyrazole-3-carbonyl chloride (100 mg) in DCM (5 ml) was added dropwise. The reaction was stirred at RT for 2 h. After this time saturated sodium bicarbonate aq (25 ml) was added and the reaction was stirred vigorously for 5 min before the DCM was passed through a hydrophobic frit then evaporated to dryness. The residue was dissolved in DCM, and then applied to the top of a 20 g silica cartridge preconditioned with cyclohexane. The column was washed with 50% cyclohexane:ether (100 ml), before the compound was eluted with ether, then 5% methanol in ether. The product containing fractions were evaporated to dryness to afford the title compound, 310 mg.
LCMS (method E); $R_t$=1.41 min, MH$^+$=560.

Intermediate 99

N-[1-(Phenylsulfonyl)-6-(trimethylstannanyl)-1H-indazol-4-yl]-2-furancarboxamide

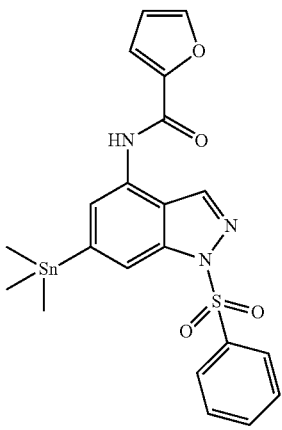 [SMILES: [CH3][Sn]([CH3])([CH3])[c]1cc(NC(=O)c2ccco2)c2cnn(S(=O)(=O)c3ccccc3)c2c1]

2-Furancarbonyl chloride (0.199 ml) was added to a stirred solution of 1-(phenylsulfonyl)-6-(trimethylstannanyl)-1H-indazol-4-amine (580 mg) in pyridine (10 ml) at RT. The mixture was stirred for 1 h. After this time, the mixture was acidified with 5 N HCl and extracted into ether (2×40 ml). The combined extracts were washed with aq sodium bicarbonate (20 ml), water (50 ml), dried (frit) and evaporated to dryness. The residual oil was purified on a 20 g Si isolute cartridge using ether as the eluent. The appropriate fractions were evaporated to give the title compound, 510 mg as a colourless solid.
LCMS (method B); $R_t$=3.41 min, MH$^+$=532.

Intermediate 100

N-{1-(Phenylsulfonyl)-6-[1-(phenylsulfonyl)-1H-pyrrolo[2,3-b]pyridin-4-yl]-1H-indazol-4-yl}-2-furancarboxamide

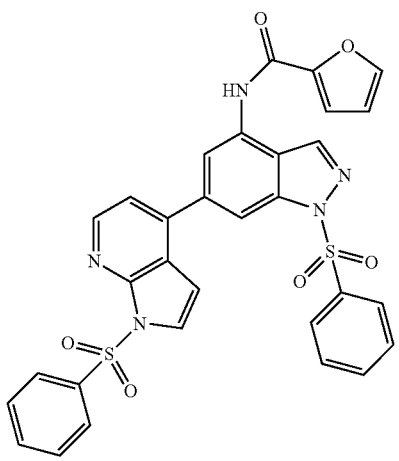 [SMILES: O=C(Nc1cc(-c2ccnc3c2ccn3S(=O)(=O)c2ccccc2)cc2c1cnn2S(=O)(=O)c1ccccc1)c1ccco1]

A stirred solution of N-[1-(phenylsulfonyl)-6-(trimethylstannanyl)-1H-indazol-4-yl]-2-furancarboxamide (216 mg) and 4-bromo-1-(phenylsulfonyl)-1H-pyrrolo[2,3-b]pyridine (182 mg) with Solvias catalyst (11 mg) in DMF (3 ml) was heated at 120° C. for 20 min in the microwave. The solvent was evaporated and the residue was purified on 20 g silica cartridge using ether and then 10% ethyl acetate:ether. The appropriate fractions were evaporated to dryness and triturated with ether to give the title compound, 90 mg as an off-white solid.
LCMS (method B); $R_t$=3.32 min, MH$^+$=624.

Intermediate 101

2-(Chloromethyl)-N-[6-(1H-indol-4-yl)-1-(phenyl-sulfonyl)-1H-indazol-4-yl]-1,3-thiazole-4-carboxamide

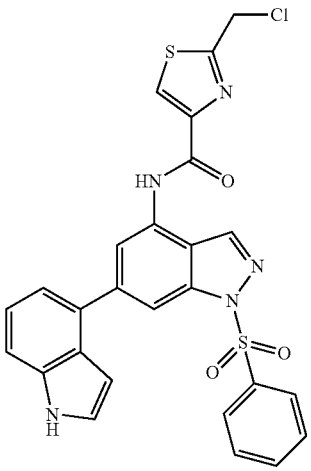 [SMILES: O=C(Nc1cc(-c2cccc3[nH]ccc23)cc2c1cnn2S(=O)(=O)c1ccccc1)c1csc(CCl)n1]

To solution of 6-(1H-indol-4-yl)-1-(phenylsulfonyl)-1H-indazol-4-amine (1.5 g) in chloroform (20 ml) at 0° C. was added DIPEA (1.35 ml). 2-(Chloromethyl)-1,3-thiazole-4-carbonyl chloride (1.8 g) in chloroform (20 ml) was added dropwise and the mixture was stirred at 0° C. for 1 h 15 min. The mixture was allowed to warm to RT and stirring continued for 18 h. A further portion of 2-(chloromethyl)-1,3-thiazole-4-carbonyl chloride (0.2 g) was added to the mixture which was stirred at RT for 30 min. Water (50 ml) was added and the mixture was extracted with DCM (2×100 ml), separating the layers using a hydrophobic frit. The organics were collected and solvent removed in vacuo to give a brown solid which was triturated with ether (10 ml). The solid was filtered and dried in a vacuum oven overnight to afford the title compound, 1.6 g.

LCMS (Method E): $R_f$=1.26 min, MH$^+$=548.

Intermediate 102

2-(Chloromethyl)-1,3-thiazole-4-carbonyl chloride

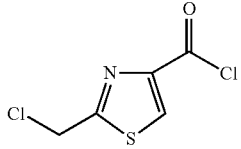

To a solution of 2-(hydroxymethyl)-1,3-thiazole-4-carboxylic acid (370 mg) in chloroform (5 ml) and DMF (0.1 ml) was added thionyl chloride (1 ml). The mixture was heated to reflux for 1 h. The mixture was cooled and the solvent removed in vacuo. The residue was azeotroped with chloroform (5 ml) and dried on a high vacuum line for 30 min to afford the title compound. The material was not suitable for long term storage at RT so was either used immediately or stored at −20° C. for up to 2 weeks.

LCMS was run as a solution in MeOH (method E); $R_f$=0.77 min, MH$^+$=191.

Intermediate 103

2-(Hydroxymethyl)-1,3-thiazole-4-carboxylic acid

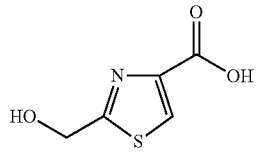

A solution of 2-{[(2,2-dimethylpropanoyl)oxy]methyl}-1,3-thiazole-4-carboxylic acid (3 g) and potassium carbonate (2.326 g) in methanol (100 ml) and water (30 ml) was heated to reflux for 4 h. The mixture was cooled and concentrated in vacuo to ~30 ml. It was then acidified with 2 M HCl (aq) (50 ml) and concentrated in vacuo. The resulting solid was treated with hot MeOH/Ethyl acetate (2:1), washing well before filtering off the remaining solid. The filtrate was concentrated in vacuo to give a brown solid which was dissolved in MeOH and added to the top of 2×70 g aminopropyl cartridge that had been preconditioned with MeOH. The cartridges were both eluted with MeOH and then with 10% HCl in MeOH. The acidic fractions were combined and the solvent removed in vacuo to give the title compound as a brown oil, 550 mg.

LCMS (method E); $R_f$=0.38 min, MH$^+$=160.

Intermediate 104

1-(Phenylsulfonyl)-6-[1-(phenylsulfonyl)-1H-pyrrolo[2,3-b]pyridin-4-yl]-1H-indazol-4-amine

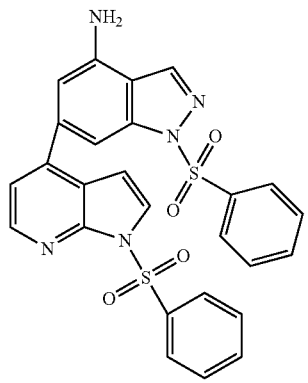 [SMILES: Nc1cc(-c2ccnc3c2ccn3S(=O)(=O)c2ccccc2)cc2c1cnn2S(=O)(=O)c1ccccc1]

4-Bromo-1-(phenylsulfonyl)-1H-pyrrolo[2,3-b]pyridine (1.546 g), 1-(phenylsulfonyl)-6-(trimethylstannanyl)-1H-indazol-4-amine (2 g) and Pd(PPh$_3$)$_4$ (0.265 g) were added to DMF (30 ml) under nitrogen. The mixture was heated at 100° C. for 2 days then cooled to RT and concentrated in vacuo. The mixture was purified by column chromatography on silica (70 g) eluting with ammonia and methanol in DCM, then again using the ISCO Companion, eluting with a gradient of 30-85% MeCN (+0.1% TFA): H2O (0.1% TFA). Fractions containing desired product were combined and the solvent was removed to afford the title compound as a brown solid (663 mg).

LCMS (Method E) $R_f$=1.17 min, MH$^+$=530.

Intermediate 105

4-Bromo-1-(phenylsulfonyl)-1H-pyrrolo[2,3-b]pyridine

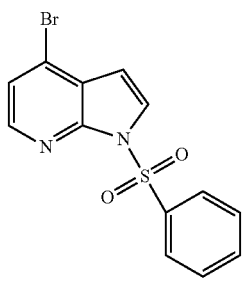 [SMILES: O=S(=O)(c1ccccc1)n1ccc2c(Br)ccnc21]

4-Bromo-1H-pyrrolo[2,3-b]pyridine (2 g) and sodium hydride (60% in mineral oil) (0.406 g) were added to DMF (30 ml) with stirring under nitrogen. After 15 min the reaction was cooled in an ice bath and benzenesulfonyl chloride (1.295 ml) was added. The reaction mixture was stirred in the ice bath for 30 min and then allowed to warm up to RT. Water (30 ml) was added and the precipitate collected by filtration to afford the title compound as an orange solid, 4.8 g.

LCMS (Method E) $R_t$=1.19 min, MH$^+$=339.

Intermediate 106

3-Fluoro-6-{6-fluoro-1-[(4-nitrophenyl)sulfonyl]-1H-indol-4-yl}-1-(phenylsulfonyl)-1H-indazol-4-amine

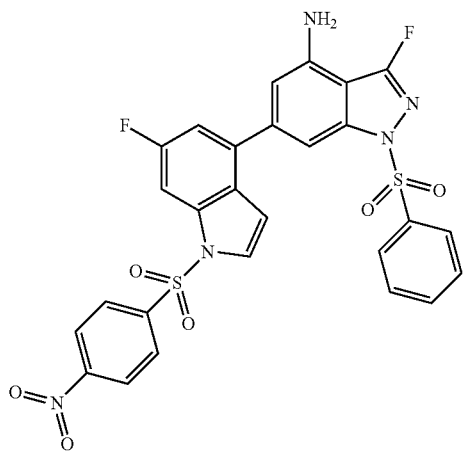 [SMILES: Nc1cc(-c2cc(F)cc3c2ccn3S(=O)(=O)c2ccc([N+](=O)[O-])cc2)cc2c1c(F)nn2S(=O)(=O)c1ccccc1]

A solution of 3-fluoro-1-(phenylsulfonyl)-6-(trimethylstannanyl)-1H-indazol-4-amine (0.65 g), 4-bromo-6-fluoro-1-[(4-nitrophenyl)sulfonyl]-1H-indole (0.69 g) and Pd(PPh$_3$)$_4$ (0.17 g) in DMF (5 ml) was heated to 120° C. for 18 h. The mixture was concentrated in vacuo and purified by silica cartridge (100 g) by Flashmaster II using a gradient of cyclohexane and ethyl acetate to give the title compound, 0.48 g as an orange solid.

LCMS (Method E): $R_t$=1.39 min.

Intermediate 107

2-(Chloromethyl)-N-{1-(phenylsulfonyl)-6-[1-(phenylsulfonyl)-1H-pyrrolo[2,3-b]pyridin-4-yl]-1H-indazol-4-yl}-1,3-thiazole-4-carboxamide

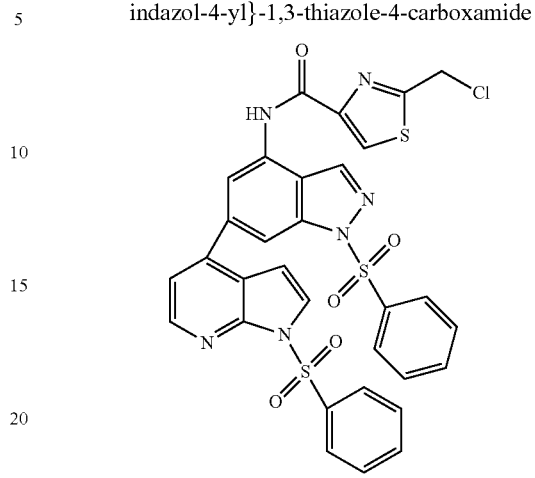

1-(Phenylsulfonyl)-6-[1-(phenylsulfonyl)-1H-pyrrolo[2,3-b]pyridin-4-yl]-1H-indazol-4-amine (663 mg) in chloroform (10 ml) was stirred at 0° C. DIPEA (0.437 ml) was added into the reaction mixture, then 2-(chloromethyl)-1,3-thiazole-4-carbonyl chloride (300 mg) in chloroform (10 ml) was added. The reaction mixture was stirred at 0° C. for 15 min. 2-(Chloromethyl)-1,3-thiazole-4-carbonyl chloride (400 mg) was added to the reaction mixture and stirring was continued. 2-(Chloromethyl)-1,3-thiazole-4-carbonyl chloride (1.6 g) was added to the reaction mixture which was stirred under nitrogen for 18 h. The solution was treated with DCM (25 ml) and saturated sodium bicarbonate aq (25 ml), and then stirred for 10 min. The organic layer was separated, washed with diluted sodium chloride aq (25 ml) and then passed through a hydrophobic frit. A part of the solvent was removed then the solution was applied to a silica column (Flasmaster II, 100 g silica cartridge) and eluted with a gradient of 0-100% ethylacetate:cyclohexane over 60 min. Fractions containing desired product were combined and the solvent was removed to afford the title compound, 111 mg as a white solid.

LCMS (Method E) $R_t$=1.34 min, MH$^+$=689.

Intermediate 108

6-(Chloromethyl)-N-[6-(1H-indol-4-yl)-1-(phenylsulfonyl)-1H-indazol-4-yl]-2-pyridinecarboxamide

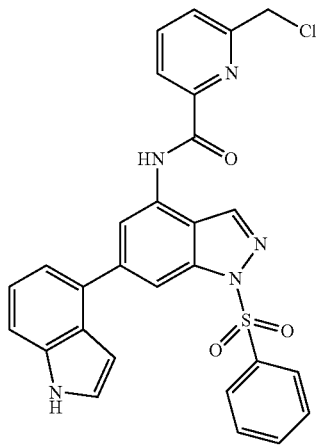 [SMILES: O=C(Nc1cc(-c2cccc3[nH]ccc23)cc2c1cnn2S(=O)(=O)c1ccccc1)c1cccc(CCl)n1]

To a solution of 6-(hydroxymethyl)-2-pyridinecarboxylic acid (500 mg) in chloroform (10 ml) and DMF (0.1 ml) was added thionyl chloride (1 ml) and the mixture heated at 65° C. for 1 h. The solvent was removed in vacuo and the residue was azeotroped with chloroform (5 ml) then dried on a high vacuum line for 30 min to afford an orange oil (650 mg), presumed to be 6-(chloromethyl)-2-pyridinecarbonyl chloride.

To solution of 6-(1H-indol-4-yl)-1-(phenylsulfonyl)-1H-indazol-4-amine (1.37 g) in chloroform (30 ml) at 0° C. was added DIPEA (1.232 ml). 6-(Chloromethyl)-2-pyridinecarbonyl chloride (1.519 g, crude) in chloroform (15 ml) was added dropwise and the mixture was stirred at 0° C. for 15 min. Water (30 ml) was added and the mixture was extracted with DCM (50 ml), separating the layers by hydrophobic frit.

The solvent was removed in vacuo and the residue was dissolved in DCM (5 ml) and added to the top of 2×100 g silica SPE cartridges. One cartridge was eluted with 0-100% Ethyl acetate:cyclohexane over 60 min on the FlashMaster II. Product-containing fractions were combined and concentrated. The resultant solid was dissolved in 1:1 DCM:methanol and loaded onto a 20 g aminopropyl cartridge that had been pre-conditioned with methanol. The cartridge was then eluted with 1:1 DCM:methanol and the fraction obtained was blown down under a stream of nitrogen. The solvent was removed in vacuo to give the title compound as a pink solid, 487 mg. The second cartridge was eluted with 0-100% Ethyl acetate:DCM over 60 min on the FlashMaster II. The product-containing fractions were combined and concentrated to give a further portion of the title compound as a pink solid, 449 mg.

LCMS (Method E) $R_t$=1.31 min, MH$^+$=542.

Intermediate 109

6-{6-Fluoro-1-[(4-nitrophenyl)sulfonyl]-1H-indol-4-yl}-1-(phenylsulfonyl)-1H-indazol-4-amine

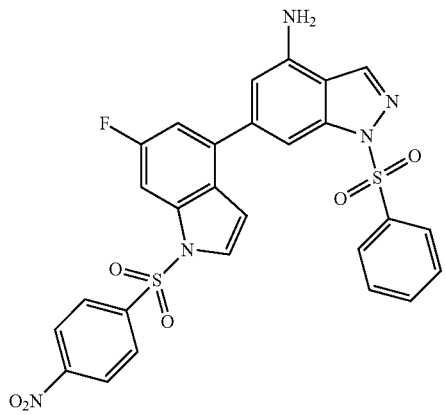 [SMILES: Nc1cc(-c2cc(F)cc3c2ccn3S(=O)(=O)c2ccc([N+](=O)[O-])cc2)cc2c1cnn2S(=O)(=O)c1ccccc1]

A mixture of 1-(phenylsulfonyl)-6-(trimethylstannanyl)-1H-indazol-4-amine (0.8 g), 4-bromo-6-fluoro-1-[(4-nitrophenyl)sulfonyl]-1H-indole (0.879 g) and Pd(PPh$_3$)$_4$ (0.212 g) in DMF (5 ml) was heated at 120° C. for 18 h. The solvent was removed in vacuo and the residue purified by silica cartridge (100 g) using a gradient of cyclohexane and ethyl acetate to give the title compound as an orange solid, 0.42 g.

LCMS (Method E); $R_t$=1.34 min.

Intermediate 110

4-Bromo-6-fluoro-1-[(4-nitrophenyl)sulfonyl]-1H-indole

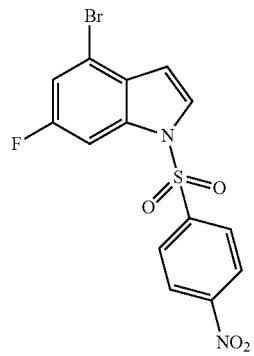 [SMILES: O=[N+]([O-])c1ccc(S(=O)(=O)n2ccc3c(Br)cc(F)cc32)cc1]

To a mixture of 4-bromo-6-fluoro-1H-indole (2 g) in DMF (5 ml) was added sodium hydride (60% in mineral oil) (0.448 g). The reaction was stirred at 20° C. for 10 min. 4-Nitrobenzenesulfonyl chloride (2.278 g) was added and the reaction was stirred at 20° C. for 1 h. The mixture was poured onto water (100 ml), and extracted with DCM (50 ml) which was separated by hydrophobic frit. Purification by silica (2×100 g) on Flashmaster II using a gradient of DCM and cyclohexane gave the title compound as a pale yellow solid, 1.54 g.

LCMS (Method E); $R_t$=1.39 min.

Intermediate 111

6-{1-[(4-Methyl phenyl)sulfonyl]-1H-pyrazolo[3,4-b]pyridin-5-yl}-1-(phenylsulfonyl)-1H-indazol-4-amine

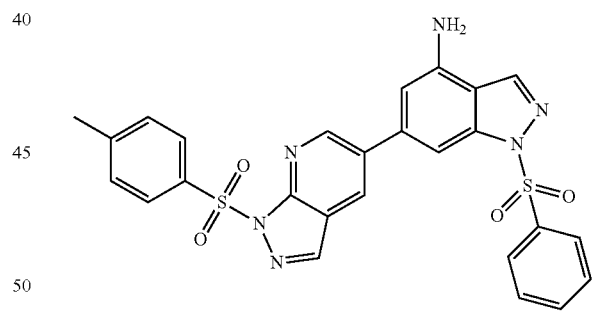

1-(Phenylsulfonyl)-6-(trimethylstannanyl)-1H-indazol-4-amine (775 mg), Pd(PPh$_3$)$_4$ (212 mg) and 5-bromo-1-[(4-methylphenyl)sulfonyl]-1H-pyrazolo[3,4-b]pyridine (775 mg) were introduced into a microwave vial and DMF (10 ml) was added. The mixture was heated in the microwave at 120° C. for 4 h. The solvent was removed in vacuo and the crude residue was placed on a high vacuum line overnight. The resulting brown oil was purified by FlashMaster II. The crude material was dissolved in chloroform and added to the top of 2×100 g silica SPE cartridges that were subsequently eluted with 0-100% ethyl acetate:cyclohexane over 60 min. The product-containing fractions were combined and the solvent was removed in vacuo. The residue was dried on a high vacuum line to give the title product, 371 mg as a cream solid.

LCMS (Method E); $R_t$=1.18 min, MH$^+$=545.

Intermediate 112

6-[2-Methyl-1-(phenylsulfonyl)-1H-pyrrolo[2,3-b]pyridin-4-yl]-1-(phenylsulfonyl)-1H-indazol-4-amine

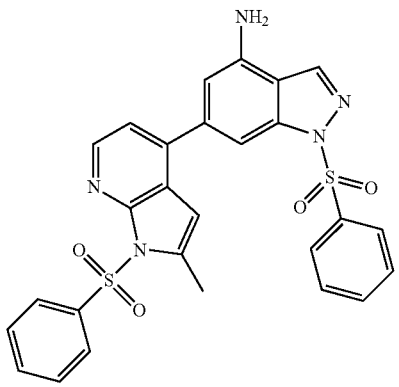 [SMILES: Cc1cc2c(-c3cc(N)c4cnn(S(=O)(=O)c5ccccc5)c4c3)ccnc2n1S(=O)(=O)c1ccccc1]

1-(Phenylsulfonyl)-6-(trimethylstannanyl)-1H-indazol-4-amine (1 g), Pd(PPh$_3$)$_4$ (0.265 g) and 4-bromo-2-methyl-1-(phenylsulfonyl)-1H-pyrrolo[2,3-b]pyridine (0.966 g) were weighed into a microwave vial and DMF (15 ml) was added. The mixture was heated in the microwave at 120° C. for 3 h. The solvent was removed in vacuo and the crude residue was dried in a vacuum oven overnight. The resulting brown oil was purified by FlashMaster II. The residue was dissolved in chloroform and added to the top of 2×100 g silica SPE cartridges that were subsequently eluted with 0-100% ethyl acetate:cyclohexane over 60 min. The product-containing fractions were combined and the solvent was removed in vacuo. The resulting pale yellow oil was dried on a high vacuum line to give the title product, 737 mg as a glassy yellow solid.

LCMS (Method E); R$_t$=1.23 min, MH$^+$=544.

Intermediate 113

4-Bromo-2-methyl-1-(phenylsulfonyl)-1H-pyrrolo[2,3-b]pyridine

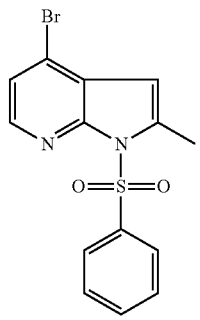 [SMILES: Cc1cc2c(Br)ccnc2n1S(=O)(=O)c1ccccc1]

To a stirring solution of 4-bromo-1-(phenylsulfonyl)-1H-pyrrolo[2,3-b]pyridine (20.08 g) in anhydrous Tetrahydrofuran (200 ml) at −50° C. was added LDA (66.2 ml) dropwise over 20 min. The resulting suspension was stirred at −50° C. for 1 h then methyl iodide (22.34 ml) was added dropwise over 20 min. The reaction mixture was stirred at −30° C. for 1 h then quenched by the addition of water. The layers were separated and the aq was re-extracted with DCM. The THF layer was concentrated in vacuo then re-dissolved in DCM. The DCM extracts were then combined and washed with water, brine, then dried over magnesium sulfate, filtered and evaporated to yield an oily residue that was recrystallised using cyclohexane:ethyl acetate (5:1) to yield a solid which was triturated using methanol, collected by filtration then dried in vacuo at 45° C. overnight to yield the title compound, 10.52 g as a pale yellow solid.

LCMS (Method E); R$_t$=1.25 min, MH$^+$=351.

Intermediate 114

3-Fluoro-6-[2-methyl-1-(phenylsulfonyl)-1H-pyrrolo[2,3-b]pyridin-4-yl]-1-(phenylsulfonyl)-1H-indazol-4-amine

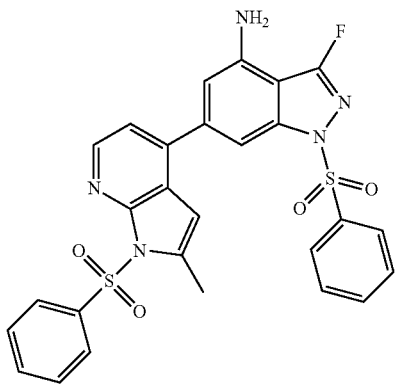 [SMILES: Cc1cc2c(-c3cc(N)c4c(F)nn(S(=O)(=O)c5ccccc5)c4c3)ccnc2n1S(=O)(=O)c1ccccc1]

3-Fluoro-1-(phenylsulfonyl)-6-(trimethylstannanyl)-1H-indazol-4-amine (660 mg), Pd(PPh$_3$)$_4$ (168 mg) and 4-bromo-2-methyl-1-(phenylsulfonyl)-1H-pyrrolo[2,3-b]pyridine (613 mg) were weighed into a microwave vial and DMF (10 ml) was added. The mixture was heated to 120° C. overnight. The mixture was then cooled to RT and the solvent was removed in vacuo. The crude material was dried in a vacuum oven overnight. The resulting dark brown oil was purified by FlashMaster II. The crude material was dissolved in chloroform and added to the top of 2×100 g silica SPE cartridges that were subsequently eluted with 0-100% ethyl acetate:cyclohexane over 80 min. The product-containing fractions were combined and the solvent removed in vacuo to give the title compound, 357 mg as a cream solid.

LCMS (Method E); R$_t$=1.31 min, MH$^+$=562.

Intermediate 115

3-Fluoro-6-{1-[(4-methylphenyl)sulfonyl]-1H-pyrazolo[3,4-b]pyridin-5-yl}-1-(phenylsulfonyl)-1H-indazol-4-amine

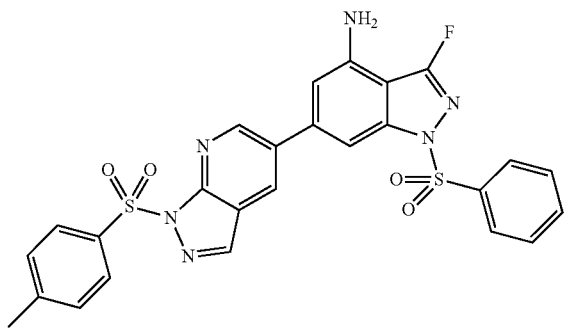 [SMILES: Cc1ccc(S(=O)(=O)n2ncc3cc(-c4cc(N)c5c(F)nn(S(=O)(=O)c6ccccc6)c5c4)cnc32)cc1]

5-Bromo-1-[(4-methylphenyl)sulfonyl]-1H-pyrazolo[3,4-b]pyridine (605 mg) in DMF (4 ml) was added to a solution of 3-fluoro-1-(phenylsulfonyl)-6-(trimethylstannanyl)-1H-indazol-4-amine (650 mg) in DMF (6 ml), treated with Pd( )Ph₃)₄ (165 mg) and then heated at 120° C. for 21 h. The solution was allowed to cool, filtered, and then evaporated. The residue was dissolved in chloroform, loaded onto a 100 g silica cartridge which was eluted with 0-100% ethyl acetate: cyclohexane over 60 min using the Flashmaster II. Appropriate peaks were combined and evaporated to give the title compound as a white solid, 0.577 g.

LCMS (Method B); $R_t$=3.28 min, MH⁺=563.

Intermediate 116

5-Bromo-1-[(4-methylphenyl)sulfonyl]-1H-pyrazolo[3,4-b]pyridine

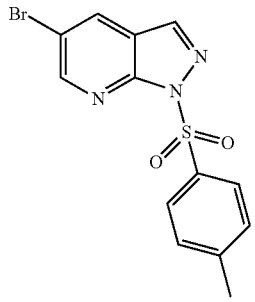 [SMILES: Cc1ccc(S(=O)(=O)n2ncc3cc(Br)cnc32)cc1]

5-Bromo-1H-pyrazolo[3,4-b]pyridine (1.39 g) in DMF (6 ml) was cooled in an ice-bath under nitrogen and treated portionwise with sodium hydride (0.308 g) (60% dispersion in oil) over a period of about 15 min. The reaction was left to stir in the ice-bath for 40 min, then treated with tosyl chloride (1.469 g) in DMF (2 ml). The reaction was left to stir in the ice-bath under nitrogen and the ice left to melt overnight. The reaction was stirred for a total of 20 h. The reaction was treated cautiously with water (6 ml) and stirred for 5 min. The reaction was poured onto water (60 ml), filtered and the residue treated with DCM (20 ml). The mixture was stirred, and then pushed through a frit into a cartridge with a hydrophobic frit. The solution was allowed to drip through, and then this procedure was repeated with further DCM (2×15 ml). The combined filtrates were evaporated to dryness to give the title compound as a brown solid, 1.802 g.

LCMS (Method B); $R_t$=2.75 min, MH⁺=354.

Intermediate 117

6-Bromo-1-methyl-1H-indazol-4-amine

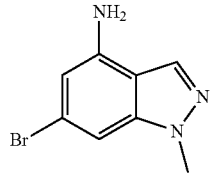

6-Bromo-1H-indazol-4-amine (available from Sinova, 300 mg, 1.42 mmol) was dissolved in THF (7.5 ml) and the mixture cooled to 0° C. Sodium hydride (60% in mineral oil) (62 mg) was then slowly added. The mixture was stirred for 15 min, then methyl iodide (221 mg) was added and stirring continued at 0° C. for 3 h. The reaction mixture was quenched by careful addition of methanol (2 ml), then water (10 ml), then extracted into ethyl acetate and the organic layer was concentrated in vacuo. The residue was purified by column chromatography on silica eluting with a gradient of 0-50% ethyl acetate in cyclohexane. Fractions containing desired product were combined and concentrated in vacuo to afford the title compound, 48 mg.

LCMS (Method E): $R_t$=0.91 min, MH⁺=227.

Intermediate 118

1-Methyl-6-{1-[(4-methylphenyl)sulfonyl]-1H-pyrrolo[2,3-b]pyridin-4-yl}-1H-indazol-4-amine

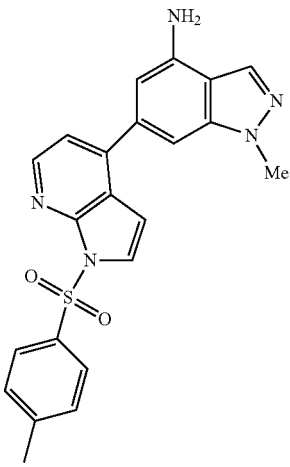 [SMILES: Cc1ccc(S(=O)(=O)n2ccc3c(-c4cc(N)c5cnn(C)c5c4)ccnc32)cc1]

6-Bromo-1-methyl-1H-indazol-4-amine (300 mg), {1-[(4-methylphenyl)sulfonyl]-1H-pyrrolo[2,3-b]pyridin-4-yl}boronic acid (482 mg), tripotassium phosphate (845 mg) and Pd(dppf)Cl₂ (97 mg) were added to 1,4-dioxane (7 ml) and water (3.5 ml). The reaction mixture was heated in the microwave at 100° C. for 15 min. After this time the reaction mixture was partitioned between water (20 ml) and DCM (20 ml). The organic layer was extracted then put through hydrophobic frits. The solvent was removed to afford a crude mixture. The residue was purified by column chromatography on silica (100 g) eluting with a gradient of 0-100% ethyl acetate: cyclohexane. Fractions containing desired product were combined and concentrated in vacuo to afford the title compound, 312 mg as an orange solid.

LCMS (Method E): $R_t$=1.1 min, MH⁺=418.

Intermediate 119

2-Methyl-N-(1-methyl-6-{1-[(4-methylphenyl)sulfonyl]-1H-pyrrolo[2,3-b]pyridin-4-yl}-1H-indazol-4-yl)-1,3-thiazole-4-carboxamide

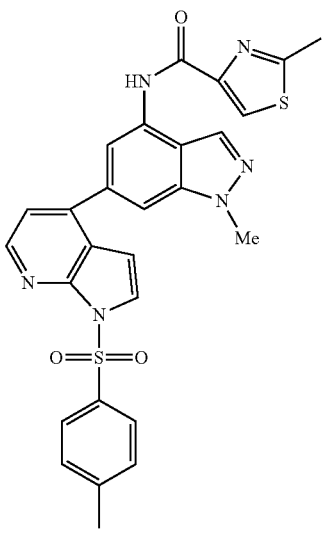 [SMILES: Cc1ccc(S(=O)(=O)n2ccc3c(-c4cc(NC(=O)c5csc(C)n5)c5cnn(C)c5c4)ccnc32)cc1]

1-Methyl-6-{1-[(4-methylphenyl)sulfonyl]-1H-pyrrolo[2,3-b]pyridin-4-yl}-1H-indazol-4-amine (75 mg) and pyridine (0.029 ml) were added to DCM (5 ml) under stirring at RT under nitrogen. 2-Methyl-1,3-thiazole-4-carbonyl chloride (38 mg) was added into the reaction mixture. The reaction mixture was partitioned between water (20 ml) and DCM (20 ml).

The organic layer was extracted and the solvent was removed to afford the title compound, 100 mg.

LCMS (Method E): $R_t$=1.27 min, MH$^+$=543.

Intermediate 120

1,4-Dimethyl-1H-pyrazole-3-carbonyl chloride

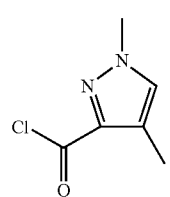

1,4-Dimethyl-1H-pyrazole-3-carboxylic acid (190 mg) was weighed to a round bottom flask and thionyl chloride (1 ml) was added. The reaction was heated to reflux for 6 h then overnight at RT. After this time thionyl chloride was evaporated and the residue azeotroped with toluene to afford the title compound, 200 mg.

$^1$H NMR (CDCl$_3$) δ 7.2 (m, 1H), 3.98 (s, 3H), 2.27 (s, 3H).

Intermediate 121

4-Bromo-1-[(4-nitrophenyl)sulfonyl]-1H-indole-6-carbonitrile

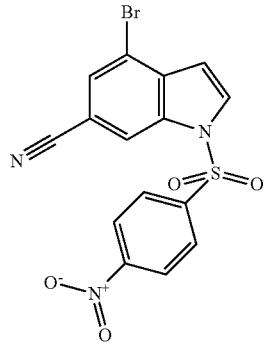 [SMILES: N#Cc1cc(Br)c2ccn(S(=O)(=O)c3ccc([N+](=O)[O-])cc3)c2c1]

4-Bromo-1H-indole-6-carbonitrile (207 mg), PS-BEMP (900 mg) and 4-nitrobenzenesulfonyl chloride (380 mg) were weighed to a round bottom flask, then N,N-Dimethylformamide (4 ml) was added and the reaction was stirred at RT. The reaction was filtered and washed with DMF. The DMF was evaporated and the residue was dissolved in DCM:methanol and passed through a 5 g SAX cartridge (preconditioned with methanol) washing with DCM:methanol. The residue was evaporated to afford the title compound, 360 mg as a pale orange solid.

LCMS (Method E): $R_t$=1.29 min.

Intermediate 122

4-Bromo-2-chloro-1H-indole

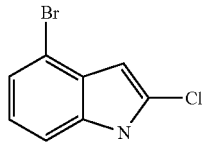 [SMILES: Clc1cc2c(Br)cccc2[nH]1]

4-Bromo-2-chloro-1-[(4-methylphenyl)sulfonyl]-1H-indole (215 mg), IPA (2.5 ml) and 2 M NaOH (aq) (2.5 ml) were mixed in a microwave vial and heated in the microwave for 30 min at 120° C. The reaction was acidified using 2M HCl (aq) and then extracted with DCM, which was passed through a hydrophobic frit, then evaporated to dryness. The residue was triturated with methanol which was then evaporated to afford the title compound, 112 mg.

LCMS (Method E): $R_t$=0.82 min.

Intermediate 123

2-Methyl-1,3-thiazole-4-carbonyl chloride

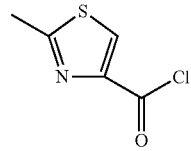

To 2-methyl-1,3-thiazole-4-carboxylic acid (1 g) was added thionyl chloride (5 ml). The mixture was heated at 80° C. for 8 h. Thionyl chloride (5 ml) was added and the mixture heated for 2 h at 80° C. Further thionyl chloride (5 ml) was added and the mixture heated for 2 h. The mixture was concentrated in vacuo and azeotroped with toluene to give the title compound, 1.12 g.

$^1$H NMR (DSMO) δ 8.34 (s, 1H), 2.80 (s, 3H).

Intermediate 124

6-Bromo-1-[(4-nitrophenyl)sulfonyl]-1H-benzimidazole

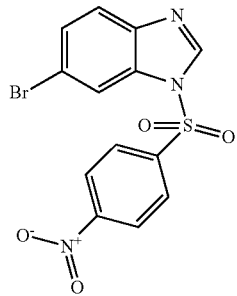 [SMILES: O=[N+]([O-])c1ccc(S(=O)(=O)n2cnc3ccc(Br)cc32)cc1]

5-Bromo-1H-benzimidazole (756 mg) was dissolved in anhydrous DMF (3 ml) and cooled in an ice bath. Sodium hydride (60% in mineral oil) (153 mg) was added in one portion. The reaction was stirred for 1 h, before addition of 4-nitrobenzenesulfonyl chloride (850 mg) in DMF (2 ml) to the reaction. The reaction was stirred for a further hour before warming to RT and addition of water (10 ml). The reaction was stirred vigorously then left at RT overnight. Ethyl acetate (ca. 10 ml) was added to the reaction mixture and was then vigorously stirred. The reaction was dissolved in DCM:methanol and passed through a 1 g SAX cartridge. The residue was purified on silica cartridge using cyclohexane:ethyl acetate with a 50-100% gradient. Fractions containing the product were combined and evaporated to dryness to afford the title compound, 401 mg.

LCMS (Method E): $R_t$=1.19 min, $MH^+$=384.

Similarly prepared from the appropriate bromide or iodide were the following;

| Intermediate No | Structure | Name | $R_t$ | $MH^+$ | Bromide or Iodide Name |
|---|---|---|---|---|---|
| 125 | 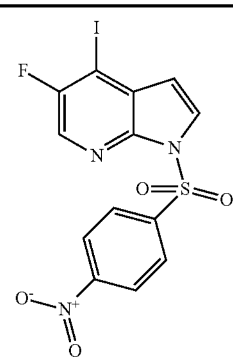 | 5-fluoro-4-iodo-1-[(4-nitrophenyl)sulfonyl]-1H-pyrrolo[2,3-b]pyridine | 1.27 | 448 | 5-fluoro-4-iodo-1H-pyrrolo[2,3-b]pyridine |
| 126 | 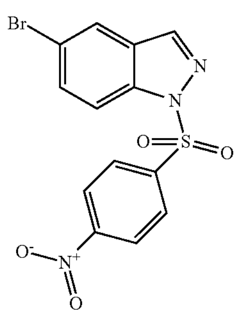 [SMILES: O=[N+]([O-])c1ccc(S(=O)(=O)n2ncc3cc(Br)ccc32)cc1] | 5-bromo-1-[(4-nitrophenyl)sulfonyl]-1H-indazole | 1.25 | N/A | 5-bromo-1H-indazole |
| 127 | 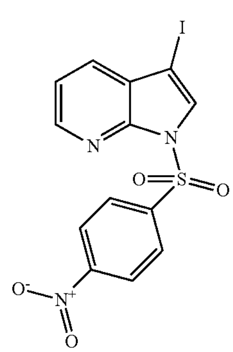 [SMILES: O=[N+]([O-])c1ccc(S(=O)(=O)n2cc(I)c3cccnc32)cc1] | 3-iodo-1-[(4-nitrophenyl)sulfonyl]-1H-pyrrolo[2,3-b]pyridine | 1.24 | 430 | 3-iodo-1H-pyrrolo[2,3-b]pyridine |

Intermediate 128

3-Bromo-1-[(4-nitrophenyl)sulfonyl]-1H-pyrrolo[2,3-c]pyridine

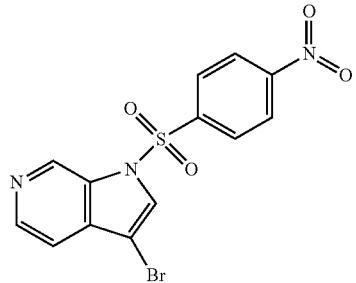 [SMILES: O=[N+]([O-])c1ccc(S(=O)(=O)n2cc(Br)c3ccncc32)cc1]

Sodium hydride (60% in mineral oil) (217 mg) was added to a stirred solution of 3-bromo-1H-pyrrolo[2,3-c]pyridine (535 mg) in DMF (5 ml) that had been cooled in an ice bath to 0° C. and placed under nitrogen. The mixture was stirred for 30 min, until hydrogen evolution ceased, and then 4-nitrobenzenesulfonyl chloride (662 mg) was added. The mixture was stirred at 0° C. for 1 hour. The mixture was then warmed to RT and stirred for a further 30 min. The solution was poured into stirring water (10 ml) and rapidly stirred for 15 min. The resulting brown solid was collected by filtration, washed with water and dried in a vacuum oven at 50° C. to give a yellow solid. This crude material was purified by FlashMaster II. The residue was dissolved in DCM:methanol (1:1) and pre adsorbed onto silica. This was added to the top of a 20 g silica SPE cartridge that was subsequently eluted with 0-50% ethyl acetate:cyclohyexane over 40 min. The product-containing fractions were combined and the solvent removed in vacuo to give the title compound, 233 mg as a white solid.

LCMS (Method E): $R_f$=1.01 min, MH$^+$=384.

Intermediate 129

1-{[(1,1-Dimethylethyl)oxy]carbonyl}-3-methyl-1H-pyrazole-4-carboxylic acid

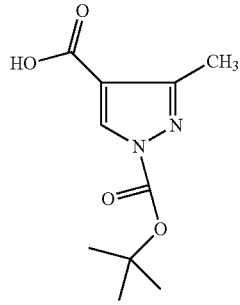 [SMILES: Cc1nn(C(=O)OC(C)(C)C)cc1C(=O)O]

3-Methyl-1H-pyrazole-4-carboxylic acid (200 mg) was dissolved in DMF (5 ml), sodium hydride (60% in mineral oil) (140 mg) was added and the mixture was stirred for 15 min at 20° C. Bis(1,1-dimethylethyl) dicarbonate (0.442 ml) was added and the mixture was stirred under nitrogen at 20° C. for 18 h. The reaction was quenched with saturated ammonium chloride aq (15 ml), extracted with DCM (3×20 ml) and separated with a hydrophobic frit. The solvent was removed in vacuo and to the residue 1% LiCl (aq) (20 ml) and diethyl ether (20 ml) were added. The phases were separated and the aq phase was extracted with diethyl ether (2×15 ml). The combined organic phases were dried over magnesium sulphate and the solvent was removed in vacuo to give the title compound, 98 mg as an off-white solid.

LCMS (Method F): $R_f$=2.53 min, MH$^+$=227.

Intermediate 130

N-[5-[4-(5-{[(2R,6S)-2,6-Dimethyl-4-morpholinyl]methyl}-1,3-oxazol-2-yl)-1-(phenylsulfonyl)-1H-indazol-6-yl]-2-(methyloxy)-3-pyridinyl]methanesulfonamide

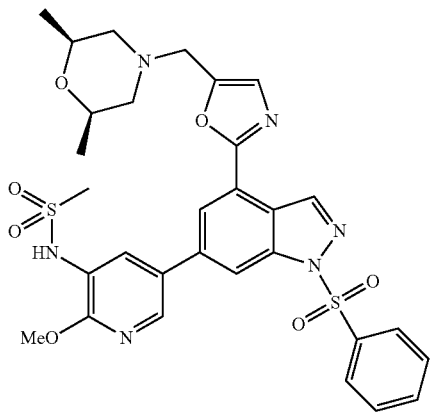 [SMILES: COc1ncc(-c2cc(-c3ncc(CN4C[C@@H](C)O[C@@H](C)C4)o3)c3cnn(S(=O)(=O)c4ccccc4)c3c2)cc1NS(C)(=O)=O]

Method A

A suspension of palladium (II) acetate (0.05 g) and tricyclohexylphosphine (0.16 g) in isopropanol (27 ml) was added to a suspension of 6-Chloro-4-(5-{[(2R,6S)-2,6-dimethyl-4-morpholinyl]methyl}-1,3-oxazol-2-yl)-1-(phenylsulfonyl)-1H-indazole (5.40 g), Potassium trifluoro{6-(methyloxy)-5-[(methylsulfonyl)amino]-3-pyridinyl}borate (6.19 g) and sodium bicarbonate (2.87 g) in isopropanol (27 ml) and water (38 ml) stirring under nitrogen at 60-65° C. The reaction mixture was stirred at 60-65° C. for 2.5 hours and was then cooled to room temperature. The resultant suspension was filtered, washed with 1:1 v/v water isopropanol (11 ml then 22 ml) and the solid dried under vacuum at 40° C. to give the title compound as a grey solid (7.73 g).

LCMS (Method B): Rt 2.59 min, MH$^+$ 653.

Method B

All weights, volumes and equivalents are relative to ((2-(6-chloro-1-(phenylsulfonyl)-1H-indazol-4-yl)oxazol-5-yl)methyl)-cis-2,6-dimethylmorpholine.

((2-(6-Chloro-1-(phenylsulfonyl)-1H-indazol-4-yl)oxazol-5-yl)methyl)-cis-2,6-dimethylmorpholine (1.00 wt, 460 g), N-(2-methoxy-5-(4,4,5,5-tetramethyl-1,3,2-dioxaborolan-2-yl)pyridin-3-yl)methanesulfonamide (0.741 wt, 1.1 eq, 341 g) and potassium phosphate (0.523 wt, 1.2 eq, 241 g) are combined in IPA (5 vol, 2.3 L) and water (5 vol, 2.3 L) in a clean CLR under nitrogen. Potassium hydrogen difluoride (0.353 wt, 2.2 eq, 163 g) is added and the mixture is heated to 75-80° C. and degassed at this temperature for at least 1 hr. In a separate vessel IPA (5 vol, 2.3 L) is degassed by being heated to reflux, then stirred for a further 20 min at this temperature under a flow of $N_2$ before being cooled to 20-25° C. under a nitrogen atmosphere. To the degassed IPA (5 vol, 2.3 L) is charged palladium (II) acetate (0.00922 wt, 0.02 eq, 4.25 g), followed by tricyclohexylphosphine (0.0230 wt, 0.04 eq, 10.6 g) and the mixture stirred at 20-25° C. for at least 0.5 hr. The resultant yellow solution is added to the reaction mixture and stirred at 75-80° C. for at least 2 hr, then monitored for completion by HPLC. The mixture is cooled to 30° C. over 1 hr and water (5 vol, 2.3 L) is added. The slurry is allowed to cool to 20° C., then aged at this temperature for at least 0.5 hr, filtered, washed with IPA:water (1:1 v/v, 2×2 vol, 2×920 ml) and sucked dry. The solid is dried in vacuo at 60° C. to constant probe temperature to afford N-(5-(4-(5-((cis-2,6-dimethylmorpholino)methyl)oxazol-2-yl)-1-(phenylsulfonyl)-1H-indazol-6-yl)-2-methoxypyridin-3-yl)methanesulfonamide as an off-white solid.

Intermediate 131

5-Bromo-2-(methyloxy)-3-nitropyridine

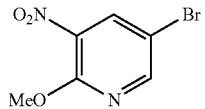

Method A

A solution of 25% wt sodium methoxide in methanol (2.1 L) was added to a suspension of 5-bromo-2-chloro-3-nitropyridine (1.70 kg) in methanol (6.6 L), stirred under nitrogen at 0-5° C. The reaction mixture was stirred at 5-10° C. for 2.75 hours and then water (8.5 L) was added. The reaction mixture was cooled to 20-25° C. The mixture was then concentrated under vacuum and the resultant suspension was filtered, washed with water (8.5 L then 2×4.25 L) and the solid dried under vacuum to give the title compound as an off-white solid (1.37 kg).

$^1$H NMR (400 MHz, Chloroform-d) δ (ppm) 8.46 (s, 1H), 8.40 (s, 1H).

Method B

All weights, volumes and equivalents are relative to 5-bromo-2-chloro-3-nitropyridine.

To a suspension of 5-bromo-2-chloro-3-nitropyridine (75.0 g, 1 wt, 1 eq) in methanol (300 mL, 4 vols), is added a solution of sodium methoxide in methanol (25 wt %, 88.6 g, 1.3 eq) over approximately 1 hour so as to maintain the internal temperature at 20±5° C. The mixture is stirred at 20° C. for at least 0.5 hr, then monitored for completion by HPLC. Water (375 mL, 5 vols) is then added to the mixture at such a rate as to maintain the internal temperature below 30° C., then aged at this temperature for at least 0.5 hr. The batch is then concentrated to 6 vols in vacuo. The resulting slurry is allowed to cool to 20-25° C., then collected by vacuum filtration, washed with water and dried in vacuo with a nitrogen bleed at 20-25° C. to constant weight to afford 5-bromo-2-methoxy-3-nitropyridine as a white solid.

Intermediate 132

5-Bromo-2-(methyloxy)-3-pyridinamine

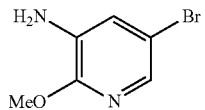

Iron powder (1.17 kg) was added to a suspension of 5-bromo-2-(methyloxy)-3-nitropyridine (1.36 kg) in IMS (6.1 L), stirred under nitrogen at 20-25° C. Water (0.8 L) was then added and the mixture cooled to less than 10° C. Aqueous hydrochloric acid (0.8 L concentrated hydrochloric acid and 0.8 L water) was then added to the reaction mixture, maintaining the temperature below 10-15° C. The suspension was warmed to 20-25° C. and then stirred at this temperature for 23 hours. The suspension was filtered, the filter cake washed with IMS (2×2.7 L) and the combined filtrates concentrated under vacuum. Water (4.1 L) was added slowly to the concentrated solution and the resulting suspension was held at 20-25° C. for 1.75 hours. The resultant suspension was filtered, washed with water (2×6.8 L) and the solid dried under vacuum to give the title compound as an off-white solid (1.13 kg).

LCMS (Method B): Rt 2.16 min, MH$^+$ 204.

Intermediate 133

N-[5-Bromo-2-(methyloxy)-3-pyridinyl]methanesulfonamide

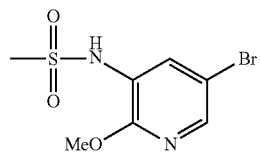

Method A

Pyridine (540 ml) was added to a suspension of 5-bromo-2-(methyloxy)-3-pyridinamine (902.0 g) in acetonitrile (2.1 L), stirred under nitrogen at less than 25° C. The mixture was cooled to less than 10° C. and methanesulfonyl chloride (605.3 g) was added maintaining the temperature below 25° C. The reaction mixture was stirred at 15-25° C. for 3 hours. Water (3.6 L) was added slowly to the mixture over 1 hour, maintaining the temperature below 25° C. The resultant suspension was filtered, washed with 3:1 v/v water:acetonitrile (2×1.35 L and the solid dried under vacuum at 45±5° C. to give the title compound as an off-white solid (1.13 kg).

LCMS (Method B): Rt 1.42 min, MH$^+$ 282.

Method B

All weights, volumes and equivalents are relative to 5-bromo-2-methoxypyridin-3-amine hydrochloride.

5-Bromo-2-methoxypyridin-3-amine hydrochloride (100 g, 1 wt, 1 eq) is charged to a CLR containing a mixture of acetonitrile (220 mL, 2.2 vols) and pyridine (101 mL, 1.01 vols, 99 g, 0.99 wt) at room temperature. Methanesulfonyl chloride (56.4 g, 0.564 wt, 1.18 eq) is then added to the mixture over 20 minutes whilst maintaining the temperature at 20° C. Having stirred at 20° C. for a further 1.5 hours, the mixture is sampled and analysed by HPLC. The completed reaction is quenched by the addition of water over 1 hour, maintaining the mixture at 20° C. and with increased stirrer speed. The resulting slurry is stirred for 17 hours and then filtered in vacuo. The cake is washed with 3:1 water:acetonitrile (2×50 mL, 2×0.5 vols) and then dried under vacuum at 40-45° C. to afford N-(5-bromo-2-methoxypyridin-3-yl)methanesulfonamide.

Intermediate 134

Potassium trifluoro{6-(methyloxy)-5-[(methylsulfonyl)amino]-3-pyridinyl}borate

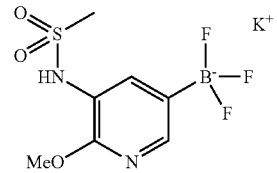 [SMILES: COc1ncc([B-](F)(F)F)cc1NS(C)(=O)=O ; [K+]]

N-[5-bromo-2-(methyloxy)-3-pyridinyl]methanesulfonamide (499.4 g), bis(pinacolato)diboron (498.2 g) and potassium acetate (361.8 g) were charged to the reaction vessel.

The reaction vessel was purged with nitrogen for 10 min before 1,4-dioxane (8.0 L) was added. The resultant solution was heated to 95±5° C. and stirred under nitrogen at this temperature. A degassed solution of tris(dibenzylidene acetone) dipalladium (0) (16.6 g) and tricyclohexylphosphine (25.0 g) in 1,4-dioxane (2.5 L) was added to the reaction vessel over 30 min. The reaction mixture was then stirred at 95±5° C. for 14 hours. The mixture was cooled to 20±3° C. and held at this temperature for 1 hour. The reaction mixture was filtered and concentrated under vacuum. Water (1.0 L) and potassium hydrogenfluoride (555.0 g) were added and the resultant mixture was stirred for 1 hour. Water (2.0 L) was added to the suspension, the aqueous layer was removed and the remaining organic layer was filtered. 1,4-dioxane (12.0 L) was added to the solution which was then dried by azeotropic vacuum distillation. Upon complete distillation the mixture was cooled to 20±3° C. and held at this temperature for 30 min. The resultant suspension was filtered, washed with 1,4-dioxane (2×1 L), then t-butyl methyl ether (2×1.0 L) and the solid dried under vacuum to give the title compound as an off-white solid (708.3 g).

LCMS (Method C): Rt 2.26 min, MH+ 247.

Intermediate 135

Ethyl oxazole-5-carboxylate

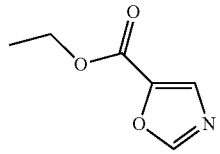

All weights, volumes and equivalents are relative to toluenesulfonylmethyl isocyanide.

Toluenesulfonylmethyl isocyanide (TosMIc) (12.31 g, 1 wt, 1 eq) is dissolved in DCM (61.6 ml, 5 vols) at 0° C. under $N_2$. In a separate vessel, ethyl glyoxalate (50 wt % solution in toluene, 20.6 g, 20.0 ml, 1.67 wt) is diluted with DCM (61.6 ml, 5 vols) under $N_2$ and DBU (12.48 g, 12.35 ml, 1.3 eq, 1.01 wt) is added resulting in a purple solution. The second solution is added to the TosMIc solution over 1 hr, maintaining temperature at 0° C., then checked by HPLC for completion after a further 20 mins. The reaction is quenched by slow addition of 2M HCl (10 vols, 123 ml) and the DCM layer separated. The aqueous layer is re-extracted with DCM (5 vols, 61.6 ml), and the combined organics dried over $Na_2SO_4$, then evaporated on Buchi, 25° C., 100 mbar to remove DCM and toluene. Distilled at 12 mbar, jacket temperature 105° C., vapour temperature 60-80° C. to afford ethyl oxazole-5-carboxylate as a colourless oil.

Intermediate 136

5-Bromo-2-methoxypyridin-3-amine

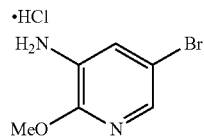

All weights, volumes and equivalents are relative to 5-bromo-2-methoxy-3-nitropyridine.

To a nitrogen-purged flask is charged 5-bromo-2-methoxy-3-nitropyridine (1 wt, 5.0 g) and iron powder (325 mesh, 0.86 wt, 4.31 g). IMS (12 vols, 60 ml) is added water (0.6 vols, 3 ml) and the mixture is heated to 35-40° C. with vigorous stirring. A mixture of concentrated HCl (37 wt %, 0.146 vols, 0.73 ml) and water (0.56 vols, 2.8 ml) is prepared. The acid solution is added to the reaction over at least 2.5 hrs at 35-40° C. The reaction is stirred for at least a further 1.5 hrs and sampled for completion test by HPLC. The reaction is cooled, filtered through Celite and the vessel and bed washed with IMS (2×2 vols, 2×10 ml). The combined filtrates are distilled under vacuum to 5 vols and toluene (10 vols, 50 ml) is added, the mixture is distilled, this is repeated until the level of IMS is <5% by NMR. The solution is cooled and 5M HCl in IPA (0.9 vols, 1.05 eq, 4.5 ml), is added over at least 30 mins. The resultant slurry is stirred for at least 60 mins, filtered and the cake washed with toluene (2×2 vols, 2×10 ml). The cake is dried under vacuum at 40° C. overnight to afford 5-bromo-2-methoxypyridin-3-amine hydrochloride as a white solid.

Intermediate 137

N-(2-Methoxy-5-(4,4,5,5-tetramethyl-1,3,2-dioxaborolan-2-yl)pyridin-3-yl)methanesulfonamide

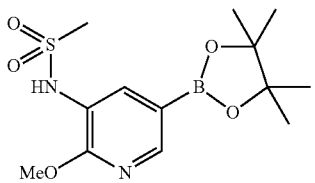 [SMILES: COc1ncc(B2OC(C)(C)C(C)(C)O2)cc1NS(C)(=O)=O]

All weights, volumes and equivalents are relative to N-(5-bromo-2-methoxypyridin-3-yl)methanesulfonamide.

Tricyclohexylphosphine (0.1191 g, 0.425 mmol, 0.008 eq, 0.008 wt) and $Pd_2(dba)_3$ (0.1438 g, 0.157 mmol, 0.003 eq, 0.01 wt) are mixed together and then toluene (15.00 mL, 1 vol, 0.86 wt, sparged with nitrogen for 1 hr) is added. The mixture is stirred and heated to 40-45° C. for 45 mins before being allowed to cool back to room temp and sit under nitrogen to give an orange-gold solution with suspended black particulates. In a separate vessel, N-(5-bromo-2-methoxypyridin-3-yl)methanesulfonamide (15.0323 g, 53.5 mmol, 1 wt, 1 eq), bis(pinacolato)diboron (16.2962 g, 64.2 mmol, 1.2 eq, 1.08 wt) and potassium acetate (10.4879 g, 107 mmol, 2 eq, 0.70 wt) are mixed together with toluene (150 mL, 10 vols, 8.6 wt). The resultant slurry is stirred and heated to 90° C. under a flow of nitrogen. Having reached the desired temperature, the catalyst mixture is added over 10 minutes followed by a wash of toluene (7.50 mL, 0.5 vol, 0.43 wt). The mixture is stirred at 90° C. for at least one hour and then sampled for HPLC analysis. Once complete, the reaction mixture is cooled to 50° C. and filtered to remove inorganic material. The filtered solid is washed with toluene (2×15 mL, 2×1 vol, 2×0.86 wt) and the liquors and washes combined and distilled down to 5 vols. The product solution is allowed to cool to room temperature by which stage it has become a slurry. Heptane (75 mL, 5 vols, 3.4 wt) is slowly added to the slurry. The slurry is aged and the supernatant analysed by HPLC to ensure sufficient crystallisation has occurred. The slurry is filtered and the solid product is washed with 1:1 toluene: heptane (2×15 mL, 2×1 vol) and dried under vacuum at 40-50° C. to afford N-(2-methoxy-5-(4,4,5,5-tetramethyl-1,3,2-dioxaborolan-2-yl)pyridin-3-yl)methanesulfonamide as an off-white solid.

Recrystallisation—All weights, volumes and equivalents are relative to N-(2-methoxy-5-(4,4,5,5-tetramethyl-1,3,2-dioxaborolan-2-yl)pyridin-3-yl)methanesulfonamide.

A stirred suspension of N-(2-methoxy-5-(4,4,5,5-tetramethyl-1,3,2-dioxaborolan-2-yl)pyridin-3-yl)methanesulfonamide (1 wt, 1.01 kg) in propan-2-ol (4 vol, 4.05 L) is heated to 70-75° C. under a nitrogen atmosphere, then aged at this temperature for at least 2 hr. The batch is allowed to cool to 20-25° C. over at least 1 hr, then the suspension is aged at this temperature for a further 1 hr. The liquors are sampled by HPLC to ensure complete crystallisation, then the resulting solids are filtered, washed with propan-2-ol (2×1 vol, 2×1.01 L) before being sucked dry for 0.5 hr, then the batch is dried in vacuo at 50° C. to constant probe temperature to afford N-(2-methoxy-5-(4,4,5,5-tetramethyl-1,3,2-dioxaborolan-2-yl)pyridin-3-yl)methanesulfonamide as a white solid.

Intermediate 138

6-(1H-Indol-4-yl)-4-(5-{[4-(1-methylethyl)-1-piperazinyl]methyl}-1,3-oxazol-2-yl)-1-(phenylsulfonyl)-1H-indazole

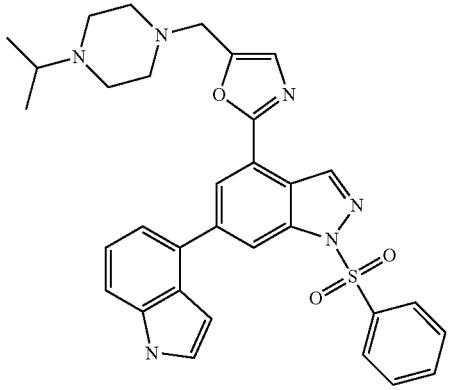 [SMILES: CC(C)N1CCN(Cc2cnc(-c3cc(-c4cccc5[nH]ccc45)cc4c3cnn4S(=O)(=O)c3ccccc3)o2)CC1]

A solution of sodium bicarbonate (228.0 g) in water (2.7 L) was added to a suspension of 6-Chloro-4-(5-{[4-(1-methylethyl)-1-piperazinyl]methyl}-1,3-oxazol-2-yl)-1-(phenylsulfonyl)-1H-indazole (271.2 g) and 4-(4,4,5,5-tetramethyl-1,3,2-dioxaborolan-2-yl)-1H-indole (263.2 g, available from Apollo Scientific Limited) in isopropanol (2.7 L) stirred under nitrogen at ambient temperature. After degassing, via evacuation and flushing with nitrogen, 2'-(dimethylamino)-2-biphenylyl-palladium(II) chloride dinorbornylphosphine complex (29.83 g) was added. The mixture was degassed again and was then heated to 90±3° C. and held at this temperature for 2 hours. The mixture was cooled to 20±5° C. over 25 minutes and aged at this temperature overnight. The resultant suspension was filtered, washed with water (1.35 L) and then slurried with toluene (4×1.35 L). The solid was dried under vacuum at 50° C. to give the title compound as grey solid (302.7 g).
LCMS (Method B): Rt 3.20 min, MH+ 581.

Example 1

6-(1H-Indol-4-yl)-4-[5-(4-morpholinylmethyl)-1,3,4-oxadiazol-2-yl]-1H-indazole

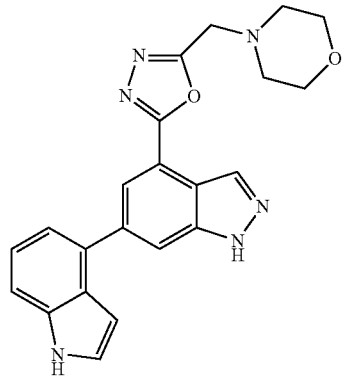 [SMILES: c1cc(-c2cc(-c3nnc(CN4CCOCC4)o3)c3cn[nH]c3c2)c2cc[nH]c2c1]

A stirred solution of 6-(1H-indol-4-yl)-1-[(4-methylphenyl)sulfonyl]-4-[5-(4-morpholinylmethyl)-1,3,4-oxadiazol-2-yl]-1H-indazole (25 mg, 0.045 mmol) and 2M sodium hydroxide (3 ml) in isopropanol (10 ml) was stirred at room temperature for 1 h. The solution was treated with 2M hydrochloric acid (3 ml) and evaporated to low bulk until the product was precipitated. The resulting solid was collected by filtration and washed with water to give the title compound as a cream coloured solid (15 mg).
LCMS (Method B): Rt 1.84 mins, MH+ 401.

Example 2

N-(2-Chloro-5-{4-[5-(4-morpholinylmethyl)-1,3,4-oxadiazol-2-yl]-1H-indazol-6-yl}-3-pyridinyl)methanesulfonamide

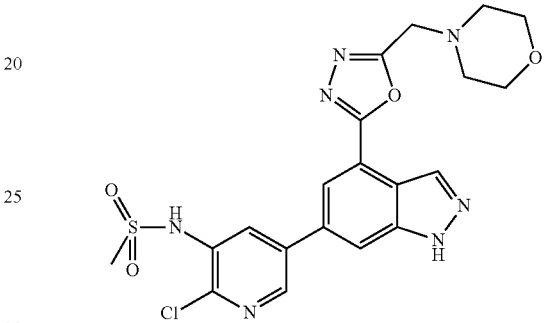

N-(2-Chloro-5-{1-[(4-methylphenyl)sulfonyl]-4-[5-(4-morpholinylmethyl)-1,3,4-oxadiazol-2-yl]-1H-indazol-6-yl}-3-pyridinyl)methanesulfonamide (52 mg, 0.081 mmol) was placed in isopropanol (3 ml) and 2M sodium hydroxide (1 ml, 2.0 mmol) added. The mixture was stirred at room temperature overnight and blown to dryness under a stream of nitrogen. The mixture was dissolved in water (10 ml) and washed with dichloromethane (10 ml). The organic layer was acidified by the addition of 2M hydrochloric acid and the solvent removed. The residue was purified by Mass Directed Automated Preparative HPLC (Method B) to give the title compound (8 mg).
LCMS (Method B): Rt 0.66 mins, MH+ 490.

Example 3

4-(5-{[(2R,6S)-2,6-Dimethyl-4-morpholinyl]methyl}-1,3,4-oxadiazol-2-yl)-6-(1H-indol-4-yl)-1H-indazole

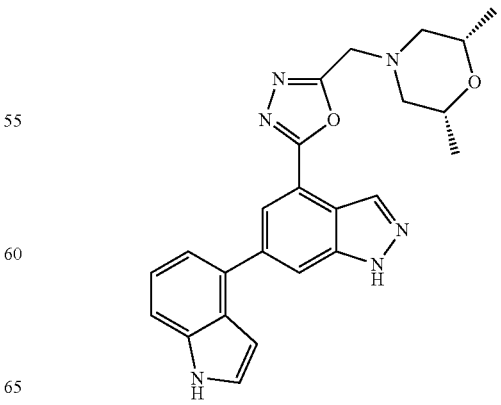

(2R,6S)-2,6-Dimethylmorpholine (12.57 mg, 0.11 mmol) and 4-[5-(chloromethyl)-1,3,4-oxadiazol-2-yl]-6-(1H-indol-4-yl)-1-(phenylsulfonyl)-1H-indazole (51 mg, 0.104 mmol) were dissolved in acetonitrile (0.5 ml) and N,N-diisopropyl-ethylamine (0.0262 ml, 0.15 mmol) was added, followed by sodium iodide (14.99 mg, 0.1 mmol). The solution was stirred at 70° C. for 18 h and blown to dryness under a stream of nitrogen. Isopropanol (0.5 ml) was added followed by 2M sodium hydroxide (0.5 ml) and stirred for 18 h when the mixture was neutralised and the solvent removed under a stream of nitrogen. The crude product was dissolved in dimethylsulphoxide (0.5 ml) and purified by Mass Directed Automated Preparative HPLC (Method F) and the solvent was evaporated in vacuo using Genevac to give the title compound (4 mg).

LCMS (Method B): Rt 2.11, MH+ 429.

The compounds listed below were synthesised using the general method above.

| Example Number | Monomer | Structure | Rt min | MH+ | Name |
|---|---|---|---|---|---|
| Example 4 | 2-(1-piperazinyl)pyrimidine dihydrochloride (available from Fluka) | 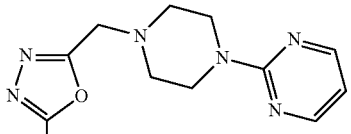 | 2.11 | 478 | 6-(1H-indol-4-yl)-4-(5-{[4-(2-pyrimidinyl)-1-piperazinyl]methyl}-1,3,4-oxadiazol-2-yl)-1H-indazole |
| Example 5 | 4,4-dimethyl-piperidine hydrochloride (available from MicroChemistry Ltd) | 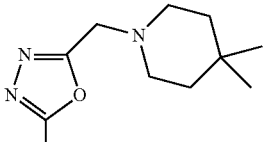 | 1.71 | 427 | 4-{5-[(4,4-dimethyl-1-piperidinyl)methyl]-1,3,4-oxadiazol-2-yl}-6-(1H-indol-4-yl)-1H-indazole |
| Example 6 | 1-(2-methylpropyl)piperazine (available from Fluorochem) | 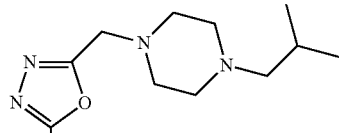 | 1.55 | 456 | 6-(1H-indol-4-yl)-4-(5-{[4-(2-methylpropyl)-1-piperazinyl]methyl}-1,3,4-oxadiazol-2-yl)-1H-indazole |

-continued

| Example Number | Monomer | Structure | Rt min | MH+ | Name |
|---|---|---|---|---|---|
| Example 7 | 4-(1-methylethyl) piperidine (available from ChemBridge Building Block Library) | 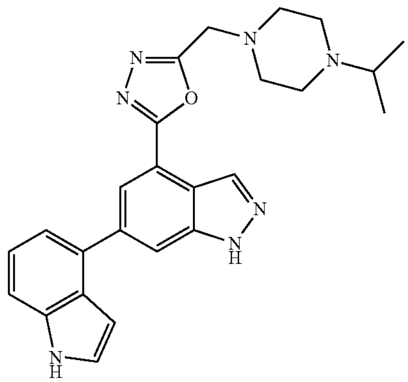 [SMILES: CC(C)N1CCN(Cc2nnc(-c3cc(-c4cccc5[nH]ccc45)cc4[nH]ncc34)o2)CC1] | 1.86 | 441 | 6-(1H-indol-4-yl)-4-(5-{[4-(1-methylethyl)-1-piperidinyl]methyl}-1,3,4-oxadiazol-2-yl)-1H-indazole |
| Example 8 | 2-(1-pyrrolidinyl methyl) piperidine (available from Fluorochem) | 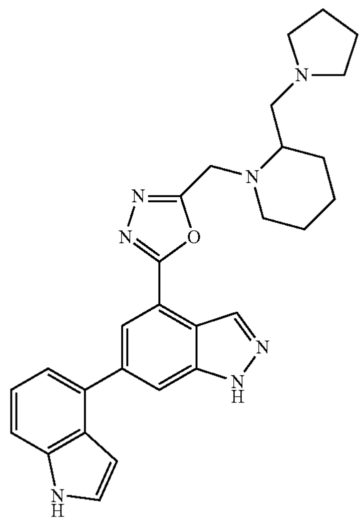 [SMILES: c1cc(-c2cc(-c3nnc(CN4CCCCC4CN4CCCC4)o3)c3cn[nH]c3c2)c2cc[nH]c2c1] | 1.69 | 482 | 6-(1H-indol-4-yl)-4-(5-{[2-(1-pyrrolidinylmethyl)-1-piperidinyl]methyl}-1,3,4-oxadiazol-2-yl)-1H-indazole |

The following examples were synthesised as above with additional purification steps as follows:

The solutions from the previous purification were neutralised and the solvent removed then purified by Mass Directed Automated Preparative HPLC (Method G) and the solvent was evaporated in vacuo using Genevac to give the following title compounds. (LCMS Method B)

| Example Number | Monomer | Structure | Rt min | MH+ | Name |
|---|---|---|---|---|---|
| Example 9 | 1-(4-fluorophenyl) piperazine hydrochloride (available from Aldrich) | 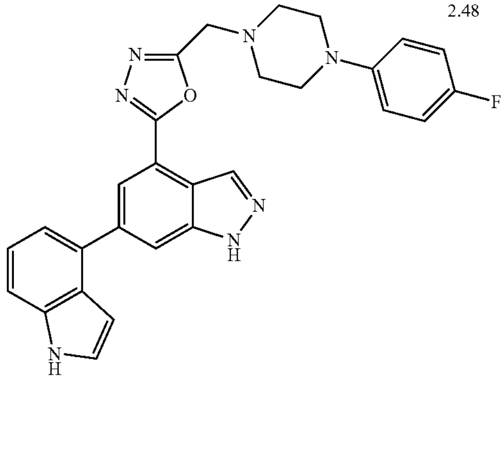 [SMILES: Fc1ccc(N2CCN(Cc3nnc(-c4cc(-c5cccc6[nH]ccc56)cc5[nH]ncc45)o3)CC2)cc1] | 2.48 | 494 | 4-(5-{[4-(4-fluorophenyl)-1-piperazinyl]methyl}-1,3,4-oxadiazol-2-yl)-6-(1H-indol-4-yl)-1H-indazole |

| Example Number | Monomer | Structure | Rt min | MH+ | Name |
|---|---|---|---|---|---|
| Example 10 | (1S,4S)-2-methyl-2,5-diazabicyclo[2.2.1]heptane hydrobromide (available from Aldrich) | 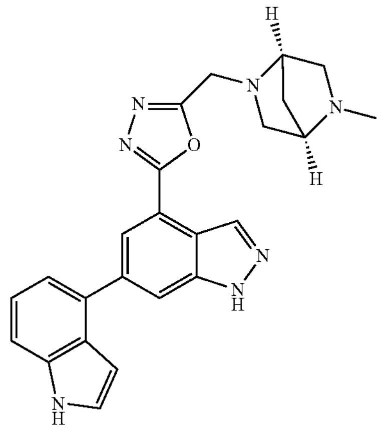 [SMILES: CN1C[C@H]2C[C@@H]1CN2Cc1nnc(-c2cc(-c3cccc4[nH]ccc34)cc3[nH]ncc23)o1] | 1.39 | 426 | 6-(1H-indol-4-yl)-4-(5-{[(1R,4R)-5-methyl-2,5-diazabicyclo[2.2.1]hept-2-yl]methyl}-1,3,4-oxadiazol-2-yl)-1H-indazole |
| Example 11 | 2-(1-pyrrolidinyl-methyl)morpholine (available from AB Chemicals Inc.) | 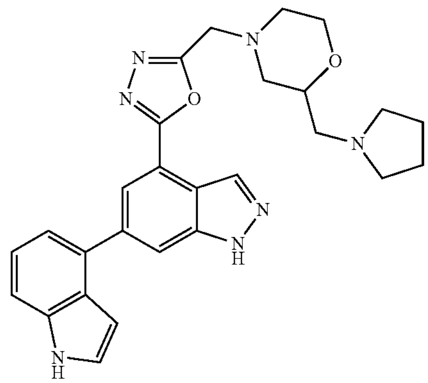 [SMILES: c1cc(-c2cc(-c3nnc(CN4CCOC(CN5CCCC5)C4)o3)c3cn[nH]c3c2)c2cc[nH]c2c1] | 1.41 | 484 | 6-(1H-indol-4-yl)-4-(5-{[2-(1-pyrrolidinylmethyl)-4-morpholinyl]methyl}-1,3,4-oxadiazol-2-yl)-1H-indazole |

Example 12

6-(1H-Indol-4-yl)-4-[5-({4-[2-(4-morpholinyl)ethyl]-1-piperazinyl}methyl)-1,3,4-oxadiazol-2-yl]-1H-indazole

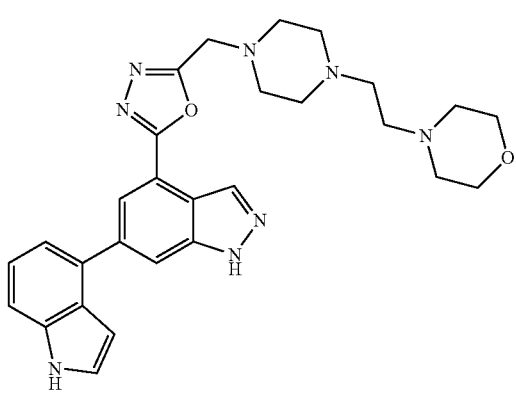 [SMILES: c1cc(-c2cc(-c3nnc(CN4CCN(CCN5CCOCC5)CC4)o3)c3cn[nH]c3c2)c2cc[nH]c2c1]

4-[2-(1-piperazinyl)ethyl]morpholine (14.1 mg, 0.11 mmol) and 4-[5-(chloromethyl)-1,3,4-oxadiazol-2-yl]-6-(1H-indol-4-yl)-1-(phenylsulfonyl)-1H-indazole (50 mg, 0.102 mmol) were dissolved in acetonitrile (0.5 ml) and N,N-diisopropylethylamine (0.026 ml, 0.15 mmol) was added, followed by sodium iodide (15.3 mg, 0.102 mmol). The solution was stirred at 70° C. for 18 h and blown to dryness under a stream of nitrogen. Isopropanol (0.3 ml) was added followed by 2M sodium hydroxide (0.3 ml) and stirred for 5 h when the mixture was neutralised and the solvent removed under a stream of nitrogen. The crude product was dissolved in dimethylsulphoxide (0.3 ml) and methanol (0.15 ml) with formic acid (0.05 ml) then purified by Mass Directed Automated Preparative HPLC (Method F) to give the title compound (26.4 mg).

LCMS (Method B): Rt 1.30, MH+ 513.

The following examples were synthesised as above with additional deprotection and purification steps as follows:

Isopropanol (0.3 ml) was added followed by 2M sodium hydroxide (0.3 ml) and stirred overnight when the mixture was neutralised and applied onto a Bicarbonate SPE (0.5 g) cartridge pre-conditioned with methanol (1 ml) then eluted with methanol (2 ml). The solvent was removed under a stream of nitrogen to give the following title compounds.

(LCMS Method B)

| Example Number | Monomer | Structure | Rt min | MH+ | Name |
|---|---|---|---|---|---|
| Example 13 | 4-(1-methylethyl)piperazine (available from Aldrich) | 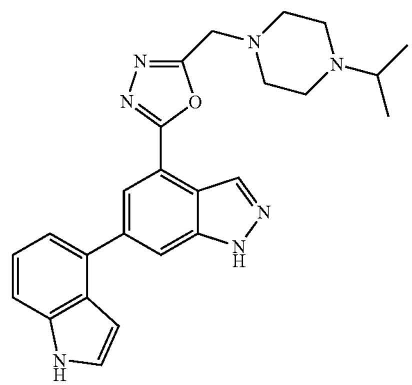 [SMILES: CC(C)N1CCN(Cc2nnc(-c3cc(-c4cccc5[nH]ccc45)cc4[nH]ncc34)o2)CC1] | 1.45 | 442 | 6-(1H-indol-4-yl)-4-(5-{[4-(1-methylethyl)-1-piperazinyl]methyl}-1,3,4-oxadiazol-2-yl)-1H-indazole. |
| Example 14 | (2R,6S)-2,6-Dimethyl-piperidine (available from Aldrich) | 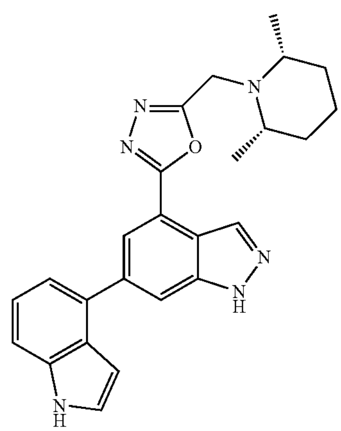 [SMILES: C[C@@H]1CCC[C@H](C)N1Cc1nnc(-c2cc(-c3cccc4[nH]ccc34)cc3[nH]ncc23)o1] | 1.62 | 427 | 4-(5-{[(2R,6S)-2,6-dimethyl-1-piperidinyl]methyl}-1,3,4-oxadiazol-2-yl)-6-(1H-indol-4-yl)-1H-indazole |
| Example 15 | (1s,4s)-7-azabicyclo[2.2.1]heptane hydrochloride (available from Enamine Ltd | 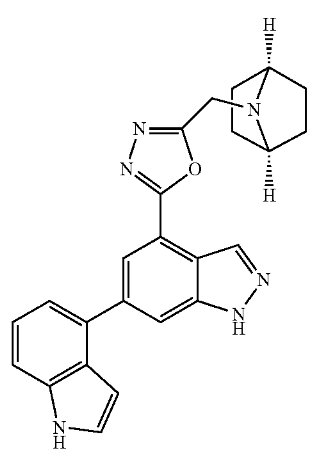 [SMILES: c1cc(-c2cc(-c3nnc(CN4[C@H]5CC[C@@H]4CC5)o3)c3cn[nH]c3c2)c2cc[nH]c2c1] | 1.46 | 411 | 4-{5-[(1s,4s)-7-azabicyclo[2.2.1]hept-7-ylmethyl]-1,3,4-oxadiazol-2-yl}-6-(1H-indol-4-yl)-1H-indazole |

| Example Number | Monomer | Structure | Rt min | MH+ | Name |
|---|---|---|---|---|---|
| Example 16 | Octahydro-2H-1,4-benzoxazine (available from Chemical Block Ltd) | 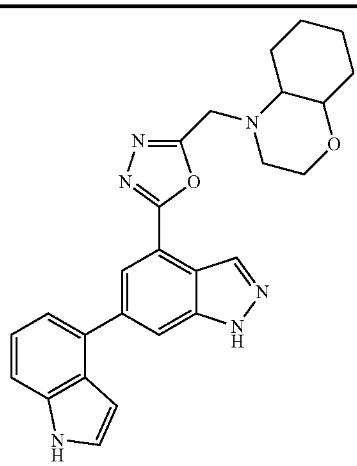 | 2.24 | 455 | 4-({5-[6-(1H-indol-4-yl)-1H-indazol-4-yl]-1,3,4-oxadiazol-2-yl}methyl)octahydro-2H-1,4-benzoxazine |
| Example 17 | 2-(2-methylpropyl)morpholine (available from ChemBridge Corp.) | 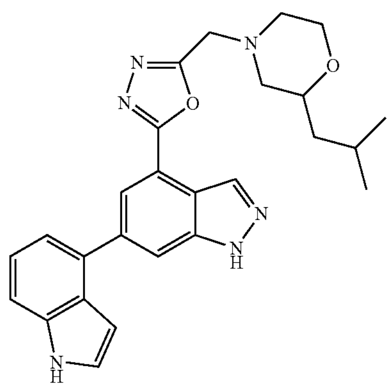 [SMILES: CC(C)CC1CN(Cc2nnc(-c3cc(-c4cccc5[nH]ccc45)cc4[nH]ncc34)o2)CCO1] | 2.55 | 457 | 6-(1H-indol-4-yl)-4-(5-{[2-(2-methylpropyl)-4-morpholinyl]methyl}-1,3,4-oxadiazol-2-yl)-1H-indazole |

Example 18

N-{2-Chloro-5-[4-(5-{[4-(1-methylethyl)-1-piperazinyl]methyl}-1,3,4-oxadiazol-2-yl)-1H-indazol-6-yl]-3-pyridinyl}methanesulfonamide N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide (25 mg, 0.042 mmol) and 1-(1-methylethyl)piperazine (500 mg, 3.90 mmol) were placed a vial and heated in a microwave at 90° C. for 15 mins. The 1-(1-methylethyl)piperazine was blown off under a stream of nitrogen and the residue suspended in isopropanol (2 ml) and 2M sodium hydroxide (1 ml) added. The mixture was stirred at room temperature for 2 h. The solvent was blown off under a stream of nitrogen and the residue purified by Mass Directed Automated Preparative HPLC (Method B) to give the title compound as a pale yellow gum (4 mg).

LCMS (Method A): Rt 0.63 mins, MH+ 531.

Example 19

N-{2-Chloro-5-[4-(5-{[(2R,6S)-2,6-dimethyl-4-morpholinyl]methyl}-1,3,4-oxadiazol-2-yl)-1H-indazol-6-yl]-3-pyridinyl}methanesulfonamide N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide (50 mg, 0.084 mmol) and (2R, 6S)-2,6-dimethylmorpholine (0.5 ml, 0.084 mmol) were placed a vial and heated in a microwave at 90° C. for 15 mins. The reaction was heated in the microwave for a further 20 mins. The (2R,6S)-2,6-dimethylmorpholine was removed and the residue placed into isopropanol (3 ml) and 2M sodium hydroxide (1 ml) and the mixture stirred at room temperature for 3 h. The solvent was removed and the residue purified by Mass Directed Automated Preparative HPLC (Method B). The desired product was not collected so the waste was concentrated in vacuo and the residue purified by Mass Directed Automated Preparative HPLC (Method B) to give the title compound as white solid (12 mg).

LCMS (Method A): Rt 0.72 mins, MH+ 518.

Example 20

N-(2-Chloro-5-{4-[5-(4-morpholinylmethyl)-1,3,4-oxadiazol-2-yl]-1H-indazol-6-yl}-3-pyridinyl)methanesulfonamide

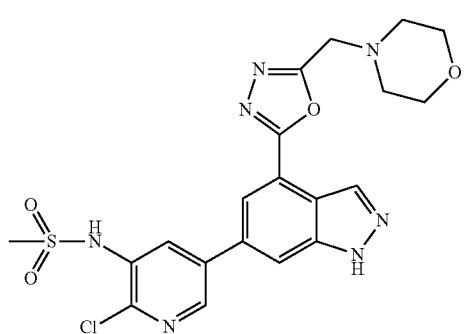 [SMILES: CS(=O)(=O)Nc1cc(-c2cc(-c3nnc(CN4CCOCC4)o3)c3cn[nH]c3c2)cnc1Cl]

N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide (30 mg, 0.051 mmol) and morpholine (1 ml, 11.48 mmol) were placed a vial and heated in a microwave at 90° C. for 15 mins. The morpholine was blown off under a stream of nitrogen and the residue suspended in isopropanol (2 ml) and 2M sodium hydroxide (1 ml) added. The mixture was stirred at room temperature for 2 h. The solvent was blown off and the residue purified by chromatography on a silica gel (20 g) cartridge, eluting with 0-25% methanol in dichloromethane over 30 mins. The solvent was removed in vacuo and the residue loaded onto a SCX (10 g) cartridge and eluted with methanol and then 2M ammonia in methanol. The residue was purified by Mass Directed Automated Preparative HPLC (Method B) to give the title compound as a white solid (5 mg).

LCMS (Method A): Rt 0.67 mins, MH+ 490.

Example 21

N-[5-[4-(5-{[(2R,6S)-2,6-Dimethyl-4-morpholinyl]methyl}-1,3,4-oxadiazol-2-yl)-1H-indazol-6-yl]-2-(methyloxy)-3-pyridinyl]methanesulfonamide

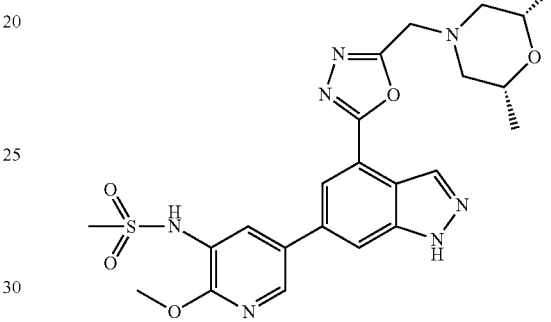

To a solution of N-[5-[4-(5-{[(2R,6S)-2,6-dimethyl-4-morpholinyl]methyl}-1,3,4-oxadiazol-2-yl)-1-(phenylsulfonyl)-1H-indazol-6-yl]-2-(methyloxy)-3-pyridinyl]methanesulfonamide (106 mg, 0.162 mmol) in 1,4-dioxane (1 ml) was added 2M sodium hydroxide (1 ml, 2.000 mmol) and the mixture stirred at 20° C. for 18 h. The mixture was evaporated in vacuo and the residue partitioned between ethyl acetate (10 ml) and saturated ammonium chloride (5 ml), separated by hydrophilic frit and purified by silica (5 g) cartridge using a gradient of dichloromethane and methanol to give a pale brown solid 50 mg which was purified by MDAP to give the title compound as a white solid (32 mg).

LCMS (Method A) Rt 0.73 mins, MH+ 514.

Similarly prepared was

| Example Number | Starting material | Structure | Rt min | MH+ | Name |
|---|---|---|---|---|---|
| Example 22 | N-[5-[4-(5-{[4-(1-methylethyl)-1-piperazinyl]methyl}-1,3,4-oxadiazol-2-yl)-1-(phenylsulfonyl)-1H-indazol-6-yl]-2-(methyloxy)-3-pyridinyl]methanesulfonamide | 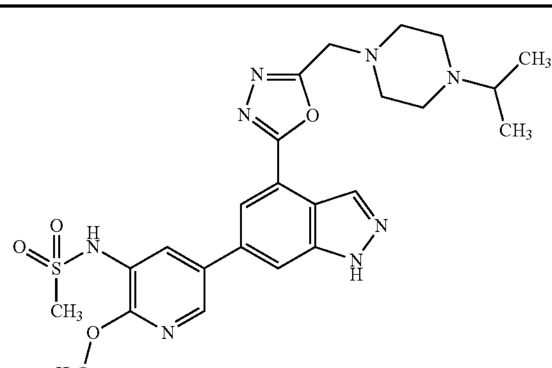 | 0.55 | 527 | N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide |

Example 23

4-(5-{[(2R,6S)-2,6-Dimethyl-4-morpholinyl]methyl}-1,3,4-oxadiazol-2-yl)-6-(1H-indol-4-yl)-1-methyl-1H-indazole

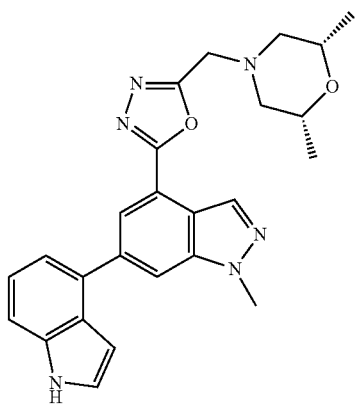 [SMILES: C[C@@H]1CN(Cc2nnc(-c3cc(-c4cccc5[nH]ccc45)cc4c3cnn4C)o2)C[C@H](C)O1]

6-Bromo-4-(5-{[(2R,6S)-2,6-dimethyl-4-morpholinyl]methyl}-1,3,4-oxadiazol-2-yl)-1-methyl-1H-indazole (50 mg, 0.123 mmol), 4-(4,4,5,5-tetramethyl-1,3,2-dioxaborolan-2-yl)-1H-indole (32.9 mg, 0.135 mmol), sodium carbonate (39.1 mg, 0.369 mmol) and 1,1-bis(diphenylphosphino)ferrocene palladium dichloride) (9.00 mg, 0.012 mmol) were added to a microwave vial and dissolved in 1,4-dioxane (0.5 ml) and water (0.5 ml). The reaction mixture was heated under microwave irradiation at 110° C. for 15 mins. The reaction mixture was passed through a 2 g silica cartridge that was then washed with methanol. The solvent was evaporated under a stream of nitrogen and the residual solid was purified by silica (20 g) cartridge using a gradient of ethyl acetate and cyclohexane to give the title compound as a white solid (5.5 mg).

LCMS (Method A): Rt 0.89 min, MH+ 443.

Example 24

6-(1H-Indol-4-yl)-1-methyl-4-(5-{[4-(1-methylethyl)-1-piperazinyl]methyl}-1,3,4-oxadiazol-2-yl)-1H-indazole

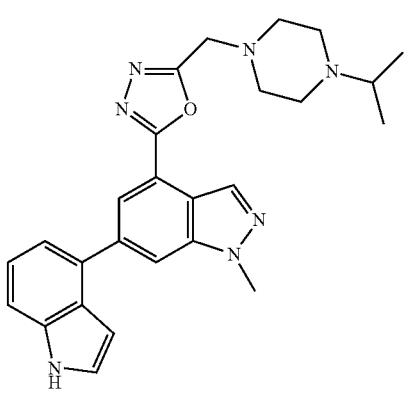 [SMILES: CC(C)N1CCN(Cc2nnc(-c3cc(-c4cccc5[nH]ccc45)cc4c3cnn4C)o2)CC1]

6-Bromo-1-methyl-4-(5-{[4-(1-methylethyl)-1-piperazinyl]methyl}-1,3,4-oxadiazol-2-yl)-1H-indazole (45 mg, 0.107 mmol), 4-(4,4,5,5-tetramethyl-1,3,2-dioxaborolan-2-yl)-1H-indole (26.1 mg, 0.107 mmol), sodium carbonate (34.1 mg, 0.322 mmol) and 1,1-bis(diphenylphosphino)ferrocene palladium dichloride (7.85 mg, 10.73 µmol) were added to a microwave vial and dissolved in 1,4-dioxane (0.5 ml) and water (0.5 ml). The reaction mixture was heated under microwave irradiation at 110° C. for 15 mins. The reaction mixture was passed through a 2 g silica cartridge that was then washed with methanol. The solvent was evaporated under a stream of nitrogen and the residual solid was purified firstly by silica (20 g) cartridge using a gradient of ethyl acetate and cyclohexane then by Mass Directed Automated Preparative HPLC (Method B). The solvent was evaporated under a stream of nitrogen to give the title compound as a white solid (20 mg).

LCMS (Method A): Rt 0.63 min, MH+ 456.

Example 25

N-[5-[1-Methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide

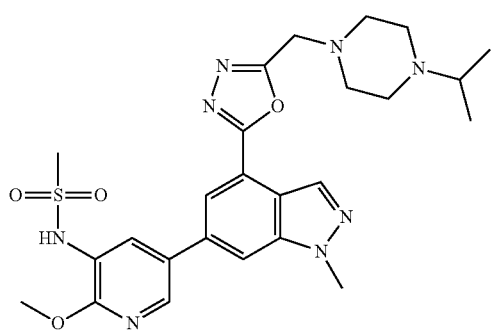 [SMILES: COc1ncc(-c2cc(-c3nnc(CN4CCN(C(C)C)CC4)o3)c3cnn(C)c3c2)cc1NS(C)(=O)=O]

6-Bromo-1-methyl-4-(5-{[4-(1-methylethyl)-1-piperazinyl]methyl}-1,3,4-oxadiazol-2-yl)-1H-indazole (40 mg, 0.095 mmol), N-[2-(methyloxy)-5-(4,4,5,5-tetramethyl-1,3,2-dioxaborolan-2-yl)-3-pyridinyl]methanesulfonamide (31.3 mg, 0.095 mmol), sodium carbonate (30.3 mg, 0.286 mmol) and 1,1-bis(diphenylphosphino)ferrocene palladium dichloride (6.98 mg, 9.54 µmol) were added to a microwave vial and dissolved in 1,4-dioxane (0.5 ml) and water (0.5 ml). The reaction mixture was heated under microwave irradiation at 110° C. for 15 mins. The reaction mixture was evaporated under a stream of nitrogen and the residual solid was dissolved in DMSO (1 ml), filtered through a frit and purified by Mass Directed Automated Preparative HPLC (Method B). The solvent was evaporated under a stream of nitrogen and the residue was dissolved in 1,4-dioxane (1 ml) and water (1 ml), frozen in a cardice bath and placed on the freeze-drier for 18 h to afford the title compound as a white solid (20 mg).

LCMS (Method A): Rt 0.56 min, MH+ 541.

Example 26

N-[5-[4-(5-{[(2R,6S)-2,6-Dimethyl-4-morpholinyl]methyl}-1,3,4-oxadiazol-2-yl)-1-methyl-1H-indazol-6-yl]-2-(methyloxy)-3-pyridinyl]methanesulfonamide

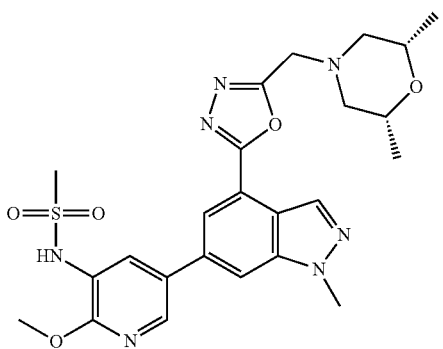 [SMILES: COc1ncc(-c2cc(-c3nnc(CN4C[C@@H](C)O[C@@H](C)C4)o3)c3cnn(C)c3c2)cc1NS(C)(=O)=O]

6-Bromo-4-(5-{[(2R,6S)-2,6-dimethyl-4-morpholinyl]methyl}-1,3,4-oxadiazol-2-yl)-1-methyl-1H-indazole (45 mg, 0.111 mmol), N-[2-(methyloxy)-5-(4,4,5,5-tetramethyl-1,3,2-dioxaborolan-2-yl)-3-pyridinyl]methanesulfonamide (36.4 mg, 0.111 mmol), sodium carbonate (35.2 mg, 0.332 mmol) and 1,1-bis(diphenylphosphino)ferrocene palladium dichloride (8.10 mg, 0.011 mmol) were added to a microwave vial and dissolved in 1,4-dioxane (0.5 ml) and water (0.5 ml). The reaction mixture was heated under microwave irradiation at 110° C. for 15 mins. The reaction mixture was passed through a 2 g silica cartridge that was then washed with methanol. The solvent was evaporated under a stream of nitrogen and the residual solid was purified by Mass Directed Automated Preparative HPLC (Method B) and the solvent was evaporated under a stream of nitrogen to give the title compound as a white solid (10 mg).

LCMS (Method A): Rt 0.77 min, MH+ 528.

Example 27

N-[5-[4-(5-{[(2R,6S)-2,6-Dimethyl-4-morpholinyl]methyl}-1,3,4-oxadiazol-2-yl)-1H-indazol-6-yl]-2-(methyloxy)-3-pyridinyl]-2,4-difluorobenzenesulfonamide

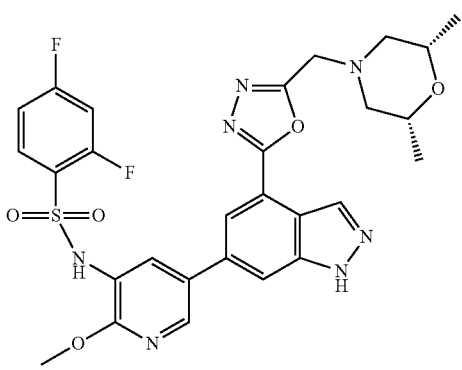 [SMILES: COc1ncc(-c2cc(-c3nnc(CN4C[C@@H](C)O[C@@H](C)C4)o3)c3cn[nH]c3c2)cc1NS(=O)(=O)c1ccc(F)cc1F]

Sodium hydroxide (2 ml, 4.00 mmol) was added to a solution of N-[5-[4-(5-{[(2R,6S)-2,6-dimethyl-4-morpholinyl]methyl}-1,3,4-oxadiazol-2-yl)-1-(phenylsulfonyl)-1H-indazol-6-yl]-2-(methyloxy)-3-pyridinyl]-2,4-difluorobenzenesulfonamide (194 mg, 0.212 mmol) in 1,4-dioxane (2 ml). The mixture was stirred at room temperature for 2 h. The solvent was evaporated under a stream of nitrogen and the residue partitioned between ethyl acetate (10 ml) and saturated ammonium chloride (5 ml). The organic layer was separated by hydrophobic frit, washed with water and the solvent removed in vacuo. The residual solid was purified by Mass Directed Automated Preparative HPLC (Method B) and the solvent was evaporated under a stream of nitrogen to give the title compound as a cream coloured solid (10 mg).

LCMS (Method A): Rt 0.89 mins, MH+ 612.

Example 28

N-[5-(4-{5-[(2,2-Dimethyl-4-morpholinyl)methyl]-1,3,4-oxadiazol-2-yl}-1H-indazol-6-yl)-2-(methyloxy)-3-pyridinyl]methanesulfonamide

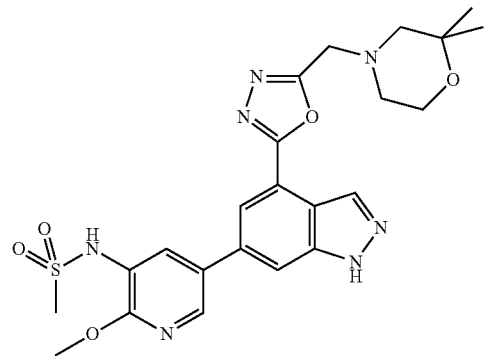 [SMILES: COc1ncc(-c2cc(-c3nnc(CN4CCOC(C)(C)C4)o3)c3cn[nH]c3c2)cc1NS(C)(=O)=O]

To a solution of 6-bromo-4-{5-[(2,2-dimethyl-4-morpholinyl)methyl]-1,3,4-oxadiazol-2-yl}-1-(phenylsulfonyl)-1H-indazole (112 mg, 0.210 mmol) was added N-[2-(methyloxy)-5-(4,4,5,5-tetramethyl-1,3,2-dioxaborolan-2-yl)-3-pyridinyl]methanesulfonamide (69.0 mg, 0.210 mmol), 1,1'-bis(diphenylphosphino)ferrocene palladium dichloride (30.8 mg, 0.042 mmol) and potassium phosphate tribasic (134 mg, 0.631 mmol). The mixture was heated under microwave irradiation at 100° C. for 20 min, then concentrated in vacuo and the residue partitioned between DCM (10 ml) and water (5 ml). The layers were separated by hydrophobic frit and the organics were concentrated, then re-dissolved in DCM and loaded on the top of a 20 g silica SPE cartridge, which was then eluted with 0-100% EtOAc/cyclohexane followed by 0-20% MeOH/EtOAc on the FlashMaster II. The desired fractions were combined and the solvent removed in vacuo to give a pale orange solid (80 mg), which was dissolved in 1,4-dioxane (0.5 ml), treated with 2M sodium hydroxide (0.5 ml, 1.000 mmol) and stirred at 20° C. for 18 h. The mixture was evaporated to dryness under a stream of nitrogen and the residue partitioned between ethyl acetate (5 ml) and saturated ammonium chloride (2 ml) and separated by hydrophilic frit. The solvent was removed under a stream of nitrogen and the residue was dissolved in DMSO (1 ml) and purified by MDAP (Method B). The product-containing fractions were evaporated to dryness under a stream of nitrogen to afford the title compound as a white solid (24 mg).

LCMS (Method A) $R_t$=0.75 min, MH+ 514.

Example 29

6-(1H-Indol-4-yl)-4-[5-(1-methylethyl)-1,3,4-oxadiazol-2-yl]-1H-indazole

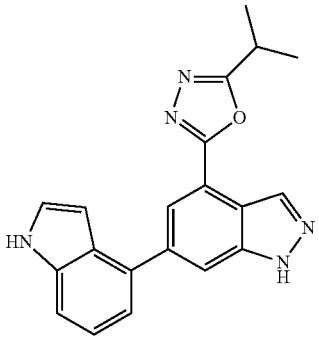 [SMILES: CC(C)c1nnc(-c2cc(-c3cccc4[nH]ccc34)cc3[nH]ncc23)o1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.084 mmol) and 2-methylpropanoyl chloride (0.175 ml, 1.672 mmol) in chloroform (4 ml), were heated under microwave irradiation at 100° C. for 30 mins, followed by 100° C. for 30 mins, followed by 100° C. for 1 h. The reaction mixture was treated with isopropanol (1 ml) then blown to dryness. The solid was dissolved in isopropanol (2 ml) and dichloromethane (2 ml) and absorbed onto Florisil. The Florisil was placed on top of a silica cartridge (10 g) and eluted with 0-100% ethyl acetate/cyclohexane. The appropriate fractions combined and concentrated to give a yellow solid, 35 mg. The solid was treated with isopropanol (1 ml) and 2M aqueous sodium hydroxide (1.003 ml) and stirred at 20° C. for 20 h. The mixture was then treated with 2M aqueous hydrochloric acid (1 ml), blown to dryness and slurried in isopropanol (2 ml) and dichloromethane (1 ml) with sonication. The mixture was absorbed onto Florisil, loaded onto a silica cartridge (10 g) and eluted with 0-100% ethyl acetate/cyclohexane. Fractions did not collect, so the waste was evaporated to dryness, the residue dissolved in dichloromethane (2 ml) and loaded onto a silica cartridge (10 g) and purified by column chromatography, eluting with 0-100% ethyl acetate/cyclohexane. Appropriate fractions were combined and evaporated to give the title compound as a white film (11 mg).

LCMS (Method B): Rt 2.63 mins, MH+ 344.

Example 30

4-(5-Cyclohexyl-1,3,4-oxadiazol-2-yl)-6-(1H-indol-4-yl)-1H-indazole

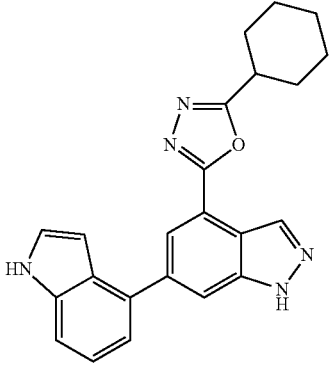 [SMILES: c1cc(-c2cc(-c3nnc(C4CCCCC4)o3)c3cn[nH]c3c2)c2cc[nH]c2c1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.084 mmol) and cyclohexanecarbonyl chloride (0.224 ml, 1.672 mmol) in chloroform (4 ml), were heated under microwave irradiation at 100° C. for 30 mins, followed by 100° C. for 30 mins, followed by 100° C. for 1 h. Additional cyclohexanecarbonyl chloride (0.114 ml, 0.849 mmol) was added and the reaction heated under microwave irradiation at 100° C. for a further 1 h. The reaction mixture was treated with isopropanol (2 ml), the solvent reduced to 2 ml by blowing down and absorbed onto Florisil. The Florisil was placed on top of a silica cartridge (10 g) and eluted with 0-100% ethyl acetate/cyclohexane. Appropriate fractions combined and concentrated to give a beige solid, 15 mg. The solid was treated with isopropanol (0.5 ml) and 2M aqueous sodium hydroxide (0.498 ml) and stirred at 20° C. for 20 h. The mixture was then treated with 2M aqueous hydrochloric acid (1 ml), blown to dryness and slurried in isopropanol (2 ml) and dichloromethane (1 ml) with sonication. The mixture was absorbed onto Florisil, loaded onto a silica cartridge (10 g) and eluted with 0-100% ethyl acetate/cyclohexane. Appropriate fractions were combined and evaporated to give the title compound as a colourless film (3 mg).

LCMS (Method B): Rt 3.06 mins, MH+ 384.

Example 31

4-[5-(Cyclohexylmethyl)-1,3,4-oxadiazol-2-yl]-6-(1H-indol-4-yl)-1H-indazole

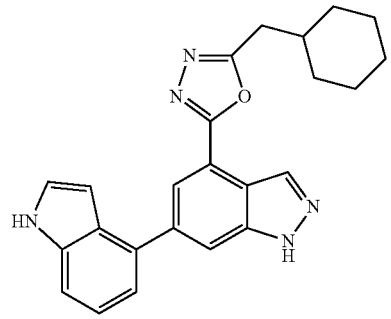 [SMILES: c1cc(-c2cc(-c3nnc(CC4CCCCC4)o3)c3cn[nH]c3c2)c2cc[nH]c2c1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.084 mmol) and cyclohexylacetyl chloride (0.257 ml, 1.672 mmol) in chloroform (4 ml), were heated under microwave irradiation at 100° C. for 1 h. The reaction mixture was treated with isopropanol (2 ml), the solvent reduced by blowing down to ~2 ml and absorbed onto Florisil. The Florisil was placed on top of a silica cartridge (10 g) and eluted with 0-100% ethyl acetate/cyclohexane. Appropriate fractions combined and concentrated to give a yellow solid, 17 mg. The solid was treated with isopropanol (0.5 ml) and 2M aqueous sodium hydroxide (0.498 ml, 0.995 mmol) and stirred at 20° C. for 20 h. The mixture was then treated with 2M aqueous hydrochloric acid (1 ml), blown to dryness and slurried in isopropanol (2 ml) and dichloromethane (1 ml) with sonication. The mixture was absorbed onto Florisil, then loaded onto a silica cartridge (10 g) and eluted with 0-100% ethyl acetate/cyclohexane. Appropriate fractions were combined and evaporated to give the title compound as an off-white solid (3.2 mg).

LCMS (Method A): Rt 1.25 min, MH+ 398 and [M+CH₃CN]⁺ 439.

Example 32

6-(1H-Indol-4-yl)-4-[5-(phenylmethyl)-1,3,4-oxadiazol-2-yl]-1H-indazole

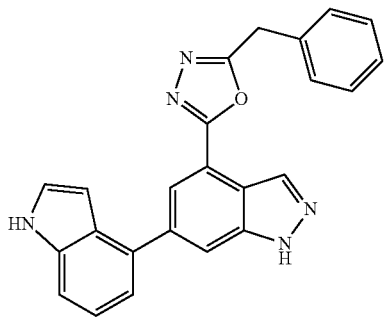 [SMILES: c1ccc(Cc2nnc(-c3cc(-c4cccc5[nH]ccc45)cc4[nH]ncc34)o2)cc1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.084 mmol) and phenylacetyl chloride (0.224 ml, 1.699 mmol) in chloroform (4 ml), were heated under microwave irradiation at 100° C. for 30 mins, followed by 100° C. for a further 30 mins. The reaction mixture was treated with methanol (5 ml) and evaporated to dryness. The residue was then dissolved in dichloromethane, loaded onto a silica cartridge (10 g) and purified by column chromatography, eluting with 0-25% methanol/dichloromethane. The appropriate fractions were combined and concentrated to give a brown solid. The solid was treated with isopropanol (0.5 ml) and 2M aqueous sodium hydroxide (0.510 ml, 1.019 mmol) and stirred at 20° C. for 1 h. Additional isopropanol (0.5 ml) and 2M aqueous sodium hydroxide (0.510 ml) were added, the mixture sonicated and then stirred at 20° C. for a further 18 h. The mixture was neutralised with 2M aqueous hydrochloric acid, evaporated to dryness and azeotroped with isopropanol (5 ml). The residue was dissolved in isopropanol (5 ml), absorbed onto Florisil, then placed on top of a silica cartridge (10 g) and eluted with 0-100% ethyl acetate/cyclohexane. Appropriate fractions were combined and evaporated to give the title compound as an off-white solid (9 mg).

LCMS (Method B): Rt 2.82 mins, MH+ 392.

Example 33

6-(1H-Indol-4-yl)-4-{5-[2-(methyloxy)ethyl]-1,3,4-oxadiazol-2-yl}-1H-indazole

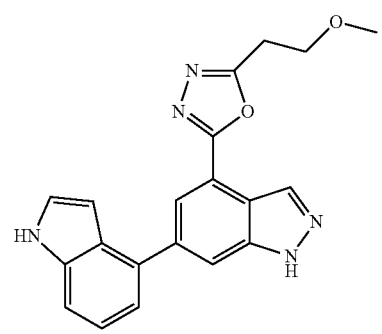 [SMILES: COCCc1nnc(-c2cc(-c3cccc4[nH]ccc34)cc3[nH]ncc23)o1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (75 mg, 0.127 mmol) and 3-(methyloxy)propanoyl chloride (31.2 mg, 0.255 mmol, available from Fluorochem) in chloroform (2 ml), were heated under microwave irradiation at 100° C. for 1 h. The solvent was blown off and the residue dissolved in isopropanol (2 ml) and 2M sodium hydroxide (1 ml) and stirred at RT for 2 h. The solvent was removed and the residue purified by column chromatography, on silica (20 g cartridge), eluting with 0-100% ethylacetate/cyclohexane followed by 0-25% methanol/dichloromethane. Further purification by Mass Directed Automated Preparative HPLC afforded the title compound (3 mg).

LCMS (Method A): Rt 0.91 mins, MH+ 360 and [M+CH₃CN]⁺ 401.

Example 34

6-(1H-Indol-4-yl)-4-(5-{[(phenylmethyl)oxy]methyl}-1,3,4-oxadiazol-2-yl)-1H-indazole

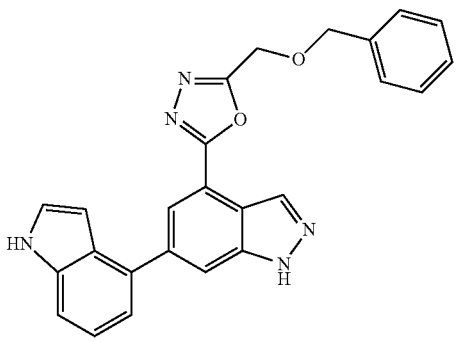 [SMILES: c1ccc(COCc2nnc(-c3cc(-c4cccc5[nH]ccc45)cc4[nH]ncc34)o2)cc1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.170 mmol) and benzyloxyacetyl chloride (62.7 mg, 0.340 mmol) in chloroform (2 ml), were heated under microwave irradiation at 100° C. for 1 h. The solvent was blown off and the residue dissolved in isopropanol (2 ml) and 2M sodium hydroxide (1 ml) and stirred at RT for 2 h. The solvent was removed and the residue purified by column chromatography, on silica (20 g cartridge), eluting with 0-100% ethylacetate/cyclohexane to give the title compound as a clear gum (5.8 mg).

LCMS (Method A): Rt 1.11 mins, MH+ 421 and [M+CH₃CN]⁺ 463.

Similarly prepared with {[(1R,2S,5R)-5-methyl-2-(1-methylethyl)cyclohexyl]oxy}acetyl chloride (available from Sigma-Aldrich) was:

| Example Number | Starting Material | Structure | Rt mins | MH+ | Name |
|---|---|---|---|---|---|
| 35 | Intermediate 37 6-Bromo-1-[(4-methylphenyl)sulfonyl]-4-(1H-tetrazol-5-yl)-1H-indazole/6-(1H-Indol-4-yl)-1-(phenylsulfonyl)-4-(1H-tetrazol-5-yl)-1H-indazole (approx 1:1) | 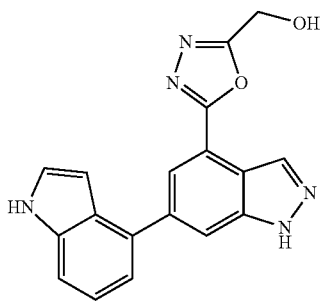 [SMILES: OCc1nnc(-c2cc(-c3cccc4[nH]ccc34)cc3[nH]ncc23)o1] | 1.42 | 470 | 6-(1H-indol-4-yl)-4-[5-({[(1R,2S,5R)-5-methyl-2-(1-methylethyl)cyclohexyl]oxy}methyl)-1,3,4-oxadiazol-2-yl]-1H-indazole |

Example 36

{5-[6-(1H-Indol-4-yl)-1H-indazol-4-yl]-1,3,4-oxadiazol-2-yl}methanol

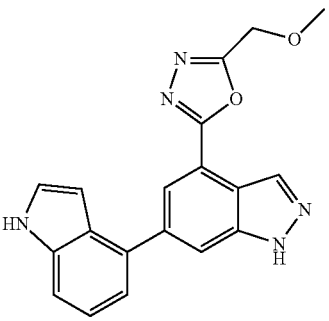 [SMILES: COCc1nnc(-c2cc(-c3cccc4[nH]ccc34)cc3[nH]ncc23)o1]

4-[5-(Chloromethyl)-1,3,4-oxadiazol-2-yl]-6-(1H-indol-4-yl)-1-(phenylsulfonyl)-1H-indazole (25 mg, 0.051 mmol), cyclohexylmethanol (17.48 mg, 0.153 mmol) and potassium carbonate (21.16 mg, 0.153 mmol) were placed in N-methyl-2-pyrrolidone (1 ml) and the mixture heated under microwave irradiation at 100° C. for 20 mins. Additional cyclohexylmethanol (17.48 mg, 0.153 mmol) was added and the mixture heated at 110° C. for 20 mins, followed by 110° C. for a further 20 mins. The solvent was removed and the residue purified by Mass Directed Automated Preparative HPLC to give the title compound as a white solid (5 mg).

LCMS (Method A): Rt 0.77 mins, MH+ 332.

Example 37

6-(1H-Indol-4-yl)-4-{5-[(methyloxy)methyl]-1,3,4-oxadiazol-2-yl}-1H-indazole

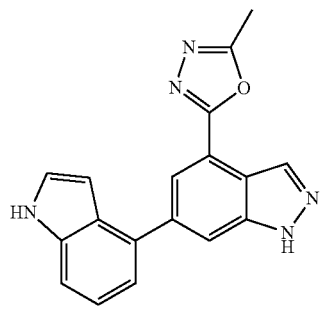 [SMILES: Cc1nnc(-c2cc(-c3cccc4[nH]ccc34)cc3[nH]ncc23)o1]

4-[5-(Chloromethyl)-1,3,4-oxadiazol-2-yl]-6-(1H-indol-4-yl)-1-(phenylsulfonyl)-1H-indazole (25 mg, 0.051 mmol) was placed in methanol (1.5 ml, 37.1 mmol) and potassium carbonate (7.05 mg, 0.051 mmol) added. The mixture was heated under microwave irradiation at 110° C. for 20 mins. The solvent was removed and the residue purified by Mass Directed Automated Preparative HPLC to give the title compound as a white solid (3 mg).

LCMS (Method A): Rt 0.91 mins, MH+ 346 and [M+CH$_3$CN]+ 387.

Example 38

6-(1H-Indol-4-yl)-4-(5-methyl-1,3,4-oxadiazol-2-yl)-1H-indazole

6-Bromo-4-(5-methyl-1,3,4-oxadiazol-2-yl)-1-[(4-methylphenyl)sulfonyl]-1H-indazole (70 mg, 0.162 mmol) was dissolved in 1,4-dioxane (1.2 ml) and 4-(4,4,5,5-tetramethyl-1,3,2-dioxaborolan-2-yl)-1H-indole (47.1 mg, 0.194 mmol, available from Frontier Scientific Europe), 1,1'-bis(diphenylphosphino)ferrocenedichloropalladium(II) (5.91 mg, 8.08 µmol), water (0.8 ml) and 2M aqueous sodium bicarbonate (0.242 ml, 0.485 mmol) were added. The reaction mixture was heated under microwave irradiation at 150° C. for 15 mins. The solution was loaded onto a silica cartridge (0.5 g) and eluted with methanol. The eluant was concentrated, the residue dissolved in methanol and absorbed onto Florisil. This was placed on top of a silica cartridge (10 g) and eluted with 25-50% ethyl acetate/cyclohexane. Appropriate fractions were evaporated to give the title compound as a yellow solid (27 mg).

LCMS (Method B): Rt 2.22 mins, MH+ 316.

Example 39

N-{2-Chloro-5-[4-(5-methyl-1,3,4-oxadiazol-2-yl)-1H-indazol-6-yl]-3-pyridinyl}methanesulfonamide

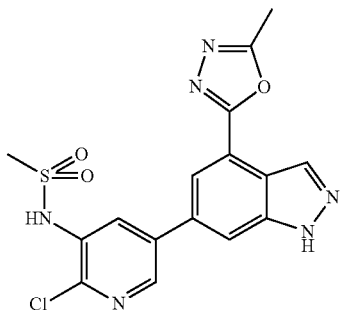 [SMILES: Cc1nnc(-c2cc(-c3cnc(Cl)c(NS(C)(=O)=O)c3)cc3[nH]ncc23)o1]

N-(2-chloro-5-{4-(5-methyl-1,3,4-oxadiazol-2-yl)-1-[(4-methylphenyl)sulfonyl]-1H-indazol-6-yl}-3-pyridinyl)methanesulfonamide (16 mg, 0.029 mmol) and 2M sodium hydroxide (1 ml, 2.0 mmol) were placed in isopropanol (5 ml) and the mixture stirred at room temperature overnight. The solvent was removed and the residue partitioned between water (5 ml) and dichloromethane (5 ml). The aqueous was acidified to ~pH 1 with 2M hydrogen chloride, then extracted with dichloromethane (20 ml). The organic layer was concentrated to give the title compound as a white solid (10 mg).

LCMS (Method A): Rt 0.76 mins, MH+ 405 and $[M+CH_3CN]^+$ 446.

Example 40

6-(1H-Indol-4-yl)-4-{5-[(methylsulfonyl)methyl]-1,3,4-oxadiazol-2-yl}-1H-indazole

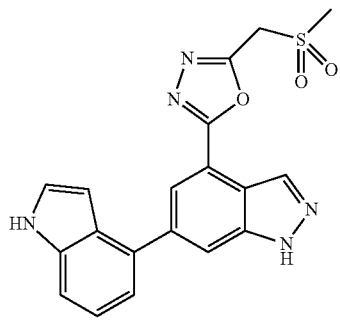 [SMILES: CS(=O)(=O)Cc1nnc(-c2cc(-c3cccc4[nH]ccc34)cc3[nH]ncc23)o1]

4-[5-(Chloromethyl)-1,3,4-oxadiazol-2-yl]-6-(1H-indol-4-yl)-1-(phenylsulfonyl)-1H-indazole (50 mg, 0.102 mmol) and sodium methanesulfinate (10.42 mg, 0.102 mmol) in ethanol (0.8 ml) were heated under microwave irradiation to 100° C. for 30 mins then 150° C. for 30 min, followed by 150° C. for a further 30 mins. Additional sodium methanesulfinate (10.42 mg, 0.102 mmol) was added and the reaction heated to 150° C. for a further 30 mins. The solvent was removed and the resultant beige solid treated with isopropanol (1 ml) and 2M aqueous sodium hydroxide (1.003 ml, 2.006 mmol) and stirred at 20° C. for 20 h. The mixture was neutralised with 2M aqueous hydrogen chloride, evaporated to dryness and azeotroped with isopropanol (2 ml). The residue was partitioned between dichloromethane (5 ml) and water (5 ml) and shaken vigorously. The aqueous phase was pipetted off, then the heterogeneous solution was treated with methanol (5 ml), absorbed onto Florisil and the solvents removed. The Florisil was placed on top of a silica cartridge (10 g) and eluted with 0-3% methanol/dichloromethane. Appropriate fractions were combined and concentrated to give a beige solid, 16 mg. Further purification by Mass Directed Automated Preparative HPLC afforded the title compound as a white solid (5 mg).

LCMS (Method A): Rt 0.79 mins, [M–H]⁻ 392.

Example 41

6-(1H-Indol-4-yl)-4-{5-[(phenylsulfonyl)methyl]-1,3,4-oxadiazol-2-yl}-1H-indazole

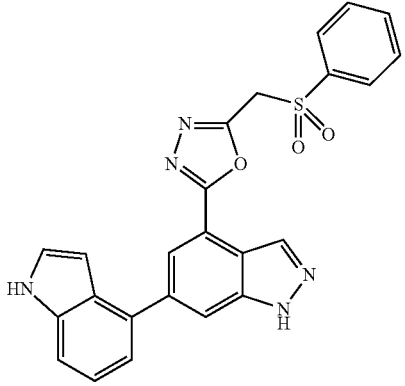 [SMILES: O=S(=O)(Cc1nnc(-c2cc(-c3cccc4[nH]ccc34)cc3[nH]ncc23)o1)c1ccccc1]

4-[5-(Chloromethyl)-1,3,4-oxadiazol-2-yl]-6-(1H-indol-4-yl)-1-(phenylsulfonyl)-1H-indazole (60 mg, 0.110 mmol) and sodium benzenesulfinate dihydrate (33.1 mg, 0.165 mmol, available from TCI Europe) in ethanol (0.8 ml) were heated under microwave irradiation to 100° C. for 30 mins then 150° C. for 20 mins. The mixture was treated with dichloromethane (3 ml) and methanol (3 ml) and absorbed onto Florisil. This was placed on top a silica cartridge (10 g) and eluted with 0-100% ethyl acetate/cyclohexane and then 0-20% methanol/ethyl acetate. Appropriate fractions were combined and concentrated to give a yellow solid, 33 mg. The solid was treated with isopropanol (1 ml) and 2M aqueous sodium hydroxide (0.999 ml, 1.998 mmol) and stirred at 20° C. for 22 h. The mixture was neutralised with 2M aqueous hydrochloric acid, blown to dryness and purified by Mass Directed Automated Preparative H PLC. Appropriate fraction was evaporated, then azeotroped with methanol to give the title compound as a white solid (8 mg).

LCMS (Method A): Rt 0.95 mins, MH+ 456.

Example 42

N-(2-(Methyloxy)-5-{4-[5-(6-oxa-9-azaspiro[4.5]dec-9-ylmethyl)-1,3,4-oxadiazol-2-yl]-1H-indazol-6-yl}-3-pyridinyl)methanesulfonamide

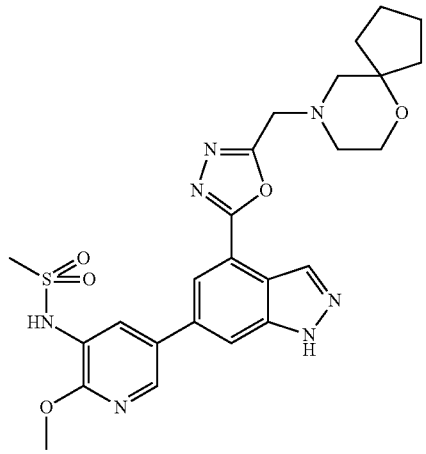 [SMILES: COc1ncc(-c2cc(-c3nnc(CN4CCOC5(CCCC5)C4)o3)c3cn[nH]c3c2)cc1NS(C)(=O)=O]

To a solution of 9-({5-[6-bromo-1-(phenylsulfonyl)-1H-indazol-4-yl]-1,3,4-oxadiazol-2-yl}methyl)-6-oxa-9-azaspiro[4.5]decane (74 mg, 0.133 mmol) in 1,4 dioxane (2.5 ml) and water (1 ml) was added N-[2-(methyloxy)-5-(4,4,5,5-tetramethyl-1,3,2-dioxaborolan-2-yl)-3-pyridinyl]methanesulfonamide (47.8 mg, 0.146 mmol), 1,1'-bis(diphenylphosphino)ferrocene palladium dichloride (19.39 mg, 0.027 mmol) and potassium phosphate tribasic (84 mg, 0.398 mmol). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The protected compound was dissolved in 1,4-dioxane (1 ml) and sodium hydroxide (1 ml, 2.000 mmol) and stirred at room temperature for 4 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the crude residue was dissolved in DMSO (1 ml) and purified by Mass Directed Automated Preparative HPLC. The appropriate fraction was blown down under a stream of nitrogen to give the title compound as a white solid (71.5 mg).

LCMS (Method A): Rt 0.82 mins, MH+ 540.

Example 43

2-[({5-[6-(1H-Indol-4-yl)-1H-indazol-4-yl]-1,3,4-oxadiazol-2-yl}methyl)amino]ethanol

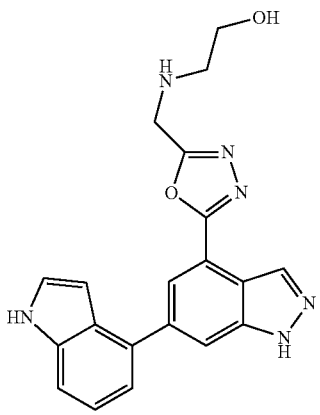 [SMILES: OCCNCc1nnc(-c2cc(-c3cccc4[nH]ccc34)cc3[nH]ncc23)o1]

4-[5-(Chloromethyl)-1,3,4-oxadiazol-2-yl]-6-(1H-indol-4-yl)-1-(phenylsulfonyl)-1H-indazole (100 mg, 0.184 mmol) in acetonitrile (2 ml) was treated with 2-aminoethanol (0.055 ml, 0.918 mmol) and heated in a microwave at 100° C. for 30 mins. The acetonitrile supernatant was pipetted off, and the solid washed with further acetonitrile (5 ml). The solid was dissolved in methanol and DMSO (1:1, 3 ml) and loaded onto a 2 g SCX cartridge. Methanol was eluted, then 2M ammonia in ethanol. Basic fractions were blown to dryness to give a brown solid. The fully-protected intermediate was treated with isopropanol (1.000 ml) followed by 2M aqueous sodium hydroxide (1.001 ml, 2.002 mmol) and stirred for 20 h at 20° C. The solution was neutralised by addition of 2M hydrochloric acid, then blown to dryness to give a brown solid. This was transferred into a small vial, and treated with DMSO/MeOH (1:1, 1 ml) then filtered and purified on MDAP (Method E). The appropriate fraction was blown to dryness to give the title compound as a beige solid (10 mg).

LCMS (Method A): Rt 0.57 mins, MH+ 375.

Example 44

1-[({5-[6-(1H-Indol-4-yl)-1H-indazol-4-yl]-1,3,4-oxadiazol-2-yl}methyl)amino]-3-(4-morpholinyl)-2-propanol

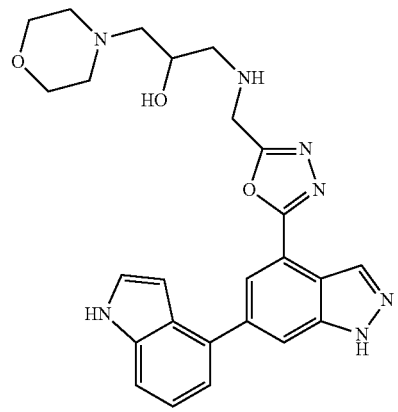 [SMILES: OC(CNCc1nnc(-c2cc(-c3cccc4[nH]ccc34)cc3[nH]ncc23)o1)CN1CCOCC1]

4-[5-(Chloromethyl)-1,3,4-oxadiazol-2-yl]-6-(1H-indol-4-yl)-1-(phenylsulfonyl)-1H-indazole (100 mg, 0.184 mmol) in acetonitrile (2 ml) was treated with 1-amino-3-(4-morpholinyl)-2-propanol (147 mg, 0.918 mmol, available from Enamine Ltd) and heated in a microwave at 100° C. for 30 mins. The solution was pipetted off the solid, then the solid was dissolved in DMSO (ml) and loaded onto a 5 g SCX cartridge. Methanol was eluted, then 2M ammonia in ethanol. Basic fractions were blown to dryness. The fully-protected intermediate was treated with isopropanol (1.000 ml) followed by 2M aqueous sodium hydroxide (1.001 ml, 2.002 mmol) and stirred for 20 h at 20° C. The solution was neutralised by addition of 2M hydrochloric acid then blown to dryness to give a brown solid. The material was purified MDAP (Method E). The appropriate fraction was blown to dryness to give the title compound as a brown film (27 mg).

LCMS (Method B): Rt 1.96 mins, MH+ 474.

Example 45

N-[5-[4-(5-{[(3R,5S)-3,5-Dimethyl-4-(1-methylethyl)-1-piperazinyl]methyl}-1,3,4-oxadiazol-2-yl)-1H-indazol-6-yl]-2-(methyloxy)-3-pyridinyl]methanesulfonamide

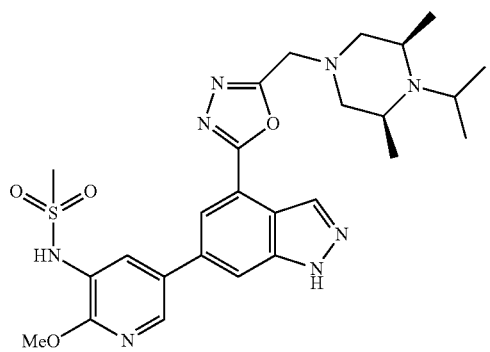 [SMILES: COc1ncc(-c2cc(-c3nnc(CN4C[C@@H](C)N(C(C)C)[C@@H](C)C4)o3)c3cn[nH]c3c2)cc1NS(C)(=O)=O]

6-Bromo-4-(5-{[(3R,5S)-3,5-dimethyl-4-(1-methylethyl)-1-piperazinyl]methyl}-1,3,4-oxadiazol-2-yl)-1-(phenylsulfonyl)-1H-indazole (172 mg, 0.300 mmol), N-[2-(methyloxy)-5-(4,4,5,5-tetramethyl-1,3,2-dioxaborolan-2-yl)-3- pyridinyl]methanesulfonamide (108 mg, 0.330 mmol), 1,1'-bis(diphenylphosphino)ferrocene palladium dichloride (43.9 mg, 0.060 mmol) and potassium phosphate tribasic (191 mg, 0.900 mmol) were added to a microwave vial and dissolved in 1,4-dioxane (2.5 ml) and water (0.25 ml). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The protected compound was dissolved in 1,4-dioxane (1 ml) and sodium hydroxide (1 ml, 2.000 mmol) and stirred at room temperature for 4 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the crude residue was dissolved in DMSO (1 ml) and purified by high pH MDAP (Method E). The appropriate fraction was blown to dryness to give the title compound as a white solid (40 mg).

LCMS (Method A): Rt 0.76 mins, MH+ 555.

The compounds listed below were synthesised using the general method above:

mg, 0.351 mmol), 1,1'-bis(diphenylphosphino)ferrocene palladium dichloride (46.7 mg, 0.064 mmol) and potassium phosphate tribasic (203 mg, 0.958 mmol) were added to a microwave vial and dissolved in 1,4-dioxane (5 ml) and water (0.5 ml). The mixture was heated under microwave irradiation at 100° C. for 20 mins. The solvent was removed under a stream of nitrogen and the residue was partitioned between DCM (10 ml) and water (10 ml), separated with a hydrophobic frit and the solvent again removed under a stream of nitrogen. The protected compound was dissolved in 1,4-dioxane (1 ml) and sodium hydroxide (1 ml, 2.000 mmol) and stirred at room temperature for 4 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the crude residue was dissolved in DMSO (2 ml) and purified by Mass Directed Automated Preparative HPLC. The appropriate fraction was blown down under a stream of nitrogen to give a yellow solid. The solid was purified further by high pH MDAP (Method E) and the appropriate fraction was blown down under a stream of nitrogen to give the title compound as a white solid (12 mg).

LCMS (Method A): Rt 0.90 mins, MH+ 514.

| Example Number | Starting Material | Structure | Rt mins | MH+ | Name |
|---|---|---|---|---|---|
| 46 | prepared with 6-bromo-4-{5-[(1,1-dioxido-4-thiomorpholinyl)methyl]-1,3,4-oxadiazol-2-yl}-1-(phenylsulfonyl)-1H-indazole) | 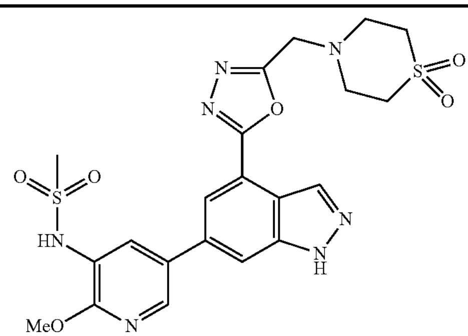 | 0.82 | 534 | N-[5-(4-{5-[(1,1-dioxido-4-thiomorpholinyl)methyl]-1,3,4-oxadiazol-2-yl}-1H-indazol-6-yl)-2-(methyloxy)-3-pyridinyl]methanesulfonamide |

Example 47

N-[5-(4-{5-[(2-Ethyl-4-morpholinyl)methyl]-1,3,4-oxadiazol-2-yl}-1H-indazol-6-yl)-2-(methyloxy)-3-pyridinyl]methanesulfonamide

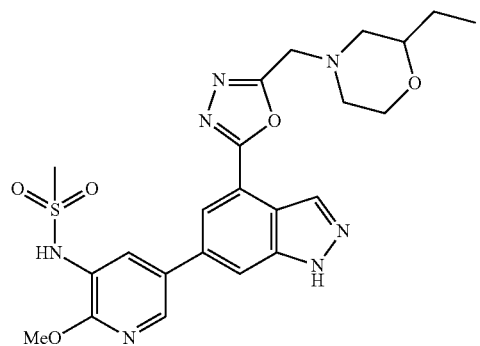 [SMILES: CCC1CN(Cc2nnc(-c3cc(-c4cnc(OC)c(NS(C)(=O)=O)c4)cc4[nH]ncc34)o2)CCO1]

6-Bromo-4-{5-[(2-ethyl-4-morpholinyl)methyl]-1,3,4-oxadiazol-2-yl}-1-(phenylsulfonyl)-1H-indazole (170 mg, 0.319 mmol), N-[2-(methyloxy)-5-(4,4,5,5-tetramethyl-1,3,2-dioxaborolan-2-yl)-3-pyridinyl]methanesulfonamide (115

Example 48

9-({5-[6-(1H-Indol-4-yl)-1H-indazol-4-yl]-1,3,4-oxadiazol-2-yl}methyl)-6-oxa-9-azaspiro[4.5]decane

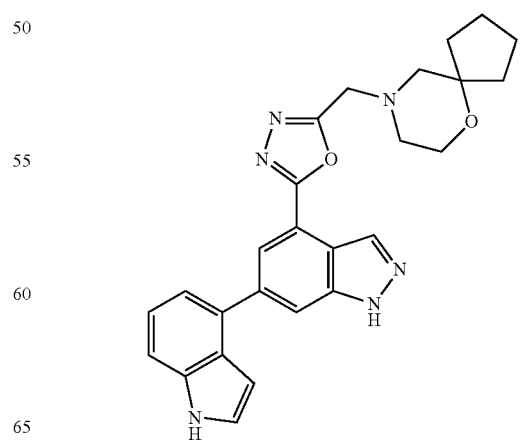

To a solution of 9-({5-[6-bromo-1-(phenylsulfonyl)-1H-indazol-4-yl]-1,3,4-oxadiazol-2-yl}methyl)-6-oxa-9-azaspiro[4.5]decane (100 mg, 0.179 mmol) in 1,4 dioxane (2.5 ml) and water (0.25 ml) was added 4-(4,4,5,5-tetramethyl-1,3,2-dioxaborolan-2-yl)-1H-indole (56.6 mg, 0.233 mmol, available from Frontier Scientific Europe), 1,1'-bis(diphenylphosphino)ferrocene palladium dichloride (26.2 mg, 0.036 mmol) and potassium phosphate tribasic (114 mg, 0.537 mmol). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The residue was dissolved in DMSO (2 ml) and purified by Mass Directed Automated Preparative HPLC. The appropriate fractions were blown down under a stream of nitrogen to give a yellow solid. The solid was dissolved in 1,4-dioxane (1 ml) and sodium hydroxide (1 ml, 2.000 mmol) and stirred at room temperature for 3 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the residue was freeze dried from 1,4-dioxane/water (1:1, 2 ml) overnight to give the title compound as a cream solid (21 mg).

LCMS (Method A): Rt 0.93 mins, MH+ 455.

Example 49

4-{5-[(2,2-Dimethyl-4-morpholinyl)methyl]-1,3,4-oxadiazol-2-yl}-6-(1H-indol-4-yl)-1H-indazole

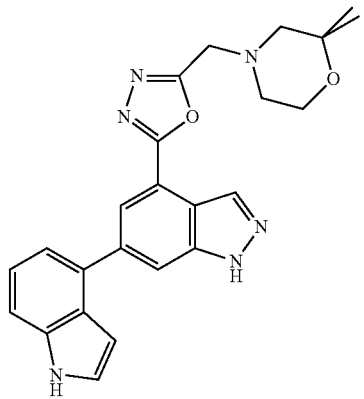 [SMILES: CC1(C)CN(Cc2nnc(-c3cc(-c4cccc5[nH]ccc45)cc4[nH]ncc34)o2)CCO1]

To a solution of 6-bromo-4-{5-[(2,2-dimethyl-4-morpholinyl)methyl]-1,3,4-oxadiazol-2-yl}-1-(phenylsulfonyl)-1H-indazole (176 mg, 0.298 mmol) in dioxane (2.5 ml) and water (0.25 ml) was added 4-(4,4,5,5-tetramethyl-1,3,2-dioxaborolan-2-yl)-1H-indole (102 mg, 0.420 mmol, available from Frontier Scientific Europe), 1,1'-bis(diphenylphosphino)ferrocene palladium dichloride (43.5 mg, 0.060 mmol) and potassium phosphate tribasic (198 mg, 0.933 mmol). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The crude residue was dissolved in DMSO (2 ml) and purified by Mass Directed Automated Preparative HPLC. The product-containing fractions were blown down under a stream of nitrogen to give a yellow solid. The protected compound was dissolved in 1,4-dioxane (1 ml) and sodium hydroxide (1 ml, 2.000 mmol) and stirred at room temperature for 3 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen to give a brown solid (31 mg) that was dissolved in DMSO (750 µL) and purified by Mass Directed Automated Preparative HPLC. The solvent was removed under a stream of nitrogen. The appropriate fraction was blown down under a stream of nitrogen to give the title compound as a pale yellow gum (2.4 mg).

LCMS (Method A): Rt 0.86 mins, MH+ 429.

Example 50

N-[5-[4-(5-{[(3R,5S)-3,5-Dimethyl-4-(1-methylethyl)-1-piperazinyl]methyl}-1,3,4-oxadiazol-2-yl)-1H-indazol-6-yl]-2-(methyloxy)-3-pyridinyl]-2,4-difluorobenzenesulfonamide

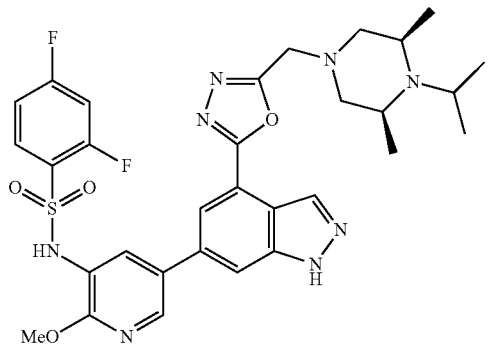 [SMILES: COc1ncc(-c2cc(-c3nnc(CN4C[C@@H](C)N(C(C)C)[C@@H](C)C4)o3)c3cn[nH]c3c2)cc1NS(=O)(=O)c1ccc(F)cc1F]

6-Bromo-4-(5-{[(3R,5S)-3,5-dimethyl-4-(1-methylethyl)-1-piperazinyl]methyl}-1,3,4-oxadiazol-2-yl)-1-(phenylsulfonyl)-1H-indazole (172 mg, 0.300 mmol), 2,4-difluoro-N-[2-(methyloxy)-5-(4,4,5,5-tetramethyl-1,3,2-dioxaborolan-2-yl)-3-pyridinyl]benzenesulfonamide (128 mg, 0.300 mmol), 1,1'-bis(diphenylphosphino)ferrocene palladium dichloride (43.9 mg, 0.060 mmol) and potassium phosphate tribasic (191 mg, 0.900 mmol) were added to a microwave vial and dissolved in 1,4-dioxane (2.5 ml) and water (0.25 ml). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The protected compound was dissolved in 1,4-dioxane (1 ml) and sodium hydroxide (1 ml, 2.000 mmol) and stirred at room temperature for 4 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the residue was dissolved in DMSO (1 ml) and purified by purified by Mass Directed Automated Preparative HPLC. The appropriate fraction was blown down under a stream of nitrogen to give the title compound as a pale yellow solid (4.9 mg).

LCMS (Method A): Rt 0.65 mins, MH+ 653.

The compounds listed below were synthesised using the general method above:

| Example Number | Starting Material | Structure | Rt mins | MH+ | Name |
|---|---|---|---|---|---|
| 51 | 6-bromo-4-(5-{[4-(1-methylethyl)-1-piperazinyl]methyl}-1,3,4-oxadiazol-2-yl)-1-(phenylsulfonyl)-1H-indazole | 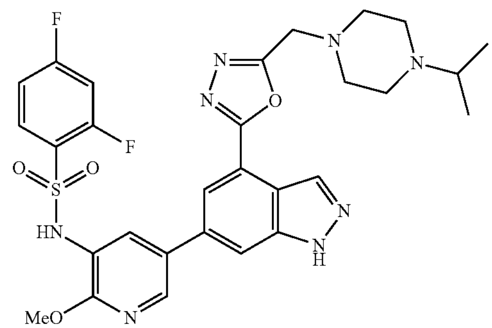 [SMILES: COc1ncc(-c2cc(-c3nnc(CN4CCN(C(C)C)CC4)o3)c3cn[nH]c3c2)cc1NS(=O)(=O)c1ccc(F)cc1F] | 0.62 | 625 | 2,4-difluoro-N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]benzenesulfonamide |

Example 52

N-[5-(4-{5-[(2-Methyl-4-morpholinyl)methyl]-1,3,4-oxadiazol-2-yl}-1H-indazol-6-yl)-2-(methyloxy)-3-pyridinyl]methanesulfonamide

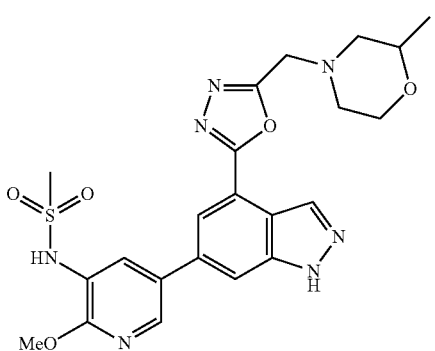 [SMILES: COc1ncc(-c2cc(-c3nnc(CN4CCOC(C)C4)o3)c3cn[nH]c3c2)cc1NS(C)(=O)=O]

6-Bromo-4-{5-[(2-methyl-4-morpholinyl)methyl]-1,3,4-oxadiazol-2-yl}-1-(phenylsulfonyl)-1H-indazole (269 mg, 0.519 mmol) was dissolved in 1,4-dioxane (5 ml) and half of this stock solution was charged to a reaction vessel. N-[2-(methyloxy)-5-(4,4,5,5-tetramethyl-1,3,2-dioxaborolan-2-yl)-3-pyridinyl]methanesulfonamide (110 mg, 0.335 mmol), 1,1'-bis(diphenylphosphino)ferrocene palladium dichloride (38 mg, 0.052 mmol), potassium phosphate tribasic (165 mg, 0.779 mmol) and water (0.25 ml) were added. The reaction mixture was heated under microwave irradiation at 100° C. for 20 mins, then 100° C. for 40 mins and lastly 100° C. for 20 mins. More N-[2-(methyloxy)-5-(4,4,5,5-tetramethyl-1,3,2-dioxaborolan-2-yl)-3-pyridinyl]methanesulfonamide (34.1 mg, 0.104 mmol), 1,1'-bis(diphenylphosphino)ferrocene palladium dichloride (7.59 mg, 10.38 μmol) and potassium phosphate tribasic (33.0 mg, 0.156 mmol) were added and the mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The crude was purified using preparative HPLC as follows:

| Column Packing | Waters Sunfire c18 |
|---|---|
| Column Particle Size | 5.0 μm |
| Column Dimensions | 100 × 19 mmID |
| Solvent A | 0.1% v/v formic acid in water |
| Solvent B | MeCN + 0.1% v/v of formic acid |
| Temperature | ambient |
| Flow Rate | 20 ml/min |
| Injection Volume | 500 μL |
| Injection Vehicle | 1:1 DMSO/MeCN |
| UV detection | Diode-array 210-400 nm (averaged) |
| MS detection | Electrospray, +ve/ −ve switching, 100-1000 amu, centroid mode |
| MS scan function | Electrospray, +ve/ −ve switching, centroid mode |

| Time (mins) | % A | % B | Flow rate (ml/min) |
|---|---|---|---|
| 0 | 65 | 35 | 20 |
| 1 | 65 | 35 | 20 |
| 15 | 65 | 35 | 20 |
| 15.5 | 100 | 0 | 20 |
| 18 | 100 | 0 | 20 |
| 18.5 | 65 | 35 | 20 |
| 20 | 65 | 35 | 20 |

The appropriate fraction were blown to dryness. 1,4-Dioxane (1 ml) was added and 2M sodium hydroxide (1 ml, 2.000 mmol) and the mixture stirred at 20° C. for 2 h. The mixture was partitioned between ethyl acetate (5 ml) and saturated ammonium chloride solution (2 ml), separated with a hydrophilic frit. The organic layer was evaporated to dryness under a stream of nitrogen to give the title compound as a cream solid (27 mg).

LCMS (Method A): Rt 0.63 mins, MH+ 500.

Example 53

6-(1H-Indol-4-yl)-4-{5-[(2-methyl-4-morpholinyl)methyl]-1,3,4-oxadiazol-2-yl}-1H-indazole

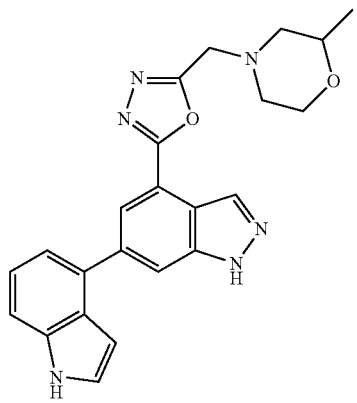 [SMILES: CC1CN(Cc2nnc(-c3cc(-c4cccc5[nH]ccc45)cc4[nH]ncc34)o2)CCO1]

6-Bromo-4-{5-[(2-methyl-4-morpholinyl)methyl]-1,3,4-oxadiazol-2-yl}-1-(phenylsulfonyl)-1H-indazole (269 mg, 0.519 mmol) was dissolved in 1,4-dioxane (5 ml) and half of this stock solution was charged to a reaction vessel. 4-(4,4,5,5-tetramethyl-1,3,2-dioxaborolan-2-yl)-1H-indole (82 mg, 0.337 mmol), 1,1'-bis(diphenylphosphino)ferrocene palladium dichloride (38 mg, 0.052 mmol), potassium phosphate tribasic (165 mg, 0.779 mmol) and water (0.25 ml) were added. The reaction mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The crude residue was purified using preparative HPLC as follows:

| Column Packing | Waters Sunfire C18 |
| --- | --- |
| Column Particle Size | 5.0 μm |
| Column Dimensions | 100 × 19 mmID |
| Solvent A | 0.1% v/v formic acid in water |
| Solvent B | MeCN + 0.1% v/v of formic acid |
| Temperature | ambient |
| Flow Rate | 20 ml/mins |
| Injection Volume | 200 μL |
| Injection Vehicle | 1:1 DMSO/MeCN |
| UV detection | Diode-array 210-400 nm (averaged) |
| MS detection | Electrospray, +ve/−ve switching, 100-1000 amu, centroid mode |
| MS scan function | Electrospray, +ve/−ve switching, centroid mode |

| Time (mins) | % A | % B | Flow rate (ml/min) |
| --- | --- | --- | --- |
| 0 | 60 | 40 | 20 |
| 1 | 60 | 40 | 20 |
| 25 | 60 | 40 | 20 |
| 25.5 | 100 | 0 | 20 |
| 27 | 100 | 0 | 20 |
| 27.5 | 60 | 40 | 20 |
| 30 | 60 | 40 | 20 |

The appropriate fractions were dried down. 1,4-Dioxane (1 ml) and 2M sodium hydroxide (1 ml, 2.000 mmol) was added and the mixture stirred at 20° C. for 2 h. The mixture was partitioned between ethyl acetate (5 ml) and saturated ammonium chloride solution (2 ml), separating the layers with a hydrophilic frit. The organic layer was evaporated to dryness under a stream of nitrogen. The residue was taken up again in 1,4-dioxane (1 ml) and 2M sodium hydroxide (1 ml, 2.000 mmol) and stirred at room temperature for 3 h. The mixture was evaporated under a stream of nitrogen. The residue was partitioned between ethyl acetate and saturated ammonium chloride solution, the organic layer was separated with a hydrophilic frit and the solvent removed under a stream of nitrogen to give the title compound as a cream solid (18 mg).

LCMS (Method A): Rt 0.75 mins, MH+ 415.

Example 54

N-({5-[6-(1H-Indol-4-yl)-1H-indazol-4-yl]-1,3,4-oxadiazol-2-yl}methyl)-3-(4-morpholinyl)-1-propanamine

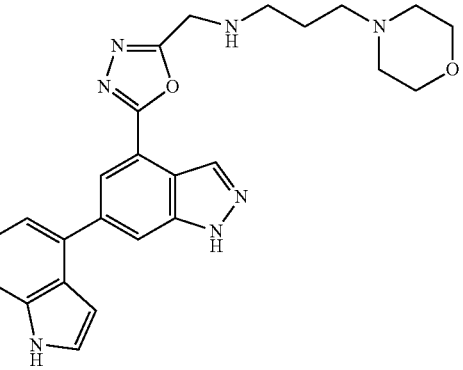

To a solution of N,N-{[5-(6-bromo-1H-indazol-4-yl)-1,3,4-oxadiazol-2-yl]methyl}-3-(4-morpholinyl)-1-propanamine (100 mg, 0.237 mmol) was added 4-(4,4,5,5-tetramethyl-1,3,2-dioxaborolan-2-yl)-1H-indole (57.7 mg, 0.237 mmol, available from Frontier Scientific Europe), 1,1'-bis(diphenylphosphino)ferrocene palladium dichloride (34.7 mg, 0.047 mmol) and potassium phosphate tribasic (151 mg, 0.712 mmol). The mixture was heated under microwave irradiation at 100° C. for 20 mins, 120° C. for 20 mins and finally 150° C. for 20 mins. The reaction mixture was filtered through a 1 g silica SPE cartridge, washing with MeOH. The solvent was evaporated under a stream of nitrogen and the residue partitioned between DCM and water, the organic layer was separated with a hydrophobic frit and the solvent again removed under a stream of nitrogen to give a brown oil (75 mg). The crude residue was purified by Mass Directed Automated Preparative HPLC and the appropriate fraction was blown down under a stream of nitrogen to give the title compound as a colourless gum (109 mg).

LCMS (Method A): Rt 0.43 mins, 458.

Example 55

N-(2-(Methyloxy)-5-{4-[5-(tetrahydro-1,4-oxazepin-4(5H)-ylmethyl)-1,3,4-oxadiazol-2-yl]-1H-indazol-6-yl}-3-pyridinyl)methanesulfonamide

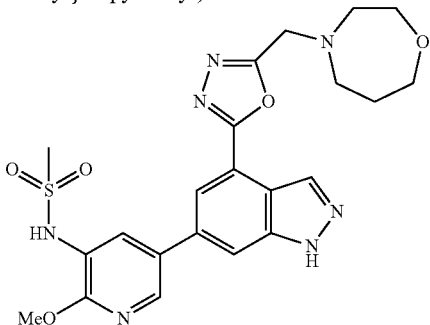

To a solution of N-(2-(methyloxy)-5-{1-(phenylsulfonyl)-4-[5-(tetrahydro-1,4-oxazepin-4(5H)-ylmethyl)-1,3,4-oxadiazol-2-yl]-1H-indazol-6-yl}-3-pyridinyl)methanesulfonamide (50 mg, 0.078 mmol) in 1,4-dioxane (1 ml) was added 2M sodium hydroxide (1 ml, 2.000 mmol) and the mixture stirred at 20° C. for 2 h. The mixture was partitioned between ethyl acetate (5 ml) and saturated ammonium chloride solution (2 ml), separating the layers with a hydrophilic frit. The organic layer was evaporated to dryness under a stream of nitrogen to give the title compound as a pale brown solid (35 mg).

LCMS (Method A): Rt 0.51 mins, MH+ 500.

The compound listed below was synthesised using the general method above:

1-[({5-[6-Bromo-1-(phenylsulfonyl)-1H-indazol-4-yl]-1,3,4-oxadiazol-2-yl}methyl)amino]-3-(4-morpholinyl)-2-propanol (100 mg, 0.346 mmol), N-[2-(methyloxy)-5-(4,4,5,5-tetramethyl-1,3,2-dioxaborolan-2-yl)-3-pyridinyl]methanesulfonamide (81 mg, 0.247 mmol), 1,1'-bis(diphenylphosphino)ferrocene palladium dichloride (25.35 mg, 0.0345 mmol) and potassium phosphate tribasic (110.5 mg, 0.5195 mmol) were added to a mixture of 1,4-dioxane (2.5 ml) and water (0.25 ml). The reaction mixture was heated under microwave irradiation at 80° C. for 30 mins and then 100° C. for 10 mins. The mixture was then passed through a 1 g silica SPE cartridge, washing with MeOH. The solvent was removed under a stream of nitrogen and the residue was partitioned between DCM (10 ml) and water (10 ml), separated by a hydrophobic frit and the solvent again removed under a stream of nitrogen. The protected compound was dissolved in 1,4-dioxane (1 ml) and sodium hydroxide (1 ml) and stirred at room temperature for 1 h. The mixture was neutralised with addition of 2M HCl, dissolved in DMSO, filtered through a filter tube and purified by high pH MDAP (Method E). The appropriate fractions and waste were evaporated to dryness in vacuo. The residue was dissolved in 1:1 DMSO/water and purified by preparative HPLC using the following method:

| Column Packing | Waters Atlantis |
|---|---|
| Column Particle Size | 5.0 μm |
| Column Dimensions | 100 × 19 mmID |
| Solvent A | 0.1% v/v TFA in water |
| Solvent B | MeOH + 0.1% v/v TFA |

| Example Number | Starting Material | Structure | Rt mins | MH+ | Name |
|---|---|---|---|---|---|
| 56 | 6-(1H-indol-4-yl)-1-(phenylsulfonyl)-4-[5-(tetrahydro-1,4-oxazepin-4(5H)-ylmethyl)-1,3,4-oxadiazol-2-yl]-1H-indazole | 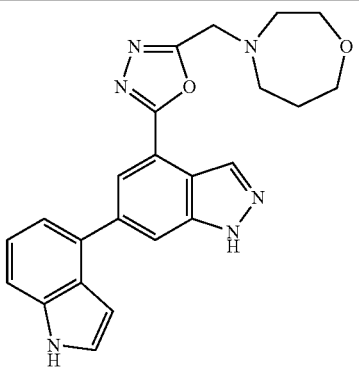 [SMILES: c1cc(-c2cc(-c3nnc(CN4CCCOCC4)o3)c3cn[nH]c3c2)c2cc[nH]c2c1] | 0.58 | 415 | 6-(1H-indol-4-yl)-4-[5-(tetrahydro-1,4-oxazepin-4(5H)-ylmethyl)-1,3,4-oxadiazol-2-yl]-1H-indazole |

Example 57

N-[5-{4-[5-({[2-Hydroxy-3-(4-morpholinyl)propyl]amino}methyl)-1,3,4-oxadiazol-2-yl]-1H-indazol-6-yl}-2-(methyloxy)-3-pyridinyl]methanesulfonamide

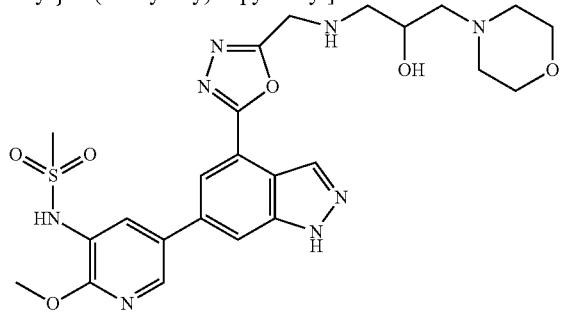

-continued

| Temperature | ambient |
|---|---|
| Flow Rate | 20 ml/min |
| Injection Volume | 500 μL |
| UV detection | Diode-array 210-400 nm (averaged) |
| MS detection | Electrospray, +ve/−ve switching, 100-1000 amu, centroid mode |
| MS scan function | Electrospray, +ve/−ve switching, centroid mode |

| Time (mins) | % A | % B | Flow rate (ml/min) |
|---|---|---|---|
| 0 | 75 | 25 | 20 |
| 1 | 75 | 25 | 20 |

| Time (mins) | % A | % B | Flow rate (ml/min) |
|---|---|---|---|
| 25 | 25 | 75 | 20 |
| 26 | 1 | 99 | 20 |
| 28.5 | 1 | 99 | 20 |
| 29 | 75 | 25 | 20 |
| 30 | 75 | 25 | 20 |

The crude residue was collected and re-purified using a similar method but using 10-30% MeCN/TFA and the following gradient.

| Time (mins) | % A | % B | Flow rate (ml/min) |
|---|---|---|---|
| 0 | 90 | 10 | |
| 1 | 90 | 10 | 20 |
| 25 | 70 | 30 | 20 |
| 26 | 1 | 99 | 20 |
| 28.5 | 1 | 99 | 20 |
| 29 | 90 | 10 | 20 |
| 30 | 90 | 10 | 20 |

The appropriate fractions were dried down give the title compound as a pale yellow solid (12 mg).
LCMS (Method A): 0.40 mins, MH+ 559.
The compound listed below was synthesised using the general method above:

| Example Number | Starting Material | Structure | Rt mins | MH+ | Name |
|---|---|---|---|---|---|
| 58 | 2,4-difluoro-N-[2-(methyloxy)-5-(4,4,5,5-tetramethyl-1,3,2-dioxaborolan-2-yl)-3-pyridinyl]benzenesulfonamide | 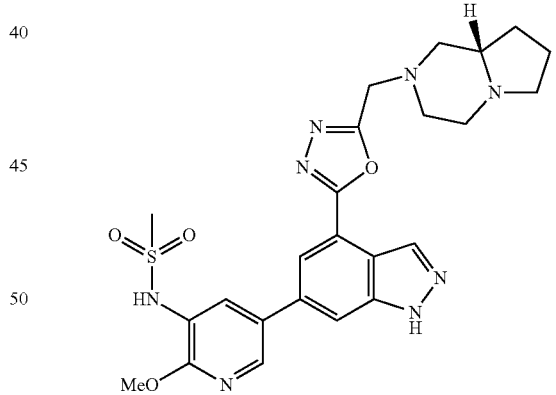 | 0.54 | 657 | 2,4-difluoro-N-[5-{4-[5-({[2-hydroxy-3-(4-morpholinyl)propyl]amino}methyl)-1,3,4-oxadiazol-2-yl]-1H-indazol-6-yl}-2-(methyloxy)-3-pyridinyl]benzenesulfonamide |

Example 59

N-[5-(4-{5-[(8aS)-Hexahydropyrrolo[1,2-a]pyrazin-2(1H)-ylmethyl]-1,3,4-oxadiazol-2-yl}-1H-indazol-6-yl)-2-(methyloxy)-3-pyridinyl]methanesulfonamide N-[5-[4-{5-[(8aS)-Hexahydropyrrolo[1,2-a]pyrazin-2(1H)-ylmethyl]-1,3,4-oxadiazol-2-yl}-1-(phenylsulfonyl)-1H-indazol-6-yl]-2-(methyloxy)-3-pyridinyl]methanesulfonamide (95 mg, 0.143 mmol) was dissolved in 1,4-dioxane (1 ml) and sodium hydroxide (1 ml, 0.143 mmol) was added. The mixture was stirred at room temperature for 1 h. The mixture was dried down under a stream of nitrogen and the residue partitioned between ethyl acetate (5 ml) and saturated ammonium chloride (2 ml). The organic layer was separated, dried by passing through a hydrophobic frit and the solvent removed in vacuo to give an orange oil. This was triturated with cyclohexane to give the title compound as an orange solid (26 mg).
LCMS (K4101903-1). Rt 0.49 mins, MH+ 525.

Example 60

2,4-Difluoro-N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]benzenesulfonamide

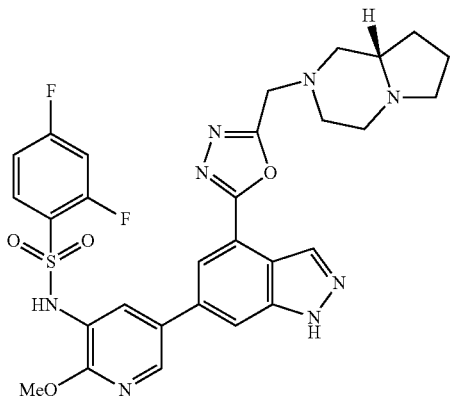 [SMILES: COc1ncc(-c2cc(-c3nnc(CN4CCN5CCC[C@H]5C4)o3)c3cn[nH]c3c2)cc1NS(=O)(=O)c1ccc(F)cc1F]

2,4-Difluoro-N-[5-[4-{5-[(8aS)-hexahydropyrrolo[1,2-a]pyrazin-2(1H)-ylmethyl]-1,3,4-oxadiazol-2-yl}-1-(phenylsulfonyl)-1H-indazol-6-yl]-2-(methyloxy)-3-pyridinyl]benzenesulfonamide (84 mg, 0.110 mmol) was dissolved in 1,4-dioxane (1 ml) and sodium hydroxide (1 ml, 0.110 mmol) was added. The mixture was stirred at room temperature for 1 h. The mixture was dried down under a stream of nitrogen and the residue partitioned between ethyl acetate (5 ml) and saturated ammonium chloride (2 ml). The organic layer was separated, dried by passing through a hydrophobic frit and the solvent removed in vacuo to give a brown gum. This was dissolved in DMSO (1 ml) and purified by high pH MDAP (Method E, extended run). The product-containing fraction was dried under a stream of nitrogen to give the title compound as a cream solid (2.4 mg).

LCMS (Method A): Rt 0.63 mins, MH+ 623.

Example 61

N-[5-[4-(5-{[(2R,6S)-2,6-Dimethyl-4-morpholinyl]methyl}-1,3,4-oxadiazol-2-yl)-1-methyl-1H-indazol-6-yl]-2-(methyloxy)-3-pyridinyl]-2,4-difluorobenzenesulfonamide

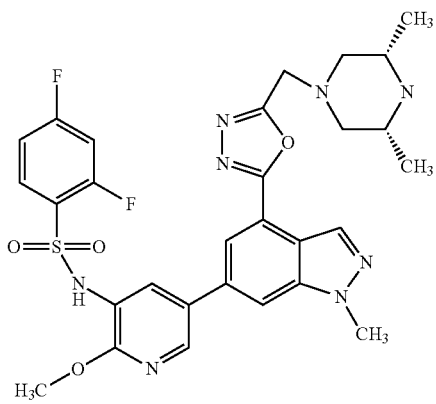 [SMILES: COc1ncc(-c2cc(-c3nnc(CN4C[C@@H](C)N[C@@H](C)C4)o3)c3cnn(C)c3c2)cc1NS(=O)(=O)c1ccc(F)cc1F]

5-[4-(5-{[(2R,6S)-2,6-Dimethyl-4-morpholinyl]methyl}-1,3,4-oxadiazol-2-yl)-1-methyl-1H-indazol-6-yl]-2-(methyloxy)-3-pyridinamine (130 mg, 0.289 mmol) was dissolved in chloroform (3 ml) then 2,4-difluorobenzenesulfonyl chloride (0.058 ml, 0.434 mmol) was added. Pyridine (0.094 ml, 1.157 mmol) was added to the reaction mixture and it was stirred at room temperature (25° C.) for 18 h. The solvent was blown down under nitrogen for 24 h to give a brown oil. Half of material was purified by column chromatography with a gradient of 0-25% MeOH/DCM over 20 mins. Fractions containing product were combined and the solvent removed to give a brown oil which was triturated in ether. The solvent was removed under nitrogen to give an orange solid. This solid was dissolved in DMSO and purified by Mass Directed Automated Preparative HPLC. The solvent was removed under nitrogen to give a white solid (5 mg). The other half of the crude material was purified by Mass Directed Automated Preparative HPLC and the appropriate fractions were combined and solvent was removed under nitrogen to give a white solid (25 mg). The two batches were combined to give the title compound as a white solid (30 mg).

LCMS (Method A): Rt 0.99 mins, MH+ 626.

Example 62

N-[5-[4-(5-{[(2R,6S)-2,6-Dimethyl-4-morpholinyl]methyl}-1,3,4-oxadiazol-2-yl)-1H-indazol-6-yl]-2-(methyloxy)-3-pyridinyl]-2-(methyloxy)benzenesulfonamide

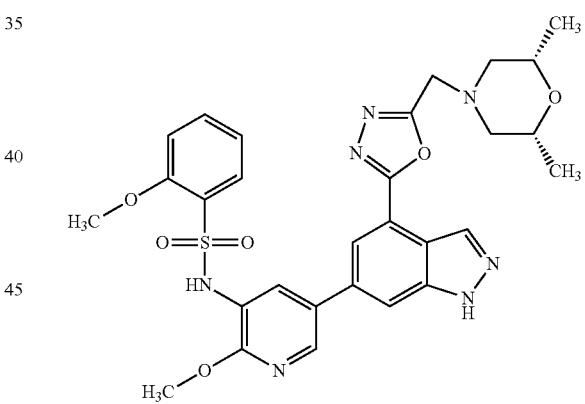

5-{4-(5-{[(2R,6S)-2,6-Dimethyl-4-morpholinyl]methyl}-1,3,4-oxadiazol-2-yl)-1-[(4-methylphenyl)sulfonyl]-1H-indazol-6-yl}-2-(methyloxy)-3-pyridinamine (150 mg, 0.254 mmol) was dissolved in chloroform (3 ml) then 2-(methyloxy)benzenesulfonyl chloride (79 mg, 0.382 mmol) was added. Pyridine (0.082 ml, 1.018 mmol) was added to the reaction mixture and it was stirred at room temperature for 5 h. The compound was dissolved in 1,4-dioxane (2 ml) and 2M sodium hydroxide (2 ml) and stirred at room temperature for 3 h. The reaction mixture was neutralized to pH 7 with 2M HCl, then the solvent was removed under a stream of nitrogen. The solid was dissolved in DMSO then filtered through a filter tube and purified by Mass Directed Automated Preparative HPLC. The solvent was removed under nitrogen to give the title compound as a white solid (60 mg).

LCMS (Method A): Rt 0.88 mins, MH+ 606.

Example 63

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide

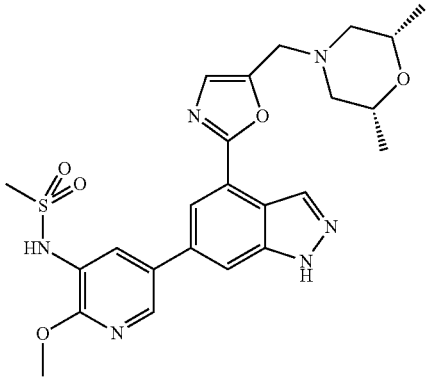

Method A

To a solution of 6-chloro-4-(5-{[(2R,6S)-2,6-dimethyl-4-morpholinyl]methyl}-1,3-oxazol-2-yl)-1-(phenylsulfonyl)-1H-indazole (0.20 g, 0.411 mmol) and N-[2-(methoxy)-5-(4,4,5,5-tetramethyl-1,3,2-dioxaborolan-2-yl)-3-pyridyl]methanesulfonamide (0.175 g, 0.534 mmol) in 1,4-dioxane (2 ml) was added chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (11.5 mg, 0.021 mmol), potassium phosphate tribasic (0.262 g, 1.23 mmol) and water (0.2 ml). The reaction mixture was heated and stirred at 120° C. under microwave irradiation for 1 h. Additional chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (11.5 mg, 0.021 mmol) and potassium phosphate tribasic (80 mg) were added and the reaction heated to 120° C. under microwave irradiation for 1 h. Additional potassium phosphate tribasic (80 mg) was added and the reaction heated under the same conditions for a further 1 h. The reaction mixture was filtered through a silica SPE and eluted with methanol. The solvent was removed in vacuo and the residue partitioned between dichloromethane (5 ml) and water (5 ml). The layers were separated and the aqueous extracted with further dichloromethane (2×2 ml). The combined organics were concentrated under a stream of nitrogen and the residue dissolved in MeOH:DMSO (3 ml, 1:1, v/v) and purified by MDAP (method H) in 3 injections. The appropriate fractions were combined and concentrated to give a white solid which was dissolved in MeOH:DMSO (1 ml, 1:1, v/v) and further purified by MDAP (method 1). The appropriate fractions were basified to pH 6 with saturated sodium bicarbonate solution and extracted with ethyl acetate (2×25 ml). The combined organics were dried and evaporated in vacuo to give a white solid which was further dried under nitrogen at 40° C. for 3 h to give the title compound as a white solid (26 mg).

LCMS (Method A): Rt 0.53 mins, MH+ 513.

Method B

N-[2-(Methyloxy)-5-(4,4,5,5-tetramethyl-1,3,2-dioxaborolan-2-yl)-3-pyridinyl]methanesulfonamide (101 g, 308 mmol), 6-chloro-4-(5-{[(2R,6S)-2,6-dimethyl-4-morpholinyl]methyl}-1,3-oxazol-2-yl)-1-(phenylsulfonyl)-1H-indazole (83.3 g, 154 mmol) and sodium bicarbonate (38.8 g, 462 mmol) were suspended in 1,4-dioxane (1840 ml) and water (460 ml) under nitrogen and heated to 80° C. Chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (8.63 g, 15.40 mmol) was added and the mixture stirred overnight at 80° C.

The reaction mixture was cooled to 45° C., sodium hydroxide 2M aq. (770 ml, 1540 mmol) added and the reaction heated to 45° C. for 4 hours. The mixture was cooled to RT and diluted with water (610 mL). Dichloromethane (920 mL) was added, and the mixture was filtered twice through Celite (washed with 200 mL 1,4-dioxane/DCM 2:1 each time). The phases were separated, and aqueous washed with 1,4-dioxane/DCM 2:1 (500 mL). The aqueous phase was neutralised with hydrochloric acid to pH ~7 and extracted with 1,4-dioxane/DCM 2:1 (1 L), then 1,4 dioxane/DCM 1:1 (2×500 mL). The organics were washed with brine (500 mL), and filtered through Celite (washed with 200 mL 1,4 dioxane/DCM 2:1), and evaporated to yield a dark black solid, which was purified in 4 batches:

Batch 1: 28 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (14.78 g).

Batch 2: 30 g was dissolved in methanol and mixed with Fluorisil. The solvent was then removed by evaporation and the solid purified by column chromatography (1.5 kg silica column, solid sample injection module), eluting with Toluene/Ethanol/Ammonia 80:20:2 to give the title compound as an off-white solid (9.44 g).

Batch 3: 31 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (17 g).

Batch 4: 29 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (21 g).

The mixed fractions from the 4 columns were combined and evaporated to yield 19 g which was dissolved in 200 mL of Toluene/Ethanol/Ammonia 80:20:2 (+additional 4 ml of 0.88 NH3 to help solubility) then purified by column chromatography (1.5 kg silica column), eluting with Toluene/Ethanol/Ammonia 80:20:2 to give the title compound as an off-white solid (6.1 g).

All pure batches were combined (68 g) and recrystallised from ethanol (1200 mL). The suspension was heated to reflux and a solution formed. The resulting solution was then cooled to room temperature overnight. The resulting solid was then collected by filtration, washed sparingly with ethanol and dried under vacuum to give the title compound as an off-white solid (56 g). This material was recrystallised again from ethanol (1100 mL). The suspension was heated to reflux and a solution formed. The resulting solution was then cooled to room temperature overnight with stirring. The resulting solid was collected by filtration and washed sparingly with ethanol. The solid was dried in vacuo at 60° C. for 5 hrs to give the title compound as an off-white solid (45.51 g).

LCMS (Method A): Rt 0.61 mins, MH+ 513.

The filtrate from the two recrystallisations was evaporated to yield ~23 g of a solid residue that was dissolved in 200 mL of Toluene/Ethanol/Ammonia 80:20:2 (+additional 4 ml of 0.88 NH3 to help solubility) then purified by column chromatography (1.5 kg silica column), eluting with Toluene/Ethanol/Ammonia 80:20:2 to give a further crop of the title compound as an off-white solid (18.5 g). This solid was then recrystallised from ethanol (370 mL). The suspension was heated to reflux then the resulting solution stirred for 20 mins before being allowed to cool to room temperature naturally overnight. The solid was then dried in vacuo at 65° C. overnight to give the title compound as an off-white solid (11.90 g).

LCMS (Method A): Rt 0.62 mins, MH+ 513.

Method C

10M Sodium hydroxide solution (0.70 ml) was added to a stirred suspension of N-[5-[4-(5-{[(2R,6S)-2,6-dimethyl-4-morpholinyl]methyl}-1,3-oxazol-2-yl)-1-(phenylsulfonyl)-1H-indazol-6-yl]-2-(methyloxy)-3-pyridinyl]methanesulfonamide (1.17 g) in water (5.8 ml). The resulting mixture was stirred at room temperature for 3.75 hours and was then washed with ethyl acetate (2×6 ml). The layers were separated and the aqueous phase was acidified to pH 6 with 2M hydrochloric acid (0.8 ml). The acidified aqueous layer was extracted twice with ethyl acetate (11 ml then 5 ml). The combined ethyl acetate extracts were dried by azeotropic distillation and diluted with further ethyl acetate (11 ml). The mixture was stirred at room temperature for 112 hours. The slurry was seeded and then stirred at room temperature for 48 hours. The resultant suspension was filtered, washed with ethyl acetate (2×2 ml) and the solid dried under vacuum at 40° C. to give the title compound as a pale yellow solid (0.58 g).

LCMS (Method B): Rt 1.86 min, MH+ 513.

Method D

To a suspension of N-[5-[4-(5-{[(2R,6S)-2,6-dimethyl-4-morpholinyl]methyl}-1,3-oxazol-2-yl)-1-(phenylsulfonyl)-1H-indazol-6-yl]-2-(methyloxy)-3-pyridinyl]methanesulfonamide (596.5 g, 0.91 mol) in water (3.8 L) is added 5M sodium hydroxide (715 ml, 3.56 mol) over 20 mins at <25° C. The mixture is stirred at 20±3° C. for 2 h 45 min then washed with EtCN (3 L). The pH of the basic aqueous phase is adjusted to pH 6.6 using 2M hydrochloric acid (1.4 L), maintaining the temperature below 30° C. The mixture is then extracted with MeTHF (2×4.8 L), and the combined MeTHF extracts are washed with water (1.2 L). The mixture is concentrated to approx 2.4 L and EtOAc (3 L) is added. This put and take distillation is repeated a further 3 times. The mixture is adjusted to 60±3° C. and seeded twice (2×3 g) 35 mins apart. The resultant is aged for 1 h 10 mins then cooled over 2 h to 20-25° C., and aged for a further 15 h 50 min. The slurry is filtered, washed with EtOAc (2×1.2 L) and dried in vacuo at 45±5° C. for approx 3 day to give the title compound.

Example 64

N-[5-[4-(5-{[4-(1-Methylethyl)-1-piperazinyl]methyl}-1,3-oxazol-2-yl)-1H-indazol-6-yl]-2-(methyloxy)-3-pyridinyl]methanesulfonamide

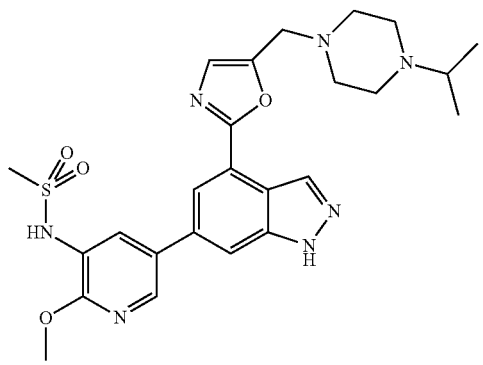 [SMILES: COc1ncc(-c2cc(-c3ncc(CN4CCN(C(C)C)CC4)o3)c3cn[nH]c3c2)cc1NS(C)(=O)=O]

To a solution of 6-chloro-4-(5-{[4-(1-methylethyl)-1-piperazinyl]methyl}-1,3-oxazol-2-yl)-1-(phenylsulfonyl)-1H-indazole (200 mg, 0.400 mmol) and N-[2-(methoxy)-5-(4,4,5,5-tetramethyl-1,3,2-dioxaborolan-2-yl)-3-pyridyl]methanesulfonamide (171 mg, 0.520 mmol) in 1,4-dioxane (2 ml) was added chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (11.2 mg, 0.020 mmol), potassium phosphate tribasic (255 mg, 1.20 mmol) and water (0.2 ml). The reaction mixture was heated and stirred at 120° C. under microwave irradiation for 3 h. The reaction mixture was filtered through a silica SPE and eluted with methanol. The solvent was removed in vacuo and the residue partitioned between dichloromethane (5 ml) and water (5 ml). The layers were separated and the aqueous extracted with further dichloromethane (2×2 ml). The combined organics were concentrated under a stream of nitrogen and the residue dissolved in MeOH:DMSO (2 ml, 1:1, v/v) and purified by MDAP (method H) in 2 injections. The appropriate fractions were combined and concentrated and the residue dissolved in MeOH:DMSO (1 ml, 1:1, v/v) and further purified by MDAP (method 1). The appropriate fractions were basified to pH 7 with saturated sodium bicarbonate solution and extracted with dichloromethane (2×20 ml). The combined organics were dried (hydrophobic frit) and concentrated to give the title compound as a white solid (22 mg).

LCMS (Method A): Rt 0.51 mins, MH+ 526.

Example 65

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]-2,4-difluorobenzenesulfonamide

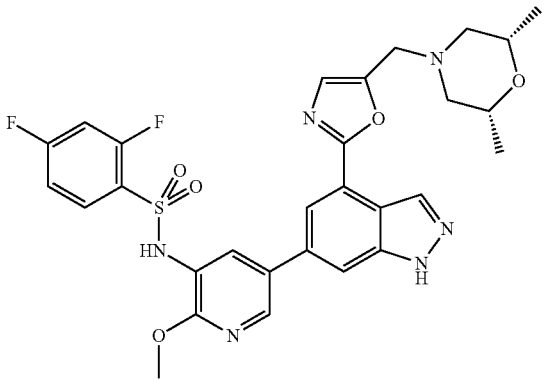 [SMILES: COc1ncc(-c2cc(-c3ncc(CN4C[C@@H](C)O[C@@H](C)C4)o3)c3cn[nH]c3c2)cc1NS(=O)(=O)c1ccc(F)cc1F]

N-[5-[4-(5-{[(2R,6S)-2,6-dimethyl-4-morpholinyl]methyl}-1,3-oxazol-2-yl)-1-(phenylsulfonyl)-1H-indazol-6-yl]-2-(methyloxy)-3-pyridinyl]-2,4-difluorobenzenesulfonamide (105 mg, 0.140 mmol) was suspended in isopropanol (2 ml) and 2M sodium hydroxide (aq) (0.699 ml, 1.399 mmol) added. The reaction mixture was stirred at RT for 2 h, the solvent removed under a stream of nitrogen and the residue dissolved in water (1 ml) and acidified to pH~6 by the addition of 2M hydrogen chloride (aq) (a black precipitate formed). The suspension was extracted with dichloromethane (3×2 ml) and the combined organics dried to give a brown solid. This was combined with the black precipitate which remained insoluble in the extraction, dissolved in MeOH:DMSO (1 ml, 1:1, v/v) and purified by MDAP (method H). The appropriate fractions were concentrated in vacuo to give the title compound as a white solid (20 mg).

LCMS (Method A): Rt 0.69 mins, MH+ 611.

Example 66

2,4-Difluoro-N-[5-[4-(5-{[4-(1-methylethyl)-1-piperazinyl]methyl}-1,3-oxazol-2-yl)-1H-indazol-6-yl]-2-(methyloxy)-3-pyridinyl]benzenesulfonamide

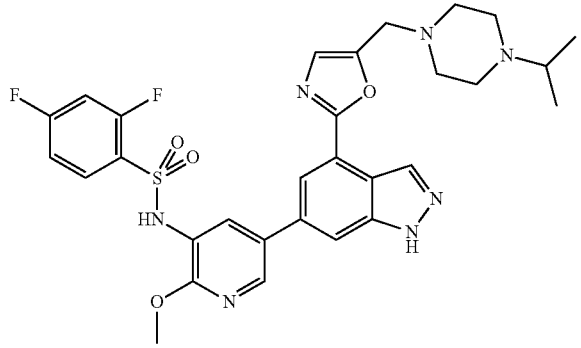 [SMILES: COc1ncc(-c2cc(-c3ncc(CN4CCN(C(C)C)CC4)o3)c3cn[nH]c3c2)cc1NS(=O)(=O)c1ccc(F)cc1F]

2,4-Difluoro-N-[5-[4-(5-{[4-(1-methylethyl)-1-piperazinyl]methyl}-1,3-oxazol-2-yl)-1-(phenylsulfonyl)-1H-indazol-6-yl]-2-(methyloxy)-3-pyridinyl]benzenesulfonamide (81 mg, 0.106 mmol) was suspended in isopropanol (2 ml) and 2M sodium hydroxide (aq) (0.53 ml, 1.060 mmol) was added. The reaction mixture was stirred at RT for 2 h, the solvent removed and the residue dissolved in water (1 ml) and acidified to pH~6 by the addition of 2M hydrogen chloride (aq). The resultant suspension was extracted with dichloromethane (3×2 ml), the organic layer separated (hydrophobic frit) and concentrated in vacuo to give a brown solid which dissolved in MeOH:DMSO (1 ml, 1:1, v/v) and purified by MDAP (method H). The appropriate fractions were concentrated in vacuo to give the title compound as a white solid (45 mg).

LCMS (Method A): Rt 0.65 mins, MH$^+$ 624.

Example 67

4-(5-{[(2R,6S)-2,6-Dimethyl-4-morpholinyl]methyl}-1,3-oxazol-2-yl)-6-(1H-indol-4-yl)-1H-indazole

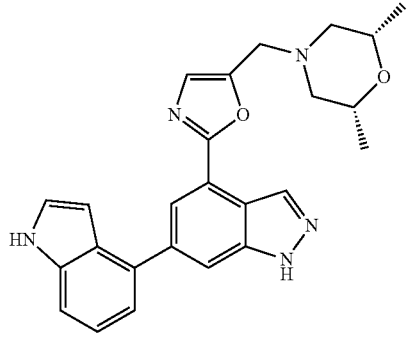 [SMILES: C[C@@H]1CN(Cc2cnc(-c3cc(-c4cccc5[nH]ccc45)cc4[nH]ncc34)o2)C[C@H](C)O1]

To a solution of 6-chloro-4-(5-{[(2R,6S)-2,6-dimethyl-4-morpholinyl]methyl}-1,3-oxazol-2-yl)-1-(phenylsulfonyl)-1H-indazole (50 mg, 0.103 mmol) in 1,4-dioxane (1.5 ml) and water (0.15 ml) was added {1-[1,1-dimethylethyl)(dimethyl)silyl]1-Hindol-4-yl}boronic acid (37 mg, 0.133 mmol), chloro[Z-(dimethylamino)-2-biphenylyl]palladium-(1R,4S)-bicyclo[2.2.1]hept-2-yl[(1S,4R)-bicyclo[2.2.1]hept-2-yl]phosphane (5.75 mg, 10.27 μmol) and potassium phosphate tribasic (65 mg, 0.308 mmol). The reaction mixture was heated under microwave irradiation at 100° C. for 40 min. The solvent was removed and the residue dissolved in 10% methanol in dichloromethane (2 ml) and purified by silica gel chromatography, eluting with a gradient of cyclohexane and ethyl acetate. The appropriate fractions were concentrated to give a brown gum which was treated directly with tetra-n-butylammonium fluoride (0.2 ml, 0.2 mmol, 1M in tetrahydrofuran) and allowed to stand at 20° C. for 18 h. The solvent was removed and the residue dissolved in 1,4-dioxane (1 ml) and treated with 2M sodium hydroxide (1 ml) and allowed to stand at 20° C. for 48 h. The solvent was removed and the residue triturated with 10% methanol in dichloromethane then purified by silica gel chromatography, eluting with a gradient of dichloromethane and methanol to give a pale brown solid which was further purified by SCX SPE (1 g), eluting with 0.5M ammonia in 1,4-dioxane. The solvent was removed and the residue further purified by MDAP to give the title compound as a white solid (14 mg).

LCMS (Method A): Rt 0.70 mins, MH$^+$ 428.

Example 68

6-(1H-Indol-4-yl)-4-(5-{[4-(1-methylethyl)-1-piperazinyl]methyl}-1,3-oxazol-2-yl)-1H-indazole

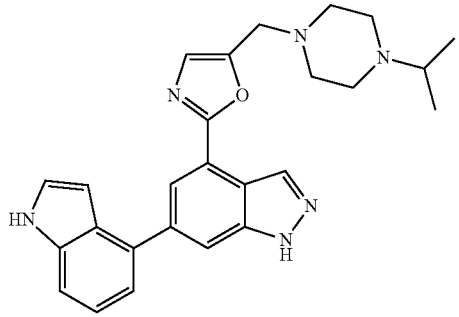 [SMILES: CC(C)N1CCN(Cc2cnc(-c3cc(-c4cccc5[nH]ccc45)cc4[nH]ncc34)o2)CC1]

Method A

6-Chloro-4-(5-{[4-(1-methylethyl)-1-piperazinyl]methyl}-1,3-oxazol-2-yl)-1-(phenylsulfonyl)-1H-indazole (97 mg, 0.194 mmol), 4-(4,4,5,5-tetramethyl-1,3,2-dioxaborolan-2-yl)-1H-indole (61.3 mg, 0.252 mmol, available from Frontier Scientific Europe), chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (10.87 mg, 0.019 mmol) and potassium phosphate tribasic (124 mg, 0.582 mmol) were dissolved in 1,4-dioxane (1 ml) and water (0.1 ml) and heated in a Biotage Initiator microwave at 100° C. for 30 min. Additional 4-(4,4,5,5-tetramethyl-1,3,2-dioxabotolan-2-yl)-1H-indole (61.3 mg, 0.252 mmol) and chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (5 mg) were added and the reaction heated at 110° C. for 30 min, then 140° C. for 30 min. The solvent was removed in vacuo and the residue purified by silica gel chromatography, eluting with 0-25% methanol in dichloromethane. The appropriate fractions were combined and concentrated to give a brown solid which was dissolved in MeOH:DMSO (1 ml, 1:1, v/v) and purified by MDAP (method H). The appropriate fractions were concentrated in vacuo to give the title compound as a white solid (30 mg).

LCMS (Method A): Rt 0.57 mins, MH$^+$ 441.

Method B

6-Chloro-4-(5-{[4-(1-methylethyl)-1-piperazinyl]methyl}-1,3-oxazol-2-yl)-1-(phenylsulfonyl)-1H-indazole (75.17 g, 150 mmol), 4-(4,4,5,5-tetramethyl-1,3,2-dioxaborolan-2-yl)-1H-indole (73.1 g, 301 mmol), sodium bicarbonate (37.9 g, 451 mmol), and chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (8.43 g, 15.03 mmol) were suspended in nitrogen purged 1,4-dioxane (1200 mL) and water (300 mL). The reaction vessel was placed under alternating vacuum and nitrogen five times with overhead stirring, then finally placed under a nitrogen atmosphere and heated to 120° C. for 2.5 h.

The reaction mixture was cooled to 45° C. and then treated with 2M aqueous sodium hydroxide (376 mL, 752 mmol). After stirring at 45° C. overnight (~13 h), the mixture was cooled to RT and DCM (600 ml) and water (400 ml) were added. The layers were separated and the aqueous re-extracted with DCM:1,4-dioxane (1:1). Brine was added and the mixture filtered through Celite, washing with DCM:1,4-dioxane (1:1). The layers were separated and 2M HCl (1000 ml) added to the organic. The mixture was again filtered through Celite washing with 500 ml 2M HCl keeping the washings separate. The filtrate layers were then separated and the organic layer was washed with the acid washings from the Celite. Layers were separated and the acidic aqueous combined. This was then back-washed with 2×500 ml of DCM; each wash requiring a Celite filtration. The acidic aqueous was then given a final filtration through Celite washing the Celite pad with 150 ml of 2M HCl.

The acidic aqueous was transferred to a beaker (5000 ml) and with vigorous stirring 2M NaOH was added to basify the mixture to pH 10-11. The mixture was then extracted using 1,4-dioxane:DCM (1:1) (5×500 ml). The combined organics were washed with brine, dried over magnesium sulphate, filtered and evaporated to yield a brown foam that was dried in vacuo at 50° C. overnight.

This material was split into three batches and each was purified by reverse phase column chromatography (3×1.9 kg C18 column), loading in DMF/TFA (1:1, 30 ml) then eluting with 3-40% MeCN in Water+0.25% TFA (Note: Columns 2 & 3 used a different gradient starting with 10% MeCN).

Appropriate fractions were combined, the acetonitrile removed in vacuo and the acidic aqueous basified to pH10 by addition of saturated aqueous sodium carbonate solution to the stirred solution. The resultant solid was collected by filtration, washed with water then dried in vacuo at 65° C. overnight to give the title compound (28.82 g) as a pale brown foam.

LCMS (Method A): Rt 0.68 mins, MH$^+$ 441.

$^1$H NMR (400 MHz, DMSO-d$_6$) d=13.41 (br. s., 1H), 11.35 (br. s., 1H), 8.59 (br. s., 1H), 8.07 (d, J=1.5 Hz, 1H), 7.90 (br. s., 1H), 7.51-7.44 (m, 2H), 7.32 (s, 1H), 7.27-7.21 (m, 2H), 6.61-6.58 (m, 1H), 3.73 (br. s., 2H), 2.64-2.36 (m, 9H), 0.97-0.90 (m, 6H)

Method C

Potassium hydroxide (145.6 g) was added to a suspension of 6-(1H-indol-4-yl)-4-(5-{[4-(1-methylethyl)-1-piperazinyl]methyl}-1,3-oxazol-2-yl)-1-(phenylsulfonyl)-1H-indazole (300.7 g) and cetyltrimethylammonium bromide (9.3 g) in tetrahydrofuran (6.0 L) and water (30 ml) stirring under nitrogen at ambient temperature. The mixture was heated at reflux for 17 hours and was then cooled to 20-25° C. Ethyl acetate (3.0 L) and water (3.0 L) were added, stirred for 10 minutes and then separated. The organic layer was extracted with hydrochloric acid (1M, 1×3.0 L, 2×1.5 L) and the acidic extracts combined and basified to ~pH 8 by the addition of saturated sodium carbonate solution (2.1 L). After ageing for 30 minutes the resultant suspension was filtered, washed with water (300 ml) and the solid dried under vacuum at 65° C. to give the title compound as a pale yellow solid (127.9

LCMS (Method B): Rt 2.44 min, MH$^+$ 441.

Example 69

6-(1H-Indol-4-yl)-4-[5-(4-morpholinylmethyl)-1,3-oxazol-2-yl]H-indazole trifluoroacetate

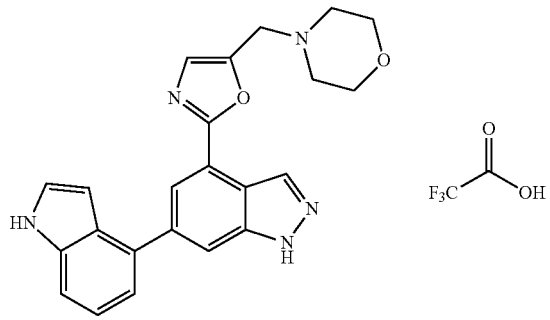 [SMILES: c1cc(-c2cc(-c3ncc(CN4CCOCC4)o3)c3cn[nH]c3c2)c2cc[nH]c2c1 ; O=C(O)C(F)(F)F]

To a solution of {2-[6-{1-[(1,1-dimethylethyl)(dimethyl)silyl]-1H-indol-4-yl}-1-(phenylsulfonyl)-1H-indazol-4-yl]-1,3-oxazol-5-yl}methanol (containing an impurity consistent with 2-[6-chloro-1-(phenylsulfonyl)-1H-indazol-4-yl]-1,3-oxazol-5-yl}methanol) (350 mg) in dichloromethane (10 ml) was added carbon tetrabromide (397 mg, 1.197 mmol). The reaction mixture was cooled to 0° C. and triphenylphosphine (314 mg, 1.197 mmol) as a solution in dichloromethane (2 ml) was added dropwise. The reaction mixture was allowed to warm to RT then the solvent partially removed and the solution purified directly by silica gel chromatography, eluting with a gradient of dichloromethane and ethyl acetate. The desired fractions were concentrated to give a brown solid (37 mg).

To a solution of the solid (30 mg, 0.056 mmol) in dichloromethane (5 ml) was added morpholine (9.8 mg, 0.112 mmol) and the mixture stirred at 20° C. for 18 h. The solvent was removed and the residue dissolved in 1,4-dioxane (2 ml) and 2M sodium hydroxide solution (1 ml, 2.0 mmol) added. The reaction mixture was stirred at 20° C. for 18 h then the solvent removed and the residue triturated with 10% methanol in dichloromethane (1 ml) and purified by silica gel chromatography, eluting with a gradient of dichloromethane and dichloromethane+1% ammonia in methanol. The desired fractions were concentrated and purified by MDAP to give the title compound as a brown solid (3 mg).

LCMS (Method A): Rt 0.65 mins, MH$^+$ 400.

Example 70

N-[5-[4-(5-{[(2R,6R)-2,6-Dimethyl-4-morpholinyl]methyl}-1,3-oxazol-2-yl)-1H-indazol-6-yl]-2-(methyloxy)-3-pyridinyl]methanesulfonamide

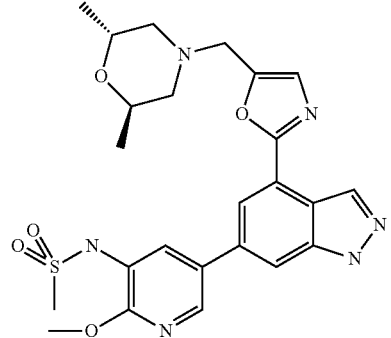 [SMILES: COc1ncc(-c2cc(-c3ncc(CN4C[C@@H](C)O[C@H](C)C4)o3)c3cn[nH]c3c2)cc1NS(C)(=O)=O]

To a solution of 6-chloro-4-(5-{[(2R,6R)-2,6-dimethyl-4-morpholinyl]methyl}-1,3-oxazol-2-yl)-1-(phenylsulfonyl)-1H-indazole (109.5 mg, 0.225 mmol), N-[2-(methyloxy)-5-(4,4,5,5-tetramethyl-1,3,2-dioxaborolan-2-yl)-3-pyridinyl]methanesulfonamide (148 mg, 0.450 mmol) and sodium bicarbonate (56.7 mg, 0.675 mmol) in 1,4-Dioxane (5 mL) and Water (1.5 mL) stirred in air at room temp was added solid Solvias Catalyst (12.60 mg, 0.022 mmol). The reaction mixture was stirred at 120° C. for 2 hr. After this time, sodium hydroxide solution (2N, 0.5 mL) was added and the reaction mixture left to stir at room temperature for two hours. On cooling, the reaction mixture was passed through a celite cartridge (10 g) and washed with ethyl acetate. The resulting solution was evaporated and the crude residue purified by MDAP (Method J). Appropriate fractions were combined and concentrated in vacuo to afford the title compound (43 mg).

LCMS (Method A) Rt 0.63 mins, MH+ 513.

Example 71

6-(1H-Indol-4-yl)-4-[5-(1-piperazinylmethyl)-1,3-oxazol-2-yl]-1H-indazole

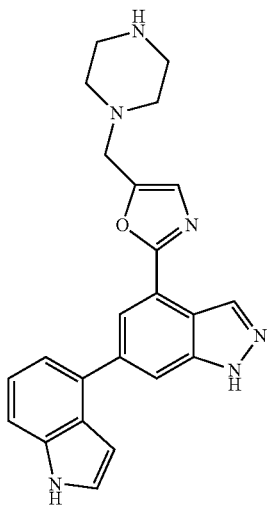 [SMILES: c1cc(-c2cc(-c3ncc(CN4CCNCC4)o3)c3cn[nH]c3c2)c2cc[nH]c2c1]

1,1-Dimethylethyl 4-({2-[6-chloro-1-(phenylsulfonyl)-1H-indazol-4-yl]-1,3-oxazol-5-yl}methyl)-1-piperazinecarboxylate (303 mg, 0.543 mmol), 4-(4,4,5,5-tetramethyl-1,3,2-dioxaborolan-2-yl)-1H-indole (172 mg, 0.706 mmol, available from Frontier Scientific), chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (30 mg, 0.054 mmol, available from Fluka) and tripotassium phosphate (346 mg, 1.629 mmol) were dissolved in 1,4-Dioxane (10 mL) and Water (2.5 mL). The reaction vessel was sealed and heated in Biotage Initiator microwave at 150° C. for 30 min. Aqueous 2M NaOH (5 ml) was then added and the mixture stirred for 2 hours. An additional portion of aqueous 2M NaOH (3 ml) was added and stirring continued until deprotection appeared complete by LCMS analysis. DCM was then added and the mixture was passed through a phase separator. The organic phase was collected. The aqueous phase was back extracted with DCM then the organic phases were combined and evaporated to give a brown oil. This was dissolved in 5 ml of 4M HCl in 1,4 dioxane and left stirring. The mixture was concentrated in vacuo and the resultant solid partitioned between DCM and 2M aqueous HCl. The aqueous phase was basified with 2M aqueous NaOH, then washed with DCM. The organic phase was concentrated in vacuo, then the residue dissolved in 2 ml DMSO/MeOH (1:1) and purified by MDAP (Method H). Combining appropriate fractions and concentrating by blow down under nitrogen at 40° C., afforded the title compound (43 mg).

LCMS (Method A) Rt 0.62 mins, MH+ 399.

Example 72

6-(1H-Indol-4-yl)-4-(5-{[4-(1-methylethyl)-1-piperazinyl]methyl}-1,3-oxazol-2-yl)-1H-indazole hydrochloride

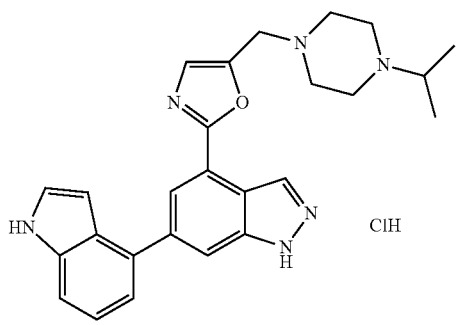 [SMILES: CC(C)N1CCN(Cc2cnc(-c3cc(-c4cccc5[nH]ccc45)cc4[nH]ncc34)o2)CC1 ; Cl]

A solution of 6-(1H-indol-4-yl)-4-(5-{[4-(1-methylethyl)-1-piperazinyl]methyl}-1,3-oxazol-2-yl)-1H-indazole in tetrahydrofuran (THF) (7.5 mL) was heated to 60° C. under nitrogen. 2M hydrochloric acid in diethyl ether (0.567 mL, 1.135 mmol) and tetrahydrofuran (THF) (0.5 mL) were mixed and added via a dropping funnel. The solution was stirred at 60° C. for 30 mins before being slowly cooled to RT. After stirring at RT for a further 30 mins the solid was filtered off, then recombined with the liquors and evaporated to dryness. THF (10 mL) was added and the slurry was cycled from RT to reflux 3 times (30 mins hold at higher/low temp). The slurry was stirred at RT for one hour then filtered under vacuum and the resultant solid dried in a vacuum oven at 50° C. overnight to give the title compound as a an off-white solid (322 mg).

LCMS (Method A): Rt 0.66 mins, MH+ 441. $^1$H NMR (400 MHz, DMSO-$d_6$) d=13.53 (s, 1H), 11.44 (br. s., 1H), 10.20 (br. s., 1H), 8.61 (s, 1H), 8.08 (s, 1H), 7.92 (s, 1H), 7.52-7.46 (m, 2H), 7.41 (s, 1H), 7.28-7.19 (m, 2H), 6.60 (br. s., 1H), 3.87 (s, 2H), 3.41-3.32 (m, 3H+, obscured by H2O), 3.10-2.93 (m, 4H), 2.71-2.58 (m, 2H), 1.23 (d, J=6.5 Hz, 6H).

Example 73

6-(1H-Indol-4-yl)-4-(5-{[4-(1-methylethyl)-1-piperazinyl]methyl}-1,3-oxazol-2-yl)-1H-indazole dihydrochloride

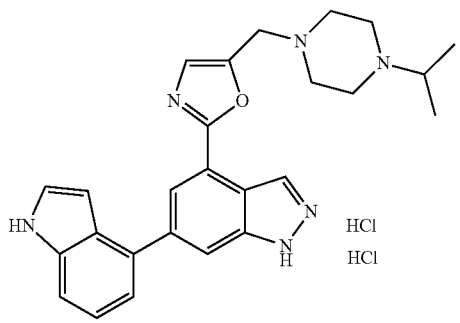 [SMILES: CC(C)N1CCN(Cc2cnc(-c3cc(-c4cccc5[nH]ccc45)cc4[nH]ncc34)o2)CC1 ; Cl ; Cl]

6-(1H-Indol-4-yl)-4-(5-{[4-(1-methylethyl)-1-piperazinyl]methyl}-1,3-oxazol-2-yl)-1H-indazole (19.4 mg, 0.044 mmol) was dissolved in tetrahydrofuran (THF) (0.5 ml) and 4M HCl in dioxane (0.022 ml, 0.088 mmol) added. The mixture was stirred at RT for 2 h, then the cream precipitate formed was filtered off and dried in a vacuum oven overnight to give the title compound as a beige solid (15.5 mg).

LCMS (Method A): Rt 0.65 mins, MH$^+$ 441.

$^1$H NMR (600 MHz, DMSO-d$_6$) d=13.47 (br. s., 1H), 11.38 (br. s., 1H), 10.17 (br. s., 1H), 8.66 (s, 1H), 8.13 (s, 1H), 7.93 (s, 1H), 7.51 (br. s., 1H), 7.49 (dt, J=1.0, 7.5 Hz, 1H), 7.47 (t, J=3.0 Hz, 1H), 7.25 (t, J=7.0 Hz, 1H), 7.23 (dd, J=1.5, 7.0 Hz, 1H), 6.60 (ddd, J=1.0, 2.0, 3.0 Hz, 1H), 4.17 (br. s., 2H), 3.50-3.39 (m, 3H), 3.35-3.25 (m, 2H), 3.22-3.11 (m, 2H), 2.99-2.76 (m, 2H), 1.24 (d, J=6.5 Hz, 6H).

Example 74

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide (R)-mandelate

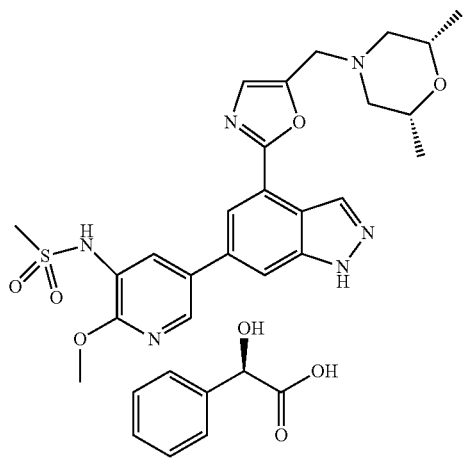

Method A

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (113 mg, 0.220 mmol) was suspended in water (18 ml) and (R)-mandelic acid (0.33M solution in water, 735 μl, 0.242 mmol) was added. The mixture was stirred at RT overnight then concentrated and dried in a vacuum oven at 50° C. overnight to give the title compound as a white solid (133 mg).

LCMS (Method A): Rt 0.60 mins, MH+ 513.

$^1$H NMR (400 MHz, DMSO-d$_6$) d=13.53 (br. s., 1H), 9.43 (s, 1H), 8.58 (s, 1H), 8.43 (d, J=2.5 Hz, 1H), 7.99 (d, J=2.5 Hz, 1H), 7.93 (d, J=1.5 Hz, 1H), 7.89 (s, 1H), 7.36 (s, 1H), 7.43-7.24 (m, 5H), 5.01 (s, 1H), 3.99 (s, 3H), 3.75 (s, 2H), 3.63-3.52 (m, 2H), 3.11 (s, 3H), 2.81 (d, J=10.5 Hz, 2H), 1.78 (t, J=10.5 Hz, 2H), 1.04 (d, J=6.5 Hz, 6H).

Note—mandelate only present at a molar ratio of 0.8.

Method B

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (3.17 mg) was suspended in 5% dextrose/water (3 ml). A 100 mg/ml aqueous solution of (R)-mandelic acid (10 μl) was added and the mixture stirred for 45 min to give the title compound as a clear solution.

Example 75

N-[6-(6-Fluoro-1H-indol-4-yl)-1H-indazol-4-yl]-6-methyl-2-pyridinecarboxamide

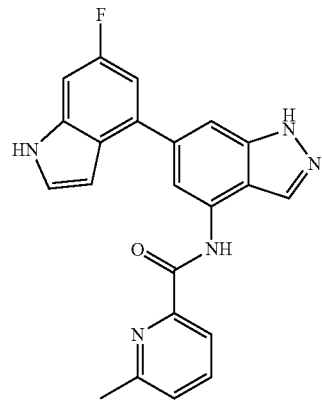 [SMILES: Cc1cccc(C(=O)Nc2cc(-c3cc(F)cc4[nH]ccc34)cc3[nH]ncc23)n1]

HATU (1.825 g) was dissolved in DMF (9.6 ml) and 1.6 ml of the resultant solution was dispensed to 6-methyl-2-pyridinecarboxylic acid (0.8 mmol) in DMF (1.6 ml). To this solution was added DIPEA (0.419 mL) and the mixture was left to stand for 5 min. 6-{6-Fluoro-1-[(4-nitrophenyl)sulfonyl]-1H-indol-4-yl}-1-(phenylsulfonyl)-1H-indazol-4-amine (0.6 mmol) was dissolved in DMF (1.2 ml) and 0.2 ml of the resultant solution was dispensed to an appropriate vial. To this vial was added the 6-methyl-2-pyridinecarboxylic acid: HATU solution, dispensed at 452 μl. The resulting solution was shaken for 5 min and left to stand at RT overnight. After this time, HATU (1.825 g) was dissolved in DMF (9.6 ml) and 1.6 ml of the resultant solution was dispensed to 6-methyl-2-pyridinecarboxylic acid (0.8 mmol) in DMF (1.6 ml). DIPEA (0.419 ml) was added and the mixture was left to stand for 5 min, then added to the reaction mixture, dispensed at 452 μl. The solution was shaken for 5 min and placed in the oven at 40° C. for 1 h. DMF was removed in Genevac (not to dryness) and the compounds were dissolved in chloroform (300 μL). The solution was loaded onto an aminopropyl SPE cartridge (500 mg) that had been preconditioned with methanol followed by chloroform (2 ml each). The column was eluted with 10% methanol in ethyl acetate (5 ml) and the fractions obtained were blown down under a stream of nitrogen. The samples were dissolved in DMSO (0.5 ml) and purified by MDAP (method D). The solvent was evaporated in vacuo using the Genevac to afford the required intermediate. This intermediate was dissolved in IPA (300 μl) and 2M sodium hydroxide (aq) (300 μl) was added. The solution was left for 32 h at RT. After this time the solution was neutralised with 2 M HCl (aq) and blown down under a stream of nitrogen. The sample was dissolved in DMSO (0.5 ml) and purified by MDAP (method L). The solvent was evaporated in vacuo using the Genevac. The residue was dissolved in 10% methanol in chloroform and added to the top of a 500 mg aminopropyl cartridge that had been pre-conditioned with methanol (1 column volume) followed by chloroform (1 column volume). The columns were eluted with 10% methanol in chloroform (1 column volume) and the fractions obtained were blown down under a stream of nitrogen to afford the title compound, 5 mg.

LCMS (method E) R$_t$=1.06 min, MH$^+$=386.

Similarly prepared from the appropriate amine and carboxylic acid were the following;

| Example No | Structure | Name | R_t | MH+ | Carboxylic Acid |
|---|---|---|---|---|---|
| 76 | 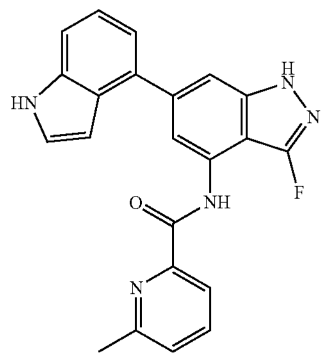 [SMILES: Cc1cccc(C(=O)Nc2cc(-c3cccc4[nH]ccc34)cc3[nH]nc(F)c23)n1] | N-[3-fluoro-6-(1H-indol-4-yl)-1H-indazol-4-yl]-6-methyl-2-pyridinecarboxamide | 1.16 | 386 | 6-methyl-2-pyridinecarboxylic acid |
| 77 | 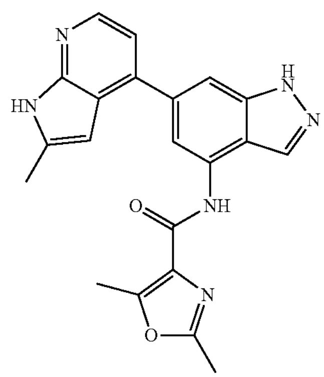 [SMILES: Cc1cc2c(-c3cc(NC(=O)c4nc(C)oc4C)c4cn[nH]c4c3)ccnc2[nH]1] | 2,5-dimethyl-N-[6-(2-methyl-1H-pyrrolo[2,3-b]pyridin-4-yl)-1H-indazol-4-yl]-1,3-oxazole-4-carboxamide | 0.71 | 387 | 2,5-dimethyl-1,3-oxazole-4-carboxylic acid |
| 78 | 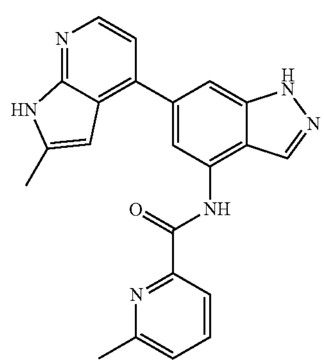 [SMILES: Cc1cccc(C(=O)Nc2cc(-c3ccnc4[nH]c(C)cc34)cc3[nH]ncc23)n1] | 6-methyl-N-[6-(2-methyl-1H-pyrrolo[2,3-b]pyridin-4-yl)-1H-indazol-4-yl]-2-pyridinecarboxamide | 0.77 | 383 | 6-methyl-2-pyridinecarboxylic acid |
| 79 | 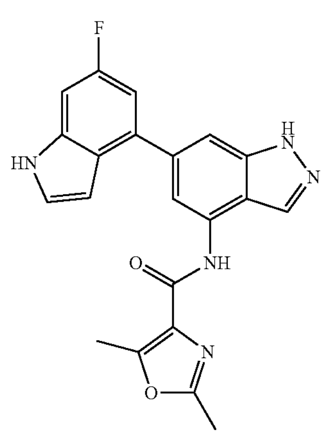 [SMILES: Cc1nc(C(=O)Nc2cc(-c3cc(F)cc4[nH]ccc34)cc3[nH]ncc23)c(C)o1] | N-[6-(6-fluoro-1H-indol-4-yl)-1H-indazol-4-yl]-2,5-dimethyl-1,3-oxazole-4-carboxamide | 0.99 | 390 | 2,5-dimethyl-1,3-oxazole-4-carboxylic acid |

-continued

| Example No | Structure | Name | R$_t$ | MH$^+$ | Carboxylic Acid |
|---|---|---|---|---|---|
| 80 | 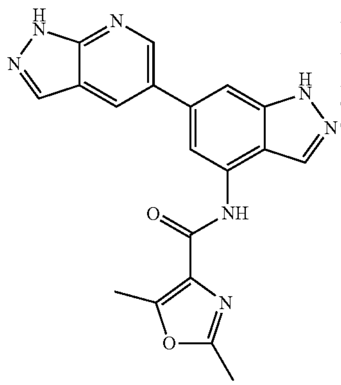 | 2,5-dimethyl-N-[6-(1H-pyrazolo[3,4-b]pyridin-5-yl)-1H-indazol-4-yl]-1,3-oxazole-4-carboxamide | 0.77 | 374 | 2,5-dimethyl-1,3-oxazole-4-carboxylic acid |
| 81 | 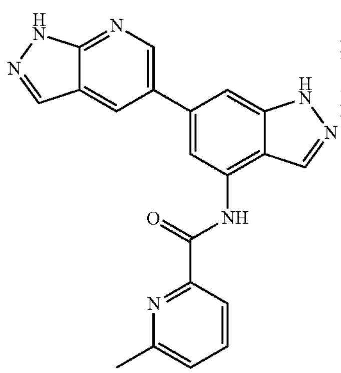 [SMILES: Cc1cccc(C(=O)Nc2cc(-c3cnc4[nH]ncc4c3)cc3[nH]ncc23)n1] | 6-methyl-N-[6-(1H-pyrazolo[3,4-b]pyridin-5-yl)-1H-indazol-4-yl]-2-pyridinecarboxamide | 0.84 | 370 | 6-methyl-2-pyridinecarboxylic acid |
| 82 | 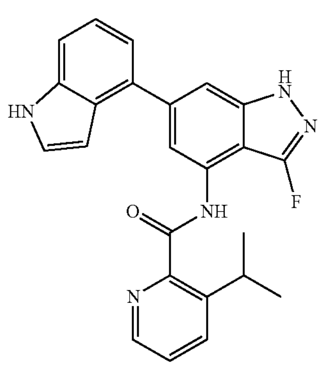 [SMILES: CC(C)c1cccnc1C(=O)Nc1cc(-c2cccc3[nH]ccc23)cc2[nH]nc(F)c12] | N-[3-fluoro-6-(1H-indol-4-yl)-1H-indazol-4-yl]-3-(1-methylethyl)-2-pyridinecarboxamide | 1.27 | 414 | 3-(1-methylethyl)-2-pyridinecarboxylic acid |

| Example No | Structure | Name | $R_t$ | MH⁺ | Carboxylic Acid |
|---|---|---|---|---|---|
| 83 | 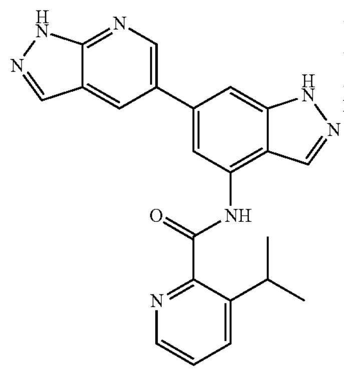 [SMILES: CC(C)c1cccnc1C(=O)Nc1cc(-c2cnc3[nH]ncc3c2)cc2[nH]ncc12] | 3-(1-methylethyl)-N-[6-(1H-pyrazolo[3,4-b]pyridin-5-yl)-1H-indazol-4-yl]-2-pyridinecarboxamide | 0.9 | 398 | 3-(1-methylethyl)-2-pyridinecarboxylic acid |
| 84 | 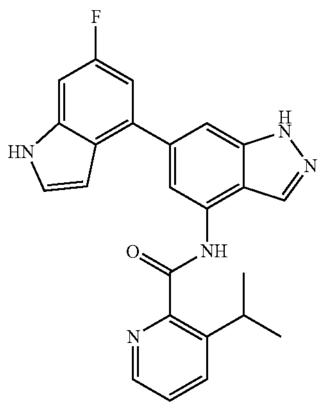 [SMILES: CC(C)c1cccnc1C(=O)Nc1cc(-c2cc(F)cc3[nH]ccc23)cc2[nH]ncc12] | N-[6-(6-fluoro-1H-indol-4-yl)-1H-indazol-4-yl]-3-(1-methylethyl)-2-pyridinecarboxamide | 1.12 | 414 | 3-(1-methylethyl)-2-pyridinecarboxylic acid |

Example 85

N-[3-Fluoro-6-(1H-pyrazolo[3,4-b]pyridin-5-yl)-1H-indazol-4-yl]-2,5-dimethyl-1,3-oxazole-4-carboxamide

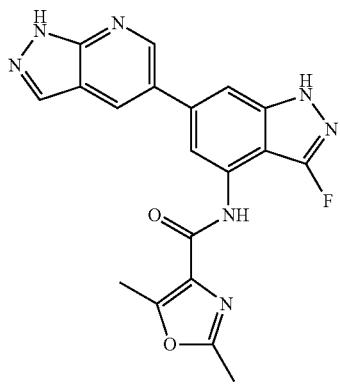 [SMILES: Cc1nc(C(=O)Nc2cc(-c3cnc4[nH]ncc4c3)cc3[nH]nc(F)c23)c(C)o1]

2,5-Dimethyl-1,3-oxazole-4-carboxylic acid was dissolved in THF (0.2 ml) and 1-chloro-N,N,2-trimethyl-1-propen-1-amine (15 µl) was added. The mixture was shaken and left to stand for 30 min. 3-Fluoro-6-{1-[(4-methylphenyl)sulfonyl]-1H-pyrazolo[3,4-b]pyridin-5-yl}-1-(phenylsulfonyl)-1H-indazol-4-amine (0.338 g) was suspended in THF (2.4 ml) and 0.4 ml of this suspension was added to the acid mixture, followed by pyridine (16 µl). The reaction mixture was shaken and left to stand for 2 h. 2,5-Dimethyl-1,3-oxazole-4-carboxylic acid was dissolved in THF (0.2 ml) and 1-chloro-N,N,2-trimethyl-1-propen-1-amine (15 µl) was added. This mixture was shaken and left to stand for 30 min, then added to the reaction mixture followed by pyridine (16 µl). The reaction was left to stand overnight. 2,5-Dimethyl-1,3-oxazole-4-carboxylic acid was dissolved in THF (0.2 ml) and 1-chloro-N,N,2-trimethyl-1-propen-1-amine (15 µl) was added. This mixture was shaken and left to stand for 30 min then added to the reaction, followed by pyridine (16 µl). The reaction was were stirred for more than 3 h. 2,5-Dimethyl-1,3-oxazole-4-carboxylic acid was dissolved in chloroform (0.2 ml) and 1-chloro-N,N,2-trimethyl-1-propen-1-amine (15 µl) was added. This mixture was shaken and left to stand for 30 min then added to the reaction, followed by pyridine (16 µl). The mixture was stirred for 30 min before blowing down under a stream of nitrogen. The sample was dissolved in DMSO (0.5 ml) and purified by MDAP (method L). The solvent was evaporated in vacuo using the Genevac to give the required intermediate. This was dissolved in IPA (300 µl) and 2M NaOH (aq) (300 µl) was added. The reaction was left over the weekend at RT. The solution was neutralised with 2M HCl (aq) and blown down under a stream of nitrogen. The sample was dissolved in DMSO (0.5 ml) and purified by MDAP (method L). The solvent was evaporated in vacuo using the Genevac to give the title compound, 2 mg.

LCMS (method B) $R_t$=2.4 min, MH⁺=392.

Similarly prepared from the appropriate amine and carboxylic acid were the following;

| Example No | Structure | Name | R$_t$ | MH$^+$ | Carboxylic Acid |
|---|---|---|---|---|---|
| 86 | 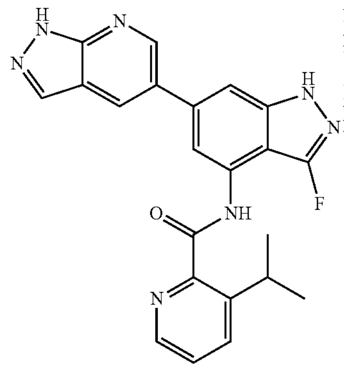 | N-[3-fluoro-6-(1H-pyrazolo[3,4-b]pyridin-5-yl)-1H-indazol-4-yl]-3-(1-methylethyl)-2-pyridinecarboxamide | 1.1 | 416 | 3-(1-methylethyl)-2-pyridinecarboxylic acid |
| 87 | 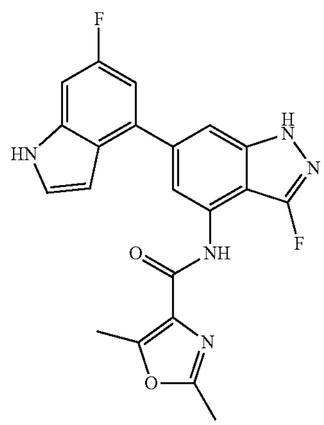 [SMILES: Cc1nc(C(=O)Nc2cc(-c3cc(F)cc4[nH]ccc34)cc3[nH]nc(F)c23)c(C)o1] | N-[3-fluoro-6-(6-fluoro-1H-indol-4-yl)-1H-indazol-4-yl]-2,5-dimethyl-1,3-oxazole-4-carboxamide | 1.17* | 408 | 2,5-dimethyl-1,3-oxazole-4-carboxylic acid |
| 88 | 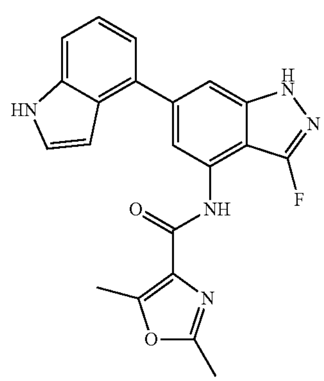 [SMILES: Cc1nc(C(=O)Nc2cc(-c3cccc4[nH]ccc34)cc3[nH]nc(F)c23)c(C)o1] | N-[3-fluoro-6-(1H-indol-4-yl)-1H-indazol-4-yl]-2,5-dimethyl-1,3-oxazole-4-carboxamide | 1.12* | 390 | 2,5-dimethyl-1,3-oxazole-4-carboxylic acid |
| 89 | 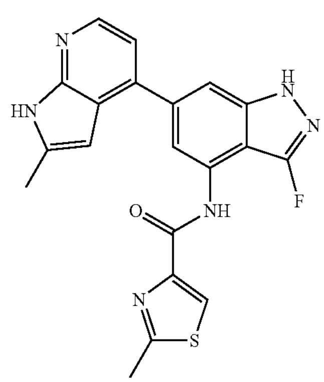 [SMILES: Cc1cc2c(-c3cc(NC(=O)c4csc(C)n4)c4c(F)n[nH]c4c3)ccnc2[nH]1] | N-[3-fluoro-6-(2-methyl-1H-pyrrolo[2,3-b]pyridin-4-yl)-1H-indazol-4-yl]-2-methyl-1,3-thiazole-4-carboxamide | 0.88 | 407 | 2-methyl-1,3-thiazole-4-carboxylic acid |

*LCMS method E

Example 90

N-[6-(6-Cyano-1H-indol-4-yl)-1H-indazol-4-yl]-1,4-dimethyl-1H-pyrazole-3-carboxamide

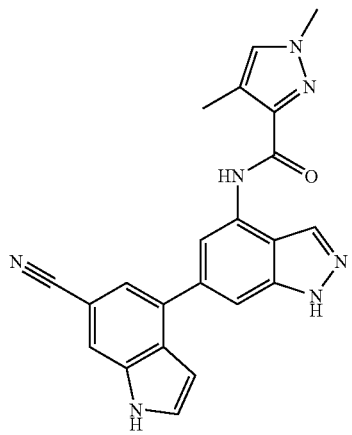 [SMILES: Cc1cn(C)nc1C(=O)Nc1cc(-c2cc(C#N)cc3[nH]ccc23)cc2[nH]ncc12]

4-Bromo-1-[(4-nitrophenyl)sulfonyl]-1H-indole-6-carbonitrile (70 mg), 1,4-dimethyl-N-[1-(phenylsulfonyl)-6-(trimethylstannanyl)-1H-indazol-4-yl]-1H-pyrazole-3-carboxamide (51 mg) and Pd(PPh$_3$)$_4$ (22 mg) were weighed to a microwave vial and DMF (1 ml) was added. The reaction was heated at 120° C. for 1 h, then cooled and passed through a silica (1 g) cartridge, which had been pre-washed with methanol and washed through with methanol:DCM. The solvent was dried under nitrogen blowdown. The residue was purified using MDAP (method K but using an isocratic 50:50 solvent mix over 10 min). Purified fraction was dissolved in methanol (1 ml) and 2M NaOH (aq) (2 ml) was added and the reaction left at RT over the weekend. The reaction was neutralised using 2M HCl (aq) and dried under nitrogen blowdown. The residue was taken into water and extracted into ethyl acetate. The ethyl acetate was passed through a hydrophobic frit, then through an SAX cartridge pre-conditioned with ethyl acetate. The solvent was evaporated by nitrogen blow down to give title compound, 12 mg.

LCMS (method E) R$_t$=0.92 min, MH$^+$=396.

Example 91

2-Methyl-N-[6-(2-oxo-2,3-dihydro-1H-indol-4-yl)-1H-indazol-4-yl]-1,3-thiazole-4-carboxamide

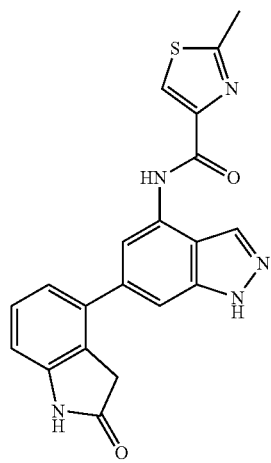 [SMILES: Cc1nc(C(=O)Nc2cc(-c3cccc4c3CC(=O)N4)cc3[nH]ncc23)cs1]

4-Bromo-2-chloro-1H-indole (24 mg), 2-methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg), Pd(dppf)Cl$_2$ (8 mg) and sodium carbonate (44 mg) were added to a microwave vial. 1,4-Dioxane (0.5 ml) and water (0.5 ml) were added and the reaction was heated in the microwave at 140° C. for 20 min. The reaction was passed through a 1 g silica cartridge washing with DCM:methanol. The solvent was evaporated in the blow down. The residue was dissolved in DMSO:methanol (1.6 ml, 1:1, v/v), passed through a C18 cartridge (1 g) washing with acetonitrile and evaporated in the blow down. The residue was dissolved in DMSO:methanol (1.6 ml, 1:1, v/v) and purified by MDAP (method M). The pure fraction was evaporated to dryness to give title compound, 8 mg.

LCMS (method E) R$_t$=0.85 min, MH$^+$=390.

Example 92

N-[6-(5-Fluoro-1H-pyrrolo[2,3-b]pyridin-4-yl)-1H-indazol-4-yl]-2-methyl-1,3-thiazole-4-carboxamide

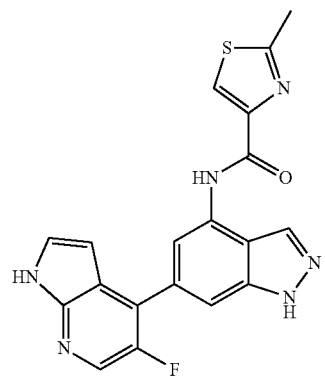 [SMILES: Cc1nc(C(=O)Nc2cc(-c3c(F)cnc4[nH]ccc34)cc3[nH]ncc23)cs1]

2-Methyl-N-[1-(phenylsulfonyl)-6-(trimethylstannanyl)-1H-indazol-4-yl]-1,3-thiazole-4-carboxamide (1 g) was dissolved in DMF (4 ml) and 400 µl of the resultant solution was dispensed to 5-fluoro-4-iodo-1-[(4-nitrophenyl)sulfonyl]-1H-pyrrolo[2,3-b]pyridine (0.18 mmol) in DMF (400 µl) in a microwave vessel. Solvias catalyst (4 mg) was added and the reaction was heated in the microwave using initial 700 W to 135° C. for 20 min. The solution was loaded onto C18 SPE (pre-conditioned with 0.1% TFA in MeCN) and flushed through with 0.1% TFA in MeCN (3 ml). The solvent was removed under nitrogen blowdown. The sample was dissolved in DMSO (0.5 ml) and purified by MDAP (method D). The solvent was evaporated in vacuo using the Genevac. The sample was dissolved in IPA (300 µl) and 2M NaOH (aq) (300 µl) was added. The reaction was left overnight. The sample was dissolved in DMSO (0.6 ml) and purified by MDAP (method M). The solvent was evaporated in vacuo using the Genevac to give title compound, 2 mg.

LCMS (method E) R$_t$=0.84 min, MH$^+$=393.

Similarly prepared from the appropriate bromide were the following;

| Example No | Structure | Name | R$_f$ | MH$^+$ | Bromide Name |
|---|---|---|---|---|---|
| 93 | 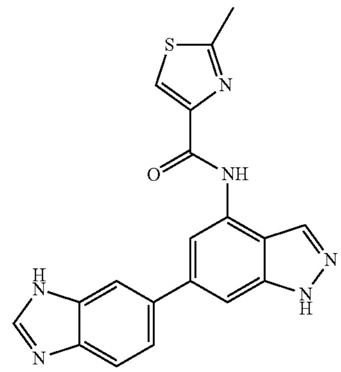 [SMILES: Cc1nc(C(=O)Nc2cc(-c3ccc4nc[nH]c4c3)cc3[nH]ncc23)cs1] | N-[6-(1H-benzimidazol-5-yl)-1H-indazol-4-yl]-2-methyl-1,3-thiazole-4-carboxamide | 0.6 | 375 | 6-bromo-1-[(4-nitrophenyl)sulfonyl]-1H-benzimidazole |
| 94 | 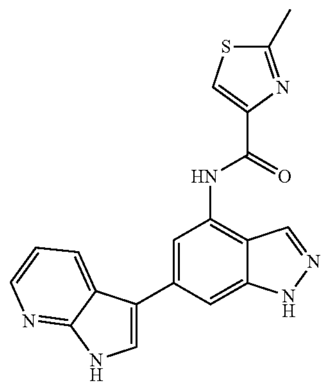 [SMILES: Cc1nc(C(=O)Nc2cc(-c3c[nH]c4ncccc34)cc3[nH]ncc23)cs1] | 2-methyl-N-[6-(1H-pyrrolo[2,3-b]pyridin-3-yl)-1H-indazol-4-yl]-1,3-thiazole-4-carboxamide | 0.73 | 375 | 3-iodo-1-[(4-nitrophenyl)sulfonyl]-1H-pyrrolo[2,3-b]pyridine |
| 95 | 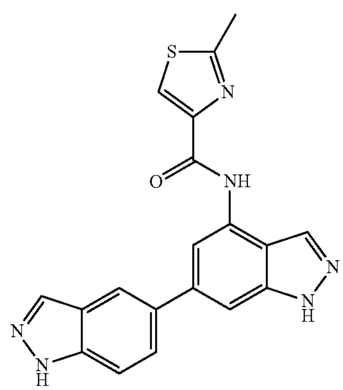 [SMILES: Cc1nc(C(=O)Nc2cc(-c3ccc4[nH]ncc4c3)cc3[nH]ncc23)cs1] | N-1H,1'H-5,6'-biindazol-4'-yl-2-methyl-1,3-thiazole-4-carboxamide | 0.82 | 375 | 5-bromo-1-[(4-nitrophenyl)sulfonyl]-1H-indazole |
| 96 | 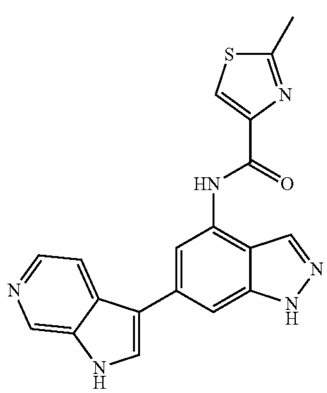 [SMILES: Cc1nc(C(=O)Nc2cc(-c3c[nH]c4cnccc34)cc3[nH]ncc23)cs1] | 2-methyl-N-[6-(1H-pyrrolo[2,3-c]pyridin-3-yl)-1H-indazol-4-yl]-1,3-thiazole-4-carboxamide | 0.59 | 375 | 3-bromo-1-[(4-nitrophenyl)sulfonyl]-1H-pyrrolo[2,3-c]pyridine |

| Example No | Structure | Name | $R_t$ | MH+ | Bromide Name |
|---|---|---|---|---|---|
| 97 | 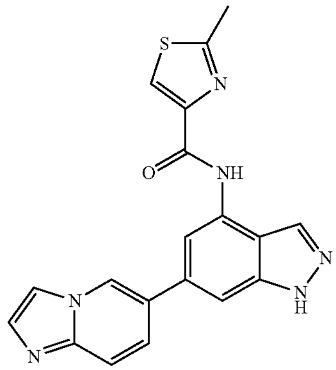 [SMILES: Cc1nc(C(=O)Nc2cc(-c3ccc4nccn4c3)cc3[nH]ncc23)cs1] | N-(6-imidazo[1,2-a]pyridin-6-yl-1H-indazol-4-yl)-2-methyl-1,3-thiazole-4-carboxamide | 0.57 | 375 | 6-bromoimidazo[1,2-a]pyridine |

Example 98
2-Methyl-N-[1-methyl-6-(1H-pyrrolo[2,3-b]pyridin-4-yl)-1H-indazol-4-yl]-1,3-thiazole-4-carboxamide

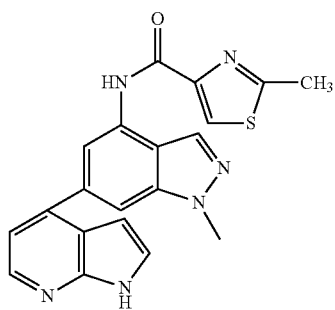 [SMILES: Cc1nc(C(=O)Nc2cc(-c3ccnc4[nH]ccc34)cc3c2cnn3C)cs1]

2-Methyl-N-(1-methyl-6-{1-[(4-methylphenyl)sulfonyl]-1H-pyrrolo[2,3-b]pyridin-4-yl}-1H-indazol-4-yl)-1,3-thiazole-4-carboxamide (44 mg) and potassium trimethyl silanolate (14 mg) were added to THF (2 ml). The reaction mixture was heated at 50° C. overnight. The reaction mixture was partitioned between water (20 ml) and DCM (20 ml). The solvent was removed. The residue was purified by FlashMaster silica cartridge (10 g) using a gradient of 0-100% ethylacetate in cyclohexane followed by 0-20% methanol in ethyl acetate over 30 min. The solvent was removed to give title compound, 31 mg.
LCMS (method E) $R_t$=0.84 min, MH+=389.

Example 99
N-(6-Furo[3,2-b]pyridin-6-yl-1H-indazol-4-yl)-2-methyl-1,3-thiazole-4-carboxamide

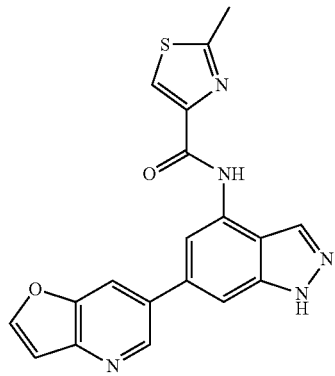 [SMILES: Cc1nc(C(=O)Nc2cc(-c3cnc4ccoc4c3)cc3[nH]ncc23)cs1]

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg), 6-bromofuro[3,2-b]pyridine (21 mg) and Pd(dppf)Cl$_2$ (8 mg) were combined in a microwave vial. 1,4-Dioxane (0.5 ml) was added followed by sodium carbonate (44 mg) dissolved in water (0.5 ml). The reaction was heated in the microwave at 140° C. for 20 min. The reaction was filtered through a silica cartridge (1 g) washing with DCM:methanol (3:1). The solvent was then removed under a stream of nitrogen. The residue was dissolved in DMSO (1200 µl) and methanol (400 µl) and MDAP (method M). The product-containing fractions were left overnight, then concentrated and the residue dissolved in 1,4-dioxane:water (2 ml, 1:1, v/v) and freeze-dried. The residue was dissolved in DCM, a few drops of TFA were added and the reaction left overnight. The residue was further purified by MDAP (method K) then dried under nitrogen blowdown to give title compound, 13 mg.
LCMS (method E) $R_t$=0.87 min, MH+=376.

Example 100
N-[6-(1H-Indol-4-yl)-1H-indazol-4-yl]-1-(1-methylethyl)-1H-pyrazole-5-carboxamide

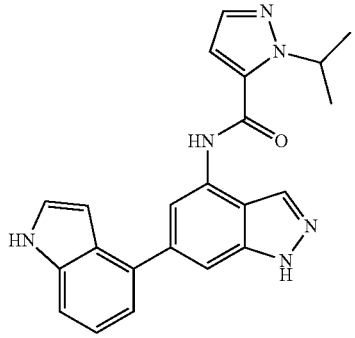 [SMILES: CC(C)n1nccc1C(=O)Nc1cc(-c2cccc3[nH]ccc23)cc2[nH]ncc12]

To a solution of HATU (0.253 g) in DMF (3 ml) was added 1-(1-methylethyl)-1H-pyrazole-5-carboxylic acid (0.102 g) and DIPEA (0.211 ml) and the mixture was left to stand for 10 min. 6-(1H-Indol-4-yl)-1H-indazol-4-amine (0.075 g) dissolved in DMF (3 ml) was added and the solution was left to stand at RT for 18 h. DMF was removed by blow down (not to dryness) and the residue was dissolved in chloroform (1 ml)

and loaded onto an aminopropyl SPE (2 g) (pre-conditioned with methanol (6 ml) and chloroform (6 ml)). The mixture was left on the column for 2 h then eluted with ethyl acetate: methanol (1:1, 10 ml). The solvent was blown down to dryness and the residue was dissolved in DMSO:methanol (1 ml, 1:1) and purified by MDAP (method K). The solvent was removed in vacuo and dried in an vacuum oven (50° C.) overnight to give title compound, 18 mg.

LCMS (method B) $R_t$=3.23 min, MH$^+$=385.

Example 101

N-[6-(1H-Pyrrolo[2,3-b]pyridin-4-yl)-1H-indazol-4-yl]-2-furancarboxamide

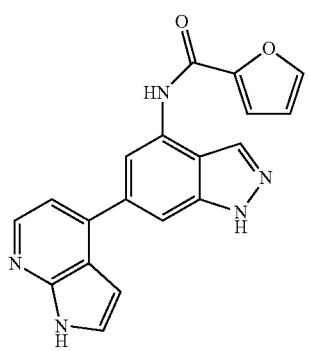 [SMILES: O=C(Nc1cc(-c2ccnc3[nH]ccc23)cc2[nH]ncc12)c1ccco1]

A solution of N-{1-(phenylsulfonyl)-6-[1-(phenylsulfonyl)-1H-pyrrolo[2,3-b]pyridin-4-yl]-1H-indazol-4-yl}-2-furancarboxamide (80 mg) and 2M sodium hydroxide (2 ml) in IPA (4 ml) was stirred for 18 h at RT. The solution was heated at 70° C. for 1.5 h. The solution was cooled, neutralized with 2M HCl (aq) (2 ml) and purged with nitrogen to remove the IPA. The resulting solid was collected by filtration and dried in vacuo at 50° C. to give title compound, 30 mg.

LCMS (method B) $R_t$=1.51 min, MH$^+$=344.

Example 102

1,1-Dimethylethyl 4-({[6-(1H-indol-4-yl)-1H-indazol-4-yl]amino}carbonyl)-3-methyl-1H-pyrazole-1-carboxylate

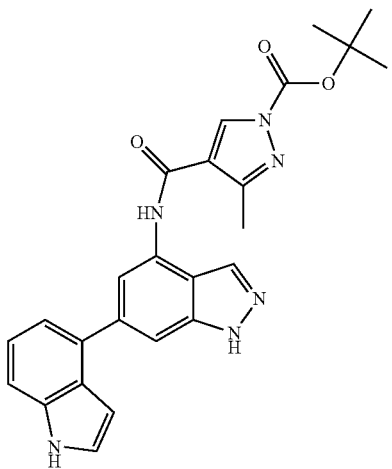 [SMILES: Cc1nn(C(=O)OC(C)(C)C)cc1C(=O)Nc1cc(-c2cccc3[nH]ccc23)cc2[nH]ncc12]

To a solution of HATU (0.162 g) in anhydrous DMF (4 ml) was added 1-{[(1,1-dimethylethyl)oxy]carbonyl}-3-methyl-1H-pyrazole-4-carboxylic acid (0.097 g) and DIPEA (0.149 ml) and the mixture was left to stand for 10 min. 6-(1H-Indol-4-yl)-1H-indazol-4-amine (0.053 gl) dissolved in anhydrous DMF (3 ml) was added and the solution was left to stand at RT for 18 h. The DMF was blown down to dryness under a stream of nitrogen and the residue was dissolved in DMSO:methanol (1 ml, 1:1) and purified by MDAP (method K). The solvent was removed in vacuo to give title compound, 6 mg.

LCMS (method B) $R_t$=3.34 min, MH$^+$=457.

Example 103

2-(1-Piperidinylmethyl)-N-[6-(1H-pyrrolo[2,3-b]pyridin-4-yl)-1H-indazol-4-yl]-1,3-thiazole-4-carboxamide

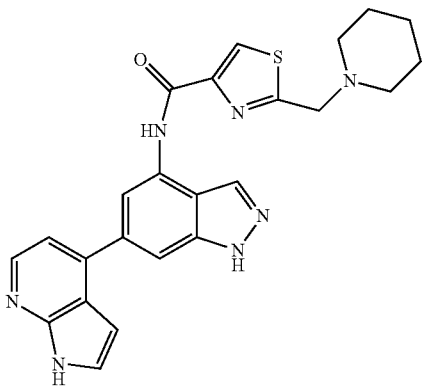 [SMILES: O=C(Nc1cc(-c2ccnc3[nH]ccc23)cc2[nH]ncc12)c1csc(CN2CCCCC2)n1]

2-(Chloromethyl)-N-{1-(phenylsulfonyl)-6-[1-(phenylsulfonyl)-1H-pyrrolo[2,3-b]pyridin-4-yl]-1H-indazol-4-yl}-1,3-thiazole-4-carboxamide (40 mg) and piperidine (0.5 ml) were added to a microwave vial then heated in the microwave for 15 min at 90° C. The solvent was blown off under nitrogen. IPA (3 ml) and 2M NaOH (aq) (2 ml) were added and the reaction mixture was stirred for 29 h. The reaction was heated to 50° C. for 5 min then cooled to RT for stirring overnight. The mixture was neutralised to pH 7 with 2M HCl (aq.) and the solvent was removed under a stream of nitrogen. The resultant solid was dissolved in DMSO (2 ml), filtered and purified by MDAP (method K). The fractions were combined and solvent was removed under nitrogen. The residue was dissolved in water:1,4-dioxane (1:1) then freeze-dried to give title compound, as an orange solid, 15 mg.

LCMS (method E) $R_t$=0.55 min, MH$^+$=458.

Similarly prepared from the appropriate chloride and amine was the following;

| Example No | Structure | Name | $R_f$ | MH⁺ | Chloride Intermediate No. | Amine Name |
|---|---|---|---|---|---|---|
| 104 | 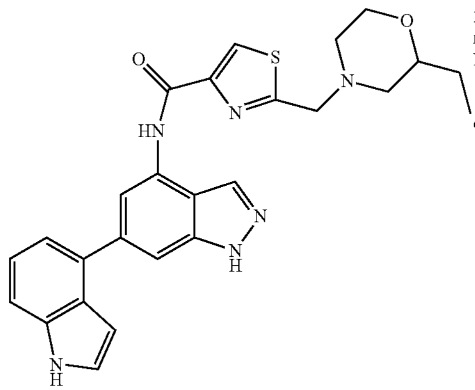 [SMILES: CCC1CN(Cc2nc(C(=O)Nc3cc(-c4cccc5[nH]ccc45)cc4[nH]ncc34)cs2)CCO1] | 2-[(2-ethyl-4-morpholinyl)methyl]-N-[6-(1H-indol-4-yl)-1H-indazol-4-yl]-1,3-thiazole-4-carboxamide | 0.71 | 487 | 18 | 2-ethylmorpholine |

Example 105

6-[(1,1-Dioxido-4-thiomorpholinyl)methyl]-N-[6-(1H-indol-4-yl)-1H-indazol-4-yl]-2-pyridinecarboxamide

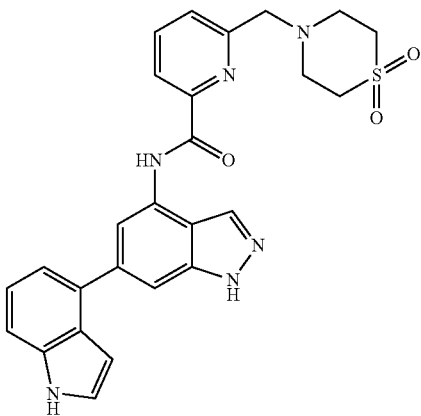 [SMILES: O=C(Nc1cc(-c2cccc3[nH]ccc23)cc2[nH]ncc12)c1cccc(CN2CCS(=O)(=O)CC2)n1]

6-(Chloromethyl)-N-[6-(1H-indol-4-yl)-1-(phenylsulfonyl)-1H-indazol-4-yl]-2-pyridinecarboxamide (75 mg), thiomorpholine 1,1-dioxide (25 mg) and sodium iodide (25 mg) were added to a small round-bottomed flask followed by MeCN (2 ml) and DIPEA (0.048 ml). The reaction mixture was heated at 70° C. for 18 h. The reaction was cooled to RT and the solvent was removed under a stream of nitrogen. The residue was suspended in IPA (2 ml) and 2M NaOH (aq) (1 ml) was added. The mixture was stirred at RT for 2 h, heated to 50° C. for 1 h, then cooled to RT to remain stirring overnight. The reaction was heated to 60° C. for 1 h. Then 2M NaOH (aq) (0.5 ml) was added and reaction was stirred at 60° C. for 2 h. The reaction was neutralised with 2M HCl (aq.) and the solvent was removed in vacuo. The residue was dissolved in DMSO (3 ml), filtered and purified by MDAP (method K). The product-containing fractions were evaporated under a stream of nitrogen and the residues were taken up in methanol, combined and blown down to give title compound, 24 mg.

LCMS (method E) $R_t$=0.85 min, MH⁺=501.

Polymorph and Salt Experimental

Example 72

X-Ray Powder Diffraction (XRPD)

The data were acquired on a PANalytical X'Pert Pro powder diffractometer, model PW3040/60, serial number DY1850 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a Si wafer (zero background) plates, resulting in a thin layer of powder.

The X-ray powder diffraction (XRPD) data are shown in FIG. 1.

Characteristic peaks for the solid state form are summarised in Table 1 with calculated lattice spacings. Peak positions were measured using Highscore software.

TABLE 1

| 2θ/° | d-spacing/Å |
|---|---|
| 5.2 | 17.0 |
| 10.3 | 8.6 |
| 12.8 | 6.9 |
| 14.8 | 6.0 |
| 15.1 | 5.9 |
| 15.6 | 5.7 |
| 16.8 | 5.3 |
| 17.2 | 5.2 |
| 18.3 | 4.9 |
| 19.6 | 4.5 |
| 20.9 | 4.2 |
| 21.3 | 4.2 |
| 21.7 | 4.1 |
| 23.2 | 3.8 |
| 24.0 | 3.7 |
| 24.9 | 3.6 |
| 26.0 | 3.4 |
| 27.1 | 3.3 |
| 27.5 | 3.2 |
| 28.2 | 3.2 |
| 28.5 | 3.1 |

Example 63

X-Ray Powder Diffraction (XRPD)

The data were acquired using a similar method to that described above.

The X-ray powder diffraction (XRPD) data for Form (I) are shown in FIG. 2.

Characteristic peaks for the solid state form are summarised in Table 2 with calculated lattice spacings. Peak positions were measured using Highscore software.

TABLE 2

| 2θ/° | d-spacing/Å |
|---|---|
| 4.5 | 19.8 |
| 6.3 | 13.9 |
| 7.8 | 11.3 |
| 8.8 | 10.1 |
| 9.9 | 8.9 |
| 10.4 | 8.5 |
| 10.7 | 8.3 |
| 11.3 | 7.8 |
| 11.7 | 7.5 |
| 12.2 | 7.3 |
| 12.9 | 6.9 |
| 14.0 | 6.3 |
| 14.5 | 6.1 |
| 15.2 | 5.8 |
| 15.4 | 5.7 |
| 16.1 | 5.5 |
| 16.5 | 5.4 |
| 16.8 | 5.3 |
| 17.7 | 5.0 |
| 17.9 | 5.0 |
| 18.5 | 4.8 |
| 19.0 | 4.7 |
| 20.7 | 4.3 |
| 21.4 | 4.1 |
| 22.4 | 4.0 |
| 22.6 | 3.9 |
| 23.4 | 3.8 |
| 23.7 | 3.8 |
| 24.9 | 3.6 |
| 25.4 | 3.5 |
| 25.7 | 3.5 |

Preparation of further polymorphs of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide Form (II)

Ethyl acetate (15 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (2.1 g) and was stirred at ambient conditions overnight. The resultant slurry was filtered and dried under vacuum at 50° C. to give a new solid state form (91% w/w).

$^1$H NMR (400 MHz, DMSO d6) d=13.49 (br s, 1H), 9.39 (s, 1H), 8.58 (s, 1H), 8.42 (d, J=2.2 Hz, 1H), 7.99 (d, J=2.2 Hz, 1H), 7.93 (d, J=1.2 Hz, 1H), 7.88 (s, 1H), 7.35 (s, 1H), 4.00 (s, 3H), 3.74 (s, 2H), 3.58 (m, 2H), 3.11 (s, 3H), 2.80 (d, J=10.3 Hz, 2H), 1.78 (t, J=10.3 Hz, 2H), 1.05 (d, J=6.4 Hz, 6H)

Form (III)

Methanol (4 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.3 g) followed by fumaric acid (0.0764 g) in methanol (2 ml). The resultant suspension was diluted further with methanol (3 ml) and stirred overnight at ambient conditions. The suspension was filtered, washed with methanol and air dried to give a new solid state form (64% w/w).

$^1$H NMR (400 MHz, DMSO d6) d=13.50 (br s, 1H), 9.39 (s, 1H), 8.58 (s, 1H), 8.42 (d, J=2.2 Hz, 1H), 7.99 (d, J=2.2 Hz, 1H), 7.93 (d, J=1.2 Hz, 1H), 7.88 (s, 1H), 7.35 (s, 1H), 4.00 (s, 3H), 3.74 (s, 2H), 3.58 (m, 2H), 3.11 (s, 3H), 2.80 (d, J=10.3 Hz, 2H), 1.78 (t, J=10.5 Hz, 2H), 1.05 (d, J=6.4 Hz, 6H)

Form (IV)

Tetrahydrofuran was saturated with N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide at room temperature and heated. The suspension was cooled to room temperature and solids filtered, washed with THF and dried under vacuum at 30° C. to give a new solid state form.

$^1$H NMR (400 MHz, DMSO d6) d=13.50 (br s, 1H), 9.39 (s, 1H), 8.58 (s, 1H), 8.41 (d, J=2.0 Hz, 1H), 7.98 (d, J=2.2 Hz, 1H), 7.93 (d, J=0.7 Hz, 1H), 7.88 (s, 1H), 7.35 (s, 1H), 4.00 (s, 3H), 3.74 (s, 2H), 3.58 (m, 2.4H), 3.11 (s, 3H), 2.80 (d, J=10.5 Hz, 2H), 1.78 (t, J=10.5 Hz, 2.4H), 1.05 (d, J=6.1 Hz, 6H)

Sample contains 0.2 molar equivalents tetrahydrofuran

X-Ray Powder Diffraction (XRPD) for Forms (II) to (IV)

The data were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a silicon wafer (zero background) plate, resulting in a thin layer of powder.

Form (III) was lightly ground with pestle and mortar to reduce preferred orientation.

Form (II)

The XRPD data are shown in FIG. 3.

Characteristic XRPD angles and d-spacings for the solid state form are summarised in Table 3. Peak positions were measured using Highscore software.

TABLE 3

| 2θ/° | d-spacing/Å |
|---|---|
| 4.6 | 19.1 |
| 9.2 | 9.6 |
| 11.4 | 7.8 |
| 12.1 | 7.3 |
| 12.7 | 7.0 |
| 13.7 | 6.5 |
| 14.0 | 6.3 |
| 16.0 | 5.5 |
| 17.1 | 5.2 |
| 17.9 | 5.0 |
| 18.5 | 4.8 |
| 18.8 | 4.7 |
| 22.3 | 4.0 |
| 20.8 | 4.3 |
| 23.8 | 3.7 |
| 25.9 | 3.4 |

Form (III)

The XRPD data are shown in FIG. 4.

Characteristic XRPD angles and d-spacings for the solid state form are summarised in Table 4. Peak positions were measured using Highscore software.

TABLE 4

| 2θ/° | d-spacing/Å |
|---|---|
| 6.7 | 13.2 |
| 8.2 | 10.8 |

241

TABLE 4-continued

| 2θ/° | d-spacing/Å |
|---|---|
| 8.8 | 10.0 |
| 9.7 | 9.1 |
| 11.1 | 8.0 |
| 12.6 | 7.0 |
| 13.6 | 6.5 |
| 14.4 | 6.1 |
| 17.0 | 5.2 |
| 17.7 | 5.0 |
| 18.8 | 4.7 |
| 20.9 | 4.2 |
| 21.3 | 4.2 |
| 22.8 | 3.9 |
| 24.4 | 3.6 |
| 25.3 | 3.5 |

Form (IV)

The XRPD data are shown in FIG. 5.

Characteristic XRPD angles and d-spacings for the solid state form are summarised in Table 5. Peak positions were measured using Highscore software.

TABLE 5

| 2θ/° | d-spacing/Å |
|---|---|
| 5.8 | 15.2 |
| 11.1 | 8.0 |
| 11.6 | 7.6 |
| 14.0 | 6.3 |
| 17.5 | 5.1 |
| 19.3 | 4.6 |
| 22.3 | 4.0 |
| 25.7 | 3.5 |

Preparation of salts of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide Sodium Salt Methanol (2 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.3 g) followed by aqueous sodium hydroxide (0.129 ml) to give a solution. Tert-butylmethylether (4 ml) was added to the solution followed by seed crystals of the sodium salt and this suspension was stirred overnight at ambient conditions. The suspension was filtered, washed with tert-butylmethylether (2 ml) and air dried to give the sodium salt (0.2312 g) as a hydrate.

NMR: Consistent with salt formation $^1$H NMR (400 MHz, DMSO d6) d=13.35 (br s, 1H), 8.53 (s, 1H), 7.90 (d, J=1.2 Hz, 1H), 7.73 (s, 1H), 7.65 (d, J=2.5 Hz, 1H), 7.62 (d, J=2.2 Hz, 1H), 7.33 (s, 1H), 4.00 (s, 3H), 3.80 (s, 3H), 3.59 (m, 2H), 2.83 (d, J=10.3, 2H), 2.61 (s, 3H), 1.78 (t, J=10.5 Hz, 2H), 1.05 (d, J=6.1 Hz, 6H)

Tosylate Salt

A solution of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.3 g) in tetrahydrofuran (3 ml) was added to p-toluenesulfonic acid (0.1224 g) to give initially a solution. A suspension formed on stirring and was diluted with tetrahydrofuran (2 ml) and stirred overnight at ambient conditions. The suspension was filtered, washed with tetrahydrofuran (2 ml) and air dried to give the tosylate (0.3759 g).

242

NMR: Consistent with mono tosylate formation $^1$H NMR (400 MHz, DMSO d6) d=13.56 (br s, 1H), 10.38 (br s, 1H), 9.43 (s, 1H), 8.69 (s, 1H), 8.43 (d, J=2.5 Hz, 1H), 8.03 (s, 1H), 7.99 (d, J=2.2 Hz, 1H), 7.96 (s, 1H), 7.69 (s, 1H), 7.46 (d, J=7.8 Hz, 2H), 7.11 (d, J=7.8 Hz, 2H), 4.69 (br s, 2H), 4.00 (s, 3H), 3.80 (br s, 2H), 3.50 (br s, 2H), 3.11 (s, 3H), 2.80 (br s, 2H), 2.28 (s, 3H), 1.05 (d, J=6.1 Hz, 6H) Sample contains 0.5 molar equivalents tetrahydrofuran NMR signals 3.60 (m, 2H), 1.76 (m, 2H)

Maleate Salt

Methanol (4 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.3 g) followed by maleic acid (0.0749 g) in methanol (2 ml). The solution was allowed to crystallise overnight at ambient conditions. The resultant suspension was filtered, washed with methanol (1 ml) and air dried to give the maleate (0.1441 g).

NMR: Consistent with mono maleate formation $^1$H NMR (400 MHz, DMSO d6) d=13.53 (br s, 1H), 9.41 (s, 1H), 8.63 (s, 1H), 8.42 (d, J=2.4 Hz, 1H), 7.99 (d, J=2.4 Hz, 1H), 7.98 (d, J=1.2 Hz, 1H), 7.92 (s, 1H), 7.51 (s, 1H), 6.16 (s, 2H), 4.16 (br s, 2H), 4.00 (s, 3H), 3.69 (br s, 2H)*, 3.11 (s+br s, 3H+2H), 2.22 (br s, 2H), 1.10 (d, J=6.4 Hz, 6H)

*Partial increase in integral due to overlap with broad HOD peak

Hemi Pamoate Salt

Tetrahydrofuran (1 ml) was added to pamoic acid (0.0759 g) to give a suspension. This suspension was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.2 g). Further tetrahydrofuran (7 ml) and water (12 ml) were added before the solution was reduced in volume by ca. 10% under a nitrogen flow. The resultant suspension was sonicated and stirred at ambient conditions overnight. The suspension was filtered, washed with water and dried under vacuum at 50° C. to give the hemi pamoate (0.092 g) containing 5% w/w water.

NMR: Consistent with hemi pamoate formation $^1$H NMR (400 MHz, DMSO d6) d=13.51 (br s, 1H), 9.40 (s, 1H), 8.60 (s, 1H), 8.42 (m, 2H), 8.13 (d, J=8.8 Hz, 1H), 7.99 (d, J=2.2 Hz, 1H), 7.95 (s, 1H), 7.90 (s, 1H), 7.85 (d, J=8.0 Hz, 1H), 7.42 (s, 1H), 7.33 (t, J=7.3 Hz, 1H), 7.18 (t, J=7.1 Hz, 1H), 4.78 (s, 1H), 4.00 (s, 3H), 3.92 (br s, 2H), 3.63 (m, 2H), 3.11 (s, 3H), 2.95 (d, J=11.0 Hz, 2H), 1.97 (m, 2H), 1.07 (d, J=6.4 Hz, 6H)

Hemi Naphthalenedisulfonate Salt

Isopropylacetate (12 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.2 g) followed by naphthalenedisulfonic acid (0.0703 g) in isopropylacetate (2 ml). The suspension was stirred at ambient temperature for 9 days prior to filtration and dried under vacuum at 40° C. for 3 hrs to give the hemi naphthalenedisulfonate.

NMR Consistent with hemi naphthalenedisulfonate formation $^1$H NMR (400 MHz, DMSO d6) d=13.56 (br s, 1H), 10.38 (br s, 1H), 9.42 (s, 1H), 8.85 (d, J=8.8 Hz, 1H), 8.69 (s, 1H), 8.43 (d, J=2.5, 1H), 8.03 (s, 1H), 7.99 (d, J=2.2 Hz, 1H), 7.96 (s, 1H), 7.93 (d, J=7.1 Hz, 1H), 7.69 (br s, 1H), 7.40 (t, J=7.8 Hz, 1H), 4.68 (br s, 2H), 4.00 (s, 3H), 3.80 (br s, 2H), 3.50 (br s, 2H), 3.11 (s, 3H), 2.80 (br s, 2H), 1.15 (d, J=6.1 Hz, 6H)

Integrals at 4.68 and 2.80 are only at 1.6H not the expected 2H

Extra peaks due to ca. 0.1 eq isopropylacetate.

Raman: Not consistent with freebase forms known

Mesitylenesulfonate Salt

A solution of mesitylenesulfonic acid dihydrate (0.0698 g, 0.295 mmol, 1.0 eq) in tetrahydrofuran (0.5 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.1505 g, 0.294 mmol) and sonicated to give a clear solution. After stirring at ambient temperature for ca. 2 mins the solution had formed a very thick suspension. This was held at ambient temperature overnight. The solids were collected by filtration and washed with tetrahydrofuran (1-2 ml) before being dried in vacuo at 50° C. overnight to give the mesitylenesulfonate salt (0.1399 g, 66.8% th).

NMR: consistent with salt formation

NMR (400 MHz, DMSO d6) d=13.56 (s, 1H), 10.39 (bs, 1H), 9.42 (s, 1H), 8.69 (s, 1H), 8.43 (d, J=2.2 Hz, 1H), 8.03 (s, 1H), 7.99 (d, J=2.2 Hz, 1H), 7.96 (s, 1H), 7.69 (s, 1H), 6.73 (s, 2H), 4.69 (bs, 2H), 4.01 (s, 3H), 3.81 (bs, 2H), 3.49 (bs, 4H), 3.11 (s, 3H), 2.79 (bs, 2H), 2.16 (s, 3H), 1.15 (d, J=6.1 Hz, 6H).

Two methyl groups from mesitylenesulfonic acid are not seen as they overlap with resonance from d$_5$H-DMSO.

Hemi Biphenyldisulfonate

A solution of biphenyldisulfonic acid (0.0465 g, 0.148 mmol, 0.5 eq) in tetrahydrofuran (0.2 ml) and water (0.2 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.1506 g, 0.294 mmol) and sonicated to give a solution which was stirred at ambient temperature overnight. After this time the solution set solid due to a precipitate. These solids were collected by filtration and washed with tetrahydrofuran (1-2 ml) before being dried in vacuo at 50° C. overnight to give the hemi-biphenyldisulfonate salt (0.117 g, 59.5% th)

NMR: consistent with salt formation

NMR (400 MHz, DMSO d6) d=13.55 (s, 1H), 10.37 (bs, 1H), 9.42 (s, 1H), 8.69 (s, 1H), 8.43 (d, J=2.2 Hz, 1H), 8.03 (s, 1H), 7.99 (d, J=2.2 Hz, 1H), 7.96 (s, 1H), 7.66 (s+d, J=8.1 Hz, 1H+2H), 7.61 (d, J=8.3 Hz, 2H), 4.69 (bs, 2H), 4.01 (s, 3H), 3.81 (bs, 2H), 3.50 (bs, 4H), 3.11 (s, 3H), 2.79 (bs, 2H), 1.16 (d, J=6.1 Hz, 6H).

2-Naphthalenesulfonate (napsylate)

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide (0.200 g, 0.390 mmol) was dissolved in tetrahydrofuran (3.2 ml) and water (0.8 ml). Separately, 2-naphthalenesulfonic acid (0.081 mg, 0.390 mmol, 1.0 eq) was dissolved in tetrahydrofuran (0.8 ml) and added to the N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide solution. This was seeded with a previous napsylate salt, however these seeds dissolved. The solution was allowed to evaporate at ambient temperature for 2 days. The white solid formed was triturated in water and sonicated before being filtered and washed with water. The damp solids were dried further in vacuo at 40-50° C. for 5 days to give the napsylate salt (254.8 mg, 91% th).

NMR: consistent with salt formation

NMR (400 MHz, DMSO d6) d=13.56 (s, 1H), 10.38 (bs, 1H), 9.42 (s, 1H), 8.69 (s, 1H), 8.43 (d, J=2.2 Hz, 1H), 8.15 (s, 1H), 8.03 (s, 1H), 8.00 (d, J=2.0 Hz, 1H), 7.96 (m, 2H), 7.86 (m, 2H), 7.71 (m, 2H), 7.53 (m, 2H), 4.68 (bs, 2H), 4.01 (s, 3H), 3.79 (bs, 2H), 3.50 (bs, 2H), 3.11 (s, 3H), 2.78 (bs, 2H), 1.14 (d, J=6.1 Hz, 6H).

NMR also shows some unidentified low level impurities and residual tetrahydrofuran (0.1 molar equivalents).

Hemi Cinnamate

Method A

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide (0.02505 g, 0.049 mmol) was treated with trans-cinnamic acid (0.01453 g, 0.098 mmol, 2.0 eq) in methanol (0.5 ml). This was heated with a hot air gun until dissolution occurred then allowed to cool to room temperature. Solids precipitated on returning to room temperature and were allowed to stir overnight. The solids were filtered and solvent removed by pulling vacuum through the cake to give the salt.

Method B

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide (80 g, 0.156 mol) and trans-cinnamic acid (58.66 g, 0.396 mol, 2.5 eq) were dissolved in methanol (3.2 L) by heating to 65° C. The solution was cooled to 60° C. and seeded with N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide hemi-cinnamate (0.0802 g), these dissolved so the solution was cooled further to 50° C. and reseeded with N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methane-sulfonamide hemi-cinnamate. This was stirred for 1 hr at 50° C. and then cooled at −0.167° C./min to 20° C. After 2 hrs a sample was taken and proved to be Form 3 by Raman analysis. The slurry was heated back to reflux to give a solution and extra methanol (100 ml) was added to make up for solvent losses incurred during the extended high temperature process. The solution was cooled to 25° C. and sample taken which was seeded with N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide hemi-cinnamate. This seeded sample was aged for 20 mins and then used to seed the bulk solution. This was allowed to stir at 25° C. for 16 hrs. The slurry was filtered and sucked dry before being dried in vacuo at 50° C. to give the salt (75.4 g, 82.5% th).

NMR: consistent with salt formation

NMR (400 MHz, DMSO d6) d=13.49 (bs, 1H), 9.40 (bs, 1H), 8.58 (s, 1H), 8.42 (d, J=2.5 Hz, 1H), 7.99 (d, J=2.2 Hz, 1H), 7.94 (s, 1H), 7.88 (s, 1H), 7.68 (m, 1H), 7.57 (d, J=16.1 Hz, 0.5H), 7.42 (m, 1.5H), 7.35 (s, 1H), 6.55 (d, J=15.9 Hz, 0.5H), 4.01 (s, 3H), 3.74 (s, 2H), 3.58 (m, 2H), 3.12 (s, 3H), 2.80 (d, J=10.5, 2H), 1.78 (t, J=10.5, 2H), 1.05 (d, J=6.1 Hz, 6H).

NMR also shows residual methanol (signal 3.18 ppm) at <0.1 molar equivalents.

Hemi Sebacate

A solution of sebacic acid (118.6 mg, 0.586 mmol, 2.0 eq) in THF (2 ml) was made up and added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methane-sulfonamide (150.6 mg, 0.294 mmol) and heated to give a clear solution. The solution was allowed to cool to room temperature with stirring and after 2 hrs solids were present. A further aliquot of THF was added at this point and the suspension stirred overnight at ambient temperature. The solids were isolated by filtration and dried in vacuo at 50° C. overnight to give the hemi-sebacate salt.

NMR: consistent with salt formation

NMR (400 MHz, DMSO d6) d=13.49 (s, 1H), 11.94 (bs, 1H), 10.38 (bs, 1H), 9.38 (s, 1H), 8.58 (s, 1H), 8.42 (d, J=2.2 Hz, 1H), 7.99 (d, J=2.0 Hz, 1H), 7.93 (s, 1H), 7.88 (s, 1H), 7.35 (s, 1H), 4.00 (s, 3H), 3.74 (s, 2H), 3.11 (s, 3H), 2.80 (d,

J=10.5, 2H), 2.18 (t, J=7.3 Hz, 2H), 1.48 (t, J=6.8 Hz, 2H), 1.25 (s, 4H), 1.05 (d, J=6.1 Hz, 6H).

Sample contains 0.85 molar equivalents tetrahydrofuran—NMR signals 3.60 ppm (m, 3.3H) and 1.76 ppm (m, 3.4H).

Hemi Pyromellitate

A solution of pyromellitic acid (0.0546 g, 0.215 mmol, 0.55 eq) was made up in tetrahydrofuran (1 ml) and added to N-[5-[4-(5-{[(2R,6S)-2,6-dimethyl-4-morpholinyl]methyl}-1,3-oxazol-2-yl]-1H-indazol-6-yl]-2-(methyloxy)-3-pyridinyl]methanesulfonamide (0.1999 g, 0.390 mmol) followed by further tetrahydrofuran (1 ml). This suspension was sonicated at which point the solids changed physical character and set solid. A further aliquot of tetrahydrofuran (2 ml) was added and the solution was heated and sonicated, however dissolution was not observed. The suspension was allowed to cool and stir overnight at room temperature. The solids were collected by filtration and washed with tetrahydrofuran (2 ml) before drying in vacuo overnight at 50° C. to give the hemi-pyromellitate salt as a tetrahydrofuran solvate.

NMR: consistent with salt formation

NMR (400 MHz, DMSO d6) d=13.52 (s, 1H), 9.39 (s, 1H), 8.61 (s, 1H), 8.42 (d, J=2.2 Hz, 1H), 8.20 (s, 1H), 7.99 (d, J=2.2 Hz, 1H), 7.96 (s, 1H), 7.91 (s, 1H), 7.45 (s, 1H), 4.01 (s, 5H), 3.60 (m, 6H), 3.11 (s, 3H), 3.02 (d, J=10.8 Hz, 2H), 2.06 (bs, 2H), 1.76 (m, 4H), 1.05 (d, J=6.1 Hz, 6H).

Tetrahydrofuran signals are 3.60 ppm (m, 4H) and 1.76 ppm (M, 4H) corresponding to 1 molar equivalent.

Hemi Benzenediacrylate 1,4-Benzenediacrylic acid (0.0431 g, 0.197 mmol, 0.5 eq) was dissolved in dimethylsulfoxide (0.5 ml) with heating, this was added to N-[5-[4-(5-{[(2R,6S)-2,6-dimethyl-4-morpholinyl]methyl}-1,3-oxazol-2-yl]-1H-indazol-6-yl]-2-(methyloxy)-3-pyridinyl]methanesulfonamide (0.2003 g, 0.391 mmol) and heated to give a solution. Tetrahydrofuran (1 ml) was added to the solution and it was then heated and sonicated before being allowed to stir at room temperature overnight. The solids were isolated by filtration and washed with tetrahydrofuran before being dried in vacuo at 65° C. overnight to give the hemi-benzenediacrylate salt (0.1385 g, 57% th).

NMR: consistent with salt formation

NMR (400 MHz, DMSO d6) d=13.49 (bs, 1H), 12.40 (bs, 1H), 9.38 (bs, 1H), 8.58 (s, 1H), 8.42 (d, J=2.2 Hz, 1H), 7.99 (d, J=2.2 Hz, 1H), 7.93 (s, 1H), 7.88 (s, 1H), 7.73 (s, 2H), 7.58 (d, J=16.1 Hz, 1H), 7.35 (s, 1H), 6.62 (d, J=16.1 Hz, 1H), 4.00 (s, 3H), 3.74 (s, 2H), 3.11 (s, 3H), 2.80 (d, J=10.5 Hz, 2H), 1.05 (d, J=6.4 Hz, 6H).

Tetrahydrofuran signals are 3.60 ppm (m, 2.7H) and 1.78 ppm (m, 2.7H) corresponding to 0.68 molar equivalent. Dimethylsulfoxide signal is 2.54 ppm (s, 0.7H) corresponding to 0.12 molar equivalents.

Preparation of polymorph of 6-(1H-Indol-4-yl)-4-(5-{[4-(1-methylethyl)-1-piperazinyl]methyl}-1,3-oxazol-2-yl)-1H-indazole 6-(1H-Indol-4-yl)-4-(5-{[4-(1-methylethyl)-1-piperazinyl]methyl}-1,3-oxazol-2-yl)-1H-indazole (25 g) was dissolved in dimethylformamide (DMF, 240 ml) and filtered (porosity 4 filter). DMF (10 ml) was used as a line rinse to wash the glassware and filtered. The material was chromatographed in 14×17-18 ml injections and a final injection of ca. 10 ml. Fractions containing 6-(1H-indol-4-yl)-4-(5-{[4-(1-methylethyl)-1-piperazinyl]methyl}-1,3-oxazol-2-yl)-1H-indazole were evaporated under vacuum at temperatures up to 40° C. The resulting solid was filtered, washed with water (100 ml) and dried at 60° C. under vacuum overnight.

Chromatography Conditions:
HPLC system Varian SD-1
Column: Phenomenex Luna C18(II), 50×243 mm
Eluent A: 0.1M ammonium acetate adjusted to pH 8.0 with 0.88 ammonia
Eluent B: Acetonitrile
Detector: 350 nm range 12
Injection: approx 17-18 ml of solution in DMF (1 g per 10 ml DMF)
NMR Concordant with Expected Spectrum:

NMR (400 MHz, DMSO d6): 13.42 (br s, 1H), 11.35 (br s, 1H), 8.60 (s, 1H), 8.08 (d J=1.2 Hz, 1H), 7.91 (s, 1H), 7.48 (m, 2H), 7.32 (s, 1H), 7.24 (m, 2H), 6.61 (s, 1H), 3.73 (s, 1H), 2.58 (m, 1H), 2.45 (br s, 4H), 0.94 (d J=6.6 Hz, 6H)

Broad singlet at 2.45 ppm is likely to contain some of the remaining aliphatic protons; however the integration is unlikely to be accurate due to the overlap with the DMSO (d5) peak. The remaining aliphatic protons are likely to be underneath the DMSO (d5) peak.

Preparation of salts of 6-(1H-indol-4-yl)-4-(5-{[4-(1-methylethyl)-1-piperazinyl]methyl}-1,3-oxazol-2-yl)-1H-indazole and polymorphs thereof Tosylate 6-(1H-Indol-4-yl)-4-(5-{[4-(1-methylethyl)-1-piperazinyl]methyl}-1,3-oxazol-2-yl)-1H-indazole (1.5013 g) was suspended in acetonitrile (10 ml) and stirred. Separately, p-toluenesulfonic acid monohydrate (679.5 mg, 1.05 eq) was dissolved in acetonitrile (5 ml) and added. Immediately a gummy precipitate formed and was sonicated and triturated to mobilise the solid mass. The suspension was seeded with crystalline tosylate salt and allowed to stir overnight. The solids were isolated and dried under vacuum at 50° C.

NMR Concordant with Expected Spectrum:

NMR (400 MHz, DMSO d6): 13.45 (br s, 1H), 11.37 (br s, 1H), 8.92 (br s, 1H), 8.64 (s, 1H), 8.11 (s, 1H), 7.94 (s, 1H), 7.48 (m, 4H), 7.43 (s, 1H), 7.24 (m, 2H), 7.12 (d J=8.1 Hz, 2H), 6.61 (s, 1H), 3.97 (s, 2H), 3.42 (m, 3H), 3.13 (m, 4H), 2.54 (m, 1H), 2.28 (s, 3H), 1.23 (d J=6.4 Hz, 6H)

Aliphatic protons not seen here are likely to be residing under the DMSO (d5) peak The Crystalline Tosylate Salt Seed May be Prepared by the Following Method:

6-(1H-Indol-4-yl)-4-(5-{[4-(1-methylethyl)-1-piperazinyl]methyl}-1,3-oxazol-2-yl)-1H-indazole (0.1003 g) was suspended in acetonitrile (1.5 ml) and stirred. Separately, toluenesulfonic acid monohydrate (45.6 mg, 1.05 eq) was dissolved in acetonitrile (0.5 ml) and added to the suspension of 6-(1H-indol-4-yl)-4-(5-{[4-(1-methylethyl)-1-piperazinyl]methyl}-1,3-oxazol-2-yl)-1H-indazole. A gummy precipitate formed which was allowed to stir for 10 mins. The sample was heated to approximately 50° C. and sonicated with little visual effect. The solids were manually agitated with a spatula to mobilise them and stirred for 4 days at room temperature. The solids were filtered and sucked dry.

Hemi Fumarate 6-(1H-Indol-4-yl)-4-(5-{[4-(1-methylethyl)-1-piperazinyl]methyl}-1,3-oxazol-2-yl)-1H-indazole (1.5014 g) and fumaric acid (217.2 mg, 0.56 eq) were suspended in IMS (15 ml) and stirred at room temperature overnight. The slurry was filtered and sucked dry before being dried under vacuum at 50° C. overnight.

NMR Concordant with Expected Spectrum:

NMR (400 MHz, DMSO d6): 13.47 (br s, 1H), 11.37 (br s, 1H), 8.60 (s, 1H), 8.08 (s, 1H), 7.92 (s. 1H), 7.48 (m, 2H), 7.34

(s, 1H), 7.24 (m, 2H), 6.61 (s, 1H), 6.56 (s, 1H), 3.76 (s, 2H), 2.74 (m, 1H), 2.58 (br s, 7H), 1.00 (d J=6.6 Hz, 6H)

Broad singlet at 2.58 ppm is likely to contain remaining aliphatic protons; however the integration is unlikely to be accurate due to the overlap with the DMSO (d5) peak.

Hemi Succinate

Industrial methylated spirits (IMS, 1 ml) was added to 6-(1H-indol-4-yl)-4-(5-{[4-(1-methylethyl)-1-piperazinyl]methyl}-1,3-oxazol-2-yl)-1H-indazole (0.1006 g) and stirred. Separately succinic acid (28.3 mg, 1.05 eq) was dissolved in IMS (1 ml) and then added to the 6-(1H-indol-4-yl)-4-(5-{[4-(1-methylethyl)-1-piperazinyl]methyl}-1,3-oxazol-2-yl)-1H-indazole suspension and stirred at room temperature over the weekend (ca. 72 hrs). The solids were isolated by filtration and washed with IMS (ca. 1 ml) before being dried under vacuum at 50° C.

NMR Concordant with Expected Spectrum:

NMR (400 MHz, DMSO d6): 13.42 (br s, 1H), 11.36 (br s, 1H), 8.61 (s, 1H), 8.09 (d J=1.2 Hz, 1H), 7.92 (s, 1H), 7.48 (m, 2H), 7.34 (s, 1H), 7.25 (m, 2H), 6.62 (s, 1H), 3.76 (s, 2H), 2.67 (m, 1H), 2.40 (s, 2H), 0.98 (d J=6.6 Hz, 6H)

Aliphatic protons not seen here are likely to be residing under the DMSO (d5) peak

X-Ray Powder Diffraction (XRPD) for the polymorph of 6-(1H-indol-4-yl)-4-(5-{[4-(1-methylethyl)-1-piperazinyl]methyl}-1,3-oxazol-2-yl)-1H-indazole and the polymorphs of the salts of 6-(1H-indol-4-yl)-4-(5-{[4-(1-methylethyl)-1-piperazinyl]methyl}-1,3-oxazol-2-yl)-1H-indazole The data were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a silicon wafer (zero background) plate, resulting in a thin layer of powder.

Polymorph of 6-(1H-Indol-4-yl)-4-(5-{[4-(1-methylethyl)-1-piperazinyl]methyl}-1,3-oxazol-2-yl)-1H-indazole The XRPD data are shown in FIG. 6.

Characteristic XRPD angles and d-spacings for the solid state form are summarised in Table 6. Peak positions were measured using Highscore software.

TABLE 6

| 2θ/° | d-spacing/Å |
|---|---|
| 8.0 | 11.0 |
| 9.0 | 9.9 |
| 9.6 | 9.2 |
| 10.4 | 8.5 |
| 12.5 | 7.1 |
| 13.3 | 6.7 |
| 14.4 | 6.1 |
| 16.5 | 5.4 |
| 19.3 | 4.6 |
| 19.7 | 4.5 |
| 20.3 | 4.4 |
| 21.6 | 4.1 |
| 22.7 | 3.9 |
| 24.4 | 3.6 |

Polymorph of the tosylate salt of 6-(1H-Indol-4-yl)-4-(5-{[4-(1-methylethyl)-1-piperazinyl]methyl}-1,3-oxazol-2-yl)-1H-indazole The XRPD data are shown in FIG. 7.

Characteristic XRPD angles and d-spacings for the solid state form are summarised in Table 7. Peak positions were measured using Highscore software.

TABLE 7

| 2θ/° | d-spacing/Å |
|---|---|
| 6.3 | 13.9 |
| 9.3 | 9.5 |
| 11.3 | 7.9 |
| 11.6 | 7.6 |
| 12.7 | 7.0 |
| 13.2 | 6.7 |
| 14.2 | 6.2 |
| 15.6 | 5.7 |
| 15.8 | 5.6 |
| 17.1 | 5.2 |
| 18.7 | 4.7 |
| 19.5 | 4.5 |
| 20.3 | 4.4 |
| 21.0 | 4.2 |
| 22.3 | 4.0 |
| 25.7 | 3.5 |

Polymorph of the hemi fumarate salt of 6-(1H-Indol-4-yl)-4-(5-{[4-(1-methylethyl)-1-piperazinyl]methyl}-1,3-oxazol-2-yl)-1H-indazole The XRPD data are shown in FIG. 8.

Characteristic XRPD angles and d-spacings for the solid state form are summarised in Table 8. Peak positions were measured using Highscore software.

TABLE 8

| 2θ/° | d-spacing/Å |
|---|---|
| 6.9 | 12.7 |
| 8.7 | 10.2 |
| 13.8 | 6.4 |
| 14.4 | 6.1 |
| 17.6 | 5.0 |
| 18.0 | 4.9 |
| 18.9 | 4.7 |
| 21.1 | 4.2 |
| 22.6 | 3.9 |
| 25.8 | 3.5 |

Polymorph of the hemi succinate salt of 6-(1H-Indol-4-yl)-4-(5-{[4-(1-methylethyl)-1-piperazinyl]methyl}-1,3-oxazol-2-yl)-1H-indazole The XRPD data are shown in FIG. 9.

Characteristic XRPD angles and d-spacings for the solid state form are summarised in Table 9. Peak positions were measured using Highscore software.

TABLE 9

| 2θ/° | d-spacing/Å |
|---|---|
| 7.2 | 12.3 |
| 13.2 | 6.7 |
| 14.0 | 6.3 |
| 18.0 | 4.9 |

TABLE 9-continued

| 2θ/° | d-spacing/Å |
|---|---|
| 19.1 | 4.6 |
| 19.7 | 4.5 |
| 20.7 | 4.3 |
| 23.2 | 3.8 |
| 26.3 | 3.4 |

Biological Data
PI3K Alpha, Beta, Delta and Gamma Assays
Assay Principle

The assay readout exploits the specific and high affinity binding of PIP3 to an isolated pleckstrin homology (PH) domain in the generation of a signal. Briefly, the PIP3 product is detected by displacement of biotinylated PIP3 from an energy transfer complex consisting of Europium (Eu)-labelled anti-GST monoclonal antibody, a GST-tagged PH domain, biotin-PIP3 and Streptavidin-APC. Excitation of Eu leads to a transfer of energy to APC and a sensitized fluorescence emission at 665 nm. PIP3 formed by PI3kinase activity competes for the binding site on the PH domain, resulting in a loss of energy transfer and a decrease in signal.

Assay Protocol

Solid compounds are typically plated with 0.1 µl of 100% DMSO in all wells (except column 6 and 18) of a 384-well, v bottom, low volume Greiner plate. The compounds are serially diluted (4-fold in 100% DMSO) across the plate from column 1 to column 12 and column 13 to column 24 and leave column 6 and 18 containing only DMSO to yield 11 concentrations for each test compound.

The assays are run using specific PI3 kinase kits from Millipore (Cat#33-001)

The assay kit consist of the following:
4×PI3K reaction buffer (Contains 200 mM Hepes pH 7, 600 mM NaCl, 40 mM Mgcl$_2$, <1% Cholate (w/v), <1% Chaps (w/v), 0.05% Sodium Azide (w/v))
PIP2 (1 mM)
3× Biotin PIP3 (50 µM)
Detection Mix C (Contains 267 mM KF)
Detection Mix A (Contains 60 µg/ml streptavadin-APC)
Detection Mix B (Contains 36 µg/ml Europium-anti-GST (Anti-GST-K) and 90 µg/ml GST-GRP1-PH-Domain and 1 mM DTT)
Stop Solution (Contains 150 mM EDTA)

Manually add 3 µl of Reaction buffer (contains 1 mM DTT) to column 18 only for 100% inhibition control (no activity)

Manually add 3 µl of 2× Enzyme solution to all wells except column 18. Preincubate with compound for 15 minutes.

Manually add 3 µl of 2× Substrate solution to all wells. (column 6 represents 0% inhibition control)

Leave plate for 1 hr (cover from light) (In the case of Gamma only a 50 min incubation is required)

Manually add 3 µl Stop/Detection solution to all wells

Leave plate for 1 hour (cover from light)

The assay is read upon the BMG Rubystar and the ratio data is utilised to calculate 11 point curves.

NB The substrate solution (concentrations) differ with each isoform (see below)

Alpha
2× substrate solution containing 500 µM ATP, 16 µM PIP2 and 0.030 µM 3× biotin-PIP3.

Beta
2× substrate solution containing 800 µM ATP, 16 µM PIP2 and 0.030 µM 3× biotin-PIP3.

Delta
2× substrate solution containing 160 µM ATP, 10 µM PIP2 and 0.030 µM 3× biotin-PIP3.

Gamma
2× substrate solution containing 30 µM ATP, 16 µM PIP2 and 0.030 µM 3× biotin-PIP3.

Analysis Method

Data processed through the XC50 4-parameter logistic curve fit algorithm in Activity Base.

Normalise to % inhibition between the high and low controls (0% and 100% inhibition respectively)

Primary Module fit: Slope, Min and Max asymptotes varies

Secondary Module fits: (1) Fix Min asymptote, (2) Fix Max asymptote, (3) Fix Min and Max asymptotes Curve Fit QC: pXC50 95% CL ratio>10
−20<Min asymptote<20
80<Max asymptote<120

The compounds and salts of Examples 1 to 72 and 74 to 105 were tested in the PI3K Alpha, Beta, Delta and/or Gamma assays above or similar assays and were found to have a mean pIC$_{50}$ in the PI3K Delta assay of at least 5 or greater.

Influenza Virus Assay

The impact of test compounds on influenza virus infection is evaluated using cytoprotection assays in A549 cells. Briefly, virus is incubated in the presence or absence of test compound with A549 cells for 7 days at a virus titre chosen to induce 85 to 95% loss of cell viability due to virus replication. Cytoprotection is a measure of antiviral efficacy as it is observed when compounds prevent virus replication. Cytoprotection and compound cytotoxicity are assessed by MTS dye reduction (CellTiter®96 Reagent, Promega, Madison Wis.). The % reduction in viral cytopathic effects is determined and the IC$_{50}$ determined. The % reduction in viability induced by compound in the absence of virus is determined as a measure of cytotoxicity and a TC$_{50}$ determined (concentration resulting in 50% cell death). Each assay includes ribavirin (RBV) and zinamavir as positive controls.

A549 cells (human epithelial) are obtained from the American Type Culture Collection (ATCC, Rockville, Md.) and are grown in DMEM/F-12K supplemented with 10% fetal bovine serum (FBS), 0.1 mM non-essential amino acids, 2.0 mM L-Glutamine, 100 units/ml Penicillin and 100 µg/ml Streptomycin ("growth medium"). Cells are sub-cultured twice a week at a split ratio of 1:4 using standard cell culture techniques. Total cell number and percent viability determinations are performed using a hemacytometer and trypan blue exclusion. Cell viability must be greater than 95% for the cells to be utilized in the assay.

A/Hong Kong/8/68 (H3N2), A/PR/8/34 (H1N1), A/Victoria/3/75 (H3N2), A/WS/33 (H1N1), B/Lee/40, and B/Russia/69 are obtained from the American Type Culture Collection (ATCC) and are grown in MDCK cells for the production of stock virus pools and titres determined in A549 cells.

The A549 cells are seeded in 96-well tissue culture plates the day before the assay at a concentration of 1×10$^4$ cells/well in DMEM/F-12K supplemented with 2% fetal bovine serum (FBS), 0.1 mM non-essential amino acids, 2.0 mM L-Glutamine, 100 units/ml Penicillin and 100 µg/ml Streptomycin, and 1.0 µg/mL TPCK trypsin and incubated at 37° C. 5% CO2. On the day of assay, an aliquot of virus is removed from the −80 freezer and allowed to thaw slowly to room temperature. The virus is resuspended and diluted into tissue culture medium such that the amount of virus added to each well is the amount determined to induce between 85 and 95% cell death at 7 days post-infection. Compounds are dissolved in DMSO at 10 mM concentrations and diluted in neat DMSO to prepare the appropriate dilution series. 5 µL of the dilution is transferred into 995 μL of media to prepare the 2× compound. 50 μL of the 2× compound is added to a 96-well plate, where it is mixed 1:1 with 50 μL of either virus or media, resulting in 1× compound in the wells (0.1, 1 and 10 μM compound, 0.25% DMSO final in-assay concentration). Compounds are tested for antiviral efficacy in triplicate, whilst duplicate measurements are also made in the absence of virus as a measure of cellular cytotoxicity. DMSO is added to control wells. Assay plates are prepared to contain cell control wells (cells only), virus control wells (cells plus virus), compound toxicity control wells (cells plus compound only), compound colorimetric control wells (compound only), as well as experimental wells (compound plus cells plus virus). At assay termination (7 days post-infection), the assay plates are stained with the soluble tetrazolium-based dye MTS (3-(4,5-dimethylthiazol-2-yl)-5-(3-carboxymethoxyphenyl)-2-(4-sulfophenyl)-2H-tetrazolium; CellTiter 96 Reagent, Promega) to determine cell viability and quantify compound toxicity. MTS is metabolized by the mitochondrial enzymes of metabolically active cells to yield a soluble formazan product, allowing the rapid quantitative analysis of cell viability and compound cytotoxicity. At termination of the assay, 20-25 μL of MTS reagent is added per well and the microtiter plates are then incubated for 4-6 hrs at 37° C., 5% $CO_2$ to assess cell viability. Adhesive plate sealers are used in place of the lids, the sealed plate is inverted several times to mix the soluble formazan product and the plate is read spectrophotometrically at 490/650 nm with a Molecular Devices Vmax or SpectraMax Plus plate reader.

The results obtained for two compounds in the above or a similar assay are shown in Table 1 below. In Table 1, Compound A is 6-(1H-indol-4-yl)-4-(5-{[4-(1-methylethyl)-1-piperazinyl]methyl}-1,3-oxazol-2-yl)-1H-indazole hydrochloride and Compound B is N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide.

TABLE 1

| Compound/Units | Influenza Virus Isolate | IC50 | TC50 | Comment |
|---|---|---|---|---|
| Compound A (μM) | A/Hong Kong/8/68 (H3N2) | — | >10 | 40.4% inhibition observed at 10 μM |
| Compound A (μM) | A/PR/8/34 (H1N1) | — | >10 | 15.9% inhibition observed at 10 μM |
| Compound A (μM) | A/Victoria/3/75 (H3N2) | 9.19 | >10 | |
| Compound A (μM) | A/WS/33 (H1N1) | — | >10 | 21.4% inhibition observed at 10 μM |
| Compound A (μM) | B/Lee/40 | 4.61 | >10 | |
| Compound A (μM) | B/Russia/69 | 3.53 | >10 | |
| Compound B (μM) | A/Hong Kon/8/68 (H3N2) | — | >10 | 13.7% inhibition observed at 10 μM |
| Compound B (μM) | A/PR/8/34 (H1N1) | — | >10 | 35% inhibition observed at 10 μM |
| Compound B (μM) | A/Victoria/3/75 (H3N2) | — | >10 | 11.4% inhibition observed at 10 μM |
| Compound B (μM) | A/WS/33 (H1N1) | — | >10 | 0.1% inhibition observed at 10 μM |
| Compound B (μM) | B/Lee/40 | 7.94 | >10 | |
| Compound B (μM) | B/Russia/69 | 4.65 | >10 | |
| Ribavirin (μg/ml) | A/Hong Kong/8/68 (H3N2) | 6.59 | >100 | Active Control Compound |
| Ribavirin (μg/ml) | A/PR/8/34 (H1N1) | 7.35 | >100 | Active Control Compound |
| Ribavirin (μg/ml) | A/Victoria/3/75 (H3N2) | 6.01 | >100 | Active Control Compound |
| Ribavirin (μg/ml) | A/WS/33 (H1N1) | 7.34 | >100 | Active Control Compound |
| Ribavirin (μg/ml) | B/Lee/40 | 6.65 | >100 | Active Control Compound |
| Ribavirin (μg/ml) | B/Russia/69 | 4.75 | >100 | Active Control Compound |
| Zanamivir (μM) | A/Hong Kong/8/68 (H3N2) | 0.871 | >100 | Active Control Compound |
| Zanamivir (μM) | A/PR/8/34 (H1N1) | 0.984 | >100 | Active Control Compound |
| Zanamivir (μM) | A/Victoria/3/75 (H3N2) | 0.832 | >100 | Active Control Compound |
| Zanamivir (μM) | A/WS/33 (H1N1) | 0.743 | >100 | Active Control Compound |
| Zanamivir (μM) | B/Lee/40 | 2.52 | >100 | Active Control Compound |
| Zanamivir (μM) | B/Russia/69 | 3.25 | >100 | Active Control Compound |

What is claimed is:

1. A method of ameliorating symptoms of influenza virus infection comprising administering a safe and effective amount of the compound N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide; or a pharmaceutically acceptable salt thereof.

2. A method of ameliorating symptoms of influenza virus infection comprising administering a safe and effective amount of the compound 6-(1H-indol-4-yl)-4-(5-{[4-(1-methylethyl)-1-piperazinyl]methyl}-1,3-oxazol-2-yl)-1H-indazole; or a pharmaceutically acceptable salt thereof.

3. A method of ameliorating symptoms of influenza virus infection comprising administering a safe and effective amount of the compound 6-(1H-indol-4-yl)-4-(5-{[4-(1-methylethyl)-1-piperazinyl]methyl}-1,3-oxazol-2-yl)-1H-indazole hemi succinate.

* * * * *